(12) United States Patent
Xu et al.

(10) Patent No.: US 12,376,822 B2
(45) Date of Patent: Aug. 5, 2025

(54) THREE-DIMENSIONAL MAPPING OF DEEP TISSUE MODULUS BY STRETCHABLE ULTRASONIC ARRAYS

(71) Applicant: THE REGENTS OF THE UNIVERSITY OF CALIFORNIA, Oakland, CA (US)

(72) Inventors: Sheng Xu, La Jolla, CA (US); Hongjie Hu, La Jolla, CA (US); Xiaoxiang Gao, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 70 days.

(21) Appl. No.: 18/562,022

(22) PCT Filed: May 26, 2022

(86) PCT No.: PCT/US2022/031048
§ 371 (c)(1),
(2) Date: Nov. 17, 2023

(87) PCT Pub. No.: WO2022/251436
PCT Pub. Date: Dec. 1, 2022

(65) Prior Publication Data
US 2024/0237965 A1    Jul. 18, 2024

Related U.S. Application Data

(60) Provisional application No. 63/193,224, filed on May 26, 2021.

(51) Int. Cl.
*A61B 8/08* (2006.01)
*A61B 8/00* (2006.01)

(52) U.S. Cl.
CPC ............ *A61B 8/0858* (2013.01); *A61B 8/403* (2013.01); *A61B 8/4488* (2013.01); *A61B 8/485* (2013.01)

(58) Field of Classification Search
CPC ..... A61B 8/0858; A61B 8/403; A61B 8/4488; A61B 8/485
See application file for complete search history.

(56) References Cited

U.S. PATENT DOCUMENTS

| | | | | |
|---|---|---|---|---|
| 5,178,147 A | * | 1/1993 | Ophir | ..................... G01N 29/07 600/437 |
| 5,293,870 A | * | 3/1994 | Ophir | .................. G01S 7/52042 600/437 |

(Continued)

FOREIGN PATENT DOCUMENTS

| | | |
|---|---|---|
| WO | 2020/215075 A1 | 10/2020 |
| WO | 2022215075 A1 | 10/2020 |

OTHER PUBLICATIONS

Sevan Goenezen et al., Linear and Nonlinear Elastic Modulus Imaging: An Application to Breast Cancer Diagnosis, IEEE Transactions on Medical Imaging, Aug. 1, 2012, pp. 1628-1637, vol. 31, No. 8.

*Primary Examiner* — Dixomara Vargas
(74) *Attorney, Agent, or Firm* — Stuart H. Mayer; Kaplan Breyer Schwarz LLP

(57) ABSTRACT

A method for determining mechanical properties of tissue in an individual includes attaching a stretchable and/or flexible ultrasound imaging device to the individual. The imaging device includes at least a one-dimensional array of transducer elements that transmit ultrasound waves into the individual. A first series of ultrasound waves are received from the tissue in the individual before applying a strain to the tissue by compression and a second series of ultrasound waves are received from the tissue after applying the com- (Continued)

pression to the tissue. Data from the first and second series of ultrasound waves are compared to obtain displacement data of the tissue from which strain data representing strain applied to the tissue is obtainable. A 2D image representing a 2D modulus distribution within the tissue is generated using the displacement data. One or more mechanical properties of the tissue is identified based on the 2D modulus distribution.

18 Claims, 108 Drawing Sheets

(56) References Cited

U.S. PATENT DOCUMENTS

| | | | |
|---|---|---|---|
| 5,474,070 A * | 12/1995 | Ophir | G01N 29/07 600/437 |
| 5,860,934 A * | 1/1999 | Sarvazyan | A61B 1/0052 600/587 |
| 5,922,018 A | 7/1999 | Sarvazyan | |
| 2006/0052696 A1 * | 3/2006 | Shiina | G01S 15/8906 600/437 |
| 2006/0173320 A1 * | 8/2006 | Radulescu | A61B 8/485 600/438 |
| 2007/0244390 A1 * | 10/2007 | Matsumura | A61B 8/463 600/437 |
| 2010/0286520 A1 | 11/2010 | Hazard et al. | |
| 2011/0125019 A1 | 5/2011 | Shiina et al. | |
| 2013/0046175 A1 | 2/2013 | Sumi | |
| 2014/0206995 A1 * | 7/2014 | Oikawa | A61B 8/403 600/438 |
| 2014/0221833 A1 * | 8/2014 | Oikawa | A61B 8/0858 600/438 |
| 2014/0288424 A1 | 9/2014 | Mukdadi | |
| 2020/0281568 A1 | 9/2020 | Hoerig et al. | |
| 2020/0286520 A1 | 9/2020 | Patry et al. | |
| 2023/0048327 A1 * | 2/2023 | Lampe | A61B 8/488 |

* cited by examiner

| Diseases | Muscles | Functions of the stretchable ultrasonic patch | Citations |
|---|---|---|---|
| Myositis | Thigh/arm muscles | Rehabilitation | 4 |
| Cerebral palsy | Lateral gastrocnemius | Rehabilitation | 5 |
| Stroke | Biceps brachii muscle | Diagnosis/Rehabilitation | 6 |
| Amyotrophic lateral sclerosis | Quadriceps muscle | Diagnosis/Rehabilitation | 7 |
| Muscle damage | Posterior thigh muscles | Diagnosis/Rehabilitation | 8 |
| Delayed onset muscle soreness | Biceps brachii muscle | Diagnosis/Rehabilitation | 9 |
| Tendinopathy | Achilles tendon | Diagnosis/Rehabilitation | 10 |
| Parkinson's disease | Biceps brachii muscle | Diagnosis/Rehabilitation | 12 |

*FIG. 6B*

| Measurement modalities | Wearability | Testing targets | Testing depths | Spatial resolutions | Mapping | Citations |
|---|---|---|---|---|---|---|
| Suction | Too bulky | Skin | <1 mm | >6 mm | 0D | 13 |
| Compression | Too bulky | Shallow tissue | <1 cm | >5 mm | 0D | 14 |
| Extension | Too bulky | Skin | <2 mm | >30 mm | 0D | 15 |
| Small-scale indentation | Too bulky | Skin | <20 μm | >5 μm | 2D | 16 |
| Rigid ultrasonic array | Too bulky | Deep tissue | >4 cm | >0.1 mm | 3D | 18, 19, 23, 24 |
| MRE | Too bulky | Deep tissue | >4 cm | >0.9 mm | 3D | 25, 26 |
| Optical coherence elastography | Too bulky | Skin | <0.6 mm | >6.1 μm | 3D | 27, 28 |
| Flexible piezoresistive cantilevers | Yes | Skin | <20 μm | >40 μm | 0D | 33 |
| Conformal piezoelectric thin film | Yes | Skin | <2 mm | >0.3 mm | 2D | 34 |
| Tactile sensor | Yes | Shallow tissue | <5 mm | >2 mm | 2D | 35 |
| Needle-shaped piezoelectrics | Invasive | Shallow tissue | <4.5 mm | >0.5 mm | 0D | 36 |
| Stretchable ultrasonic array | Yes | Deep tissue | <4 mm | >0.56 mm | 3D | This work |

FIG. 7

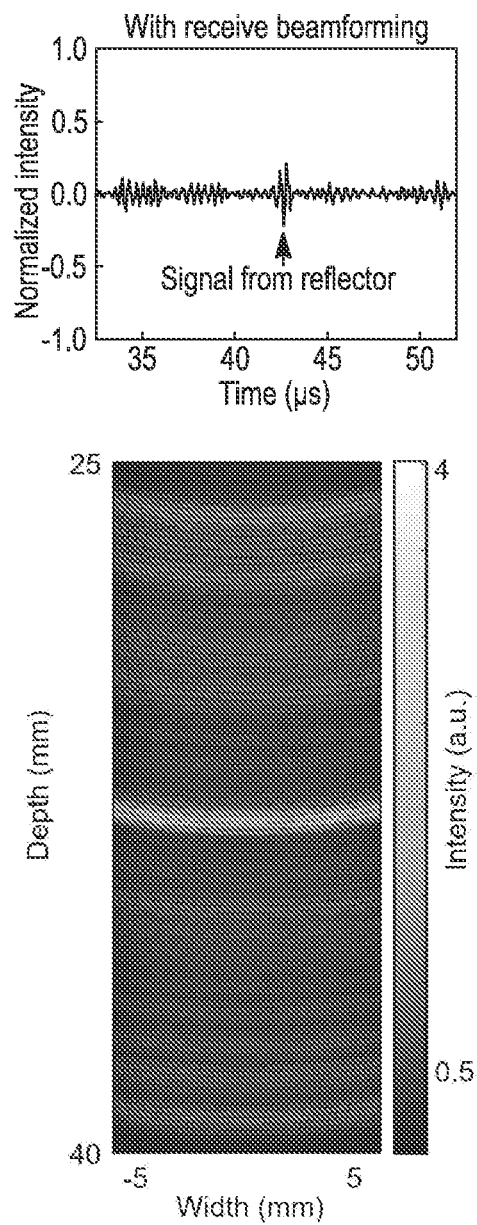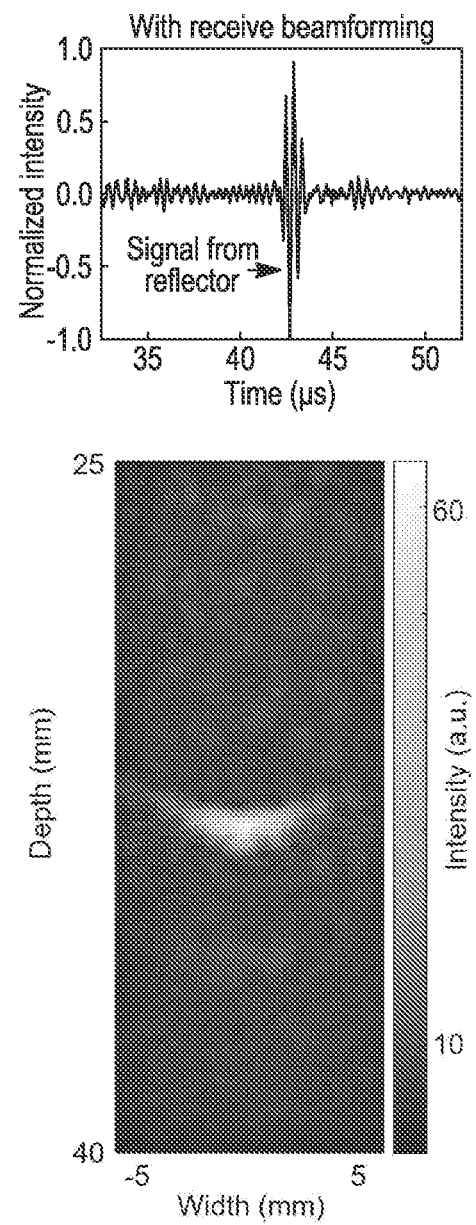
FIG. 13B
FIG. 13C

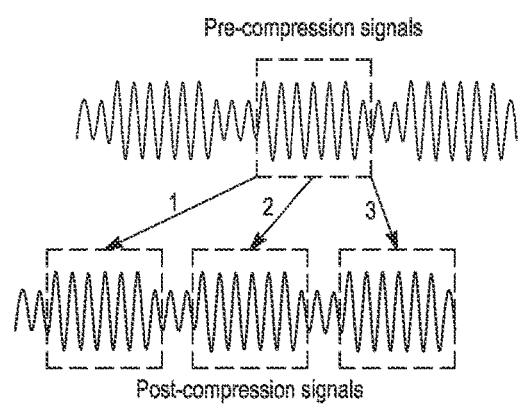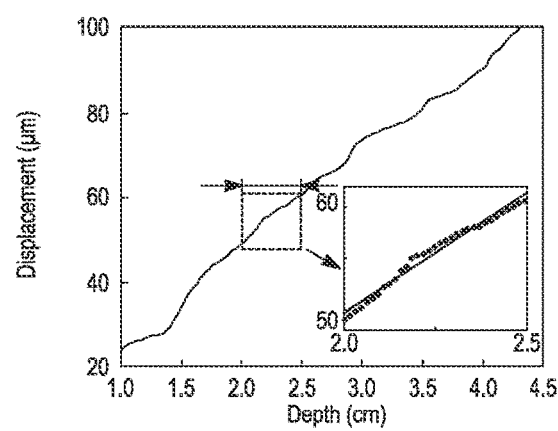
FIG. 17B
FIG. 17C

Layer 1

Layer 2

Layer 3

Layer 4

Layer 5

Layer 6

Bottom electrode 5 mm

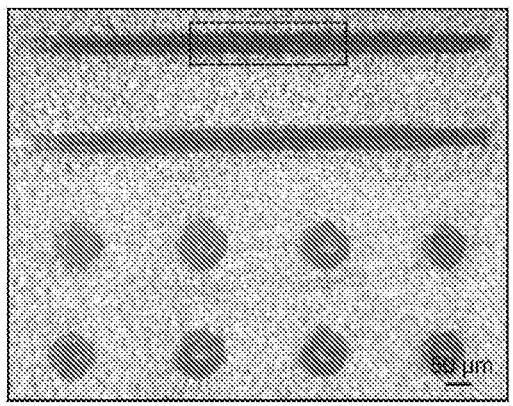
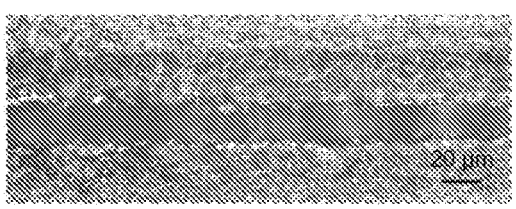
FIG. 23C
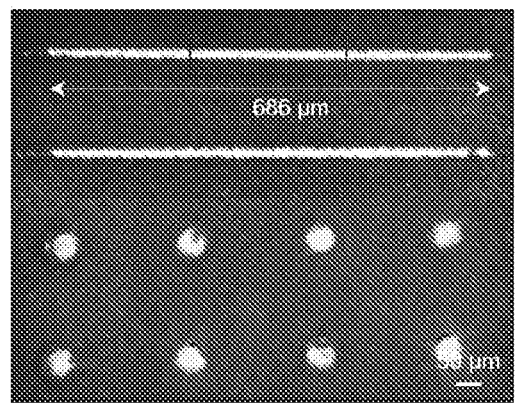
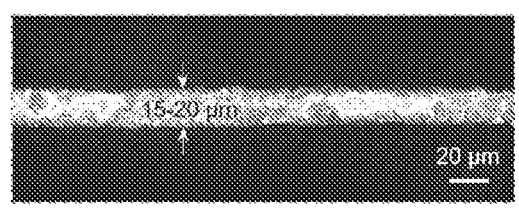
FIG. 23D

Results from a stretchable ultrasonic array

Results from a commercial ultrasound probe

Results from a stretchable ultrasonic array

Results from a commercial ultrasound probe

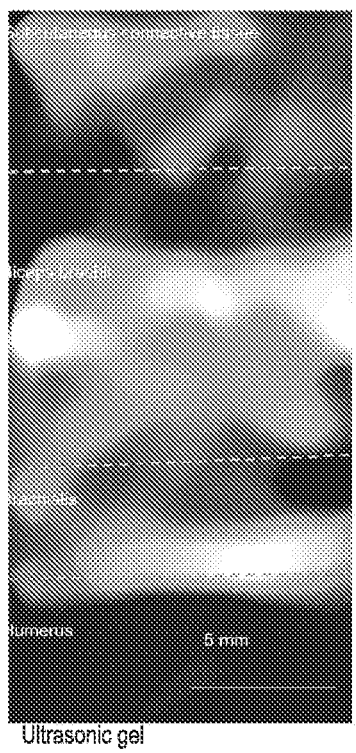 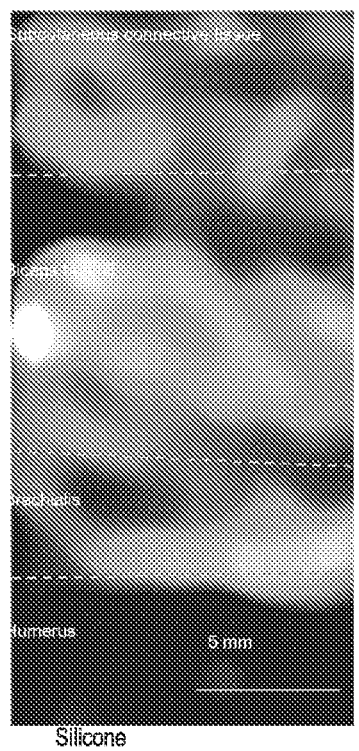 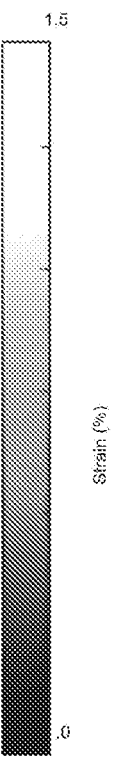
FIG. 57D  FIG. 57E

THREE-DIMENSIONAL MAPPING OF DEEP TISSUE MODULUS BY STRETCHABLE ULTRASONIC ARRAYS

GOVERNMENT FUNDING

This invention was made with government support under EB027303 awarded by the National Institutes of Health. The government has certain rights in the invention.

BACKGROUND

The mechanical properties of human tissues are vital for the structure and function of the human physiological systems. Frequent mechanical characterizations of various organs allow timely evaluation of tissue growth, metabolic state, immunologic function, and hormone regulation. Most importantly, the mechanical properties of diseased tissues can often reflect pathophysiological conditions. Monitoring of these properties can provide key information about disease progression and guide intervention in a timely manner. For instance, the stiffness of cancerous tumors is known to be different from healthy tissues. Additionally, in some tumors, changes in stiffness can occur as they grow in certain developmental stages, and these changes can happen quickly. Frequent inspections of these tumors' stiffness are required for growth stage assessment and therapy guidance. Mechanical characterization is also critical in the diagnosis and rehabilitation of many musculoskeletal diseases and injuries. Long-term monitoring of muscular moduli enables more proactive screening of the area at risk. Serial surveillance of tissue moduli has also been demonstrated to help with early detection and tracking of cardiovascular diseases. An ideal technology should provide temporal, non-invasive, and three-dimensional (3D) mapping of deep tissues with accurate location, morphology, and mechanical information. However, existing methods are unable to address this critical need.

From inflammation to cyst, fibrosis, and carcinoma, many pathological manifestations alter the mechanical properties, especially the elastic modulus, of the soft tissue, which can serve as biomarkers for clinical diagnosis. Specifically, the increase in Young's modulus is typical in the development of both benign and malignant tumors in the human breast, primarily due to the proliferation of denser collagen fibers in the extracellular matrix. Cysts filled with liquids exhibit much lower stiffness than the normal tissue. Musculoskeletal and tendinous tissues associated with injury or inflammation, such as myositis and delayed onset muscle soreness, embody distinct differences in local stiffness. Moreover, differentiation of Parkinson's disease from Parkinsonian syndrome requires strain ratio tests of biceps brachii muscles every minute, before and after drug administration. The lack of frequent examination and long-term monitoring abilities prevents quick and effective tracking of tumor growth, cysts development, and diagnosis and rehabilitation processes of multiple musculoskeletal diseases and injuries.

SUMMARY

Serial surveillance of a tissue's biomechanical properties has proven to effectively screen early pathophysiological conditions, track the evolution of lesions, and evaluate the progress of rehabilitation. Existing assessment methods are either invasive, for short-term use only, or provide limited penetration depth or spatial resolutions. Described herein is a stretchable ultrasonic array that overcomes the shortcomings of the existing methods. In some cases the stretchable ultrasonic array enables serial non-invasive elastographic measurements in regions greater than e.g., 4 cm beneath the skin. The reconstructed three-dimensional distributions of the Young's moduli in biological tissues have been quantitatively verified by magnetic resonance elastography. When applied to delayed onset muscle soreness, the stretchable ultrasonic array can detect the microstructural damage of muscles within 20 minutes after exercise, well before the sore sensation of the subject starts. The ultrasonic array also allows serial monitoring of the dynamic recovery process of the muscle injuries under different physiotherapies. The results from the wearable array and associated methods can be used to manage a wide range of diseases and conditions, with substantially improved user experience and clinical outcomes.

In one aspect, a method is provided for determining one or more mechanical properties of tissue in an individual. In accordance with the method, a stretchable and/or flexible ultrasound imaging device is attached in a removable manner to the individual. The stretchable and/or flexible ultrasound imaging device includes at least a one-dimensional array of transducer elements. Ultrasound waves are transmitted into the individual using the transducer elements. A first series of ultrasound waves are received from the tissue in the individual using the transducer elements before applying a strain to the tissue by compression and a second series of ultrasound waves are received from the tissue in the individual using the transducer elements after applying the compression to the tissue. Data from the first series of ultrasound waves is compared to data from the second series of ultrasound waves to obtain displacement data of the tissue from which strain data representing strain applied to the tissue is obtainable. At least one 2D image representing a 2D modulus distribution within the tissue is generated using the displacement data of the tissue. One or more mechanical properties of the tissue is identified based on the 2D modulus distribution.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTION OF THE DRAWINGS

FIG. 6A-6B show data demonstrating the significance of the stretchable ultrasonic array for serial tissue modulus monitoring.

FIG. 7 compares existing methods for tissue modulus mapping.

FIGS. 13A-13C shows schematics, images and data demonstrating the effects of the receive beamforming.

FIGS. 17A-17C illustrates the normalized cross-correlation and least-squares strain estimator algorithms.

FIGS. 23A-23D show schematics and data concerning the evaluation of the effective laser beam size and depth of focus.

FIGS. 57A-57E show data and images comparing the coupling performance between ultrasonic gel and Silicone.

DETAILED DESCRIPTION

Introduction

Described herein is a stretchable and/or flexible ultrasonic array with improved device engineering and imaging algorithms. A coherent compounding imaging strategy enables accurate displacement calculations, and therefore, enhanced elastographic signal-to-noise ratio ($SNR_e$) and contrast-to-noise ratio ($CNR_e$) in the entire sonographic window. By solving an inverse elasticity problem, we can derive quantitative modulus distribution, which is significant improvement upon the qualitative strain distribution obtained with conventional quasi-static elastography. The reliability of this technology is demonstrated by tests on various artificial phantom models and ex vivo biological specimens, with quantitative validation by magnetic resonance elastography (MRE). In vivo studies on delayed onset muscle soreness shows that the devices and methods described herein can track the recovery progress of muscular injury in a noninvasive, serial manner, providing therapeutic guidance. These results suggest a convenient and effective approach to monitor tissue mechanical properties, facilitating the diagnosis and treatment of a wide range of diseases and symptoms.

Figure 1A:
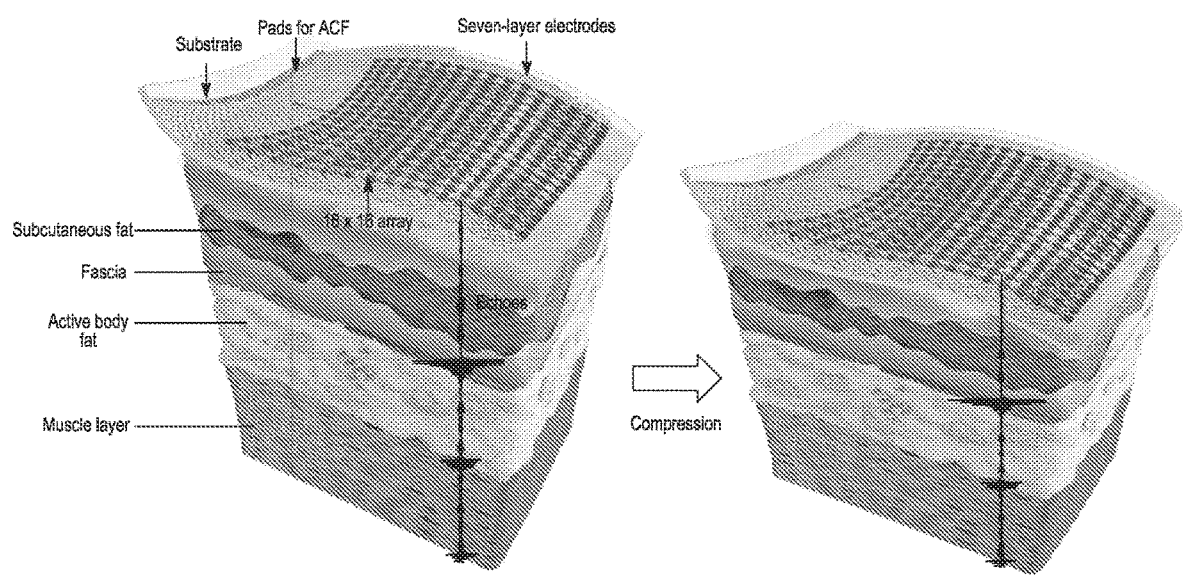
FIGS. 1A-1G shows various views and characterization data for the stretchable and/or flexible ultrasonic array described herein.
Figure 11:
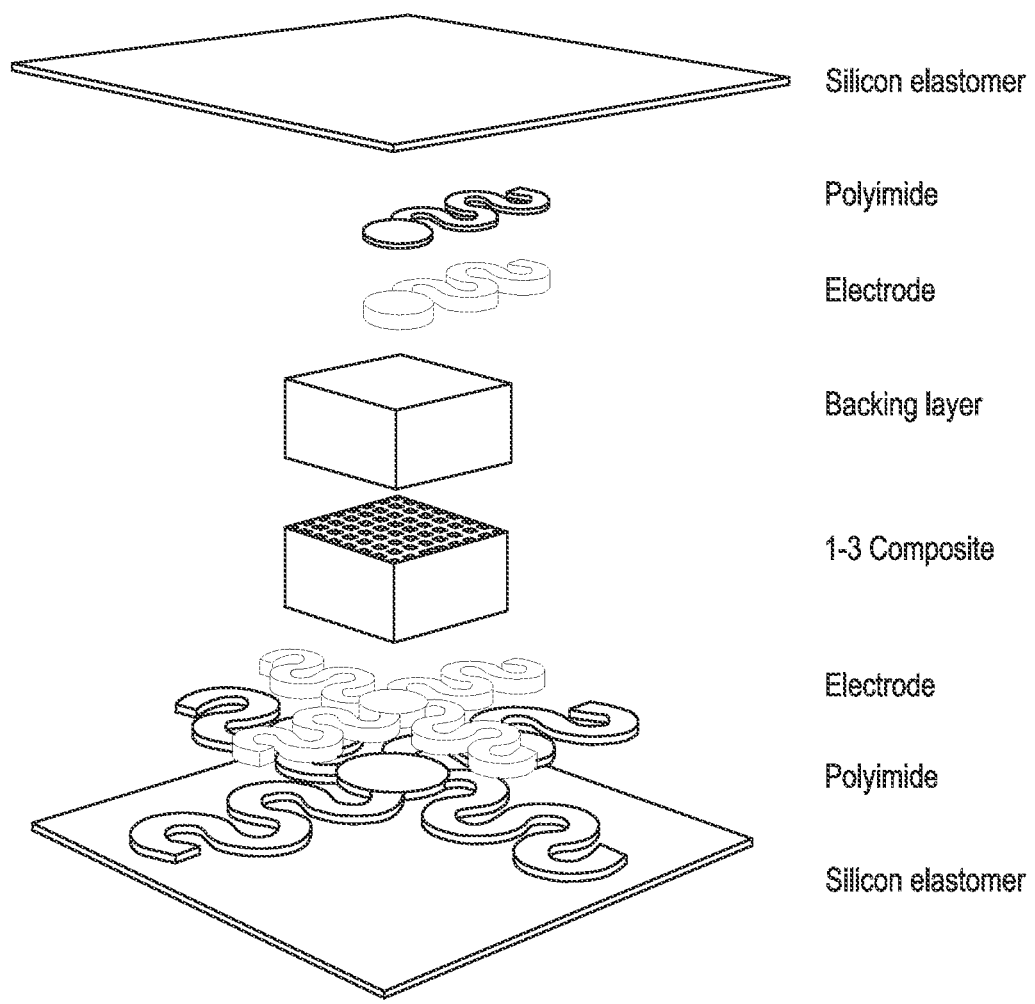
FIG. 11 is a schematic of the exploded view of one transducer element.

Measurements by traditional rigid ultrasound probes may suffer from poor acoustic coupling, because their rigid surfaces cannot accommodate the curvilinear shape of the human body. To address this problem, the stretchable and/or flexible ultrasonic array described herein can be used for modulus sensing. FIG. 1a shows the schematic working mechanism of one particular embodiment of the stretchable and/or flexible ultrasonic device that employs a 16 by 16 array of transducer elements (see FIGS. 11 and 12 for additional details, which are described below). As illustrated in FIG. 1a, the array is able to conform to and acoustically couple with the human skin via a type of silicone-based couplants for high-quality imaging (see FIGS. 10A-10F, described below). In this embodiment the transducer elements are connected in-parallel by a seven-layer electrode and encapsulated with water-proof and biocompatible silicone elastomer. An exploded view of each element is shown in FIG. 11, showing the structure and components of the element. This layout design allows activating each element individually with a particular time-delay profile and capturing the reflected echoes from scattering sources, (left) pre- and (right) post-compression. The beamformed pre- and post-compression signals are cross-correlated to derive the displacement, strain, and modulus fields. ACF: anisotropic conductive film.

After the array is activated, ultrasound waves are sent into the tissue underneath the device. Scattering sources (e.g., tissue interfaces) can reflect the ultrasound waves, which carry location information of these scattering sources. The reflected waves are then received by the transducer elements in the ultrasonic array as radiofrequency data. The collected radiofrequency data by each element are then enhanced by receive beamforming (see FIGS. 13A-E, described below). After that, strain (e.g., 0.5%~1% strain) is applied to the tissue by quasi-static uniaxial compression. The low strain ensures that the tissues exhibit linear stress-strain behavior, i.e., their Young's modulus does not vary with load. After compression, the maximum change in the array's pitch is only 0.02% (see FIGS. 14A-14B, described below). Therefore, the associated phase aberration is negligible for both transmit and receive beamforming, especially for deep-tissue inspections (see FIGS. 15A-F and FIGS. 16A-16D, described below). As a result, we can use the same time-delay profile for both post- and pre-compression receive beamforming.

A normalized cross-correlation algorithm was used to compare the radiofrequency data before and after compression, and calculate the displacements of the scattering sources with high sonographic sensitivity and accuracy (see FIGS. 17A and 17B, described below). A least-squares strain estimator was used to transform displacements to strain while minimizing possible fluctuations (see FIG. 17C, described below). A graphical user interface having real-time display windows and control panels may be used for locating the device and quantifying the compression to the subject (see FIGS. 18A-18B, described below). An inverse elasticity problem, discussed in more detail below, was solved to quantify the modulus distribution inside the tissue.

In some embodiments a center frequency of 3 MHz may be to balance the requirement of high spatial resolution and frequency-dependent linear attenuation of the ultrasound wave in tissues. The characterized mean resonant and anti-resonant frequencies show a small standard deviation, indicating the consistency across the entire array (see FIG. Tb, which shows the resonant frequency, anti-resonant frequency, and calculated effective electromechanical coupling coefficient (Ker) distribution of the 256 elements (inset).). Given the corresponding ultrasound wavelength of ~500 μm in soft tissues, we chose a pitch of 800 μm that is suitable for generating wave convergence, producing high-quality images, and minimizing crosstalk. The pitch is altered upon conformation to a curvature. However, we determined that it was reasonable to continue using the initial planar design pitch of 800 μm in the beamforming of a curved surface, due to negligible changes in pitch of no more than 0.0030% within the adoptable curvature range of the array (FIGS. 19A-19G, described below). It should be noted that all images are shown herein in grayscale and generally represent color images that depict various features using different colors.

Figure 1B:
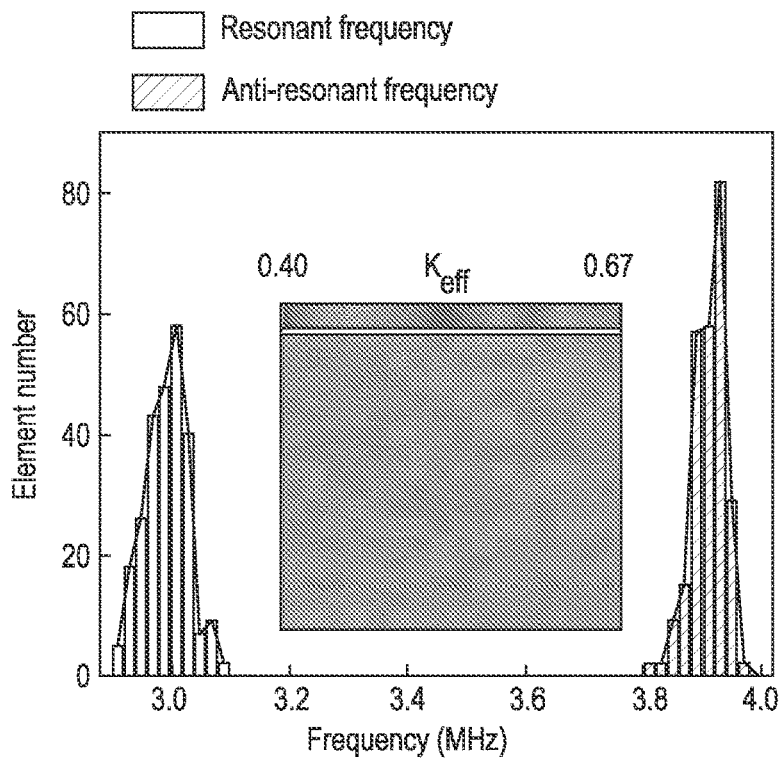

A scalable method was used to align the backing material and the transducer elements, which enhanced the fabrication throughput and performance consistency, and avoided potential phase aberrations (see FIGS. 20A and 20B discussed below). To individually address the 256 elements, six layers of activation electrodes and one layer of common ground in a serpentine shape were transfer-printed and routed to the same plane by vertical interconnect accesses (see Supplementary FIGS. 21A-23D, discussed below). A low-temperature bonding technique was used to preserve the high electromechanical coupling coefficient of the 256 elements (average 0.64, FIG. 1b inset), with performance comparable to elements in commercial ultrasound probes (0.58-0.69). The 0.022 of averaged dielectric loss of the array indicates the energy consumption caused by the heating of the transducer is minimal (see FIG. 24a, discussed below). The time- and frequency-domain characterizations with pulse-echo response and bandwidth are shown in Supplementary FIGS. 24b and 24c where the ~50% bandwidth is derived.

Figure 1C:
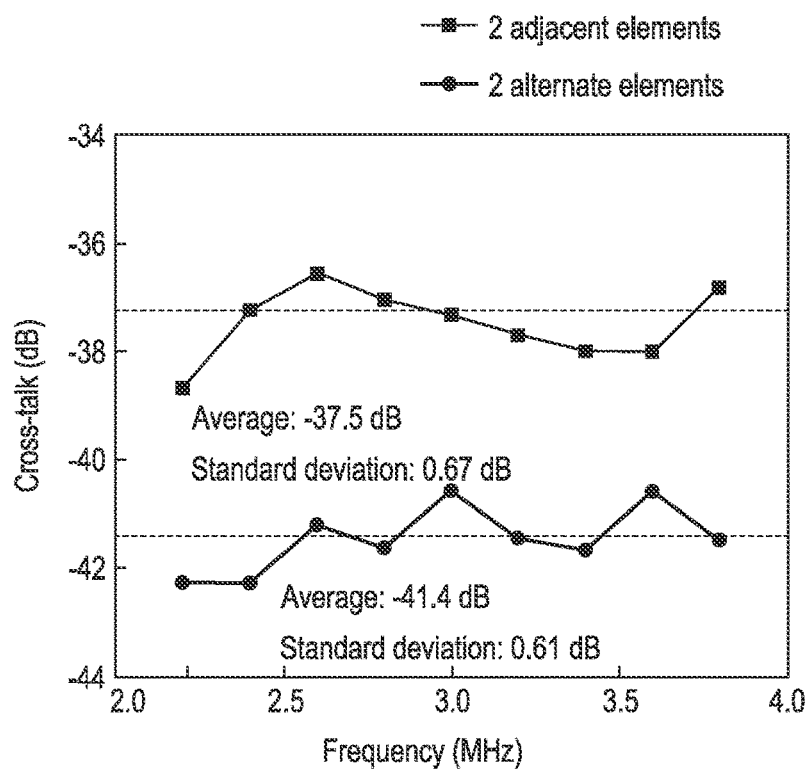
Figure 1D:
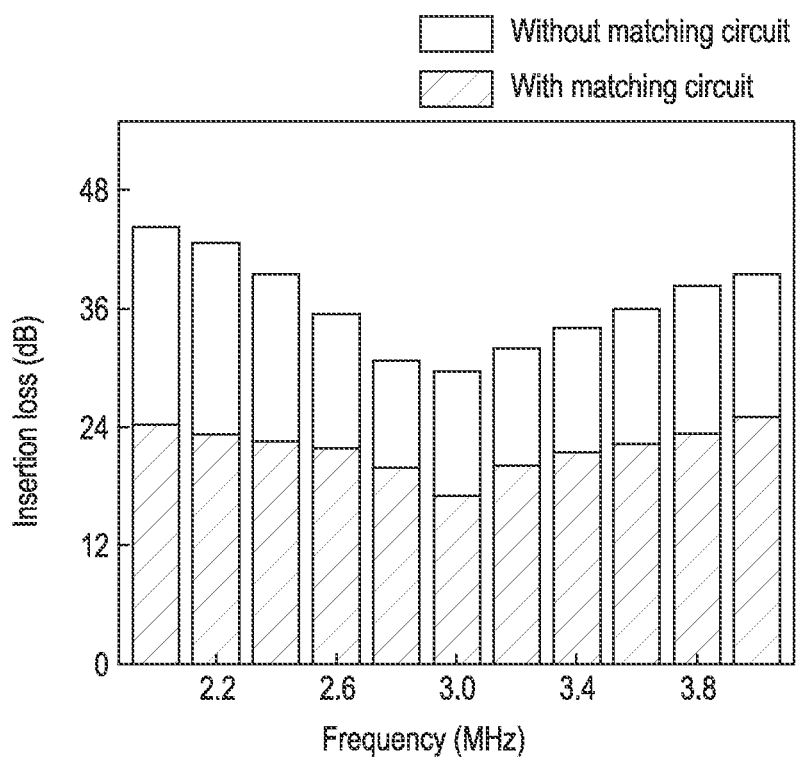
Figure 1E:
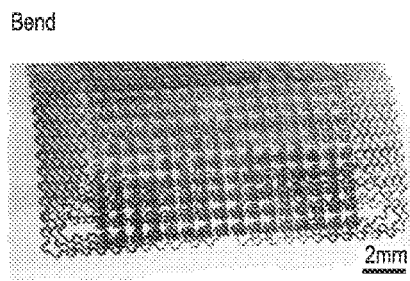
Figure 1F:
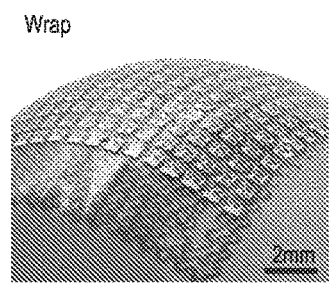
Figure 1G:
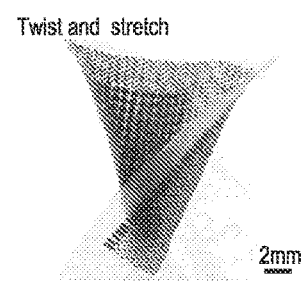

Because of the well-designed pitch, the suppression of shear vibrations by the 1-3 composite, and the damping effect of silicone elastomer between the elements, crosstalk between the elements is below the standard value of −30 dB (see FIG. 1c, which shows an evaluation of crosstalk between two adjacent elements and two alternate elements). A matching circuit effectively reduces the insertion loss to 16.98 dB at the resonant frequency (see FIG. 25, discussed below), comparable to a commercial probe (17 dB). The low insertion loss leads to excellent sonographic sensitivity, which is pivotal for modulus imaging. FIG. 1d shows the insertion loss of the transducers with and without the matching circuit. The insertion loss has a minimum value at the resonant frequency because of the maximum electrical power generated by the echoes The high-performance 1-3 composite material used, together with the innovative fabrication protocol and effective matching circuit, results in an average sonographic signal-to-noise ratio of 39 dB, comparable to a commercial probe (41 dB). The standard deviation of the sonographic signal-to-noise ratio measured underwater for two weeks is small (0.87), because of the excellent water-proof property of the encapsulating silicone elastomer (see FIG. 26A-26B, discussed below). As shown in FIGS. 1e-1g, the device can be reversibly deformed in various modes. Optical images are shown of the imaging device when bent (FIG. 1e) or wrapped (FIG. 1f) on complex-shaped surfaces, and twisted and stretched (FIG. 1g), showing its mechanical compliance and robustness. The maximum biaxial stretchability of the device without affecting its electromechanical properties is ~40%, indicating its reliability for skin integration (see FIGS. 27 and 28, discussed below).

Strategies for Elastography

Figure 2A:
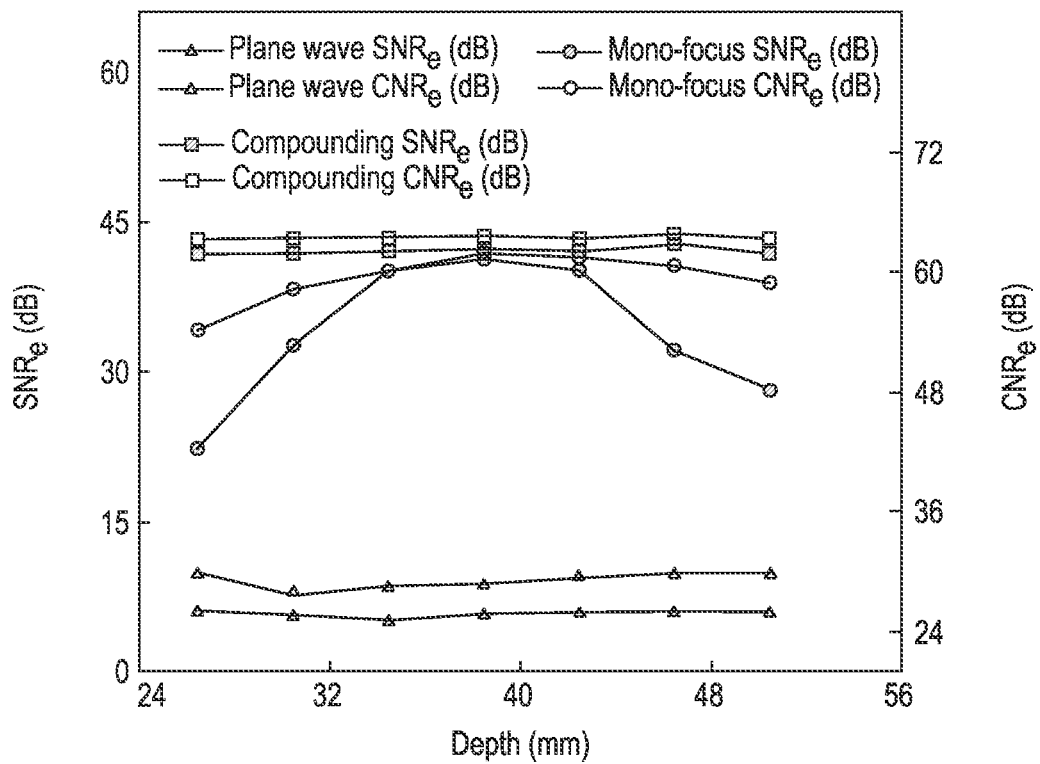
FIGS. 2A-2F show data for determining strategies for elastography
Figure 2B:
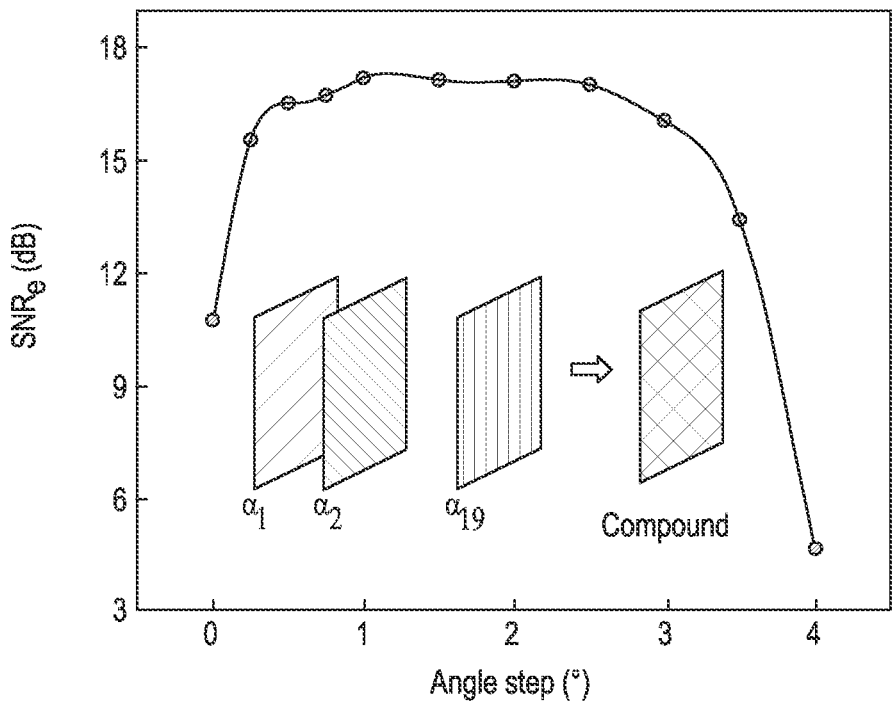
Figure 2C:
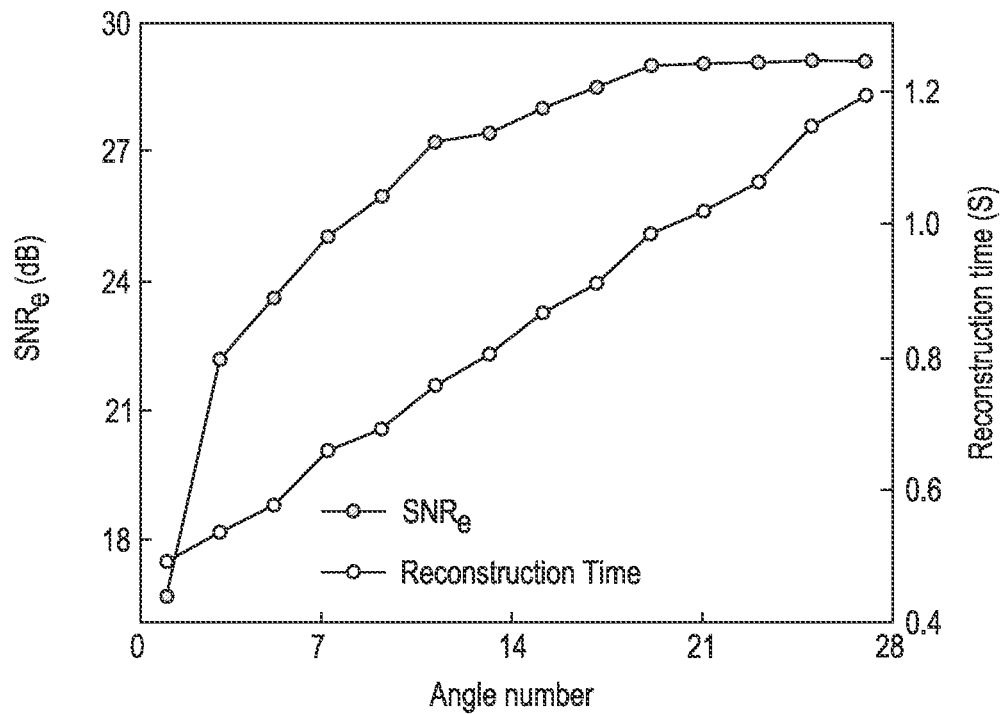

To determine the transmission mode for elastography, we simulated two-dimensional (2D) strain distributions in a bilayer phantom under three different transmission modes: single plane wave, mono-focus, and coherent plane-wave compounding (see Supplementary FIG. 24, described below), and then analyzed the $SNR_e$ and $CNR_e$, the two most critical metrics for modulus mapping . . . . Among the three modes, the single plane wave mode produces the lowest $SNR_e$ and $CNR_e$, because of the low transmission energy from non-focal scanning. FIG. 2a are simulations showing the $SNR_e$ and $CNR_e$ of the coherent plane wave compounding, mono-focus, and single plane wave transmission modes in a bilayer phantom. These data are extracted at seven different depths along the central line of strain images in Supplementary FIG. 18, discussed below. The mono-focal mode provides better $SNR_e$ and $CNR_e$, but only in regions near the focal depth. The coherent plane-wave compounding mode consists of a series of single plane waves at different transmission angles, and these steered frames are coherently integrated to reconstruct a multi-angle compounding image, with multiplex signal intensities across the entire region. The resulting $SNR_e$ and $CNR_e$ levels are significantly enhanced in all regions. The performance of the compounding strategy highly depends on the step size and the number of the steering angles used. In this work, we use 19 steering angles and a step size of 1°, which were found in experiments to give the best elastographic image quality. FIG. 2b shows the $SNR_e$ as a function of the step size of the steering angle. The inset is a schematic diagram showing the process of compounding: a set of plane waves are transmitted with different steering angles and a final compounded image is built by coherently adding all beamformed images. FIG. 2c shows the $SNR_e$ and reconstruction time with different numbers of steering angles. (see also FIGS. 30 and 31, discussed below).

Figure 2D:
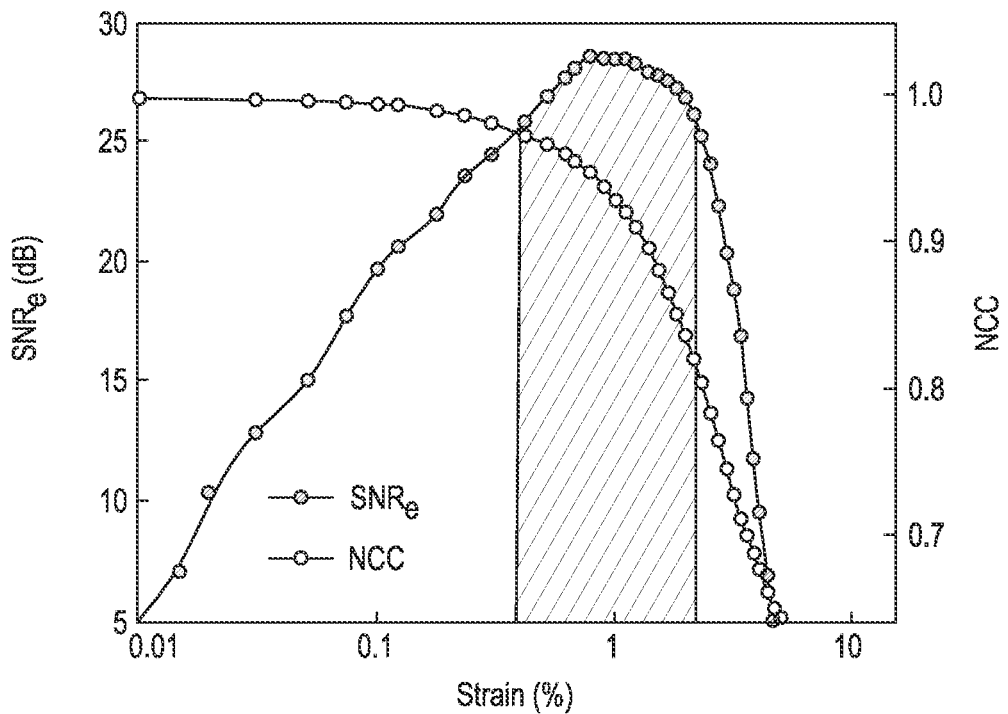

A high $SNR_e$ is important for high-quality elastographic imaging. The $SNR_e$ is influenced by the magnitude of applied strain and the normalized cross-correlation coefficient, which reflects the similarity of the radiofrequency signals before and after compression. The smallest detectable strain with $SNR_e$ of 6 dB is 0.0125%, which indicates the high elastographic sensitivity of the stretchable array. FIG. 2d shows the $SNR_e$ and normalized correlation coefficient (NCC) as a function of applied strain. The shaded area with >0.8 NCC by a −3 dB strain filter shows the dynamic range. At low strain levels, the displacement signals are small, so the relatively large intrinsic electrical noise in the radiofrequency signals leads to large deviations in the elastographic images and thus a low $SNR_e$. As the applied strain increases, the displacement signals increase proportionally, while the intrinsic electrical noise remains relatively constant, leading to an increase in the $SNR_e$. The $SNR_e$ becomes the highest at ~1% strain. Beyond 1% strain, the radiofrequency signals distort in shape and amplitude, resulting in a sharp fall in the normalized cross-correlation coefficient and therefore $SNR_e$ (see FIG. 2d). The dynamic range (i.e., the strain range with high $SNR_e$) was determined by a −3 dB cutoff from the maximum $SNR_e$, which is 0.36%~2.34% in this work, corresponding to a normalized cross-correlation coefficient>0.8.

Figure 2E:
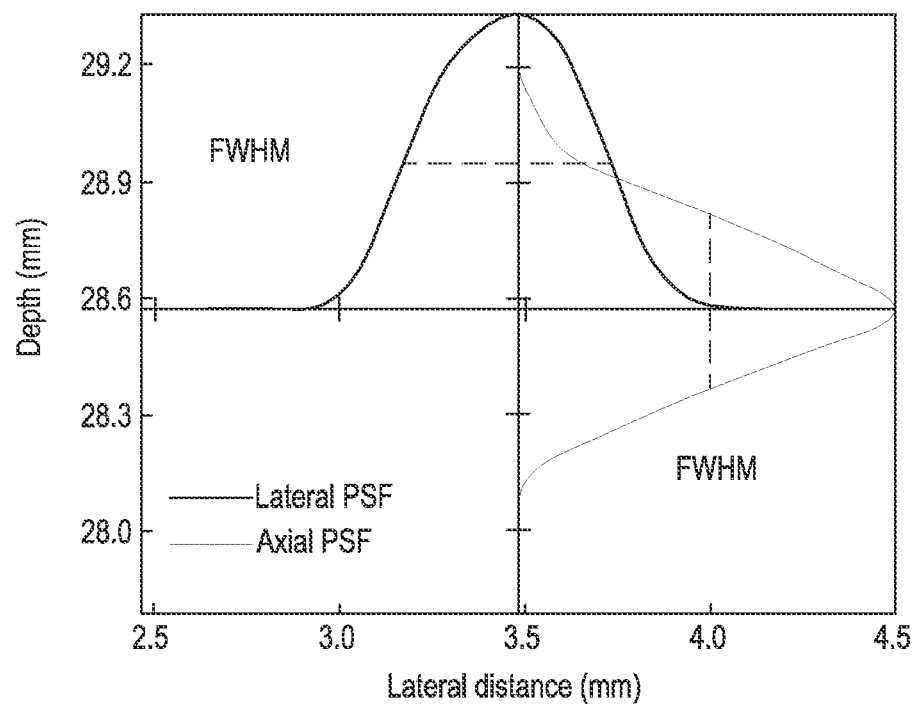

Both spatial resolution and contrast resolution are also important for elastographic imaging. To characterize the spatial resolution, we imaged and extracted the modulus distribution of the lateral and axial transition edges in an inclusion phantom (see FIG. 32, discussed below). The first derivatives of the modulus distribution yield the point spread functions (see FIG. 33, discussed below), whose full widths at half maximum are used to estimate the elastographic spatial resolutions. The spatial resolutions are then determined to be 0.56 mm in the lateral and 0.50 mm in the axial directions. FIG. 2e shows the lateral and axial resolutions of the stretchable ultrasonic array based on the full width at half maximum (FWHM) of point spread functions (PSF). Because of the synthetic focusing effect of the coherent plane-wave compounding mode, the spatial resolution remains high and consistent at different locations across the entire imaged region.

Figure 2F:
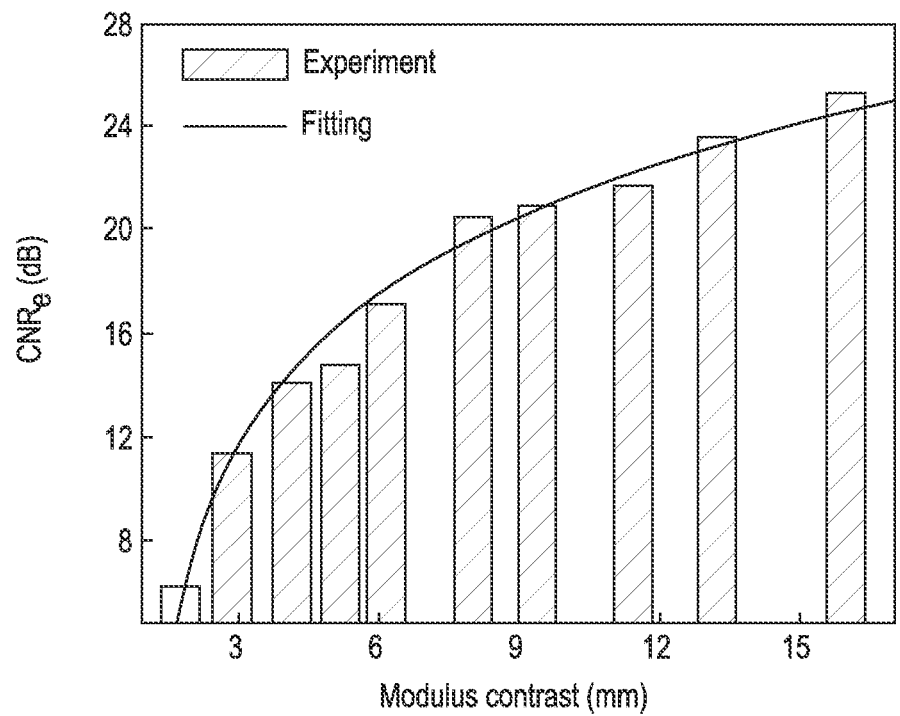

Similar to the spatial resolution, the contrast resolution is defined as the modulus contrast with a corresponding $CNR_e$ of 6 dB. To quantify the contrast resolution, we performed tests on bilayer phantoms, each composed of two homogenous gelatin phantoms with different elastic moduli. The modulus of each layer is within 10~100 kPa, covering the modulus range of all typical healthy and diseased tissues (see FIG. 34, discussed below), which creates an interfacial modulus contrast ranging from 1.79 dB to 15.94 dB. The $CNR_e$, determined by the ratio of the strain contrast to the standard deviation of strain distribution, decreases as the modulus contrast becomes lower. FIG. 2f shows the quantification of the contrast resolution based on the relationship between the $CNR_e$ and modulus contrast of phantom. Logarithmic curve-fitting, with a coefficient of determination>0.98, demonstrates the reliability of the experimental results. The contrast resolution of the device is determined to be ~1.79 dB (i.e., a modulus ratio of 1.22).

Characterizations on Phantom Models.

Following the clinical practice for tumor screening and diagnosis, we used four types of phantoms to simulate different pathological tissue environments (see FIG. 32, discussed below): a one-dimensional (1D) phantom consisting of two layers with different Young's moduli, which mimics muscles with an area of disease or injury; a 2D phantom consisting of a cylindrical cavity filled with fluid, which simulates the cysts that frequently appear in central organs; a 2D phantom with a solid cylindrical inclusion; and a commercial 3D breast phantom with a spherical mass. The last two phantoms mimic tumours and nodes with various morphologies in the breast. Young's moduli of all components have been characterized by either standard apparatus (for customized phantoms, see FIG. 34, discussed below) or a clinical ultrasound machine (for the commercial phantom, FIG. 35).

Figure 3A:
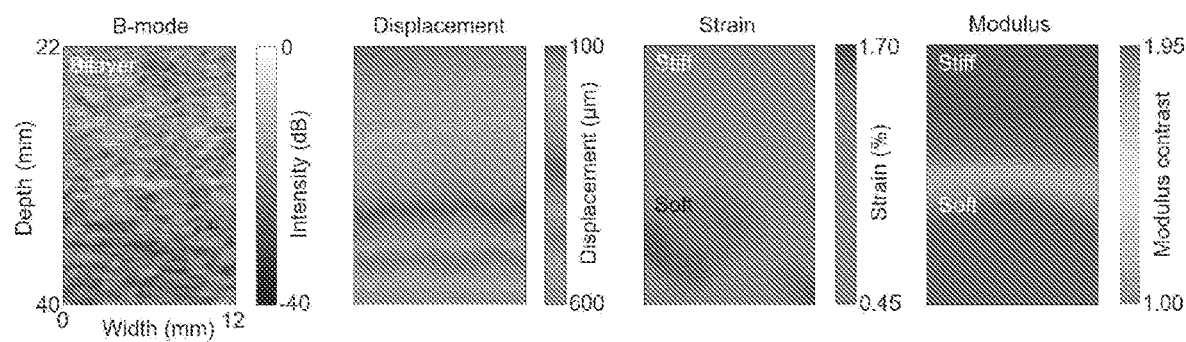
FIGS. 3A-3D show various phantom models that are used to simulate different pathological tissue environments.
Figure 3B:
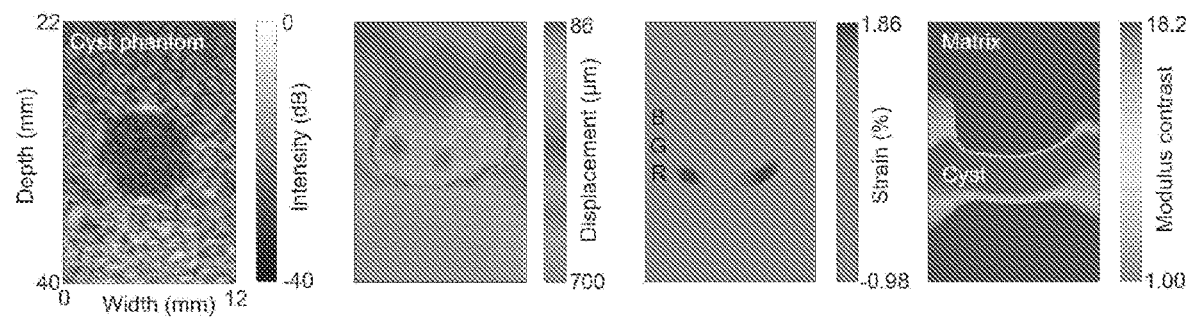
Figure 3C:
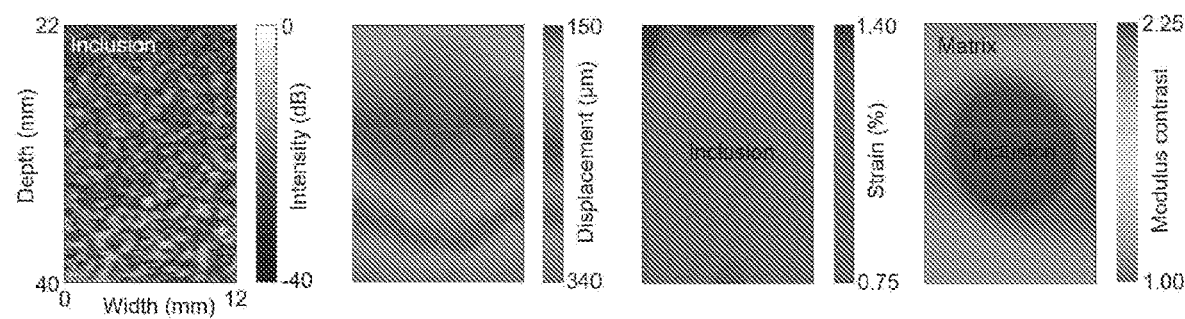
Figure 3D:
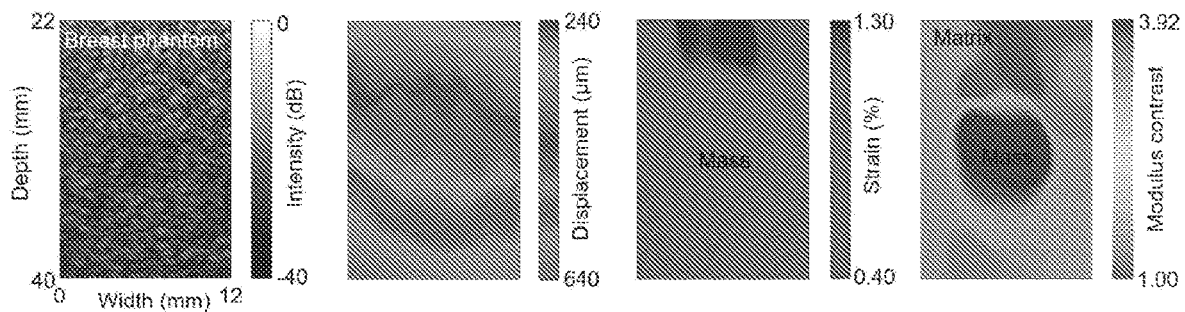

Many masses (except for the cyst phantom) have materials and constituents, and thus acoustic impedances, similar to the surrounding tissues. Thus, they exhibit a homogeneous echogenicity and a minimal sonographic contrast that can hardly be distinguished by B-mode imaging, as seen in the first column of FIGS. 3a-3d. FIG. 3 shows characterizations on phantom models. Four types of phantoms are used to simulate different pathological tissue environments: In particular, FIG. 3a shows a bilayer phantom where the top layer is 2.03 times stiffer than the bottom layer. FIG. 3b shows a cyst phantom consisting of a cylindrical cavity filled with fluid, phantoms with a cylindrical inclusion that is 1.61 times stiffer than the matrix (FIG. 3c). FIG. 3d shows a spherical mass that is 2.54 times stiffer than the matrix. B-mode images of all phantoms acquired by a commercial ultrasound probe are shown in the first column. Displacement fields estimating the motion of each scattering source in the phantoms during compression are shown in the second column. The ultrasonic array's position is defined as the origin. Corresponding strain distributions are shown in the third column. Solving the inverse elasticity problem with the displacement distributions yields quantitative modulus contrasts, shown in the fourth column.

The tests on phantom models focus on the axial displacement fields (see FIGS. 3a-3d, second column). This is because compared with the lateral and elevational displacements, the axial displacements can reflect the movement of each scattering source more accurately, since it is parallel to the direction of ultrasonic wave transmission. The strain is higher when the modulus of the component is lower (the third column in FIGS. 3a-3d). A common practice for computing strain is to take the spatial derivative of the displacement field, which amplifies small fluctuations in the displacement field (see FIG. 17b, discussed below). To remedy this problem, we applied a least-squares strain estimator with a piecewise linear curve fitting method, which allows us to calculate the 2D strain distributions while smoothing unphysical fluctuations (see FIG. 17c, discussed below). The resulting strain distributions clearly reveal the inclusion. An exception is the cyst phantom, whose strain distribution map has a clearly visible region (see FIG. 3b and FIGS. 36 and 37, discussed below) that is distinguishable in color renditions of the map by specific colors, a signature of cysts that has been used clinically to distinguish between cystic and solid lesions. To evaluate the resolution of the stretchable ultrasonic array in the elevation direction, we reconstructed 3D strain images of the phantoms by integrating 16 cross-sectional images obtained by the stretchable array. The 3D imaging results match those of a commercial ultrasound probe with a similar center frequency (2.8 MHz) (see FIGS. 38-41, discussed below). The measurements are highly reproducible, reflecting the reliability of the stretchable array (see FIG. 42, discussed below).

Strain depends on applied loads and thus strain mapping can be subjective and operator-dependent. Additionally, strain maps cannot faithfully reveal quantitative modulus information if the load is non-uniform. To avoid these issues, we quantified the spatial distribution of the shear modulus by solving an inverse elasticity problem. Specifically, we formulated the inverse elasticity problem as a constrained optimization problem. The objective is to seek a shear modulus distribution that produces a predicted displacement field that satisfies the equilibrium equation of the 2D linear elasticity model and matches the measured displacement field. We solve the optimization problem by a gradient-based minimization approach and compute the gradient efficiently using the adjoint method (see FIG. 43, discussed below). The Young's modulus distribution is three times the shear modulus distribution. For a measured displacement field, the derived modulus distribution can be accurately determined. In addition, the non-uniform external compressions do not influence the reconstructed modulus distribution because our inverse approach does not assume a uniform modulus field to a given cross-section (see FIG. 44, discussed below).

The modulus distribution maps visualize the morphology of the internal structures, which accurately match the design (see the fourth column of FIGS. 3a-3d). Shadowing artifacts, usually caused by inclusions (see FIG. 45, discussed below), do not appear in the elastograms here, because of the high transmission energy of the coherent compounding method and the excellent sonographic sensitivity of the stretchable ultrasonic array. The mean modulus contrasts between the stiff and soft components of the bilayer, inclusion, and breast phantoms are 1.94, 1.50, and 2.21, with a difference of 4.59%, 6.81%, and 12.78%, respectively, from those obtained by a standard apparatus. Note that for the cyst phantom, the acquired values only indicate that the stiffness of the cyst is much lower than that of the surrounding matrix, and do not represent the exact modulus ratios. There is a slight underestimation of modulus contrast in all cases because the total variation regularization used to solve the inverse elasticity problem tends to sacrifice the contrast in order to generate less noisy images (see FIG. 46, discussed below). The overall >87% accuracy of the results here is well above the average accuracy of 80% in the literature, because of the outstanding transducer performance and the advanced coherent compounding approach.

Validation and Serial Monitoring on Biological Tissues.

We validated the 3D imaging performance of the stretchable array against MRE on porcine abdominal tissues 4 cm thick with a multilayer structure. Each 1×16 linear array on the ultrasonic patch can map a 2D cross-sectional displacement field and the corresponding modulus distribution (see FIG. 47, discussed below).

Figure 4A:
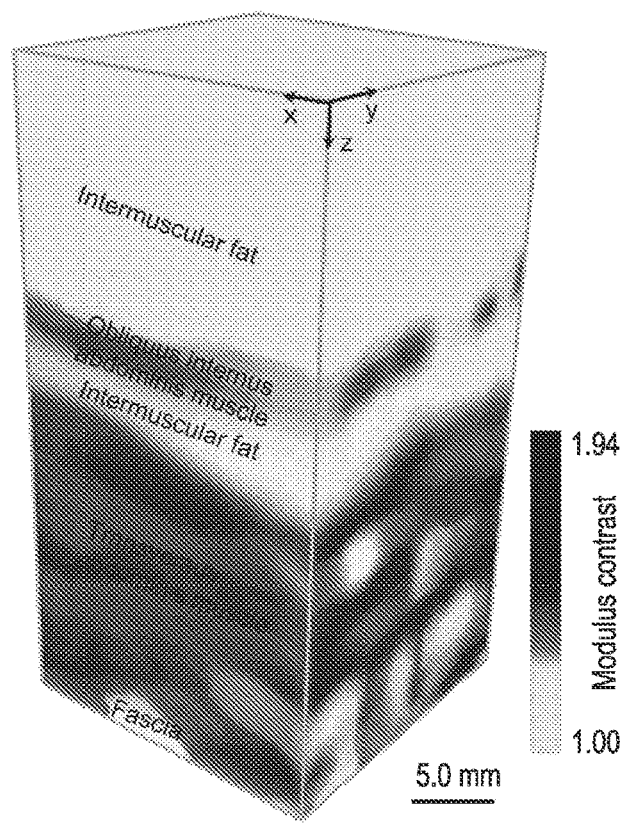
FIGS. 4A-4E show images and data for validating the 3D imaging performance of the stretchable array.
Figure 4B:
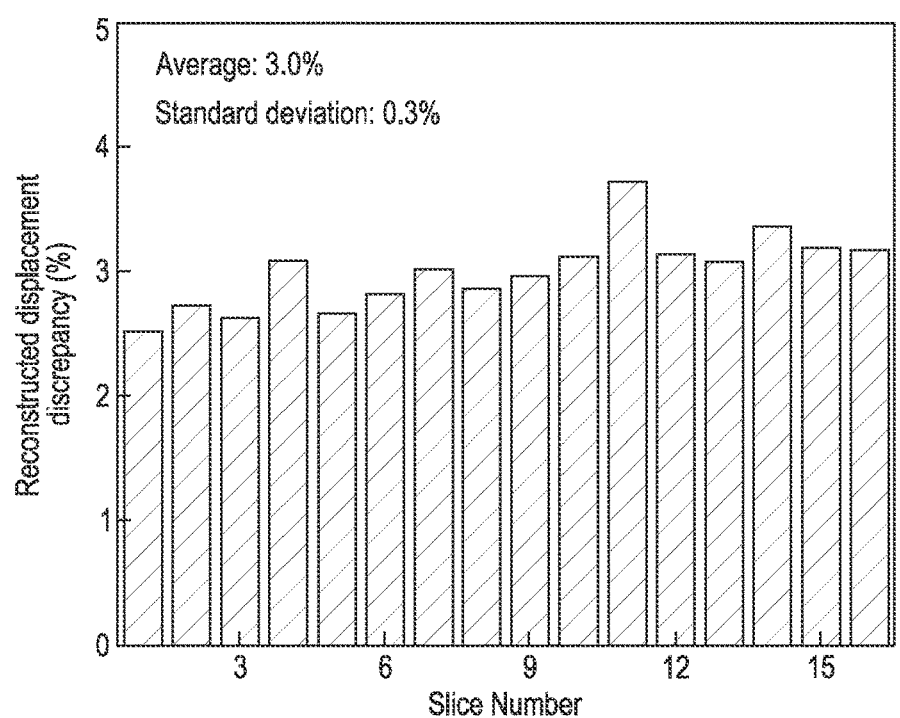
Figure 4C:
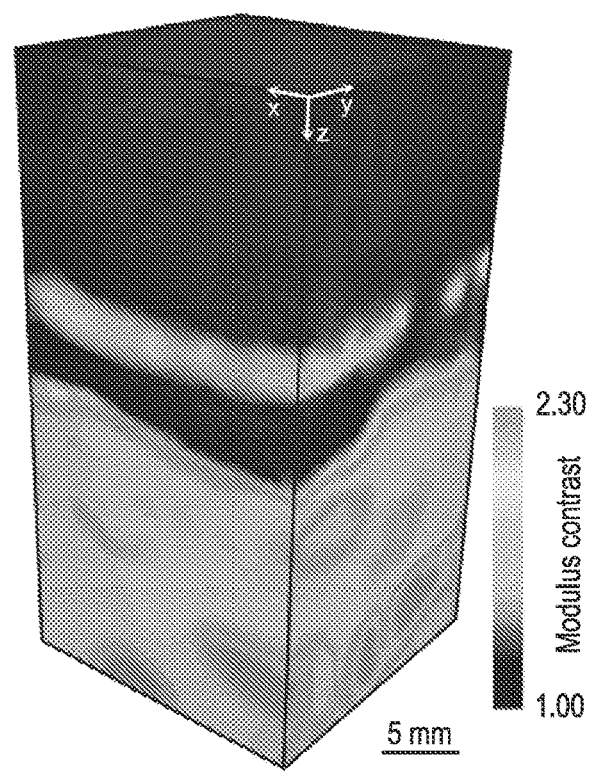
Figure 4D:
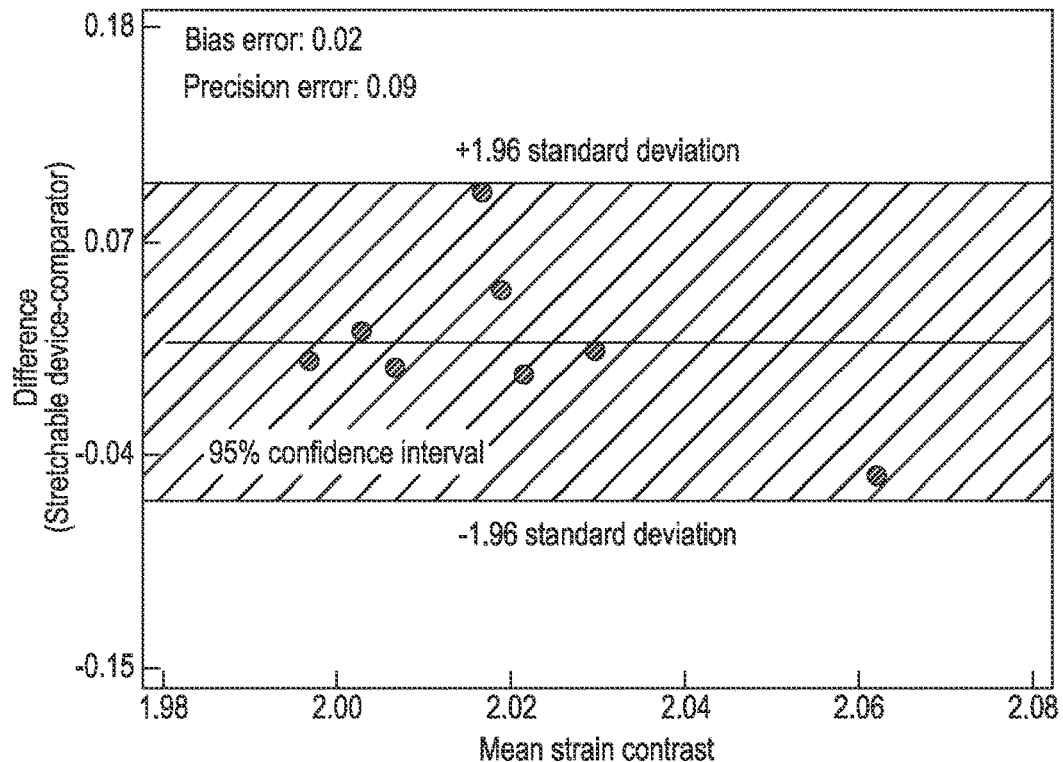
Figure 4E:
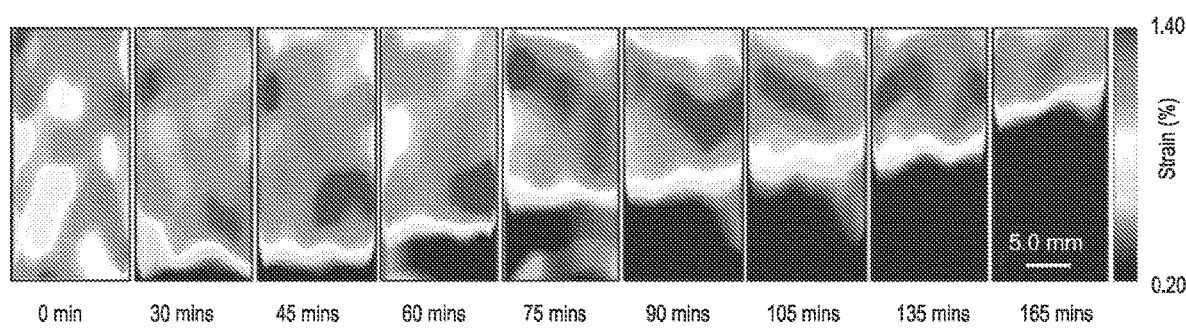

FIG. 4a shows a 3D quantitative elastographic image of a porcine abdominal tissue by the stretchable ultrasonic array. In the tissue, two muscle layers intersect with the intermuscular fat, and the fascias are embedded in the transversus abdominis muscle. The 3D elastogram embodies homogeneous, lower modulus fat layers made of glycerol and fatty acids molecules, and relatively heterogeneous, muscle groups with higher modulus made from crisscrossing and confluence fibers. FIG. 4b shows the averaged 3% discrepancy of the 16 pairs of measured and predicted displacement fields, with a high degree of correspondence between the reconstructed mechanical model by solving the inverse elasticity problem and the experimental conditions, suggesting a robust foundation for yielding the accurate modulus distributions. FIG. 4c shows a 3D MRE image of the porcine abdominal tissue. FIG. 4d shows a Bland-Altman analysis of the strain contrast of a commercial breast phantom for eight weeks. Each data point represents the difference in the measured strain contrasts between the stretchable ultrasonic array and the commercial probe. FIG. 4e shows a time-dependent stiffness variation of a piece of bovine gluteobiceps muscle under heating.

In FIG. 4a the 3D elastographic image is portrayed by integrating 16 slices of modulus maps with a 0.8 mm pitch (FIG. 4a), with an average discrepancy between measured and predicted displacement fields of 3%. (FIG. 4b and Methods). The 3D image illustrates the heterogeneous nature of the soft tissue. The same porcine abdominal tissue is then measured by MRE (see FIG. 4c). The volumetric mapping result from the stretchable array is highly comparable to that from MRE in both morphology and modulus distribution. The average measured modulus contrasts of transversus abdominis muscle, obliquus internus abdominis muscle, fascia, and intermuscular fat are approximately 1.92:1.67:1.30:1 by the stretchable array, and 2.26:1.83:1.46:1 by MRE; both are comparable to those in the literature.

A method for serial surveillance applications needs to be stable for long-term reproducibility, with a high sensitivity for picking up dynamic changes in the target tissue. A longitudinal study is carried out by testing a commercial phantom with the stretchable ultrasonic array and a commercial probe over eight weeks. We compared the strain contrast between the mass and matrix measured by the two methods and conducted Bland-Altman analysis. All data points are within 95% confidence interval, showing excellent agreement between the stretchable array and the commercial probe. Additionally, a small bias error of 0.02 shows the high accuracy of the stretchable array and a small precision error of 0.09 indicates the stability of the device for repeated measurements over the long term (see FIG. 4d and FIG. 48, discussed below). To test the elastographic sensitivity of the stretchable array, we measured a piece of bovine gluteobiceps muscle under controlled unilateral heating as its modulus gradually increases (see FIG. 49, discussed below). The measurement lasted for 165 minutes. The results clearly show that before heating, the tissue has a low modulus across the entire depth (see FIG. 4e). When heated from the bottom, the region of the tissue close to the heat source started to stiffen, because the actin in the myofibrils becomes firm and short, expelling liquid and making the structure dense. As the heating continues, the high-modulus region gradually grows, while the boundary between the high- and low-modulus regions remains clearly defined. These recordings demonstrate the capability of the stretchable array for serial monitoring of deep tissue mechanics.

Multi-Site Mapping of the Human Body

In vivo measurements can further illustrate the clinical value of the stretchable ultrasonic array. Multiple sites on the human body where muscle injuries usually happen were selected in this study (see FIG. 50, discussed below). FIGS. 5a-5d present the results of the strain mapping within 4 cm depth from the lateral side of the shoulder joint (FIG. 5a), the anterior forearm (FIG. 5b), the anterior thigh (FIG. 5c), and the posterior calf (FIG. 5d) with the anatomies labelled, juxtaposed with the corresponding B-mode images acquired by a commercial probe. Key anatomical structures are labelled in the strain images. The stretchable array can effectively resolve the mechanical properties of various tissue components.

To further demonstrate the reliability of the stretchable ultrasonic patch, we recruited ten more volunteers as human subjects (eight males and two females) with an average age of 25 for the measurements. We mapped the strain of their upper arm using the stretchable ultrasonic patch and the corresponding B-mode images acquired by a commercial ultrasonic probe are placed beside to provide a clearer structural correspondence. As shown in FIG. 51, the anatomic structure in the corresponding strain mapping results highly matches that in the B-mode imaging, and the stiffness contrast of each component is similar in the strain mapping results. The results demonstrate that the method is reliable without obvious deviations.

Serial Surveillance of Delayed Onset Muscle Soreness

Figure 5A:
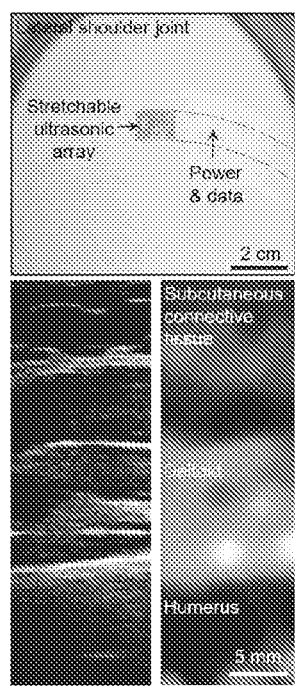
FIGS. 5A-5G show optical images, schematics and data concerning the multi-site mapping of the human body.
Figure 5B:
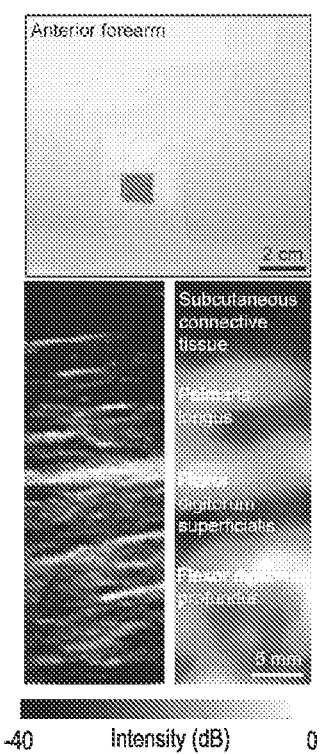
Figures 5C, 5D:
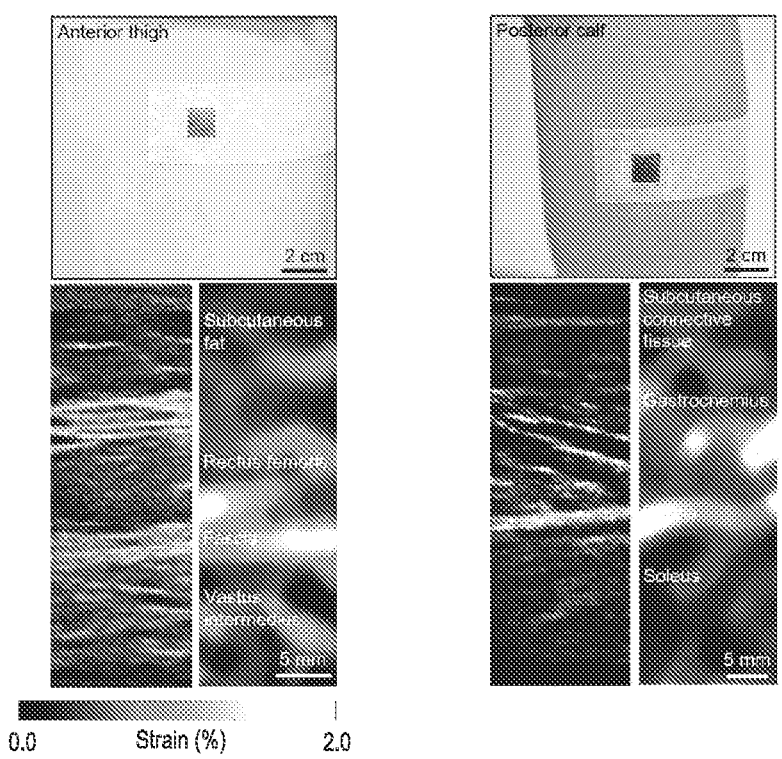
Figure 5E:
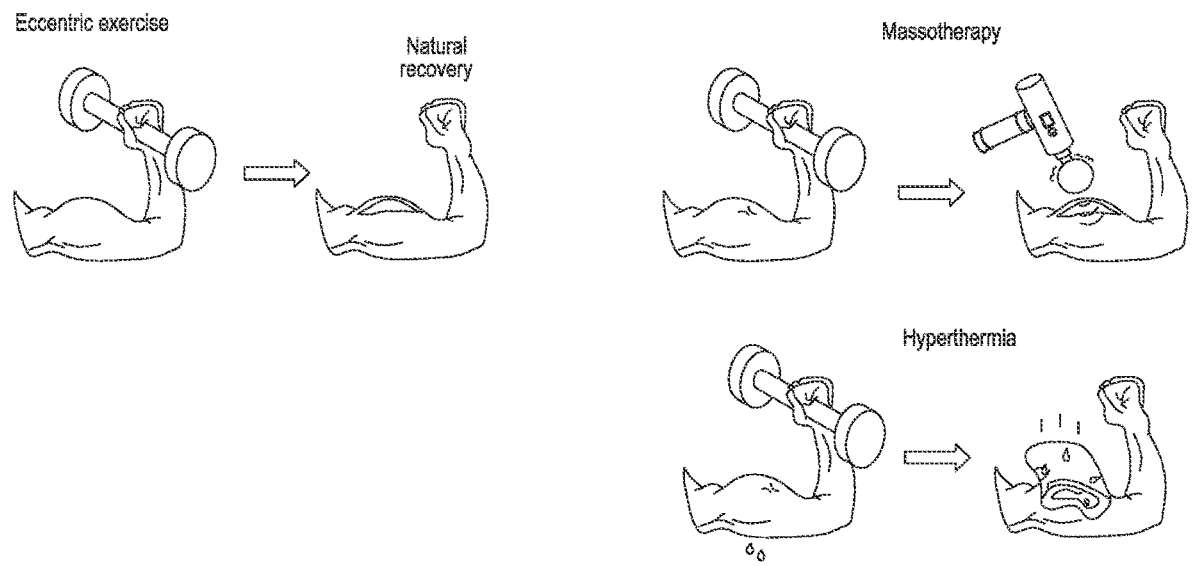

Over-exercise introduces injuries to the musculoskeletal systems, associated with damages in the sarcolemma and others. These disruptions lead to inflammation, stiffness increase, and function impairment of the tissues. Very often, the sensation of soreness doesn't occur until a few days later. The delayed onset of body responses precludes timely treatments and the injury often gets neglected and worsens. There are several studies that have reported modulus variation of the muscle after the eccentric exercise. However, the initial test was performed an hour after the participants had exercised, while by that time, muscle damage may already occur, making it impossible to pinpoint the exact time of the initial muscle damage. Additionally, the modulus changes didn't be monitored every day, but only sporadic testing over a period of time. Such a low testing frequency is easy to miss the turning point in modulus change of the muscle and fails to offer accurate trends of muscle recovery. Additionally, serial evaluation of the tissue can guide the rehabilitation strategy. MRE is frequently used to evaluate the tissue's stiffness to diagnose tissue injuries. However, MRE machine is not viable for long-term testing, which is due to its large size, limited availability, and high cost. The stretchable ultrasonic array addresses these needs. A healthy volunteer was selected to perform the eccentric elbow joint exercise to develop delayed onset muscle soreness (see FIG. 5e, which are schematics illustrating the exercise and physiotherapy protocols. See also FIG. 52, discussed below). Before exercise, well-defined anatomic components of the upper arm can be visualized three-dimensionally (see FIGS. 53 and 54 discussed below). After exercise, the muscles are either allowed to recover naturally, or treated with massotherapy or hyperthermia. In all experiments, the normalized modulus contrast of the biceps brachii was surveilled every day for five days to track the dynamic recovery process. Meanwhile, the intensity of the soreness was evaluated based on the pain visual analog scale (see FIG. 52 discussed below).

Figure 5F:
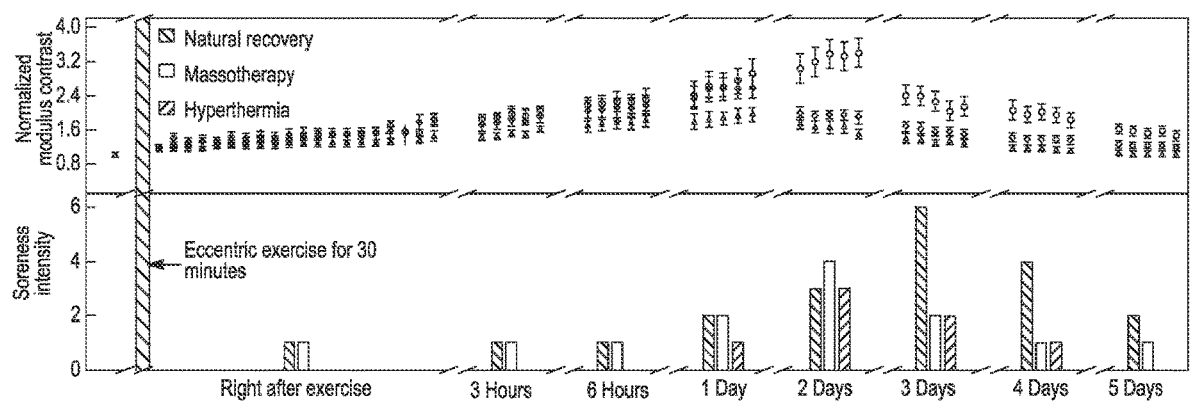
Figure 5G:
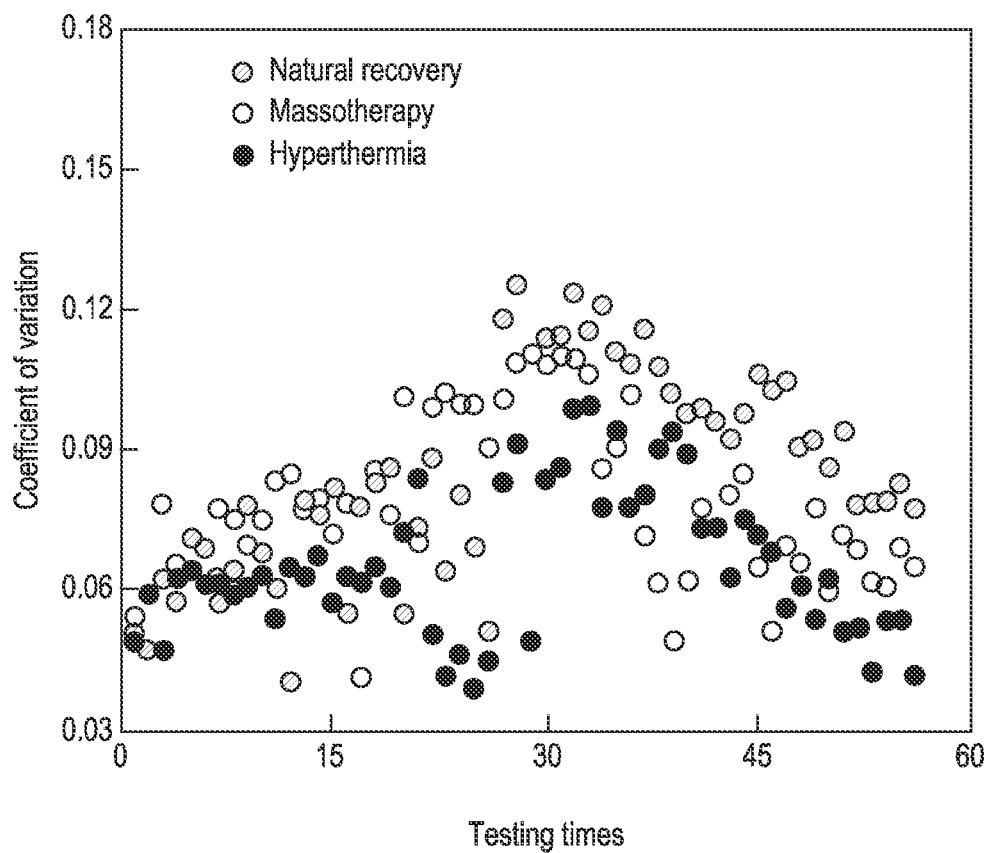

FIG. 5f shows serial monitoring results of normalized modulus contrast (top) and soreness intensity (bottom) of the biceps brachii muscle before and after the eccentric exercise. At the top panel, each point and error bar indicate the mean and standard deviation of modulus contrast of the biceps brachii muscle of every test. The time interval between adjacent tests is one minute. At the bottom panel, soreness scores were evaluated following the pain visual analog scale. The modulus of biceps brachii increased within 20 minutes after the exercise due to the muscle contracture induced by sarcolemmal disruption. However, the sensation of soreness did not arise until one day after exercise. As more time goes by, sarcolemmal disruption continued, and the muscle modulus kept increasing. Meanwhile, the circulation system delivered supplies to repair the sarcolemma, and eventually tissue modulus dropped. During natural recovery, the muscle modulus continued to increase for two days before dropping. When physiotherapies are applied, the increase only sustained for one day, with lower maximum moduli. The intensity of soreness has a latency but evolves in a trend similar to the modulus. On the fifth day, the normalized modulus contrast and soreness intensity with physiotherapies are lower than those with natural recovery. Additionally, blood cannot circulate well through the injured myofibrils, leading to involuntary tremors of the muscle during testing, which induces variations in the measurement results. The coefficient of variation of the modulus, defined as the ratio of the standard deviation to the mean, is smaller for physiotherapies than that of the natural recovery (see FIG. 5g, which shows the coefficient of variation among all tests. The lowest variation of the hyperthermia therapy indicates its best efficacy in muscle injury recovery.).

These collective results confirm that the physiotherapies promote efficient circulation, expediting the delivery of supplies to the lesion for muscle recovery. Hyperthermia has slightly higher efficacy than massotherapy in this study. Wearing the device one hour a day for five days did not induce any skin irritation (see FIG. 55, described below). The repeated bout effect could have an influence on the following exercise results after the first bout, which may cause a lower degree of muscle damage in the second and third bouts, and thus interference the evaluation of physiotherapies' efficacy. Additionally, the results may be impaired by uncertainties or coincidences introduced by individual variabilities. Therefore, three groups with randomly assigned six subjects performed eccentric exercise following with natural recovery, massotherapy, and hyperthermia, respectively (see FIG. 56, discussed below, for the detailed process and results). The results suggest that the one-month interval between exercises completely eliminates the repeated bout effect, and further demonstrate that massotherapy and hyperthermia do expedite muscle recovery.

Discussion

The stretchable ultrasonic array is able to perform serial, non-invasive 3D mapping of the mechanical properties of deep tissues, which has yet to be realized by any existing diagnosis devices. The array demonstrated high $SNR_e$, $CNR_e$, spatial resolution, and contrast resolution, which can be attributed to performance enhancement by the strategic array design, innovative microfabrication techniques, and effective ultrasound transmitting mode. Solving the inverse elasticity problem gives accurate and reliable quantitative modulus distribution in a 3D tissue. The stretchable ultrasonic array can detect muscle injuries before the subject can feel it, and therefore enable timely intervention to prevent cumulative trauma disorders. Collectively, these findings clearly demonstrate that the stretchable ultrasonic array is potentially complementary to existing clinical monitoring modalities and can be used as a unique platform technology for quantitative deep-tissue injury sensing and treatment monitoring.

In some embodiments advanced lithography, dicing, and pick-and-place techniques may be leveraged to further optimize the array design and fabrication, which can reduce the pitch and extend the aperture to achieve a higher spatial resolution and a broader sonographic window. Additionally, the stretchable ultrasonic array is currently wired for data and power transmission. Those back-end tasks, undertaken by a desktop-based interfacing system, such as electronic control, pulser and receiver, and data processing, can be achieved by a flexible printed circuit board that serves as a controller. With the advent of lower power integrated circuits and flexible lithium-polymer battery technologies, we envision the entire hardware to be fully portable while maintaining its high performance. Moving beyond muscle injuries, this technology has the potential to monitor the size and modulus of tumour real-time and inform therapeutic decisions, providing an unprecedented profiling method for both fundamental oncology research and clinical practice.

Fabrication of the Stretchable Ultrasonic Array by a New Method.

For purposes of illustration, one example of a method for fabricating the example of the stretchable and/or flexible ultrasonic array shown above will be presented. Of course, alternative methods and techniques may be used to fabricate this and other embodiments of the device. In this particular method, the fabrication of the ultrasonic array begins with preparing the multilayer stimulation electrodes. To individually control each element of the array, 256 stimulation electrodes and 1 common ground are needed. It would be very challenging to place so many electrodes in a single layer while keeping the device layout compact and stretchable. We choose to integrate the electrodes in a multilayered manner. We use AutoCAD software to design the six layers of the stimulation electrodes to individually address each element (FIG. 16), which minimizes the footprint of the entire device to a size much smaller than the stretchable ultrasound device in our previous work. The pitch of the array is shrunk from the previous 2 mm by 2 mm to the present 0.8 mm by 0.8 mm and the kerf also has been decreased from the previous 0.8 mm to the present 0.2 mm, which enhances the active component density from the previous 39.06% to the present 58.05%. To route all elements to the same plane, vertical interconnect accesses based on laser-ablation are adopted.

In this embodiment of the array, for each single element, we use 1-3 composites as the active material given the superior electromechanical coupling properties, appropriate acoustic impedance, and suppressed crosstalk between adjacent elements. We choose silver-epoxy composites as the backing material. To make the backing layer more condensed and reduce the overall device thickness (~0.8 mm), the uncured silver-epoxy mixture is centrifuged for 10 mins at 3000 rpm. This operation separates the extra liquid hardener, removes the air bubbles in existing the silver-epoxy, and improves the acoustic wave damping effect and the axial resolution.

An array with such a small footprint and large-scale requires optimized fabrication techniques. We developed a method of automatic alignment of the transducer elements to the bonding electrodes. We first bond a large piece of the backing layer to the 1-3 composite and then dice the bonded bilayer to the designed array configuration. A strong adhesion tape is used to fix the bilayer without delamination during dicing by the dicing saw (DAD3220, DISCO). The 2D array with designed element size and pitch is automatically formed. To prevent the array from tilting or moving when the array is bonded to the electrodes, a silicone elastomer (Ecoflex-0030, Smooth-On) is filled in the kerf and connects individual elements together.

Then, conductive epoxy (Von Roll 3022 E-Solder) is used to bond the copper-based stretchable interconnects with the 1-3 composite electrodes. The device is put at room temperature for 8 hours and at 40° C. for 2 hours for tight bonding. The stretchable interconnects and transducer elements are bonded by the solder paste in the previous studies. Under high temperature (over 150° C.) for over 10 minutes, the metal particles in the paste will melt and form a robust alloyed bonding. However, high-temperature bonding generates serious damages to piezoelectric materials. First, dipoles in the piezoelectric materials are lost under high temperatures, which seriously damages its ability to transmit and receive ultrasonic waves, causing low signal-to-noise ratios of the measurements. Although the dipoles can be realigned after applying an external electric field, the polarization is very time-consuming. Additionally, an excessive electrical field will break down the piezoelectric element. Second, high-temperature bonding will cause thermal damage to the epoxy in 1-3 composites. It softens and irreversibly deforms the epoxy so that the alignment of piezoelectric pillars in 1-3 composites is reduced. As a result, their electromechanical coupling performance decays. This low-temperature bonding method avoids thermal damage of the epoxy and any possible depolarization of the piezoelectric materials in the 1-3 composite, which maximizes the piezoelectric performance of the elements. Before bonding the other electrode to the transducer array, the interface between the transducer array and tape is exposed to UV light (254 nm wavelength, PSD series Digital UV Ozone System, Novascan) for 10 mins for surface de-adhesion. Then the array can be delaminated from the tape and bond with the other electrode using the same method.

Preparation and Mechanical Characterization of Phantoms.

The tissue-mimic phantoms are made by gelatin (Type A, Fisher Chemical) and silicon dioxide particles (325 mesh, Amazon) with different concentrations. We control different Young's moduli of the phantoms by tuning the concentration of gelatin in water. Concentrations of gelatin including 5%, 7%, 8%, 9%, 10%, 12%, 13%, and 14% are selected and the corresponding Young's moduli are 10.24 kPa, 21.82 kPa, 30.41 kPa, 39.66 kPa, 49.12 kPa, 64.27 kPa, 81.25 kPa, and 99.89 kPa, respectively.

As shown in FIG. 32, gelatin is added into boiling deionized water. 1-Propanol (Sigma-Aldrich) is dropped into the solution (9.2 g per 100 g deionized water) to facilitate the cross-linking of gelatin. Silicon dioxide particles (3% mass fraction of all ingredients) are added into the solution after the solution becomes clear. The particles serve as the markers for displacement tracking. After thorough mixing for 10 mins, the suspension is poured into specific modes for cooling. When we make the bilayer phantoms for measurements of $CNR_e$ and those in FIG. 3a, the bottom layer is cured into a cuboid geometry first and then the suspension of the second layer is poured and cured on the cuboid. Before pouring, the solution needs to be cooled to −40° C. to prevent melting and osmosis of the bottom layer phantom by the hot solution.

The process of making the cyst and inclusion phantoms is different from making the bilayer phantom. To build up a cylindrical cavity into the matrix, a tube with a 9.2 mm outer diameter has been inserted into the uncured matrix solution. The tube is then removed after the matrix is cured. Solution or water is filled into the cavity to form the inclusion or cyst.

To calibrate the phantom modulus, eight pieces of homogenous phantoms, including all concentrations of gelatin, are made. Compressive testings are performed to characterize the Young's modulus of each component (Instron 5965, Norwood, MA, USA). The testing rate is 0.05/min and the total compressive strain is ~2%. In this region, the phantoms obey the linear stress-strain behavior and the Young's moduli are the slope of the stress-strain curves (see FIG. 34, discussed below).

Characterization Details of the Device

We measure the frequency-dependent electrical impedance and phase angle curves following the conventional methods to characterize the electromechanical coupling performance of the ultrasound transducers (see FIG. Tb). A network analyzer (Hewlett-Packard 4195A) is used to do the testing with a frequency range of 1 MHz to 5 MHz. The effective electromechanical coupling coefficient $k_{eff}$ is a parameter of evaluating the electromechanical conversion efficiency of the transducer, which can be derived based on the resonant ($f^r$) and anti-resonant ($f_a$) frequencies of the transducers:

$$K_{eff} = \sqrt{1 - \frac{f_r^2}{f_a^2}} \quad (1)$$

Crosstalk is characterized by calculating the ratio between the measured and reference voltages. A peak-to-peak voltage of 5 V under a sinusoid burst mode is applied by the function generator (Keithley 3390) to excite the element. The reference voltage signal received by neighboring elements is collected with the frequency increment step of 0.2 MHz. The voltage ratio is transformed to the logarithmic scale.

Insertion loss is used to reflect the sonographic sensitivity of the transducer and these two variables are inversely proportional. The measurement is done in water using a functional generator with an output impedance of 50Ω and an oscilloscope (Rigol DS 1104) in a 1 MΩ coupling mode. A tone burst of a sine wave from 1.5 MHz to 4.5 MHz is generated to excite the element, and the ultrasound echoes reflected from a quartz crystal are captured by the same element. After compensating the 1.9 dB energy loss of transmitting into the quartz crystal and $2.2 \times 10^{-4}$ dB/mm $MHz^2$ loss due to the attenuation in water, the insertion loss can be calculated by:

$$\text{Insertion loss} = \left| 20 \log \frac{V_r}{V_t} + 1.9 + 2.2 \times 10^{-4} \times 2d \times f_r^2 \right| \quad (2)$$

where $V_r$ and $V_t$ are the transmitting and receiving voltages, respectively, d is the distance between the transducer and the quartz crystal, and $f^r$ is the resonant frequency. The matching circuit significantly improves the received signal amplitude, yielding a high sonographic sensitivity of the transducer (FIG. 1d and FIG. 25, discussed below).

To characterize its waterproof performance, the device is put underwater for two weeks (see FIG. 26, discussed below). Pulse-echo signals are collected every day to analyze the variation in the sonographic signal-to-noise ratio. During the measurements, the transmitting distance and the ultrasound incident angle are kept consistent all the time to ensure the accuracy of the testing results.

Figure 24A:
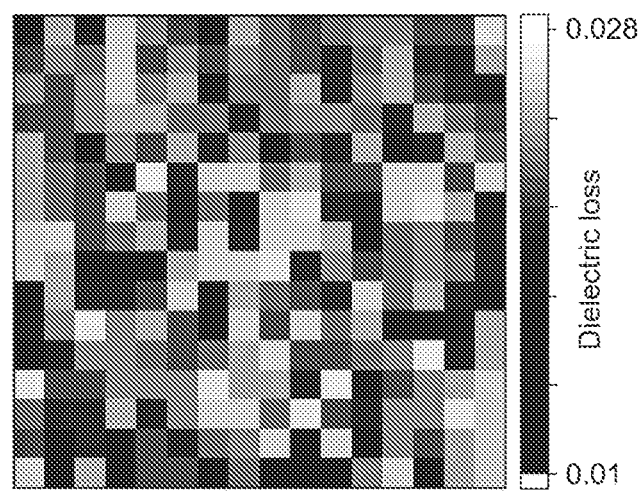
FIGS. 24A-24C show data concerning electromechanical characterizations of the transducer array.
Figure 24B:
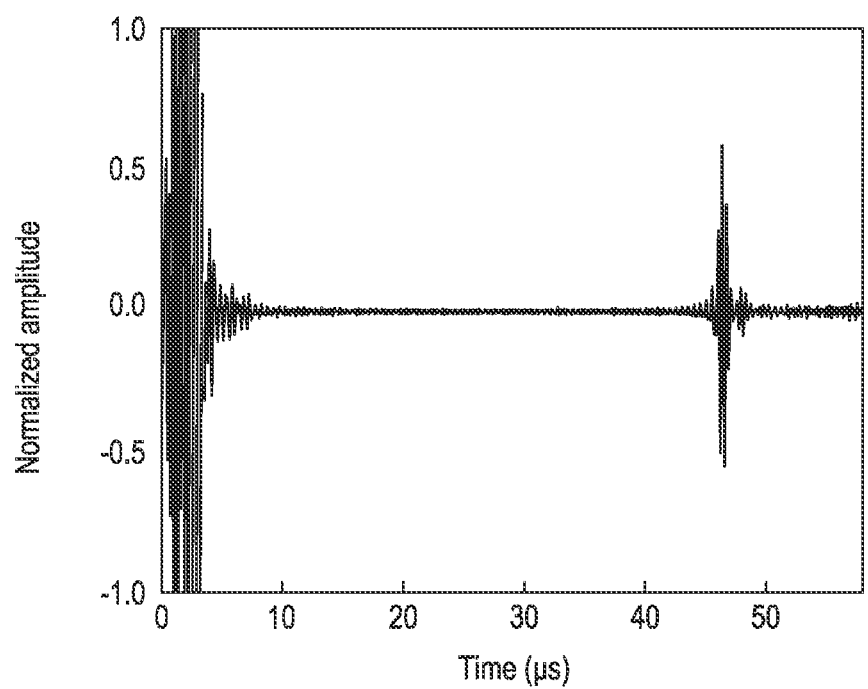
Figure 24C:
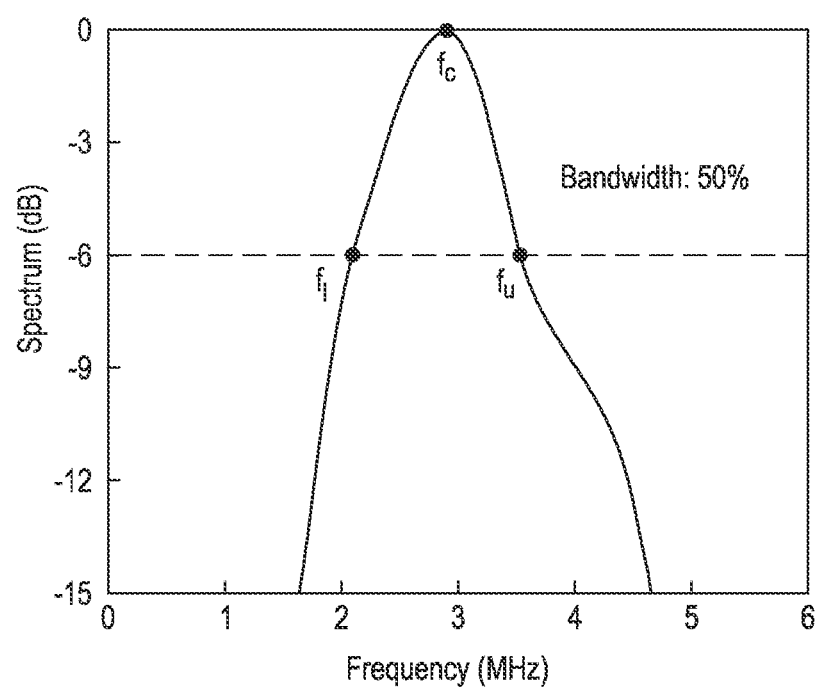

The time- and frequency-domain characterizations with pulse-echo response and bandwidth are shown in FIGS. 24b and 24c. An experimental setup, including a multi-channel control system (Verasonics 256) and an aluminium block, was used to obtain the raw data. We put the aluminium block into the water and ultrasonic waves were transmitted and received by the same transducer element. After getting the radiofrequency signal, a fast Fourier transform was applied to convert the signals from the time domain to the frequency domain. The frequency bandwidth of the signals at −6 dB was determined by:

$$BW = \frac{f_u - f_l}{f_c} \times 100\% \quad (3)$$

where $f_u$ is the upper frequency, $f_l$ is the lower frequency, and $f_c$ is the central frequency. The signal-to-noise ratio of the transducer element can be calculated from FIG. 24b, which is around 39 dB. Such a high signal-to-noise ratio is mainly attributed to the superior electromechanical coupling properties of the 1-3 composite, the low-temperature bonding technique, and the electrical matching circuit. The bandwidth of the element is around 50% (see FIG. 24c), which still has room to improve. The relatively thin backing layer cannot completely dampen the excessive vibrations of the piezoelectric materials, leading to a long spatial pulse length. However, a thick backing layer will compromise the mechanical compliance of the device. Therefore, future improvements will focus on the development of new backing materials with high acoustic attenuation coefficients and good attenuation capabilities while maintaining a small thickness of the backing layer.

The spatial resolution is characterized based on the point spread function of the transitional edges of an inclusion phantom. The modulus distribution curves along the lateral and axial transition edges (i.e., edges between inclusion and matrix that are perpendicular and parallel to the ultrasound propagation direction, respectively) are extracted from the reconstructed 2D modulus mapping image (FIG. 33). Then we apply the first derivative of the modulus distribution curves to derive the point spread function, whose full-width-at-half-maximum is defined as the spatial resolution. Simulation of different imaging modes.

The Matlab software allows simulating the three different ultrasound imaging modes: coherent plane-wave compounding, mono-focus, and single plane wave. The model of 2 cm by 5 cm is built up for the simulations, where a bilayer structure with random points filling the entire region is set up. 1.5% and 0.5% of strain are added to the top and bottom layers with different moduli, respectively, and a new model with the compressed configuration is generated. Then, the ultrasound wave is excited using the three transmission modes. Corresponding radiofrequency signals from pre- and post-compression are collected. The toolbox of Matlab, Field II, is used to simulate the radiofrequency signals. These radiofrequency signals are beamformed to enhance the signal-to-noise ratio. Displacement fields are derived using the normalized cross-correlation algorithm. Finally, the spatial strain is mapped using the least-squares strain estimator (see FIG. 2a and FIG. 29, discussed below).

System Setup and Data Collection.

Figure 12:
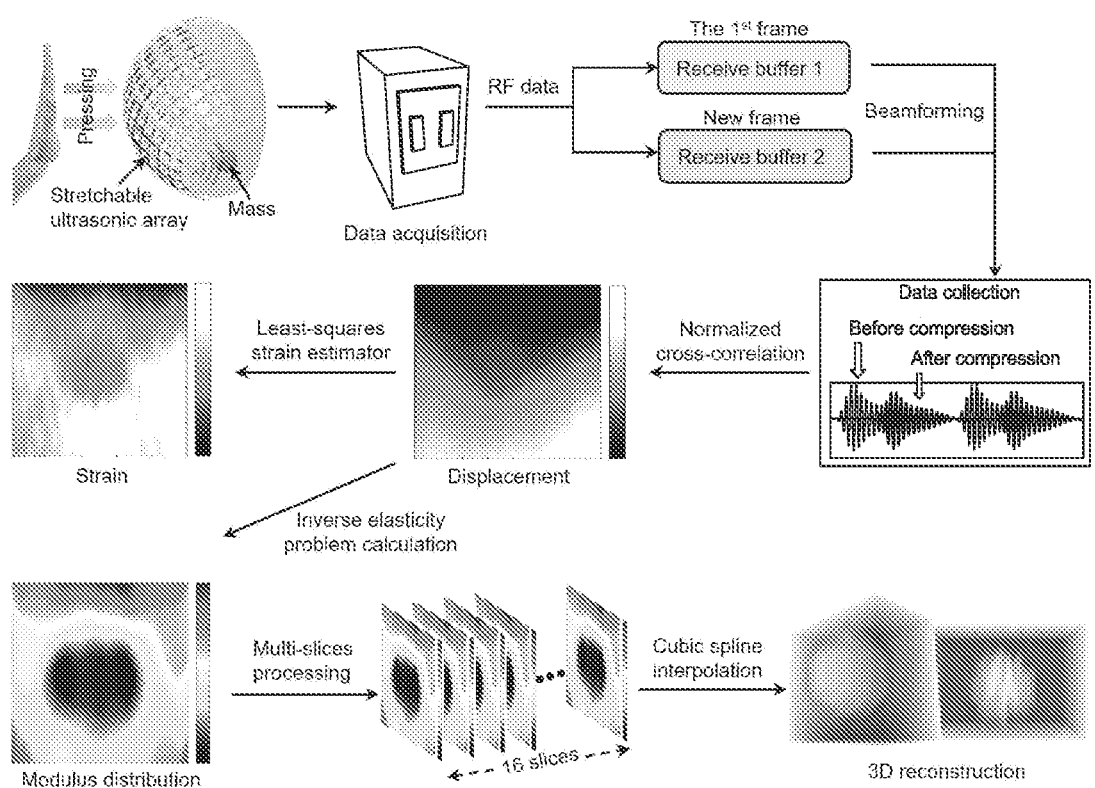
FIG. 12 is a workflow for reconstructing elastographic images by the stretchable ultrasonic array.

The stretchable and/or flexible ultrasonic imaging system is mainly composed of two parts: the front end and the back end. The stretchable ultrasonic array as the front-end device transmits and receives ultrasound waves. The back-end device may be any suitable controller and was demonstrated using a commercial multichannel controller (Verasonics Vantage 256 system, Kirkland, WA) that can be programmed to generate the arbitrary waveform. Cables are used to connect both ends for power supplying and data transmission. In alternative embodiments wireless data transmission may be employed. The Matlab software (MathWorks, Natick, MA) is used to code to control the back-end hardware and drive the front-end stretchable patch, involving the processes of plane wave compounding excitation, echo signals collection and storage, and data processing. As shown in FIG. 12, two receive buffers are designed by the Matlab to collect and store the radiofrequency signals. The first and second receive buffers are used to store the radiofrequency signals before and after compression, respectively. Then these stored radiofrequency data are retrieved and processed to form the displacement fields.

Phantom Verifications by the Commercial Probe and Ex Vivo Testing Protocols

The commercial probe that is used for verifying and reconstructing the 3D phantom images is a 64-element phased array transducer (P4-2v, Verasonics, Kirkland, WA) with 2.8 MHz resonant frequency that is almost on a par with that of the stretchable ultrasonic array ($f^r$=3 MHz). During the experiments, a 3D linear stage (Newport, West Coast, CA, USA) is used to fix the commercial ultrasound probe, apply pressure to get 2D strain images, and move to the next position. Each moving step is 0.8 mm, the same as the elevational pitch of the stretchable patch. 16 slices of the 2D images are post-processed to reconstruct the 3D images (FIGS. 39b and 41b). 3D rendering is accomplished with the Amira software (Visualization Sciences Group, Burlington, USA). All ex vivo studies are approved by the Institutional Animal Care and Use Committee at the University of California, San Diego. A frozen food-grade porcine abdominal tissue is used for ex vivo testing by the stretchable ultrasonic array and MRE. The porcine abdominal tissue is selected as a model because of the well-defined anatomy and modulus distributions. When the device is in conformal contact with the tissue surface, 0.5%~1% strain is applied, which can be followed in real-time by a customized graphical user interface. If needed, the large strain with high normalized cross-correlation coefficients can potentially be achieved by combining successive steps of small strain. Then, 16 slices of 2D displacement fields are collected sequentially under the compressive strain. The inverse elasticity problem model yields the modulus mapping images when the predicted displacement fields match the measured ones (see FIG. 47, discussed below). More details of the inverse elasticity problem calculation will be discussed below.

The MRE test (General Electric Discovery MR750 3.0T) is performed right after the ultrasound test. A hermetic bag is used to preserve the porcine abdominal tissue during traveling and testing to prevent any dehydration-induced changes in the modulus. A mechanical vibration paddle is tightly bonded to the sample tissue to generate shear waves in the tissue. Fifteen scanning slices with 0.9 mm×0.9 mm spatial resolutions of each are obtained. The total measuring time is about 30 minutes. The shear modulus of each slice can be displayed in the ImageJ software. Specifically, Young's modulus equals to three times of shear modulus in soft tissues. The modulus ratios of all slices are then calculated to compare with the results from the stretchable ultrasound arrays. The Amira software is applied to combine all slices (reconstructed in y and z directions) of ultrasound elastographic images and MRE results along the x direction, respectively, to generate the 3D volumetric image. Cubic spline interpolation is used to compensate and smooth the image in the x direction. The possible sacrifice of contrast due to the variation regularization and the 2D finite element model may have resulted in the slightly higher modulus contrast of MRE. Besides, the 2D elasticity model used in solving the inverse elasticity problem may introduce unavoidable discrepancies when applied to cross-sections of anisotropic 3D samples. Additionally, different imaging equipment manufacturers using proprietary data processing algorithms may also bring systematic deviations.

Existing Sensors and Approaches for Modulus Testing

Conventional approaches for measuring tissue modulus can be divided into two main categories. The first are those relying on Hooke's law to derive elastic modulus through establishing the relationship between the displacement and the applied force, such as vacuum-based suction, compression, extension, and micro-/nano-indentation (FIG. 7). These methods are either limited to shallow regions beneath the skin or lack of fine spatial resolution for anisotropic human tissues. Currently, elastography can be done using 3 modalities, magnetic resonance imaging (MRI), ultrasound, and optical coherence imaging. Elastography itself is split into 2 types, static and dynamic methods. Static methods use strain elastography and can be imaged using ultrasound and optical coherence imaging.

Quasi-static elastography is an imaging modality that can assess the stiffnesses of tissues using ultrasound imaging or optical coherence tomography. From the perspective of its working principle, it relies on applying tractions to generate and measure a small quasi-static deformation (strain) in the target tissue. Two different sets of signals are acquired before and after deforming the target tissue and the displacement vectors between the two signals are estimated to map the strain distributions within the tissue. From the perspective of how this measured deformation is used subsequently, quasi-static elastography includes strain-based elastography, which provides strain distributions to qualitatively reconstruct the stiffness within the tissue using a least-squares strain estimator algorithm, and modulus-based elastography, which generates modulus distributions by solving the inverse elasticity problem to quantify the stiffness mapping results. In the strain-based elastography approach, it is assumed that the stress in the tissue is uniform, and Hooke's Law ($\sigma=\varepsilon E$) is used to determine the Young's modulus as the reciprocal of axial strain. This approach can lead to artifacts in the resulting modulus map. When the stress distribution is not uniform this assumption is violated. In contrast to this, modulus-based elastography (the approach used in this manuscript) does not make the assumption of uniform stress. Instead, it involves solving an inverse problem to determine the spatial distribution of the modulus that is consistent with the measured displacement and the equations of equilibrium, which are valid under any stress distribution.

When compared with dynamic elastography, quasi-static elastography requires fewer external parts (i.e., no external oscillators required) and no high energy for the generation of acoustic radiation force, and is thus safe for long-term use. The strain-based version of quasi-static elastography suffers from the drawback that its results depend on applied traction and are therefore subjective and operator-dependent. However, the modulus-based version eliminates this drawback and yields a spatial map of the modulus that is independent of the applied tractions and is equal to the true modulus distribution up to a multiplicative factor. In doing so, it comes closer to the absolute modulus obtained using dynamic elastography while retaining the advantages of quasi-static elastography. Finally, we note that when compared with dynamic elastography, ultrasound-based quasi-static elastography is much more viable in wearable devices. It makes wearable ultrasound transducers a platform technology for serial, non-invasive, and three-dimensional mapping of mechanical properties of deep tissues.

Dynamic methods, by contrast, are based on time-varying forces. Some dynamic methods can provide an absolute measure by quantifying the tissue modulus parameters. There are 2 main types of dynamic elastography techniques: shear wave elastography and vibro-acoustography.

Shear wave elastography generates shear waves within a tissue that travel perpendicularly to the excitation force, and relates their speed of propagation to the stiffness of the tissue, as shear waves travel faster within stiffer tissues. This can be imaged using ultrasound, MRI, or optical coherence imaging. The shear waves are generated using external vibrators, or in the case of ultrasound, acoustic radiation force impulse, in which high intensity ultrasound beams are focused on a single point to excite a shear wave. Acoustic radiation force impulse has the advantage of not needing external vibrators due to its use of ultrasound transducers, but is very slow due to the singular focal point. Furthermore, it transfers a significant amount of energy into the tissue, and due to the long scan time, can cause significant heating of the tissue. Thus neither form of shear wave elastography is suitable for wearable devices—external vibrators are too bulky, and the heat generation of acoustic radiation force impulse-based devices is not fit for long-term usage.

Shear wave elastography can also suffer from wave interference as the transmitted waves are reflected at the boundaries and interfere with the main signal. The main advantage of MRI over ultrasound shear wave elastography is the very wide field of coverage that can provide a more comprehensive diagnosis. However, MRI-based shear wave elastography is expensive, bulky, and slow compared to other methods of elastography. Besides, effective diagnostic ultrasound measurements based on shear-wave ultrasound elastography are highly operator-dependent (see FIG. 8, described below). Results are prone to errors due to mishandling of the probe, such as moving the probe too quickly, offsetting scanning angle (by ~10 degrees), and pressing the probe too hard (~50 Newtons) against the human body. Professional technicians are required to properly position the probe perpendicular to the surface and scan slowly, being careful not to press on the target region excessively.

The robotic-assisted ultrasound procedure is an emerging technology by integrating the robotic arm with an ultrasound probe, which can achieve semi-automatic ultrasound scanning by an external machine instead of an operator. The robotic arm can control the scanning trajectory, area of interest, and holding forces, and is more stable than human operators, which is a promising candidate for long-term monitoring. However, the robotic system is still far away from personalized healthcare because the overall system is already heavy and inaccessible to most healthcare providers. Moreover, the system has to be coupled with complicated cameras, algorithms, and a software interface to compensate for subject movement. Specifically, in an ideal case, the robotic-assisted ultrasound monitoring system has to be coupled with a complicated ultrasound image guiding program, which uses machine learning algorithms to evaluate the image quality and recognize human motions to adjust the robotic holding. However, such an ideal long-term monitoring system has yet to be demonstrated.

In addition, the window for selecting the region of interest in the ultrasonic shear-wave elastography is very limited, which can only locate a small area of human tissue for elastographic measurements (see FIG. 9, described below). This is because the energy of acoustic radiation force and thus shear wave generated by focused ultrasound is pretty low, leading to the limited propagation range and quick attenuation of the shear wave. Therefore, the test area is limited to only the region close to the focused ultrasound. It is not applicable for simultaneous surveillance of multiple tissues and muscles (e.g., biceps brachii and brachialis in the upper arm).

Vibro-acoustography uses 2 different vibrational sources placed apart from each other, which vibrate at slightly different frequencies. The resulting interference of the two waves produces a radiation force at the focal point which oscillates at the difference of the two frequencies. The dynamic response of the tissue to this low-frequency excitation produces an acoustic emission that is detected by a hydrophone. The acoustic emission of the tissue is a function of its size, shape, stiffness, damping, and mass. The major advantages of this method are its high contrast and high spatial resolution. However, it has slow scan times and heats the tissue similarly to acoustic radiation force impulse due to the point-by-point scanning. In addition, the received signals reflect multiple different tissue properties at the same time, and the stiffness parameter cannot be fully isolated. Therefore, vibro-acoustography can also only qualitatively gauge the relative tissue stiffness.

Many portable ultrasound probes with miniaturized post-end for precision healthcare have been developed substantially in recent years. Those portable ultrasound probes are powerful and versatile to accomplish various tests outside the clinics. But no matter how portable/compact the existing ultrasound systems could be (such as Butterfly, Lumify, SonoQue, etc.), the necessity of being a long-term and continuous stable holding by the operator during usage prevents those systems from providing continuous monitoring.

Recent developments in wearable technologies are based on piezoresistance, piezoelectrics, or capacitors. Flexible piezoresistive microcantilevers allow mechanical measurements of diseased breast tissues. But the small testing depth (<4 µm) limits them for measuring only epithelial and stromal areas of the specimen. Wearable piezoelectric systems achieve conformal contact with the human skin and rapid tests of mechanical properties of the tissue through the responses of the piezoelectric actuator-sensor pairs. However, they are only suitable for the shallow tissue under the epidermis, lacking resolution in the depth dimension (FIG. 7). Additionally, laminating on the dynamic surface of human skins may cause inaccurate results since the amplitude of the sensing voltage changes when the distance between actuators and sensors is varied. Compliant tactile sensors permit non-invasive detection of soft tissues and present their mechanical imaging, using capacitance-based pressure sensing array. Although providing 2D qualitative mapping of internal strain distribution, they suffer from a similar limitation in detection depth (<5 mm). Besides, for lump-containing tissues, the embedded depth of the lumps influences the capacitance response, leading to misdiagnosis of the lesion. Flexible needle-shaped microsystems based on piezoelectricity can be used to measure and distinguish the modulus of shallow tissues (<4.5 mm). This device for invasive biopsy mainly works in an in-patient environment, which is inappropriate for long-time serial monitoring in 3D spaces (see FIG. 7, described below).

Review of Flexible/Stretchable Ultrasonic Transducers and Advantages of the 2D Array Previously reported flexible ultrasonic transducers have been made of either intrinsically flexible piezoelectric polymers or micromachined ultrasonic transducers. Piezoelectric polymers have outstanding performance as ultrasound receivers due to their similar acoustic impedance to human tissues and broad bandwidth. However, they are poor ultrasound transmitters due to their low piezoelectric coefficient ($d_{33}$), low dielectric constants, and high dielectric loss. Micromachined transducers use the bending motion of a thin membrane to achieve their low device profile and flexibility but sacrifice their electromechanical coupling properties in doing so. There are two types of micromachined transducers: capacitive and piezoelectric. In the capacitive micromachined transducers, the membrane is caught between two opposing forces—an attractive electrostatic force pulling it towards the substrate and a mechanical restoring force opposing the deformation, which dampens the vibration amplitude significantly and reduces energy conversion efficiency. Piezoelectric micromachined transducers have a bi-layer unimorph structure, with one layer providing actuation and the other providing passive mechanical support. The actuation layer is an active piezoelectric layer working in the $d_{31}$ mode, while the passive layer creates strain asymmetry along the thickness direction. The device sensitivity of piezoelectric micromachined transducers is compromised by the passive layer, as it is unable to convert between mechanical and electrical energies like the actuation layer, but still consumes mechanical energies during the bending process.

As a result, while flexible ultrasonic arrays are a major step towards optimal acoustic coupling between the device and nonplanar surfaces, they sacrifice some of the transducer performance of traditional devices. Furthermore, they still lack one more critical aspect—stretchability. A flexible array can only conform to a developable surface (e.g., cylinders), while the surface of the human body is nondevelopable (e.g., spheres). To conform to a nondevelopable surface, the device must possess stretchability in addition to flexibility. Thus, previously reported flexible ultrasonic transducers are still not fully compatible with the surfaces of the human body. To achieve stretchability, in some embodiments we integrate high-performance piezoelectric materials linked by an "island-bridge" structure where the piezoelectric "islands" are connected by serpentine-shaped metallic "bridges". The array is then encapsulated by thin elastomers. The islands are locally stiff, but their connective serpentine bridges give the overall array stretchability and flexibility. Thus, we can preserve the advantages of traditional rigid transducers, while granting the device mechanical compliance. This approach offers >40% biaxial stretchability with little sacrifice to the performance of the transducers and allows the array to closely conform to the nondevelopable surface of the human body.

There are multiple reasons why we provide a 2D array though still providing non-real time 3D imaging. First, the traditional and typical linear probe can hardly generate reliable 3D images. The only way to reconstruct a 3D image based on the linear probe is to slice the target into segments and slightly move the probe to acquire the data. However, this method can introduce a lot of errors: (1) The movement of the linear array along the elevational direction generates errors, because it's challenging to control the interval distance, the compression force and angles to be the same every time; (2) Even with the help of a linear motor or robotic arm, the complicated process for equipment setup and the dozens of times for moving the probe are considerably time-consuming. A 2D array is absolutely preferred for 3D imaging, because there is no need to move around the 2D array on the surface of the target. Also, the applied strain to all slices is the same and we don't have to worry about the related discrepancies. Besides, it takes less time to acquire the data for the image reconstruction than the linear probe.

In some embodiments the 3D reconstruction may be performed in real-time, depending on the amount of data processing resources available. There are roughly four steps for a single 3D image reconstruction: raw data acquisition, elastography computation for each slice, solving the inverse elasticity problem, and reconstruction from 2D to 3D. In some cases the data processing can be accelerated using technologies like parallel computing, graphics processing unit accelerating, and/or supercomputers.

Discussions on Qualitative and Quantitative Elastography

Strain-based elastography is regarded as a qualitative method because it assumes that stress is uniform in the subject, so that strain is inversely proportional to modulus. Since the stress in heterogeneous samples is non-uniform, strain maps typically do not reflect accurate modulus distributions, offering only qualitative information about the relative stiffness of the subject. In other words, we can only know that one component is softer than another, rather than quantitative information about tissue stiffness. Additionally, because different external loads may cause different strain distributions inside the same subject, strain-based elastography is considered to be subjective and operator-dependent. As a result, this method can only show the morphology of the lesion and its relative stiffness to the surrounding tissues.

On the other hand, modulus-based elastography is quantitative because it can reflect the objective biomechanical properties of tissues. There are two types of modulus-based elastography in existing studies. One type is shear-wave elastography, which can map the quantitative, absolute values of the shear modulus using detected shear wave velocity. Another type combines the quasi-static elastography and an inverse elasticity problem, which can accurately provide the modulus ratio of each component. Specifically, based on the displacement field of the tissue in response to quasi-static compressions, one can solve an inverse elasticity problem to determine modulus distributions, but only up to a multiplicative parameter. While this method does not provide the absolute values of the shear modulus, it generates quantitative, "normalized" values of the shear modulus that are objective and insensitive to external loadings. In this work, we used the second type, thereby performing quantitative, modulus-based elastography.

Coupling Conditions of Traditional and Stretchable Ultrasonic Devices on Curved Surfaces Traditional rigid ultrasound probes have flat or convex bases, which cannot achieve a solid interfacial contact and good coupling with irregular nonplanar surfaces, which are ubiquitous in the human body. Because of the geometric mismatch of the base of the probe and the curved surface of the subject, air gaps will inevitably appear at the interface between them (see FIG. 10, discussed below). The large mismatch of acoustic impedance between air and human skin prevents the acoustic energy from transmitting into the deep tissues of the subject, causing artifacts and information loss.

There are two common ways to solve this problem. First, for those tissues that are compressible, clinicians usually press the probe to fit the curvature of the skin and achieve a good acoustic coupling situation. However, the pressing introduces pain in some cases and may also cause changes in the shape, position, and intrinsic properties of the target area, leading to test results of little diagnostic significance. A typical example is the stiffness measurement using ultrasonic shear-wave elastography, where improper operation caused by pressure can easily make the stiffness value abnormal (see FIG. 8, discussed below) and then generate data of no use when evaluating the stages of tumors. Second, tissues close to bones are hard to be compressed to accommodate the geometric mismatch. Therefore, clinicians always place a gel pad between the probe and the skin to enhance acoustic coupling. However, too much ultrasonic gel will serve as a high-pass filter, filtering out some weak but useful signals from tiny structures. Additionally, the redundant gel will lead to significantly higher measurement results than the real modulus in the elastogram. The development of stretchable ultrasonic probes completely solves this problem. The mechanical compliance of the device can accommodate all kinds of curvature without any mechanical damages and maintain a robust and intimate contact to the human skin via Van der Waals, offering a stable interface for ultrasound waves transmission and receiving.

Although the stretchable device conforms tightly to the human skin, tiny air bubbles may still exist at the interface of the device and the skin. To achieve the best acoustic coupling condition, in some embodiments we added couplants underneath the device. However, traditional hydrophilic ultrasonic gels are volatile and cannot provide adequate acoustic coupling for long-term monitoring of stretchable ultrasonic probes. Therefore, we selected a type of uncured silicone called Silbione as the couplant. Its acoustic impedance (1.03 MRayl) is very close to the skin, and it does not volatilize at room temperature, which can provide a good acoustic coupling environment for a long time.

Figure 57A:
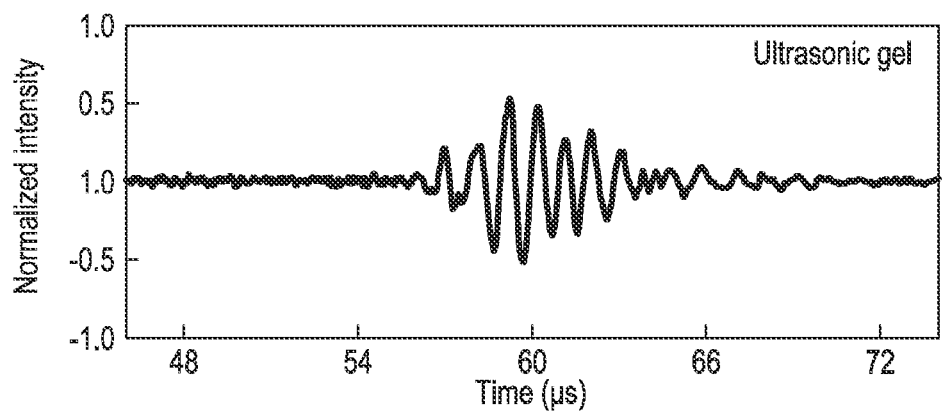
Figure 57B:
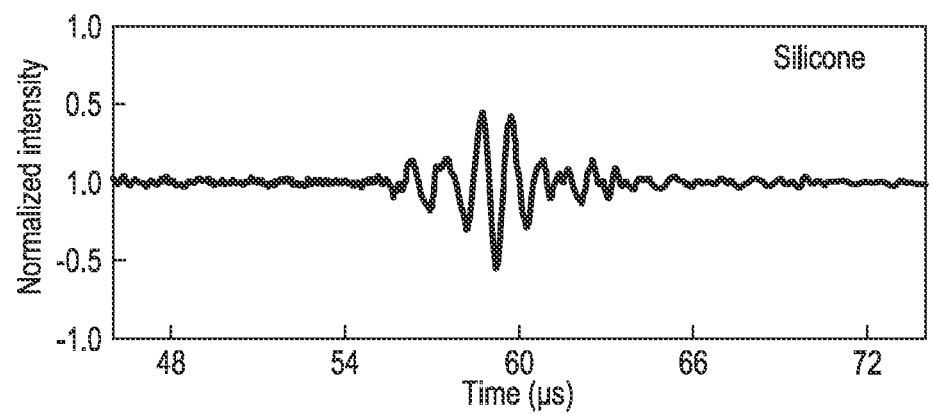
Figure 57C:
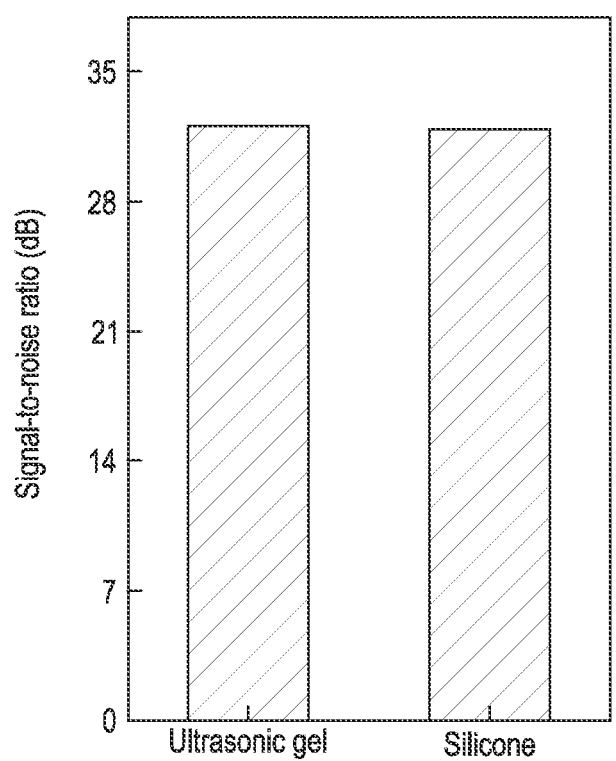

To investigate the coupling performance of the silicone couplant, we first made the most basic comparison experiment using a single transducer to sense a specific target under both traditional ultrasonic gel and silicone, and then compare the signal-to-noise ratio of the received signals. We did the experiments on a commercial phantom (CIRS Model 539) where there was a reflector 40 mm deep inside. The results in FIGS. 57a to 57c show a comparable signal-to-noise ratio with ultrasonic gels and silicone, indicating the good acoustic coupling performance of the silicone.

We then compared the imaging performance of the stretchable array on the human body (the upper arm) with ultrasonic gels and silicone. As FIGS. 57d and 57e show, the imaging results with clear anatomic structures and similar strain distributions reveal the comparable performance of those two couplants. Characterization of human tissues shows the practicability and excellent coupling conditions of silicone-based couplant for the stretchable ultrasonic array.

Characterization of the Skin Curvature on a Breast Phantom Pre- and Post-Compression We take a commercial breast phantom as a typical example since its skin surface has a large curvature. Before mapping the modulus distribution of the breast phantom, the skin curvatures are characterized to determine the correct time-delay profile to be added to the array elements before and after compression. The skin surface of the breast phantom is scanned using a 3D scanner (HDI Advances, LMI Technologies, Vancouver, Canada), by which a digital model with 3D meshes is built to portray the surface morphology. This digital model is then imported into the Catia software (Dassault Systemes, France) for curvature extraction. Forty-two data planes are drawn to intersect at the normal direction to the skin surface, producing forty-two intersection curves with 2 mm interval along the y direction (see FIG. 15b, discussed below). The intersection interfaces are used to identify the maximum curvature of the surface. To obtain quantitative curvature distribution across the entire skin, the minimum curvature radii with 12 mm aperture among the forty-two intersection interfaces are calculated by applying circular curve-fitting. The curve with the minimum curvature radius of 69 mm in this study has been selected to represent the maximum curvature of the skin (see FIG. 15d, discussed below). The coordinates of the curve are extracted by the Catia software (the black curve in FIG. 15f). To study the morphology of the skin after compression, the breast phantom model with relevant physical properties (e.g., density: 1000 kg/m$^3$, Young's modulus: 50 kPa, and Poisson's ratio: 0.5) is established by the COMSOL Multiphysics software (COMSOL Inc, USA). 1% uniaxial strain along the z direction is exerted to the model. The coordinates of the curve after compression are extracted by the Catia software (the dashed curve in FIG. 15f). The compression flattens the skin curvature to a certain degree.

Coordinates of the skin surface before and after compression are input into the Field II for ultrasonic elastography simulations (see FIG. 16, discussed below). The time-delay profiles of the array elements on the planar surface are applied to the array elements on the curvilinear surfaces, for both pre- and post-compression. Beamformed radiofrequency signals from these curvilinear surfaces are obtained (red curves in FIGS. 16a and b). To quantitatively evaluate the influence of the time-delay profiles, the beamformed radiofrequency signals from the planar surfaces are simulated (black curves in FIGS. 16a and b), which are then compared with the corresponding radiofrequency signals from the curvilinear surfaces (red curves in FIGS. 16a and b). The correlation coefficients are calculated (FIG. 16c). The displacement field of the entire breast phantom model with the curvilinear surface is reconstructed and compared with that of the model with the planar surface. The difference in displacement distribution between the two fields is plotted to evaluate the image difference and quality (see FIG. 16d).

Figure 15F:
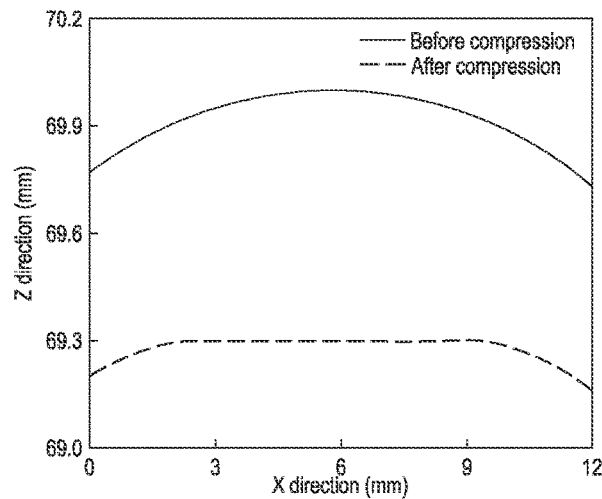
Figure 16A:
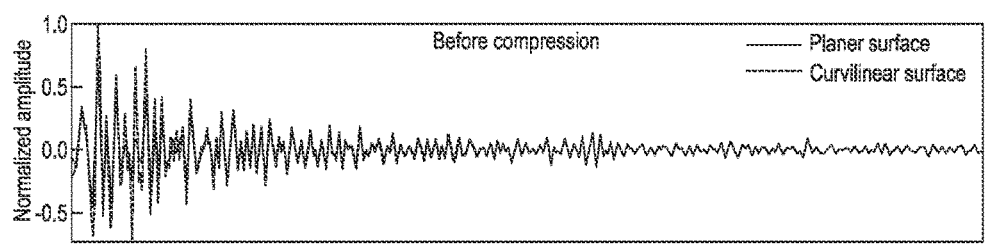
FIGS. 16A-16D shows data concerning the determination of the time-delay profile.
Figure 16B:
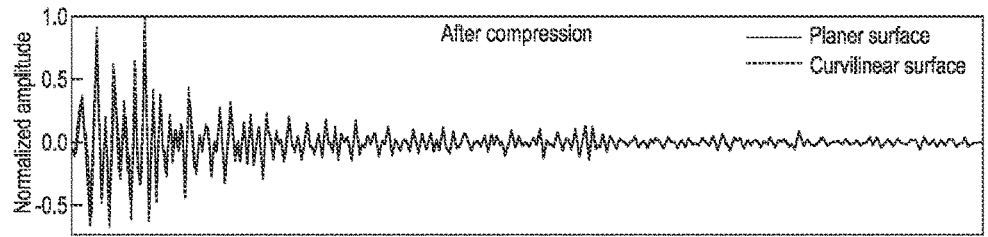
Figure 16C:
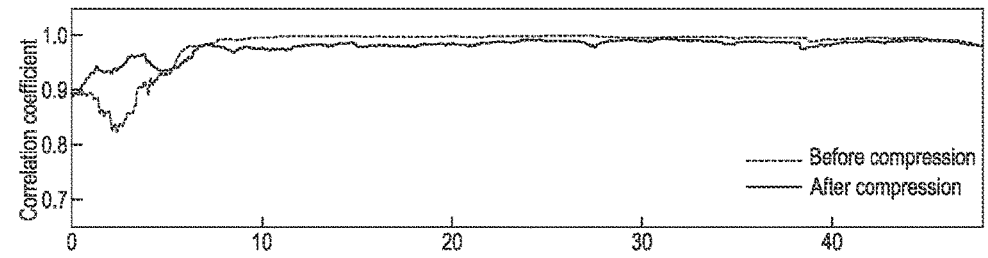

As illustrated in FIGS. 16a and 16b, most parts of the beamformed radiofrequency signals on planar and curvilinear surfaces overlap very well. The corresponding correlation coefficients are more than 0.9 for both pre- and post-compression. The major discrepancy in the near field (within 3.40 µs, corresponding to 2.62 mm depth in the soft tissue) is due to the relatively large difference in the transmission distances between the target area and the transducer elements on planar and curvilinear surfaces. The correlation coefficient of beamformed signals in the near field after compression is slightly higher than that before compression, because the compression flattens the skin curvature to a certain degree (FIG. 15f). When the imaging area is in the far field, the difference in the transmission distances on planar and curvilinear surfaces becomes small.

Figure 16D:
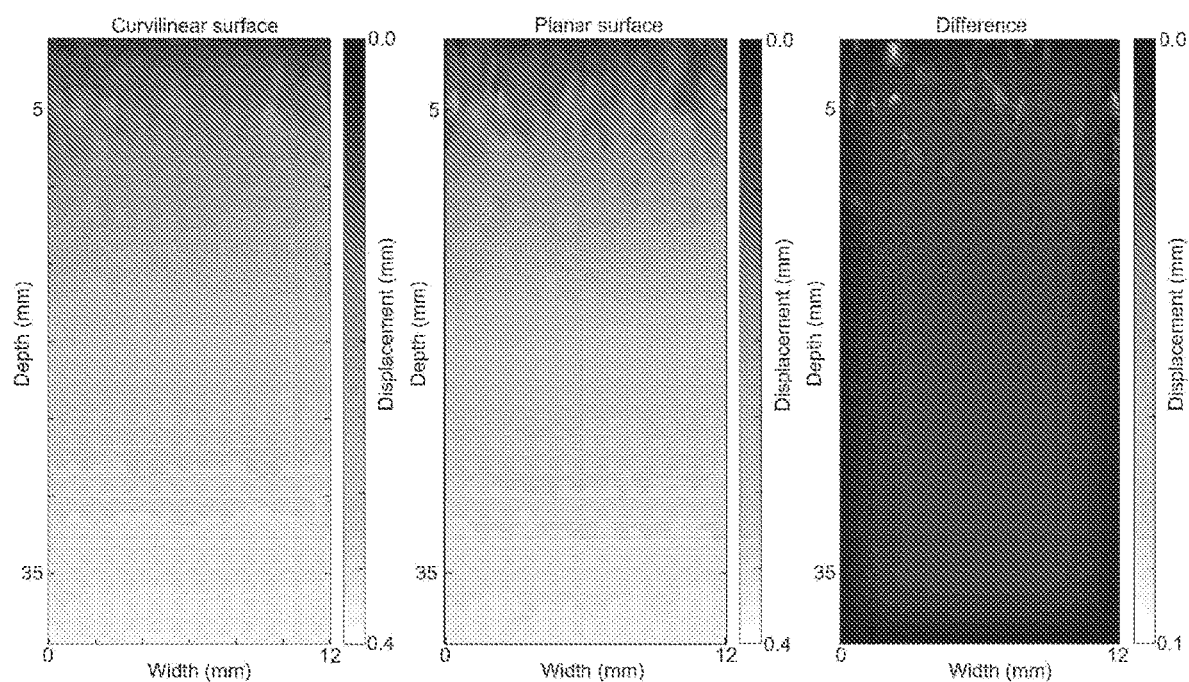

The same phenomenon is also present in the displacement distribution (see FIG. 16d). The difference between two fields is very small across the entire image, with sporadic moderate values in the near field region. To further evaluate the difference quantitatively, the structural similarity index measure and mean squared errors are introduced to evaluate the similarity and average square difference between the two fields, respectively. The structural similarity index measure can be calculated by:

$$\text{Structural similarity index measure} = \frac{(2\mu_x\mu_y + c_1)(2\sigma_{xy} + c_2)}{(\mu_x^2 + \mu_y^2 + c_1)(\sigma_x^2 + \sigma_y^2 + c_2)} \quad (1)$$

where $\mu_x$, $\sigma_x^2$ are the average and the variation of the displacement field from the curvilinear surface, respectively. $\mu_y$, $\sigma_y^2$ are the average and the variation of the displacement field from the planar surface, respectively. $\sigma_{xy}$ is the covariance of these two fields. $c_1$ and $c_2$ are constants. The mean squared errors can be calculated by:

$$\text{Mean squared errors} = \frac{1}{n}\sum_{i=1}^{n}(x_i - y_i)^2 \quad (2)$$

where the n is the number of the pixels, $x_i$ and $y_i$ are the values in both fields. The 0.9880 structural similarity index measure and $5.4 \times 10^5$ mean squared error demonstrate high correspondence of the two fields. This high correspondence is attributed to the 3 MHz resonant frequency with 500 μm wavelength of the transducer elements, which provides significant tolerance to the phase aberration induced by the geometry deformation and yields accurate displacement measurements.

Displacement Calculation by the Normalized Cross-Correlation Algorithm

Only uniaxial displacement along the compression direction is considered in this study. The normalized cross-correlation algorithm estimates the displacement based on the beamformed signals before and after compression, which are denoted as $p_a(n)$ and $p_b(n)$, n=1, 2, . . . , and N, respectively, where n is the index of sampling point, and N is the total length of the signal. To detect the detailed local displacement at different depths, a rectangular window slides from the beginning to the end of the signals to choose the signal interval. The normalized cross-correlation between the signals before and after compression is:

$$R_{NCC}(m, l) = \frac{\sum_{n=m}^{m+W-1} p_a(n)p_b(n+l)}{\sqrt{\sum_{n=m}^{m+W-1} p_a^2(n) \cdot \sum_{n=m}^{m+W-1} p_b^2(n+l)}}, (l_{min} \leq l \leq l_{max}) \quad (3)$$

where m is the index of the sampling starting point of signal $p_a(n)$, l is the time shift between the signals before and after compression, $l_{max}$ and $l_{mm}$ are the lower and upper boundaries of the time shift, and W is the window length. As shown in the equation, a period of signal $p_a(n)$ (m≤n≤m+W−1) before compression is selected. Another period of signal $p_b(n)$ (m−$l_{mm}$≤n≤m−$l_{mm}$+W−1) with the same length is then selected to calculate the similarity between the two periods. The values of l determine the possible range where the algorithm will search the right time shift, which corresponds to the maximum $R_{NCC}(m, l)$. A strain filter (see FIG. 2d) can screen the appropriate window length and step size when using the normalized cross-correlation algorithm to analyze the radiofrequency data. By sliding m from 1 to N with a step size L, the displacement curve will be derived. For the displacement calculation, the window length W and the step size L are critical. A wider window will reduce the jitter error but result in lower spatial resolution. A smaller step size L can improve the spatial resolution but increase the computation time. Based on these considerations, we set the window length W and step size L to be 5 and 0.5 of the ultrasound wavelength, respectively (see FIG. 17, discussed below).

Strain Calculation by a Least-Squares Strain Estimator Algorithm

According to the strain-displacement equation, the strain can be calculated by:

$$\varepsilon = \frac{1}{2}[\nabla u + (\nabla u)^T] \quad (4)$$

where ε is strain, and u is displacement. The right side of the equation is called the symmetric part of the displacement gradient. However, the fluctuations in the displacement will be amplified in the strain images if this equation is directly used. Therefore, the least-squares strain estimator algorithm is applied to calculate the strain because of the improvement of the signal-to-noise ratio compared to the simple gradient operation. Assuming the displacement is d(i), where 1≤i≤N, a window with a length of N will slide from the beginning to the end to choose a period of displacement for computing the strain. The window length N is called the kernel size. The least-squares strain estimator algorithm will derive the precise linear fitting of the displacement curve within the window. For a period of displacement, it can be expressed as:

$$d(n) = a \cdot z(n) + b, n = 1, 2, \ldots, N \quad (5)$$

where z is the depth, and a and b are constants to be derived. The slope a is the strain to be obtained. The equation can be transformed to the matrix format:

$$\underline{d} = A\begin{bmatrix} a \\ b \end{bmatrix} \quad (6)$$

A is an N×2 matrix, where the first column is the depth z, and the second column values are all one. The least-squares solution to this equation will be:

$$\begin{bmatrix} \hat{a} \\ \hat{b} \end{bmatrix} = [A^T A]^{-1} A^T \underline{d} \quad (7)$$

where â and b̂ are the estimated values of the least-squares strain estimator algorithm (see FIG. 17, discussed below).

Graphical User Interface Design

In some implementations the palm may be used to provide uniaxial compression to the device. To guide and quantify the external compression, a graphical user interface can be provided that displays the current maximum strain in real-time (see FIG. 18, discussed below). The graphical user interface consists of two parts: the left part that consists of three display windows, and the right part that is the control panel. The display window can show B-mode imaging, a displacement field, and a strain map in real-time. The maximum strain is shown on the top of the strain window, from which we can quantitatively control the external compression applied to the subject.

The Verasonics system provides the control panel with sufficient room for adjustment in the experiments. On the upper left of the control panel is the TGC (Time gain compensation) control center, where we may adjust the TGC in different segmentations on the image (by the eight bars above) or all together (by the TGC All Gain bar). TGC is a setting applied in diagnostic ultrasound imaging to account for sound-dampening of human tissues. It will increase the amount of gain given to an input signal as its sampling time increases monotonically. Above the TGC control center is the voltage control named 'High Voltage P1', which adjusts the exciting voltages of the ultrasonic array. On the lower left are two buttons of 'Rcv Data Loop', which controls receiving and storing of the radiofrequency signals from the transducers. The 'Simulate' button changes the mode from experiment to simulation, where effects of different probe designs can be foreseen. In the middle of the panel is the Processing area. The 'Acquire' bar determines how many frames we are going to store in the memory, and the 'Lock Rcv1' button can lock the first frame of radiofrequency signals before compression. The 'Freeze' button will pause the whole system without any data extraction. On the right are the 'Tools' dropdown and the 'Save'/'Load' buttons, which allow us to customize the filter parameters of the Verasonics system. Under 'Tools', we can select the filter parameters we want to edit, such as the center frequency and cutoff frequency, to generate the best raw radiofrequency data. We can then save and load these settings as presets using the 'Save' and 'Load' buttons. By default, the system applies a low-pass filter to remove noise.

We used B-mode imaging to find the target area and guide the compression without deviating from the imaging plane. Although the B-mode imaging quality is limited due to the small number of elements, big structures with strong reflections, such as interfaces between brachialis and humerus, can still be visualized. Those big structures are regarded as references for proper transducer location and compression guidance. Any deviations from the imaging plane will be seen as increased curvature of the interface between brachialis and humerus, suggesting the transducers have rotated during the compression and thus need to be corrected immediately.

Before compression, we click the "Lock Rcv1" in the graphical user interface to receive the initial radiofrequency signals. One frame of pre-compression radiofrequency signals will be temporally saved in the receive buffer 1. Then, we mildly compress the device, and 10 consecutive post-compression radiofrequency signals will be temporally saved in the receive buffer 2 and each of these signals is paired with the pre-compression radiofrequency signal to generate a series of strain images. According to FIG. 2d, the signal-to-noise ratio of the strain images becomes the highest at ~1% strain. Therefore, the displacement and strain mapping results with ~1% maximum strain will be selected for further modulus calculations.

Inverse Elasticity Problem Formulation

After measuring the displacement field in a sample in response to uniaxial compressions, we determine the shear modulus of the sample that generates—under the same loading conditions—a predicted displacement field that best matches the measured displacement field; this class of problems is often called inverse elasticity problems. We formulate the inverse elasticity problem as a constrained optimization problem, with the objective of finding the shear modulus distribution that minimizes the objective function:

$$\pi = \frac{1}{2} \int_\Omega |u_y - \tilde{u}_y|^2 d\Omega + \alpha \int_\Omega \sqrt{|\nabla \phi|^2 + \beta^2} \, d\Omega \qquad (8)$$

where the first term on the right represents the data mismatch between the measured and predicted displacement fields. More specifically, $\Omega$ is a chosen cross-section of the sample over which the shear modulus $\mu$ is computed, $\tilde{u}_y$ is the measured displacement field along the direction of compression, and $u_y$ is the corresponding displacement field predicted by a computational model of the deformation of a sample with a shear modulus distribution $\mu$. We utilize only the axial displacement because of the high noise level in the lateral and elevational displacements relative to the axial displacements.

The second term on the right side of the equation 8 denotes regularization that ameliorates the ill-posedness of the inverse elasticity problem. In most cases, this term penalizes unphysical spatial oscillations of unknown fields, thus serving to ensure a certain smoothness of the solution to the inverse elasticity problem. In particular, we use a smoothened version of the total variation (TV) regularization, where $\phi = \log(\mu/\mu_{ref})$ with $\mu$ being the shear modulus and $\mu_{ref} = 1$ kPa being the reference shear modulus, and $\beta$ is a small numerical parameter ($\beta \ll |\nabla \phi|$) that ensures the differentiability of the regularization term when $|\nabla \phi| = 0$. In this study, $\beta$ is chosen to be $1 \times 10^{-12}$. In particular, it has been verified that $\beta \ll |\nabla \phi|$ in regions where $\phi$ varies significantly, and that the smoothened version of the TV term closely approximates the TV term. Further, $\alpha$ is the regularization parameter, which is noise dependent and must be chosen in such a way that the regularization term is balanced against the data mismatch term. If $\alpha$ is too small, one would tend to overfit measurement noise yielding a shear modulus distribution with unphysical oscillations. On the other hand, if $\alpha$ is too large, one would obtain an over-smoothed modulus distribution at the expense of significantly increasing the displacement mismatch. Thus, we select $\alpha$ using the standard L-curve approach. Specifically, we solve the inverse elasticity problem for different $\alpha$, and plot the data mismatch term against $\alpha$ on a log-log scale, with the goal of identifying the data point that lies at the bend of this curve (i.e., the point of the maximum curvature). The regularization parameter that corresponds to this point is thought to optimally balance the data mismatch term and the regularization term. Finally, we note that the TV regularization suppresses large oscillations of the shear modulus regardless of its steepness. Since the shear modulus of a sample may vary significantly especially at the internal boundaries between different phases, the TV regularization is useful in preserving the sharp transition of the shear modulus.

The computational model of sample deformation can be described by a boundary-value problem:

$$\nabla \cdot \sigma = 0 \text{ in } \Omega \qquad (9)$$

$$u_y = \tilde{u}_y \text{ on } \partial \Omega \qquad (10)$$

$$t_x = 0 \text{ on } \partial \Omega \qquad (11)$$

Here the equation 9 represents the balance of linear momentum, where σ is the 2D Cauchy stress tensor given by a constitutive law that describes intrinsic sample properties (see below). On the other hand, equations 9 and 10 are the associated boundary conditions, where the axial displacements on the boundary, 85, are prescribed to be equal to the corresponding measured axial displacements, while the lateral tractions $t_x$, on $\partial\Omega$, are set to zero, meaning that the sample is allowed to freely move in the lateral directions with no friction. Note that the traction vector t=σn, where n is the unit outward normal vector of the boundary $\partial\Omega$.

The constitutive law of the sample is given by an incompressible, linear elasticity model under the assumption of plane stress, which is appropriate because all of the samples used in this study are unconstrained in the elevational direction and the resulting stress in this direction is expected to be small. In particular, the constitutive law can be written as:

$$\sigma = 2\mu[tr(\varepsilon)I + \varepsilon] \qquad (12)$$

where $\varepsilon=\frac{1}{2}[\nabla u+(\nabla u)^T]$ (the equation 4) is the 2D linear strain tensor (T denotes the transpose of a given tensor), $tr(\varepsilon)=\varepsilon_{xx}+\varepsilon_{yy}$ is the trace of the strain tensor, and I is the 2D second-order identity tensor ($I_{xx}=I_{yy}=1$; $I_{xy}=I_{yx}=0$). Then, it can be seen that the Cauchy stress tensor σ depends on the displacement field u through ε in the equation 12. Thus, it is clear that equations 9 to 12 constitute a well-defined boundary-value problem for the displacement field u in the region Ω. That is, given an initial guess of the shear modulus μ, along with the constitutive law (the equation 12) and boundary conditions (equations 10 and 11), we can uniquely determine the displacement field u in Ω by solving the set of partial differential equation (the equation 9).

The problem of minimizing π is reduced to a discrete optimization problem with nonlinear constraints once all of the field variables are represented using finite element basis functions, and the constraint equations are discretized using the finite element method. Thus, the optimization variables are then the nodal values of $\phi=\log(\mu/\mu_{ref})$. The optimization problem is solved iteratively by means of a quasi-Newton method, L-BFGS-B, which requires—at each iteration—both the value of the objective function π and its gradient vector. This gradient vector is computed efficiently using the adjoint method. The L-BFGS-B iterations are considered to be converged when the relative change in the displacement mismatch over the last five iterations is less than $1\times10^{-8}$ (see FIGS. 43 and 45, discussed below). In summary, the steps to solve the inverse elasticity problems are as follows (see FIG. 43):

1. For a given measured displacement field, and an initial guess of the shear modulus μ (and thus φ), solve the forward, boundary-value problem (equations 9 to 12) to obtain a predicted displacement field.
2. Solve the adjoint problem driven by the mismatch between the predicted and measured displacement fields.
3. Evaluate the objective function π and its gradient with respect to φ, making use of the solutions of the forward and adjoint problems.
4. Use the objective function and its gradient to update φ.
5. Repeat steps 1-4 until convergence.

Finally, it is important to note that while in the embodiments described herein uniaxial compression is manually applied, the inverse formulation described herein is also applicable to embodiments in which applied loadings are non-uniform (e.g., different levels of compression or tension at different locations) as long as the resulting displacement field is accurately measured. This is important because our inverse approach does not assume a uniform stress distribution; instead, it properly accounts for the balance of linear and angular momentums under arbitrary external loadings. In particular, by solving the inverse elasticity problem under the plane-stress assumption, the shear-modulus distribution of a given cross-section can be uniquely determined up to a multiplicative parameter. In other words, the contrast between the shear moduli can be uniquely determined. Thus, if the measured displacement fields correspond to the response of the same material, the modulus contrast obtained by solving the inverse elasticity problem will always converge to the same solution, regardless of the external loading conditions. This feature is also consistent with the fact that the shear modulus (at small strains) is an intrinsic material property independent of loading conditions.

We used simulation to demonstrate that the shear modulus, obtained by solving the inverse elasticity problem, is practically independent of the applied loading conditions (e.g., uniformity of the applied compression). Briefly, we started from a "known" shear modulus distribution. We built a model with a specimen and determined the resulting displacement field in the specimen by solving the forward elasticity problem (see equations 9 to 12). To make such a simulated displacement field close to real measurements, we added noise to it to generate the "measured" displacement field. Thereafter, we use these "measured" displacements to reconstruct the spatial distribution of strain by using the least-squares strain estimator algorithm and the shear modulus by solving the inverse problem (the flow chart of the process is in FIG. 43). Finally, we compared these reconstructions with the "known" distributions to assess the performance of the approach. We performed the above procedures for (1) a uniform compression and (2) a non-uniform compression.

Figure 44A:
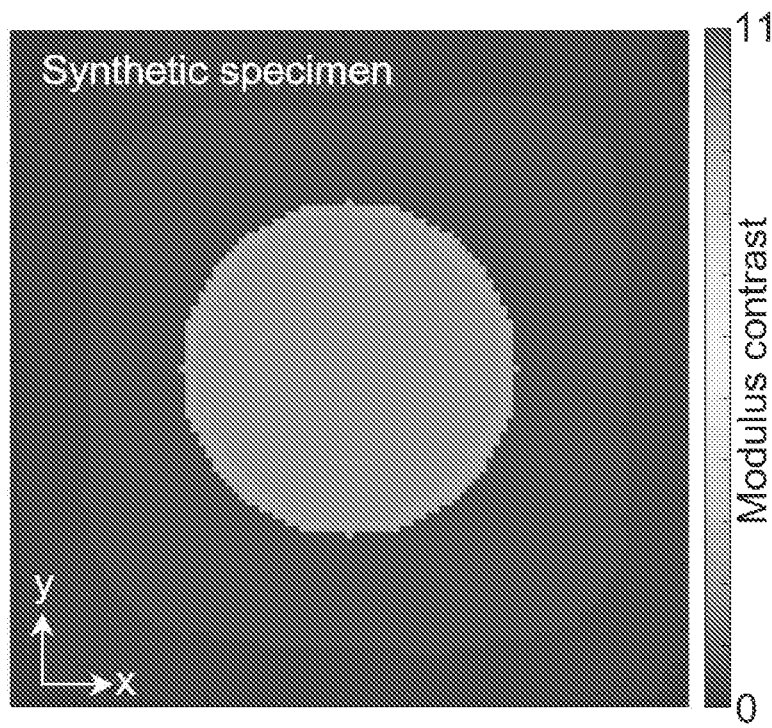
FIGS. 44A-44H show simulation results of uniform and nonuniform compressions.
Figure 44B:
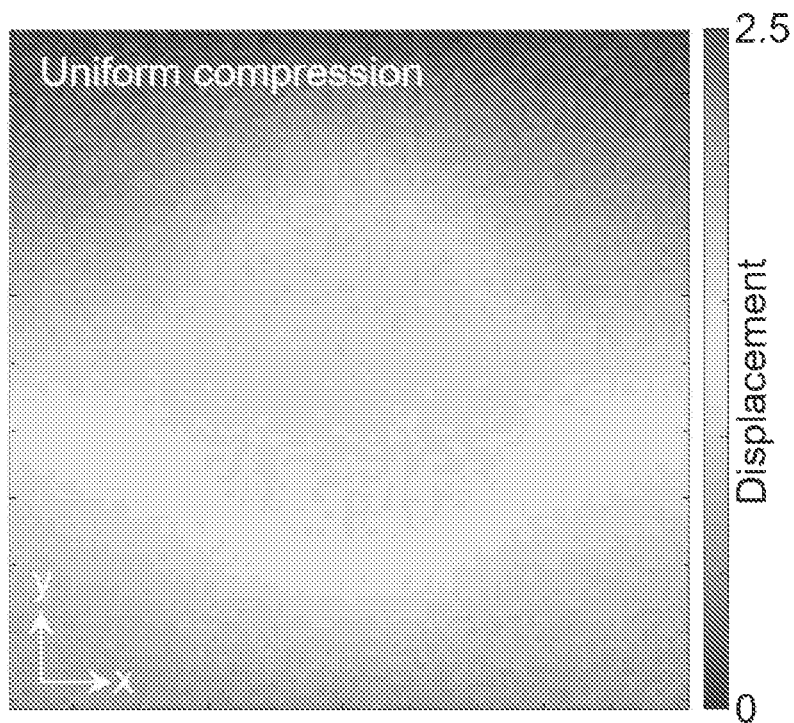
Figure 44C:
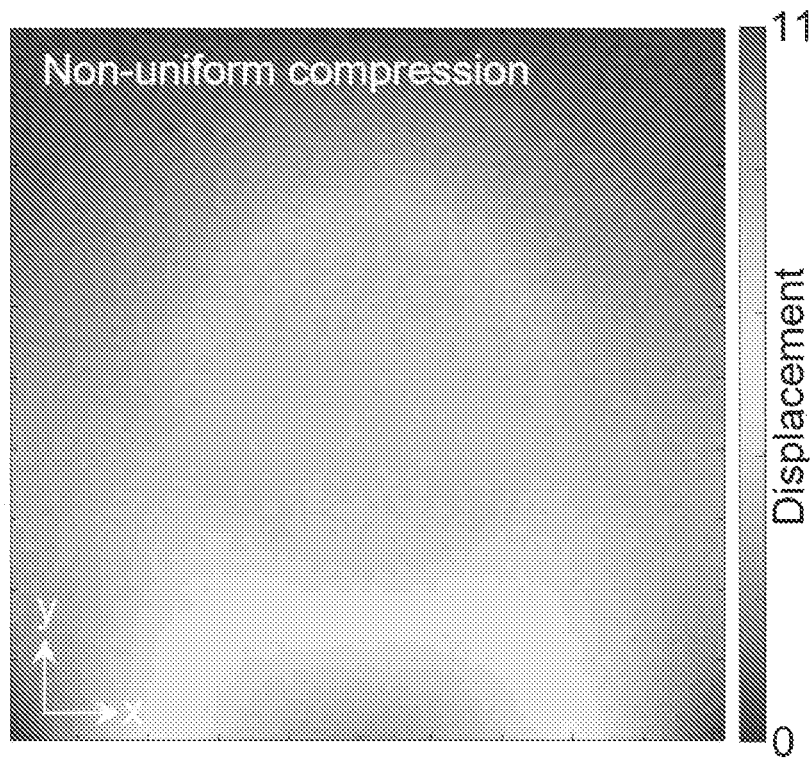
Figure 44D:
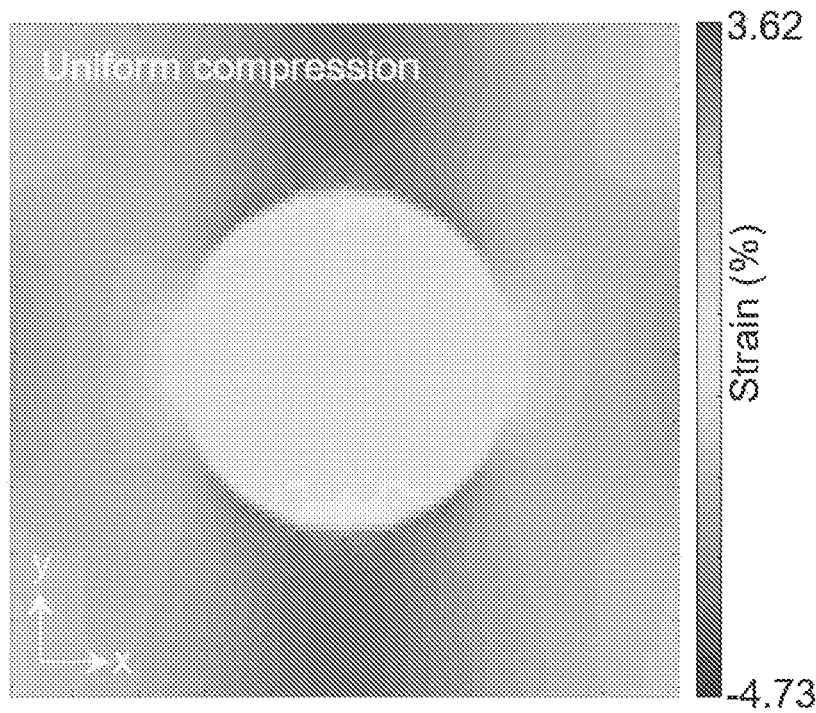
Figure 44E:
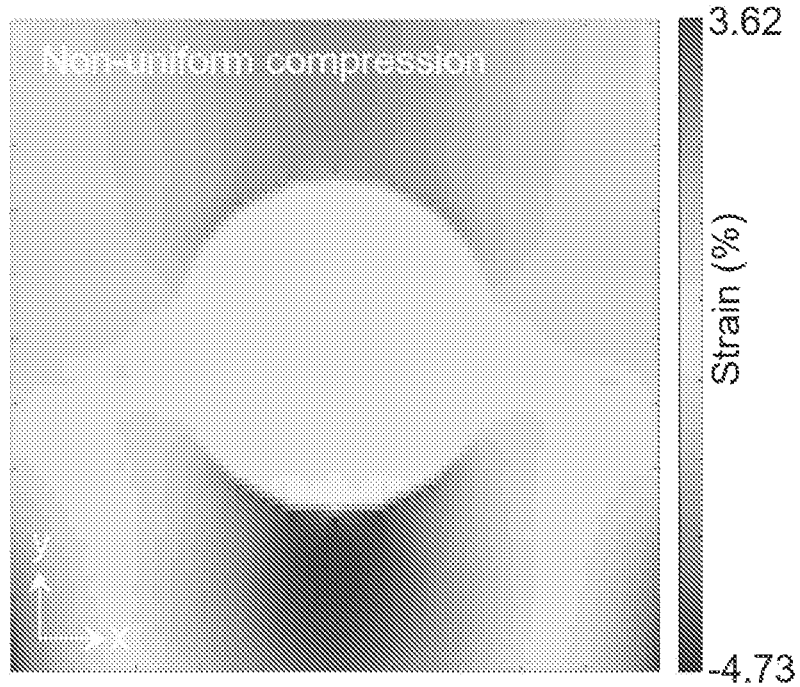
Figure 44F:
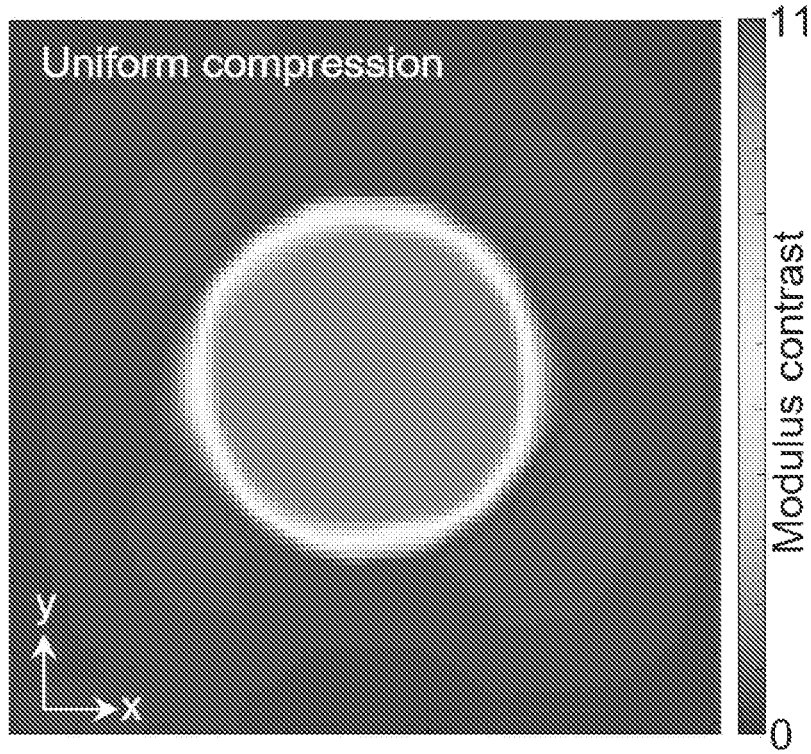
Figure 44G:
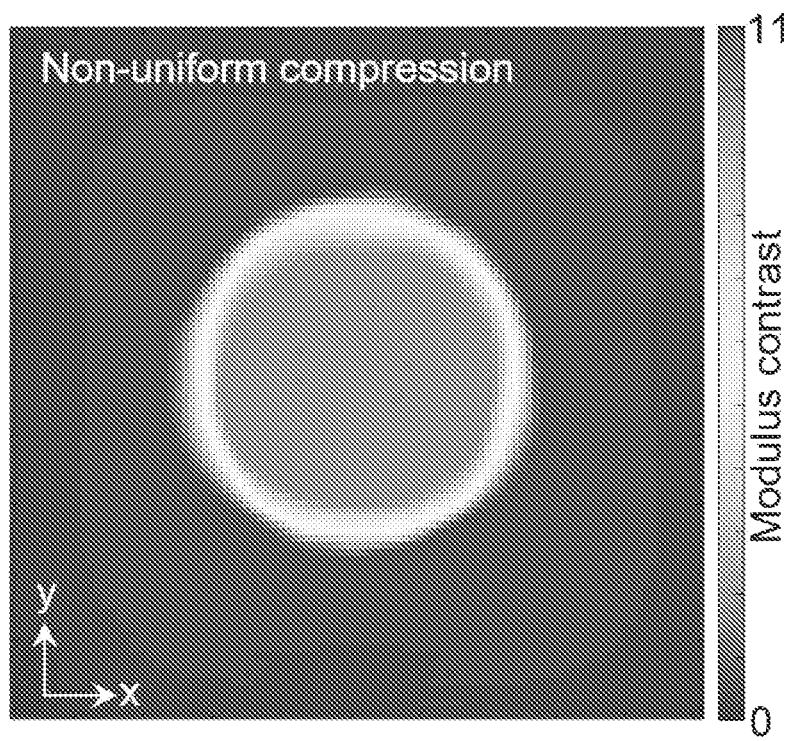
Figure 44H:
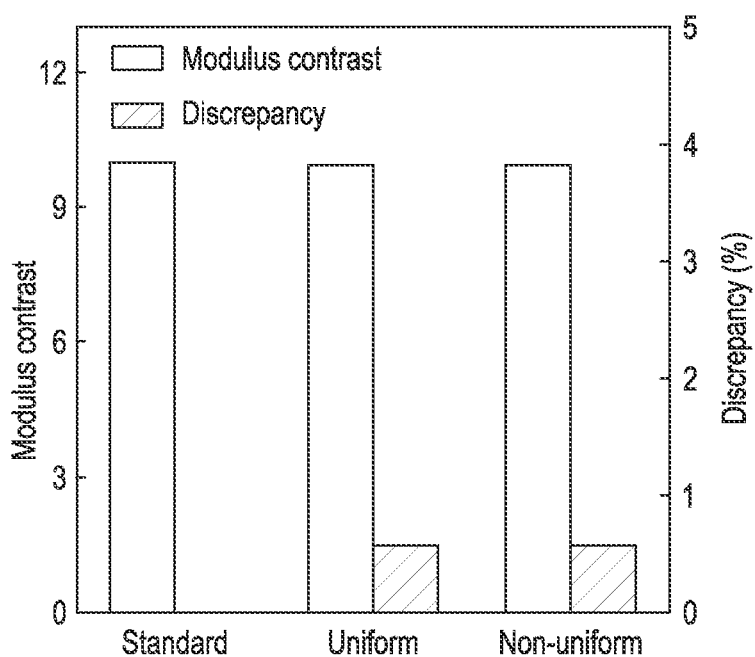

FIG. 44a shows the shear modulus distribution of the synthetic sample, with a stiff inclusion embedded in a homogeneous and soft surrounding matrix. In particular, the matrix is a unit square and the inclusion is a circle with a radius that is a quarter of the edge length of the matrix. Moreover, the inclusion has a shear modulus of 10 and the background has a shear modulus of 1. Note that all these values are taken to be dimensionless because our calculations are insensitive to specific units (e.g., mm or cm, Pa or kPa). Such a sample mimics the one probed by the ultrasonic patch.

In the first case, we uniformly compressed the specimen in the vertical direction by applying to the bottom edge a uniform movement along the positive Y direction, while keeping the top edge fixed. Both the top and bottom edges are free to move in the X direction, and the two lateral edges are taken to be stress-free. The uniform, vertical movement applied to the bottom edge is assumed to be 0.02 units, corresponding to an overall compressive strain of 2% (such a small strain is ensured to be in the linear elastic regime). In the second case, we used the same setting as in the first case, except that we applied to the bottom edge a non-uniform, sinusoidal movement in the positive Y direction. This sinusoidal movement has an amplitude of 0.02 units and a wavelength of 2 units. For the exact displacement, $u_{exact}$, obtained by solving the forward elasticity problem, we added to it about 1% Gaussian noise to generate the "measured" displacement, $u_{noise}$, following reported methods. Note that the noise level, e, can be derived using the $L_2$ norm and is given by $$e = \frac{\|u_y - u_{noise}\|_2}{\|u_y\|_2} = 1\% \quad (13)$$

with $\|p\|_2 = \sqrt{\int_\Omega p^2 d\Omega}$ being the $L_2$ norm of a quantity p, and $\Omega$ being the specimen domain. Having obtained the "measured" displacement field $u_{noise}$, we utilized the inverse algorithm to reconstruct the shear modulus for each loading case. Guided by the L-curve method described above, we chose the optimal regularization parameter to be $\alpha=5\times10^{-4}$ for both cases.

As seen in FIGS. 44b to 44h, the uniform and non-uniform compressions yield rather different displacement and strain distributions, which indicate that the strain-based elastography is a qualitative method only reflecting a relative stiffness of each component for a subject with inhomogeneous structures. On the contrary, the modulus distributions obtained by solving the inverse problem for the two cases are very similar. Concretely, the reconstructed inclusion moduli based on uniform and nonuniform compressions are the same: $\mu_{inclusion}=10.2905$. The reconstructed moduli of the surrounding matrix based on uniform and non-uniform compressions are $\mu_{matrix}=1.0352$ and 1.0350, respectively. Furthermore, the modulus ratio between the inclusion and matrix under uniform and non-uniform compressions are 9.940 and 9.942, respectively, very close to each other. Most importantly, the differences between the reconstructed modulus ratios and the exact ratio (i.e., 10) are very small (<0.6%), demonstrating that the accuracy of the results is practically insensitive to non-uniform external loadings.

While the embodiments described above do not provide the absolute modulus value for each component, due to the unknown magnitude of the applied stress, in alternative embodiments this limitation can be solved by integrating a calibration layer with known elastic properties with the stretchable ultrasonic array, or a force sensor on the back of the device.

Determination of the Adoptable Range of Curvatures of the Stretchable Array

Figure 19A:
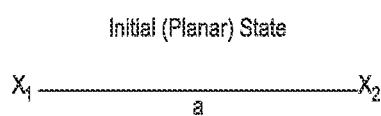
FIG. 19A-19G shows schematics and data concerning the determination of the curvature range of the stretchable array.
Figure 19B:
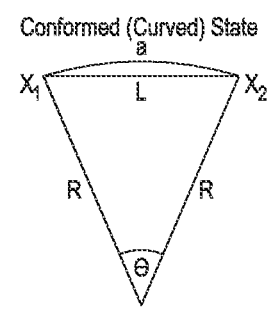

A single pair of adjacent transducers within the array is examined and called $x_1$ and $x_2$ (see FIGS. 19a and 19b, discussed below). $x_1$ and $x_2$ are initially separated by a straight distance defined by the initial design pitch, a=0.8 mm in their initial planar state. When conformed to a curved surface, the straight distance between $x_1$ and $x_2$ changes to a shortened length, L, while a conforms to the curvature and becomes the arc length between $x_1$ and $x_2$. This arc has a radius of curvature, R, corresponding to the curvature of the surface being conformed to. Transducers $x_1$ and $x_2$ are separated by the arc angle, $\theta$. L represents the conformed array pitch. Thus, we solve for L as follows:

First, we find the angle, $\theta$, of the arc between transducers $x_1$ and $x_2$:

$$\frac{a}{R} = \theta \quad (14)$$

Then, we can find the conformed array pitch, L, based on our surface's known radius of curvature:

$$L = \sqrt{2R^2 - 2R^2 \cos\frac{a}{R}} \quad (15)$$

In this study, a=0.8 mm. Thus L can be reduced to a function of R:

$$L(R) = \sqrt{2R^2 - 2R^2 \cos\frac{0.8 \text{ mm}}{R}} \quad (16)$$

For the breast phantom used in this study, the curvature is 70 mm. Thus, at this curvature:

$$L(R = 70 \text{ mm}) = \sqrt{2(70^2) - 2(70^2)\cos\frac{0.8 \text{ mm}}{70 \text{ mm}}} = 0.7999956 \text{ mm} \quad (17)$$

This is only a 0.00054% difference from the initial design pitch of 0.8 mm. Additionally, according to our simulations below, the stretchable array can conform to surfaces of curvature $$\kappa \leq \frac{1}{30} \text{mm}^{-1},$$

or radii of curvature R≥30 mm. At this maximum allowable curvature of $$\kappa = \frac{1}{30} \text{mm}^{-1},$$

we find:

$$L(R = 30 \text{ mm}) = \sqrt{2(30^2) - 2(30^2)\cos\frac{0.8 \text{ mm}}{30 \text{ mm}}} = 0.7999763 \text{ mm} \quad (18)$$

This is still only a 0.0030% difference from the initial design pitch of 0.8 mm. Therefore, due to such a negligible difference in pitch generated within the allowed curvature range of our array, we consider it appropriate to use a constant 0.8 mm pitch for beamforming even when the array is conformed to a curved surface.

For the curvature range of the surfaces the stretchable array can be conformed to, there are two limiting factors. First is the mechanical limit of the copper serpentine interconnects. When the array is conformed to a curved surface, the serpentine interconnects are strained. This strain is positively correlated with the surface curvature, so there is a maximum curvature where the copper serpentines would reach their mechanical limits, i.e., the copper yield strength, beyond which plastic deformation takes place.

The second limitation is the ultrasonic strain imaging performance of the device. For this study, we used a planar beamforming algorithm. At small curvatures, this is a reasonable assumption that does not produce many errors, especially for deep tissues. At large curvatures, the transducers are no longer be in the same plane, which causes the delays that are used to align the ultrasound signals from each transducer to be erroneous in the algorithm. The amount of error increases with the surface curvature. Thus, there is a curvature limit where the errors produced in the displacement fields are no longer acceptable. For our study, we would like to retain an image structural similarity index of >95%, referenced against the image taken from a flat surface. We take this value because a structural similarity of 95% is the threshold where human observers are unable to tell whether or not an image has been distorted.

Figure 19C:
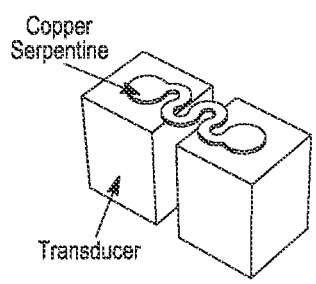

A single pair of adjacent transducer elements within the array is examined, connected by a copper serpentine electrode (see FIG. 19c, discussed below). In the planar scenario, this unit is consistent with the initial design. Once strained, one end of the transducers angles away from each other, while the other end angles toward each other, which creates strain and stress distributions along the serpentine. We would like to determine the curvature at which the maximum stress along the serpentine reaches the yield strength of copper.

The parameters used for this simulation are as follows:

| Material | Parameter | Value |
|---|---|---|
| Copper | Young's Modulus | 119 GPa |
| | Poisson Ratio | 0.34 |
| | Yield Strength | 357 MPa |
| 1-3 composite | Young's Modulus | 71 GPa |
| | Poisson Ratio | 0.31 |

Figure 19D:
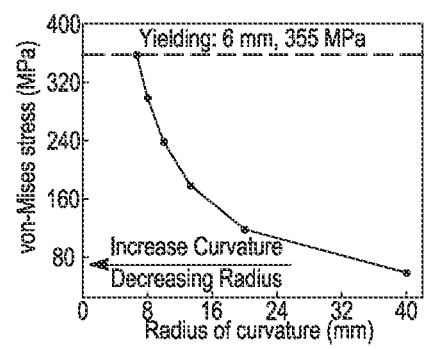
Figure 19E:
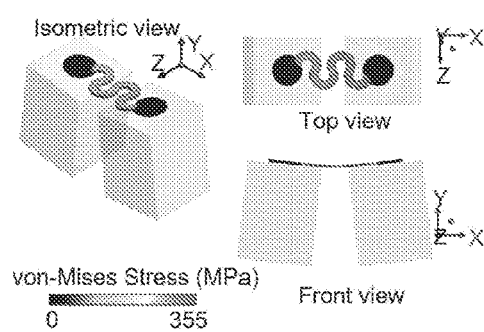

An ideal elastic-bilinear relationship was used for the copper behaviour. For each simulation in ANSYS, the two transducers and serpentine unit would begin in the planar configuration, and then be subjected to the deformation produced by a surface of a prescribed radius of curvature. The simulations began from a surface of 80 mm radius curvature and were repeated for various decreasing radii. The graphed data from the simulation trials are shown in FIG. 19d. At a curvature of $$\kappa = \frac{1}{6.6} \text{mm}^{-1},$$

the maximum stress along the copper serpentine reaches 355 MPa, which is effectively right below the yielding limit (see FIG. 19e, discussed below).

A single row of 16 transducers in the array is examined. After conforming to the curved surface, the transducers are displaced out-of-plane, which causes the time delay used for aligning ultrasound signals from each transducer to be no longer accurate. The algorithm's perceived distances from the transducers to the scatterer are incorrect. Thus, we would like to determine the maximum curvature at which the strain image of the conformed array maintains >95% accuracy with respect to the planar reference image.

Figure 19F:
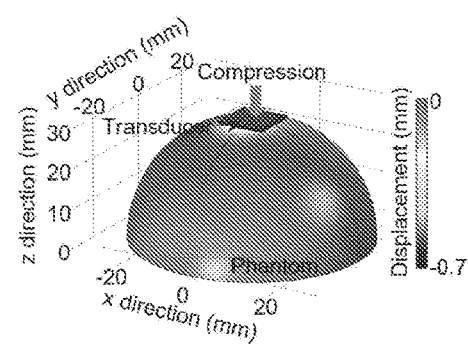
Figure 19G:
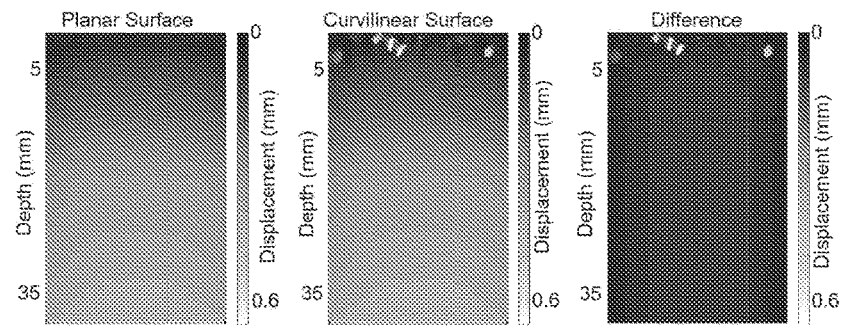

For this simulation, we used a similar methodology to that described above. In quasi-static strain elastography, the displacement differences between a pre-compression and post-compression image are compared to map the strain distributions. Thus, we first simulate the phantom tissue compression, followed by the corresponding ultrasound displacement fields. A computer phantom was generated in COMSOL Multiphysics with identical properties to the commercial breast phantom used in this study. Its radius of curvature was decreased in steps until the resulting simulated strain image no longer maintained a >95% structural similarity index with respect to the planar reference image. In each simulation, a stiff square plate of 12 mm×12 mm×0.8 mm was used to exert a downwards compression of 1% uniaxial strain on the breast phantom. The simulation setup and results are shown in FIG. 19f.

Following the compression simulation, we extracted the coordinates of the breast phantom's surface curvature from both before and after compression. The transducers' coordinates in each state were then derived from these surface curvatures, and input into Field II for ultrasonic elastography simulations. A similar process was performed on a phantom with a planar surface. The image taken by the conformed array is compared against that from the planar phantom to get a structural similarity index.

The final results of our simulation show that the strain images (see FIG. 19g, discussed below) of a phantom with $\frac{1}{30}$ mm$^{-1}$ curvature result in a 95% structural similarity. Thus, the imaging performance constraint limits the curvatures to be below $\frac{1}{30}$ mm$^{-1}$, which is smaller than the curvature $$\left(\frac{1}{6.6}\text{mm}^{-1}\right)$$

allowed by the mechanical performance constraint. It is worthy to note that the errors in the conformed array imaging are confined almost entirely to the near field, <5 mm below the tissue surface, and are almost absent in the far field. The difference in signal travel time imposed by the curvature (as compared to a planar surface) makes up a significant error percentage in shallow tissues, where the signal travel time is very short, while the long signal travel time in deep tissues makes the error percentage very small. Thus, despite using a planar algorithm, the device can maintain near-perfect image accuracy in deep tissues. The errors in the near field can be further reduced by using lower transducer frequencies, which allows more tolerations for curvature-induced dislocations of the elements.

Based on the simulations and analyses of the mechanical limited and imaging performance limited curvature of the ultrasonic array, we determine that this device is limited to curvatures of $$\kappa \le \frac{1}{30}\text{mm}^{-1},$$

imposed by the imaging performance limitation.

Elastographic and Sonographic Signal-to-Noise Ratios and Contrast-to-Noise Ratios The quality of the resulting elastogram is typically quantified by the elastographic signal-to-noise ratio ($SNR_e$) and the elastographic contrast-to-noise ratio ($CNR_e$) (FIGS. 2a to f). $SNR_e$ reflects the ratio between the mean intensity and the variance of the strain image. The formula for calculating $SNR_e$ is:

$$SNR_e = \frac{s}{\sigma} \quad (19)$$

where s is the mean of the strain and σ is the standard deviation. There are some differences and relationships between the sonographic signal-to-noise ratio and $SNR_e$. The sonographic signal-to-noise ratio is the signal and noise ratio of radiofrequency signals, which is only attributed to the performance of the ultrasonic probe, i.e., the hardware. Piezoelectric materials with high electromechanical coupling coefficient and good fabrication technologies improve the sonographic signal-to-noise ratio of the radiofrequency data. On the other side, excellent $SNR_e$ depends not only on the good hardware performance, but also on the transmitting mode and the imaging algorithms involved.

The sonographic contrast-to-noise ratio reflects the echo intensity difference of two regions. Unlike the sonographic contrast-to-noise ratio, $CNR_e$ reflects the ratio between strain contrast and standard deviation, which is defined as:

$$CNR_e = 20\log_{10}\left(\frac{2(S_{in} - S_{out})^2}{\sigma_{in}^2 + \sigma_{out}^2}\right) \tag{20}$$

where $S_{in}$ and $G_{in}$ are the mean and standard deviation strain values inside the target region, respectively; $S_{out}$, and $\sigma_{out}$ are the mean and standard deviation strain values outside the target region, respectively.

The values of $SNR_e$ and $CNR_e$ are attributed to the combined contributions of transducer performance, the imaging method, and the post data processing algorithms. The function of fitting the $CNR_e$ versus modulus contrast is:

$$f(x) = 14.77\log_{10}(x-1) + 7.156 \tag{21}$$

With the coefficient of determination of >0.98, the measured data highly match the fitting function, indicating the reliability of the experimental results.

The Transmission Mode of Coherent Plane Wave Compounding

One row of the linear array is composed of M transducer elements with the pitch of $x_{pitch}$. Thus, the position of $i^{th}$ element is defined as $(x_i, 0)$, where $x_i$ equals $x_{pitch} \cdot (i-1)$. The detection region will be a rectangle below the array. By applying different time delays to each element, the array will emit K plane waves towards different directions with an angular interval of 1°. Each element starts to receive the echoes immediately after the transmission (FIG. 2b inset). Assuming the angle between the plane wave and the linear array is $a_k$, k=1, 2, . . . , and K, the wave propagation time from the beginning of the transmission to the element pixel (x, z) will be:

$$t_{i,k}^e = (z\cos\alpha_k + x\sin\alpha_k)/c \tag{22}$$

This transmission time delay is constant for all elements. The reflection time delay from the pixel (x, z) to the i-th element can be estimated as:

$$t_{i,k}^r = \sqrt{z^2 + (x - x_i^t)^2}/c \tag{23}$$

The total time delay will be:

$$t_{i,k}^{delay} = t_{i,k}^e + t_{i,k}^r \tag{24}$$

which determines the round-trip time of ultrasound waves from the emission to the moment received by the element i. The measured ultrasound signal by the i-th channel can be expressed as $s_i(t)$, i=1, 2, . . . , and M. Therefore, by applying the Delay-and-Sum algorithm, the reconstructed signal at pixel (x, z) corresponding to angle $\alpha_k$ will be:

$$p_{\alpha_k}(x, z) = \Sigma_{i=1}^{M} s_i\left(t - t_{i,k}^{delay}\right) \tag{25}$$

Without applying any envelope calculation or other post-processing, all of the images of different angles are added coherently, yielding the final beamformed signal (FIG. 13):

$$p(x, z) = \Sigma_{k=1}^{K} p_{\alpha_k}(x, z) \tag{26}$$

The coherent compounding method adds the beamformed radiofrequency signals from the multi-angle transmissions before the demodulation process, which keeps phase information when executing the compounding process, and thus effectively removes the random noise and enhances the signal intensity. We use 19 steering angles with 1° step size to reconstruct images. Plane waves with a smaller step size than 1° cannot achieve a synthetic focusing effect. The imaging contents are too similar for each angle and the accumulated artifacts caused by side-lobes lead to a low $SNR_e$. When the step size is too big, the overlap between plane waves, and thus the $SNR_e$, decrease (see FIG. 30, discussed below). The most appropriate step size (1° in this work) yields the most constructive interference of different plane waves in the tested region, ensuring the highest $SNR_e$ (see FIG. 2b). Large angle numbers enhance the $SNR_e$ because the coherent superposition of all steered images contribute to the compounding elastographic image. When extra plane waves cannot contribute substantially to the central rectangular region directly beneath the transducer array, the $SNR_e$ saturates. However, the time required for reconstructing the images grows linearly with the number of steering angles. To save the time for image reconstruction, especially the time for ultrasound wave transmitting/receiving and post-processing of receive beamforming (see FIG. 31, discussed below), we use 19 steering angles in this work (see FIG. 2c).

Differences in Strain Distributions Obtained by the Stretchable and Commercial Probes The reasons why the two strain distributions differ in some details, though having the same shape, can be categorized into two parts. One is from the different testing methods, and the other is due to the differences in probe properties.

First of all, the stretchable array described herein is able to attach to the surface and acquire all radiofrequency signals from different slices at one time. While the commercial probe (Verasonic P4-2v) is linear-shaped, and we had to manually move the probe along the elevation direction slicing the project into multiple segments for the reconstruction. Unlike the stretchable ultrasonic probes, the commercial probes cannot always be perpendicular to the curved irregular surface of the breast phantom when testing multiple cross-sections. Such various testing angles cause the different tumour sizes and locations in 2D images compared with those from the stretchable array.

Secondly, the spatial resolutions in lateral, axial, and elevational directions of the commercial ultrasonic probe are better than those of the stretchable ultrasonic array. The lateral resolution of ultrasonography depends on the beamwidth of the ultrasound wave. Specifically, finer pitch and longer aperture improve the focusing effect, which narrows the ultrasound beam at the focal point. Since the commercial probe is superior to the stretchable array in both pitch and aperture, it achieves a better lateral resolution than the stretchable array. The axial resolution depends on the frequency and bandwidth of the array element. The commercial and stretchable probes have the same resonance frequency (3 MHz). However, the commercial probe has a thick backing layer of centimetres, which endows it with a narrow spatial pulse length and a wide bandwidth (>75%). As a result, it has a high axial resolution. However, the backing layer of the stretchable probe is relatively thin, mainly for the benefit of better mechanical compliance to tightly conform to the human skin. Therefore, the bandwidth of the stretchable array is relatively narrow, causing inferior axial resolution. The commercial probe also performs better in the elevational resolution than the stretchable ultrasonic probe since the length of each element is larger than that of the stretchable probe. It improves the convergent ultrasonic beam in the elevational direction so that the interferences from adjacent slices are less in each 2D image. These factors collectively lead to differences between the original 2D images of the commercial and stretchable probe, further influencing the 3D reconstruction. An optimized transducer design with finer pitch, larger aperture, and longer elevational length will be explored in future studies to compensate for the performance weakness of the stretchable array.

The Modulus Contrast Mapping of the Cyst Phantom

Figure 36A:
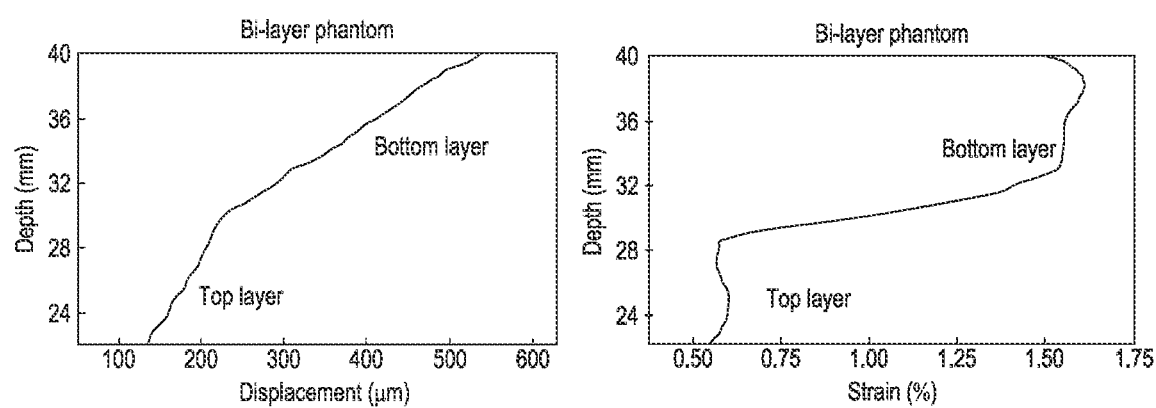
FIGS. 36A-36D show displacement and strain curves at the central lines of different phantoms.
Figure 36B:
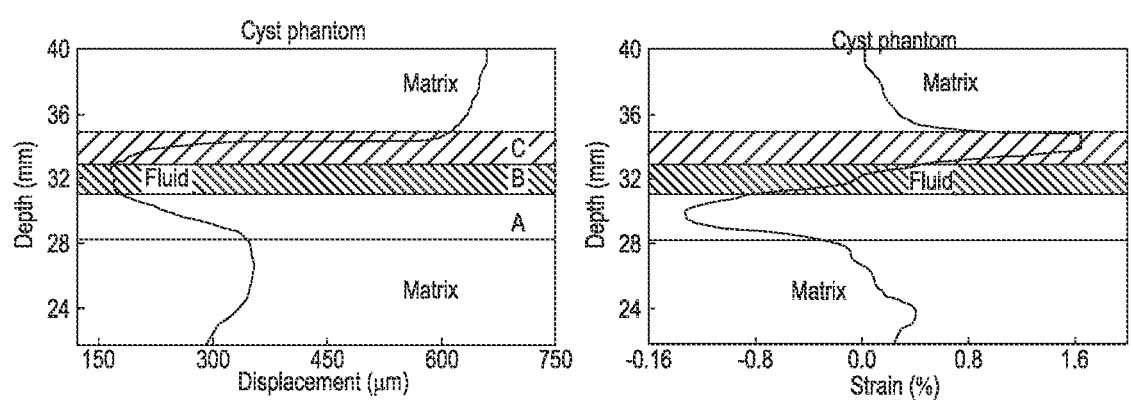
Figure 36C:
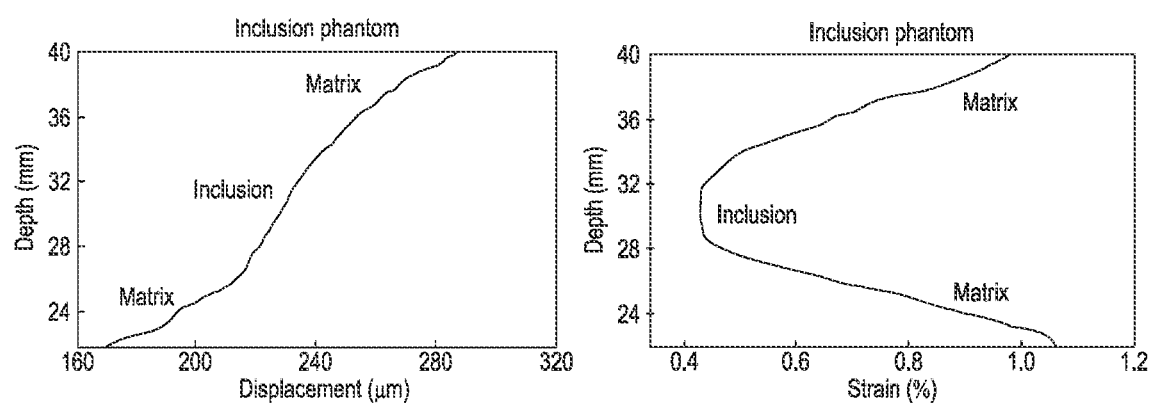
Figure 36D:
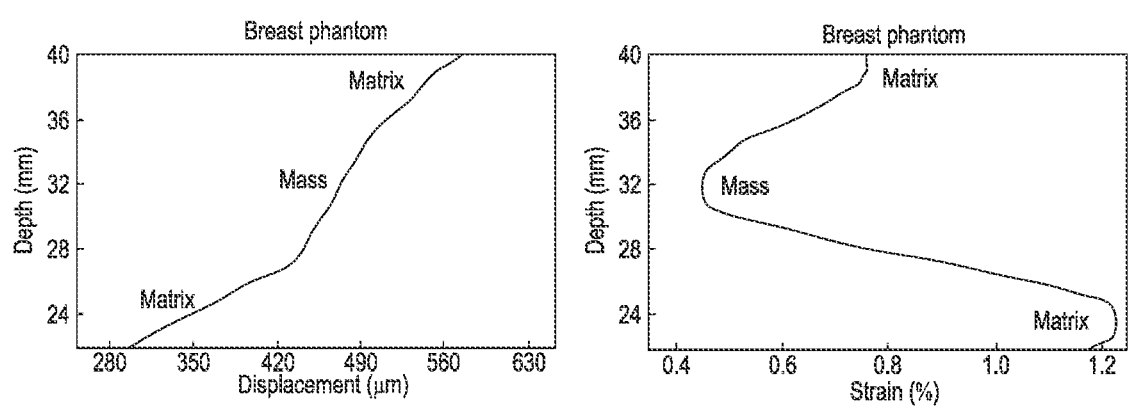

The mapped modulus contrast of the cyst phantom does not reflect the actual modulus ratio, but only demonstrate the relative stiffness of the cyst and surrounding matrix, because there is only fluid inside the cyst and is absent of scattering particles or echogenic signals from the fluid (see FIG. 3b, FIG. 36b, and FIG. 37). Noises in the radiofrequency lines from the fluid are used for calculating cyst displacements. Therefore, the measured displacements in the cyst are artifacts. Those artifacts generate modulus ratio mapping that can only provide a relative modulus distribution. The relative modulus distribution provides only a qualitative structural appearance of the cyst that facilitates its recognition and diagnosis in clinics.

Multi-Site Tissue Mapping and Protocols of the Exercise and Physiotherapy

We mapped the tissue modulus at five different locations on the human body. For measuring the shoulder joint, the upper limb was drooped naturally in relaxation, with the palm facing inward. The device was applied conformally to the lateral side of the shoulder joint, on the midpoint of the medial head of the deltoid. For measuring the forearm, the upper limb was fully stretched on the table with the palm upward. Since the palmaris longus tendon is an essential anatomical landmark, the location of the device was recognized easily by exploring along the tendon, which was the midpoint of the muscle belly of the palmaris longus. For measuring the thigh, the subject laid on the back with the lower limbs stretched and relaxed, keeping the feet upwards. The device was placed on rectus femoris, at the medium level between the upper pole of patella and the greater trochanter of femur. For measuring the calf, the subject stood vertically with feet together and forward. The location of the device was the midpoint of the muscle belly of the gastrocnemius medial head. For measuring the upper arm, the elbow joint was passively flexed at ninety degrees, with the upper arm lying on the table and the palm towards back. The device was placed at the midpoint of the muscle belly of the biceps brachii. In all tests, the device was placed on the medium site of the medial and lateral edges of all of the muscle bellies, parallel to the long axis of the upper or lower limbs.

Muscle has a heterogenous structure. To avoid anatomical differences as much as possible, in this study we have measured muscles, such as in the belly areas, which have a relatively homogenous structure and high measurement repeatability on different individuals. Due to the small footprint (12 mm×12 mm) of the stretchable ultrasonic array, the full scope of the anatomic structure of the upper arm cannot be displayed. To demonstrate the relevance of the measurements, we mapped the upper arm on the same subject using a commercial ultrasonic shear-wave elastography system (GE Logiq E9 Ultrasound System, C1-6 probe), due to its higher spatial resolution than MRE. Additionally, MRE is also based on shear-wave elastography, which uses a paddle-like device to transmit the vibrations into the subject. The paddle has a large, rigid base that is not suitable for the upper arm, leading to poor coupling and many artifacts. Due to its relatively larger footprint, the commercial probe can provide a broader sonographic window than the wearable patch. As seen in FIG. 54, the entire anatomic structure of the upper arm is visualized in both transverse and longitudinal views. Key components have been labelled in the B-mode images. To correlate the results from the commercial system with those from the patch, we did more elastographic measurements in longitudinal view, with a zoomed-in window focusing on bicep brachii and brachialis (FIG. 54b). We have taken multiple slices of B-mode images along the short axis of the upper arm, from which representative structures, such as the fascia in the bicep brachii and the interface between the bicep brachii and brachialis, highly match with slices from the patch. Additionally, we have measured the modulus of muscles using the commercial system. Due to the limited size of the window for selecting the region of interest, the modulus of bicep brachii and brachialis can only be measured separately. We have calculated the stiffness ratios of two muscles, which are very close to those tested by the patch (see FIG. 54b, discussed below). The high correspondence between the results from the commercial system and the patch demonstrates the high relevance of the measurements by the stretchable ultrasonic patch to the real-world applications.

For in vivo studies, a healthy volunteer without any upper extremity injuries or soreness was selected to perform eccentric contractions of the elbow flexor muscles. The human experiments in this study are carried out following reported protocols. All subjects signed informed consent forms. To ensure the effectiveness of the unaccustomed exercise, the subject was required to use the non-dominant arm to do the exercise. The measurements of experimental groups started when the muscle soreness caused in the control group has completely gone. Following the existing model, the subject maintained a seated position and performed the exercise with a 7.1 kg dumbbell. The forearm was forcedly extended from a fully flexed position. The exercise was consisted of six sets of ten maximum eccentric contractions of the elbow flexors with 90 seconds rests between sets. For collecting the data of the control group, the biceps brachii was tested immediately after the exercise. We ran a total of 20 tests with one per minute, which demonstrated the serial monitoring of the device within a short period of time. We did the same measurements 3 hours, 6 hours, and 1 to 5 days after the exercise. For each measurement, we ran five tests with one per minute (FIG. 52b). Massotherapy and hyperthermia were applied every day before each testing. For the massotherapy, a massage gun (Zfitei, China) was used for 20 minutes to vibrate the biceps brachii. For the hyperthermia, a hot towel was wrapped around the upper arm for 20 minutes. The modulus distribution of each test was reconstructed, from which a 12 mm×5 mm window was picked and the mean and standard deviation of the modulus were calculated. The normalized modulus contrast (FIG. 5f) could be calculated by equation 21, which intuitively reflects the degree of muscle rehabilitation from injury. The coefficient of variation among all tests could be calculated by the equation 22.

$$\text{Normalized modulus contrast} = \frac{\mu_{after}}{\mu_{before}} \quad (27)$$

$$\text{Coefficient of variation} = \frac{\sigma}{\mu_{after}} \quad (28)$$

where $\mu_{after}$ and $\mu_{before}$ are the average modulus of biceps brachii before and after exercise, respectively, and $\sigma$ is the standard deviation of the modulus distribution. Lower variation of the hyperthermia (FIG. 5g) indicates its better efficacy of recovering the muscle injury.

The muscle has different mechanical properties in different directions. In our study, the applied compressions are perpendicular to muscle fibers. However, because muscles are typically incompressible with a Poisson's ratio of 0.5, the applied compression also caused significant extension of fibers along the axial direction (axial is the direction along the long axis of the arm. see FIG. S53). As a result, the axial stiffness of fibers is also sensed by the applied compression. Because we use an isotropic model to infer tissue modulus, the obtained modulus should be interpreted as an "effective" modulus that measures the average stiffness over all orientations. This is likely why traditional clinical diagnosis can still identify damaged muscle regions with increased stiffness through characterizations that are only perpendicular to the muscle fiber directions. For instance, in abdominal palpation, as an essential physical examination in clinical practice, the condition of the abdominal muscles is tested by applying compression and manually feeling for the tissues' mechanical responses. Any abnormally stiff muscles can then be differentiated because muscle damage leads to increased stiffness of muscle fibers in all directions, and thus to increased "effective" stiffness of muscles. Therefore, the characterization perpendicular to the muscle fiber directions in this study is valuable for identifying regions of muscle damage.

Additionally, the serial measurements in this study are consistent with the temporal evolution of exercise-induced muscle injuries reported using other methods. Clinical observations of muscle performance following exercise and histological analysis both confirm the respective metrics in this study. Moreover, both massotherapy and hyperthermia are shown to significantly mitigate muscle damage and increase the recovery speed, consistent with our results. Collectively, it is evident that the characterization of muscle stiffness along the direction perpendicular to the muscle fibers can accurately track muscle recovery from exercise-induced injuries.

Mechanism of Delayed Onset Muscle Soreness

Delayed onset muscle soreness is a common muscle injury that can be classified as an overexertion-functional muscle disorder. There are many clinical mechanisms to explain this disease, and the injury mechanism is the one that is widely accepted among the others. The external load applied in the eccentric exercise is much more than the isometric force generated by the muscle fibers. The overload causes muscle fibers to be lengthened and exposed to the elevated tension, which results in the loss of myofibrillar integrity and micro-structural damage of sarcoplasmic reticulum, transverse tubules, and sarcolemma. The disruption of the sarcolemma induces the increase in the concentration of intracellular calcium, enabling the myosin to attach to the actin and forming the cross-bridge. The thin filaments slide over the thick filaments when the myosin heads pull the actin, which causes muscle contracture and leads to the increase in muscle stiffness. The movement of the calcium ions, on the other hand, activates the pathway of myofibrillar repairing. The remodeling of the protective proteins and the formation of the sarcoplasmic reticulum progressively preclude the osmosis of the calcium ions. The modulus peak occurs when the sarcolemma is completely repaired, followed by the accelerated recovery of myofibril and the relief of the symptoms of delayed onset muscle soreness.

The inflammation response following the ultrastructural damage of muscle is accepted as another important mechanism for the interpretation of the delayed soreness perception. The symptom caused the subject to feel mild fatigue after one day and an intensive soreness two to three days after exercise, as it took time for inflammatory cytokines to accumulate and abruptly release. The accumulation of leukocytes (primarily neutrophils) is observed in the muscle in 3 to 24 hours after exercise. Mast cells, playing an essential role in the inflammation response, are also infiltrated into the muscle in the same period. Increased monocytes/macrophages are observed 48 hour after eccentric exercise, lasting for five days or even longer.

Moreover, the proposed two treatments have the capability to not only alleviate the muscle pain, but also facilitate the recovery of the muscle damage and force production capability. It has been observed that massotherapy is able to decrease the serum level of some muscle damage and inflammatory markers, such as creatine kinase (CK), lactate dehydrogenase (LDH), interleukin-4, interleukin-6, and interleukin-10 (IL-4, IL-6, IL-10). Additionally, with the specific application, massotherapy improves the outcomes of muscle performance during delayed-onset muscle soreness regarding muscle maximal isometric force and peak torque. The current explanation for this effect is that massotherapy increases blood and lymph flow, which facilitates the clearance of the biomarkers from the damaged tissue and blood, thus reducing the inflammatory response and promoting muscle recovery.

Also, it has been indicated that immediate low-level heat therapy significantly improves the physical functions of muscles, including plasma myoglobin level, muscle strength, range of motion, and pain scales. One underlying mechanism of heat therapy is that it may contribute to pain relief via interacting with transient receptor potential vanilloid-1 (TRPV1) while transducing heat through neurons. Meanwhile, heat-induced increase in tissue blood flow promotes the clearance of inflammatory mediators and facilitates the supply of nutrients and oxygen to the injured sites, which accelerates muscle healing.

Evaluation of Repeated Bout Effect

The repeated bout effect could have an influence on the following exercise results after the first bout. But this effect is highly dependent on the intensity of the exercise and the time elapsed from the initial exercise bout. Specifically, if the interval between two bouts is shorter, the bout effects to the second exercise will be stronger, causing a lower degree of muscle damage. It indicates that a long duration between bouts plays an important role in the reduction of this side effect.

Figure 51A:
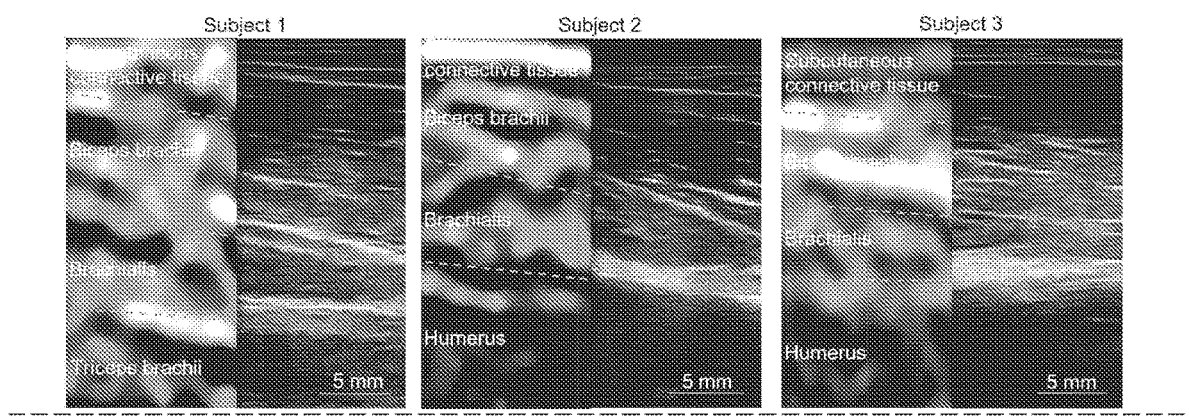
FIGS. 51A-51D show images validating the device reliability on 10 subject
Figure 51B:
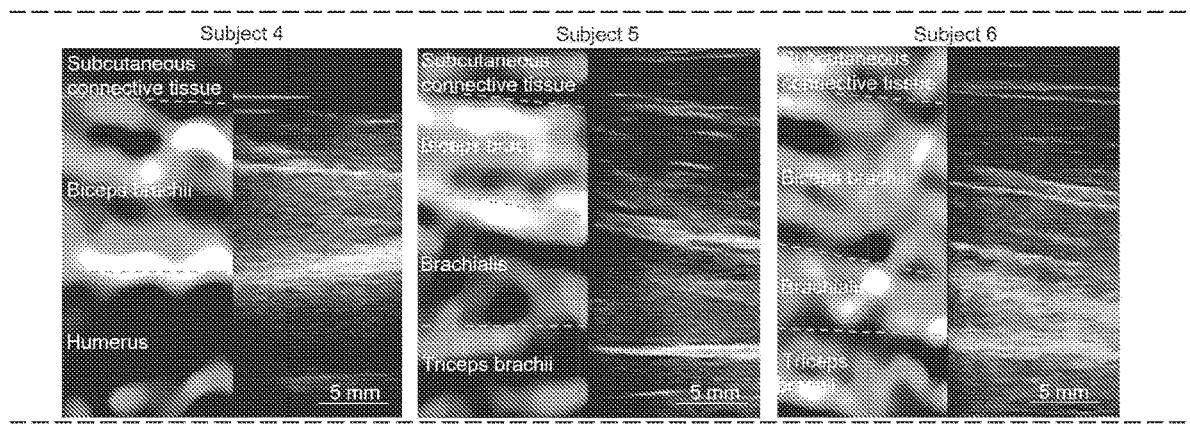
Figure 51C:
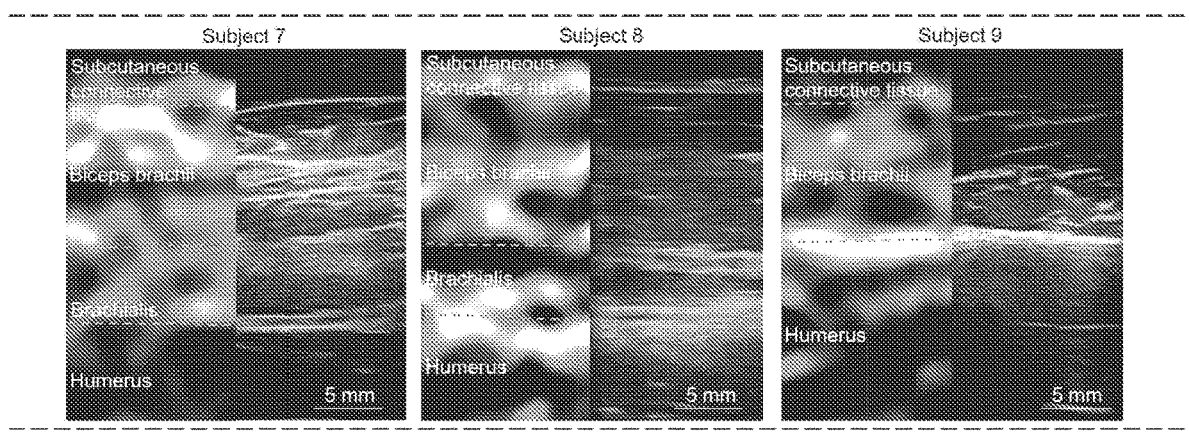
Figure 51D:
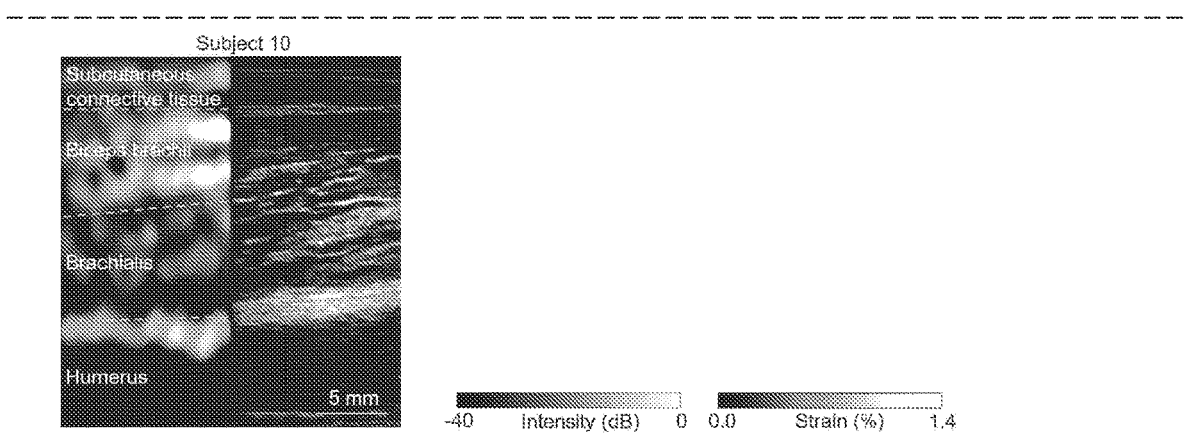

To further verify the influence of repeated bout effects and efficacy of different physical treatments, we designed extra experiments to figure out if our experiment settings would suffer from the repeated bout effect on subjects 1 and 2. Results and analysis are shown in the following paragraphs and figures. These two subjects have firstly exercised and performed natural recovery, and then repeated the exact same procedure one month later. Note that both subjects did not feel obvious fatigue or pain before repeating the exercise. The normalized modulus contrasts for each subject are shown in FIGS. 51a and 51b. For both subjects, there is no significant difference between the results of the two experiments. Specifically, for subject 1, the normalized modulus contrast was ~1.0 before exercising, increased right after the exercise, continued gradually rising to ~3.0 until the second day, and then started to decrease since the third day to almost the original value on the fifth day. Subject 2 shows the trend alike. From the results above, we can tell that the experiments of exercise with natural recovery procedure will not be influenced by the repeated bout effect after one full month rest, which is consistent with the previous studies.

To further demonstrate the effectiveness of both treatments for muscle recovery, we then had another four subjects randomly divided into two groups, one for the massotherapy and the other for the hyperthermia (see FIGS. 51c to 51f, discussed below). In the initial bout, all of them had the same procedure of the eccentric exercise followed by natural recovery. After one month's rest, one group had the eccentric exercise with massotherapy and the other had the exercise with hyperthermia for treatment. For the first group of subjects 3 and 4, the modulus contrast before exercise was 1.0. During the natural recovery, the value reached the peak on the first day after exercise, and gradually decreased to the original state within the subsequent four days. As a contrast, we applied massotherapy to the subjects in their second round of experiments. It's noticeable that the peak value was at the sixth hour right after their exercise, when the modulus contrast began to decrease on the first day, instead of the second day with natural recovery. The overall values at each time stamp are averagely smaller than the first round of experiments, showing that the massotherapy indeed helped the muscle recovery, and predictably it took less time for a full recovery. Like the first group, the second group of subjects 5 and 6 had gone through all the same procedures only with hyperthermia instead of massotherapy. Without hyperthermia, the modulus contrast reached the peak on the first day after exercise, followed by a continuous decline. With hyperthermia, the overall modulus contrast was comparably smaller and there was no dramatic change during recovery. Those two groups with randomly assigned four subjects showed a similar trend to that in the original manuscript, fully demonstrating that massotherapy and hyperthermia do expedite muscle recovery and the repeated bout effects are not influencing our conclusions.

Figure 58:
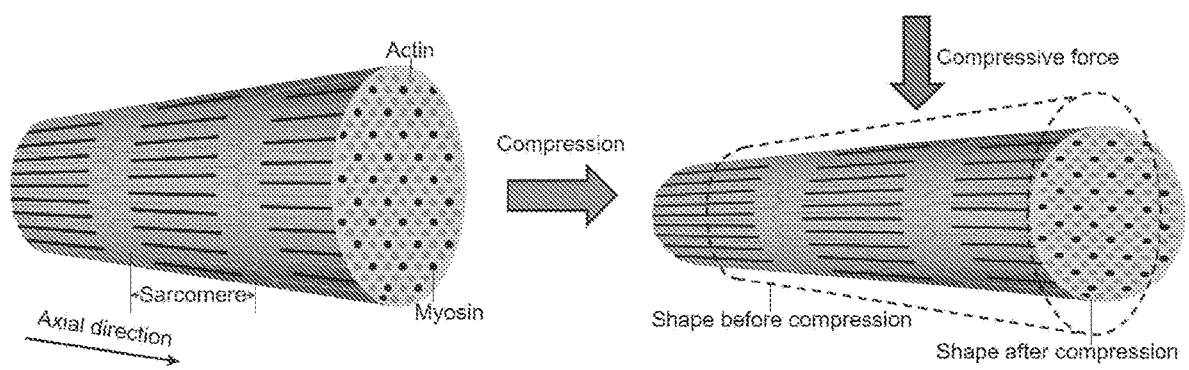
FIG. 58 is a schematic showing the length of the muscle fiber before and after compression.

Additional Description of FIGS. 6-58

Figure 6A:
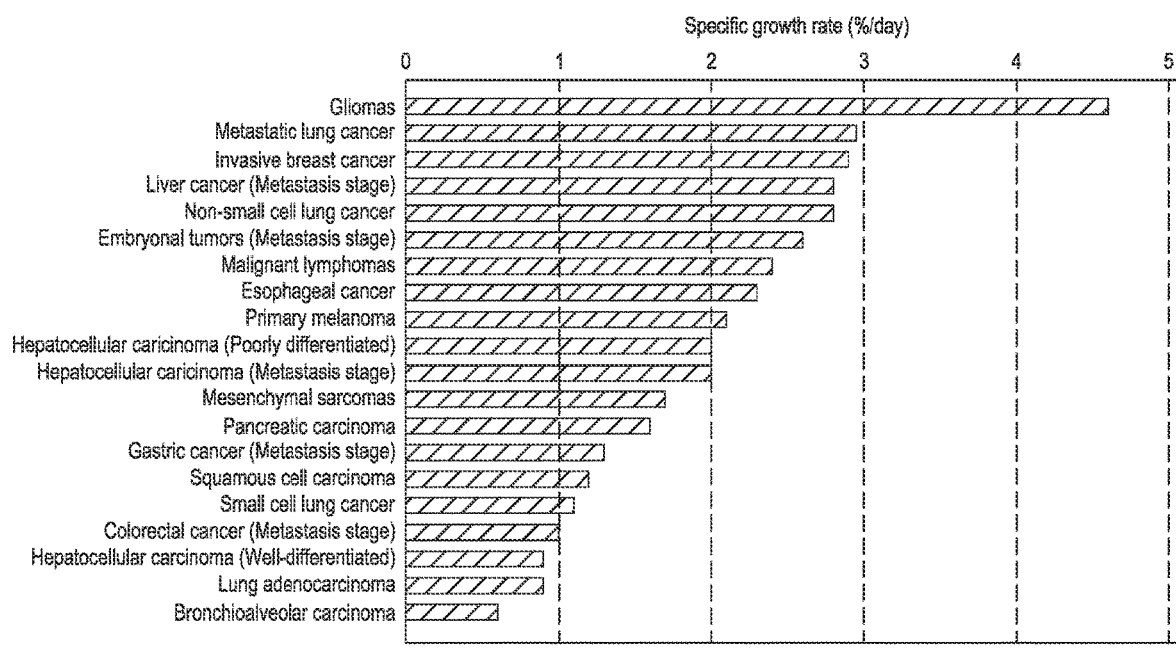
Figure 8A:
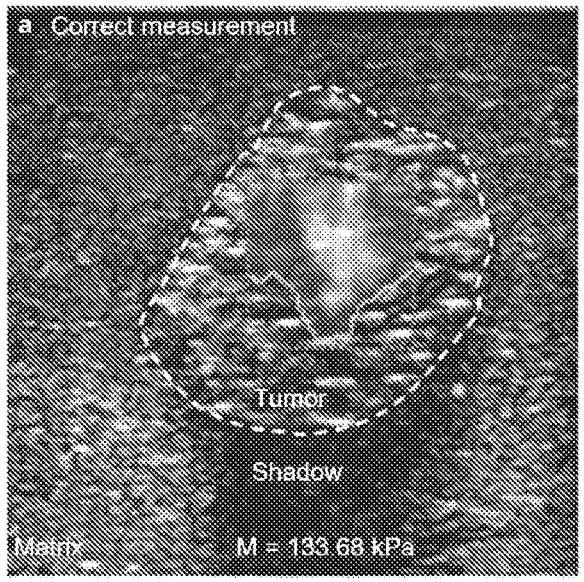
FIGS. 8A-8D show images illustrating common pitfalls in commercial ultrasonic shear-wave elastography operations.
Figure 8B:
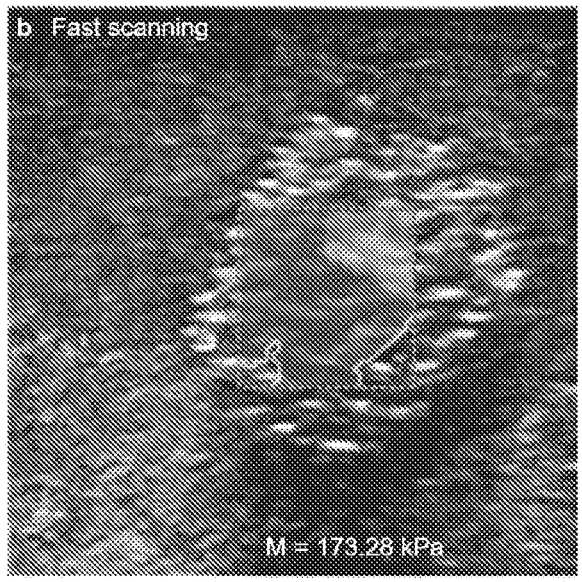
Figure 8C:
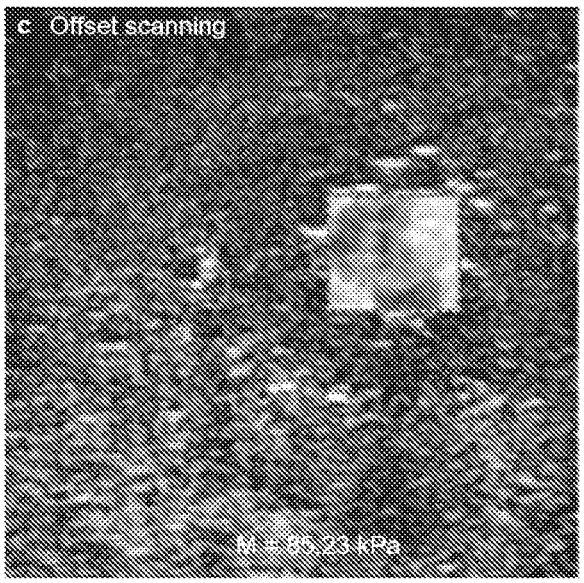
Figure 8D:
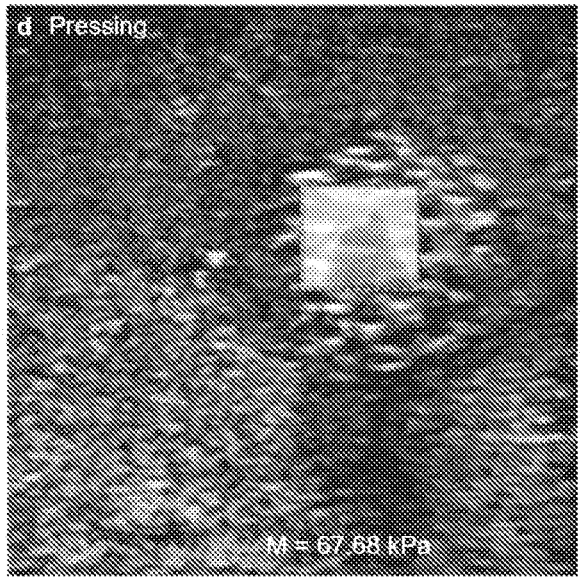

FIG. 6 illustrates the significance of the stretchable ultrasonic array for serial tissue modulus monitoring. In particular, FIG. 6(a) shows statistics of over 20 types of cancers with a high specific growth rate. The lack of serial, long-term monitoring prevents quick and effective tracking of tumor growth, which represents a critical unmet need in clinics. FIG. 6(b) shows a summary of some common muscle diseases relevant to the muscle modulus. The diagnosis and rehabilitation processes of multiple musculoskeletal diseases and injuries also require frequent examinations and long-time monitoring of the muscle modulus. A stretchable ultrasonic array can meet those needs that cannot be addressed by any existing approaches.

FIG. 7 shows a comparison among all existing methods for tissue modulus mapping. Different comparison metrics and relevant citations are listed in different columns. The major advantage of the stretchable ultrasonic array in comparison with the conventional methods is the combined merits of being wearable for serial, non-invasive, and 3D monitoring of deep tissues.

FIG. 8 shows common pitfalls in commercial ultrasonic shear-wave elastography operations. Images of a breast tumour phantom (FIG. 8a) with standard scanning, shows the correct size and stiffness of a tumour, with fast scanning (FIG. 8b), offset scanning angle (by ~10 degrees) (FIG. 8c), and moderate pressing (~50 Newtons) (FIG. 8d), causing blurry images, size deformation, and inaccurate stiffness measurements of the tumour. M in FIG. 8 denotes Young's modulus.

Figure 9:
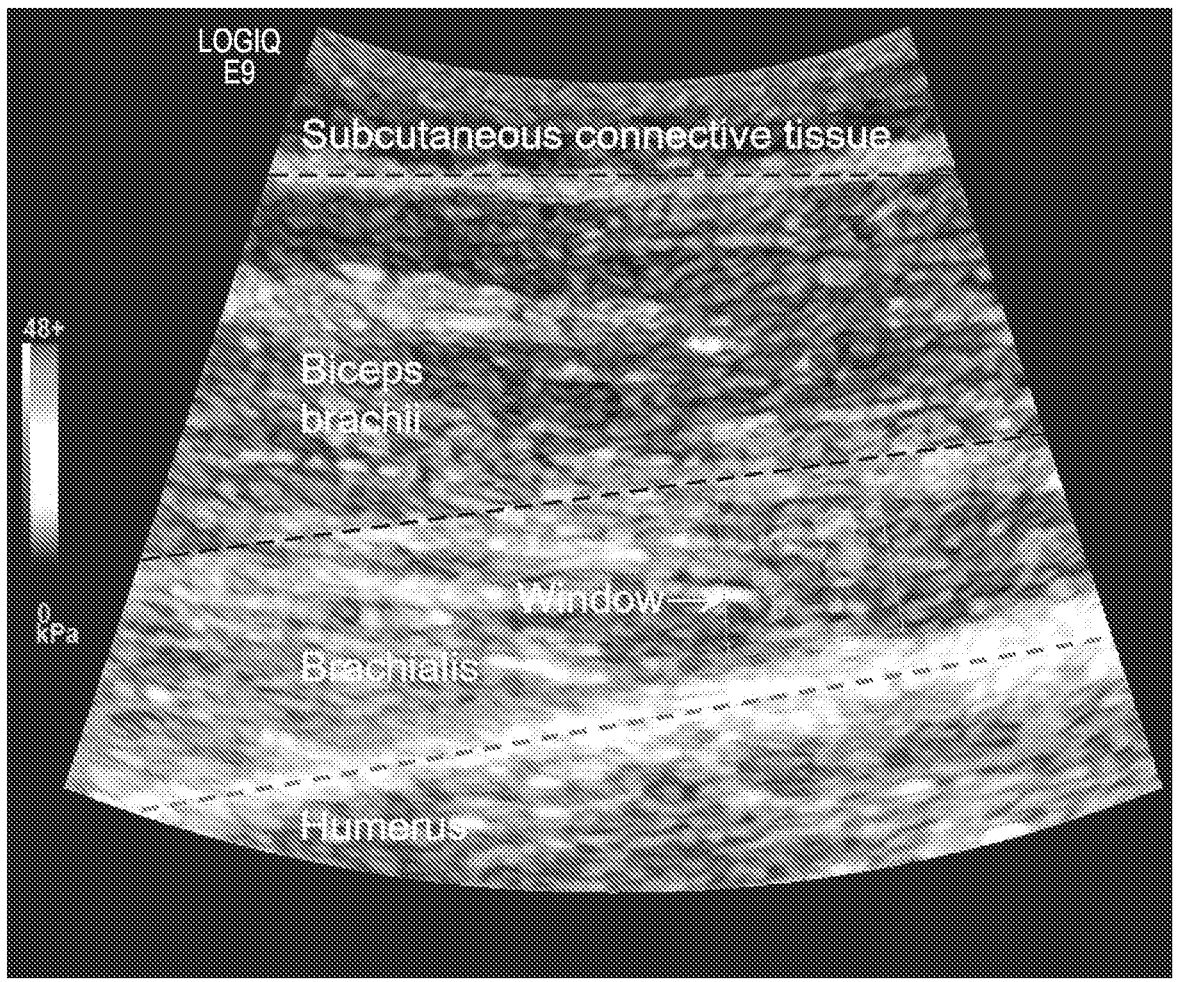
FIG. 9 shows modulus imaging by a commercial ultrasonic shear-wave elastography machine.
Figure 10A:
FIGS. 10A-10F show images illustrating the testing performance of the conventional rigid ultrasound probe and the stretchable ultrasonic array on curved surfaces.
Figure 10C:
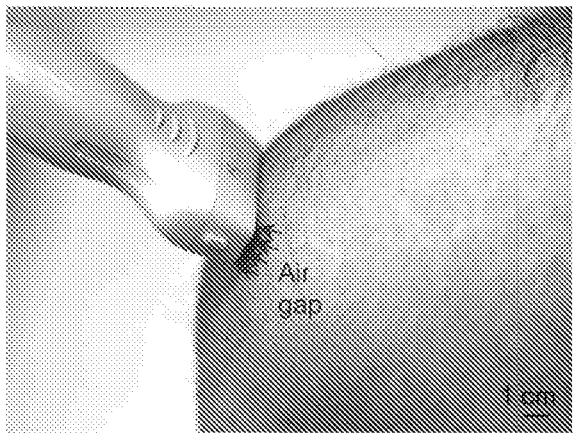
Figure 10B:
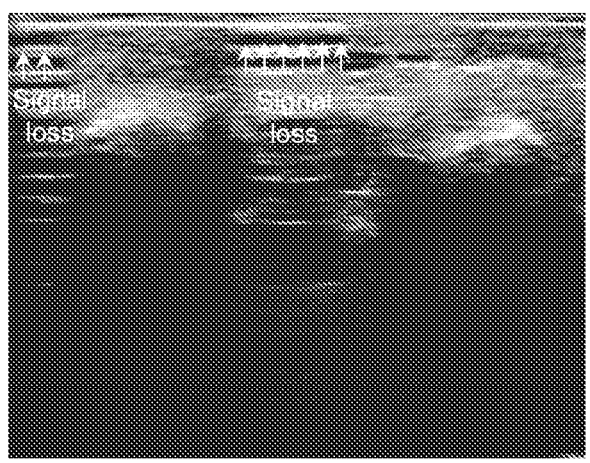
Figure 10D:
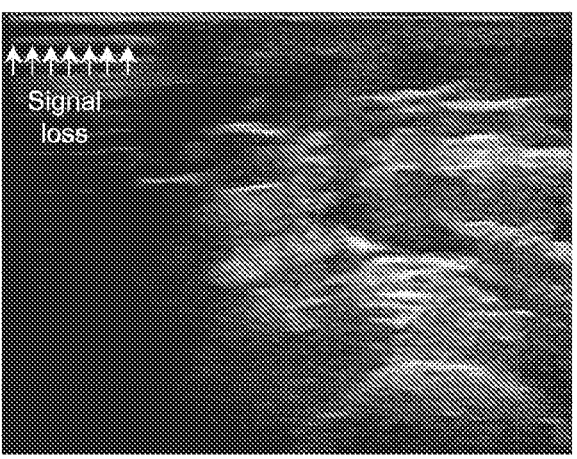
Figures 10E, 10F:
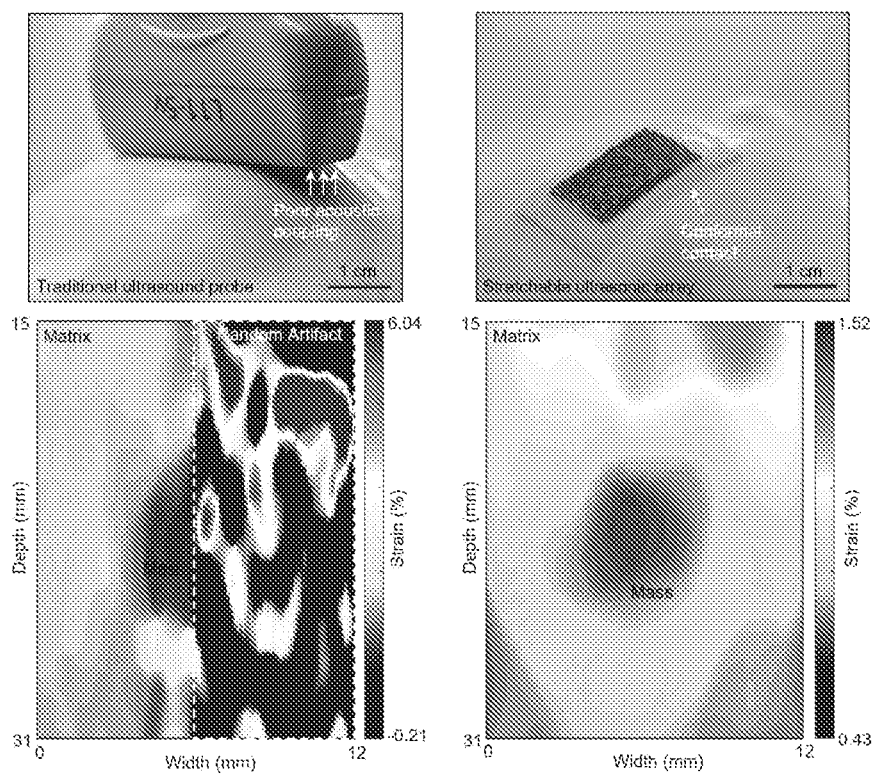

FIG. 9 shows modulus imaging by a commercial ultrasonic shear-wave elastography machine. The window to select the region of interest is too limited to map all components and tissues simultaneously.

FIG. 10 illustrates the testing performance of a traditional rigid ultrasound probe and the stretchable ultrasonic array on curved surfaces. In particular, FIG. 10(a) shows an optical image showing the testing of a commercial rigid probe on joints of the hand and FIG. 10(b) shows its corresponding B-mode image. FIG. 10(c) is an optical image showing the testing of a commercial rigid probe on the knee and FIG. 10(d) shows its corresponding B-mode image. Poor acoustic coupling caused by curved surfaces leads to signal loss in B-mode images. In addition, a breast phantom was tested by a traditional rigid ultrasound probe (FIG. 10e) and a stretchable ultrasonic array (FIG. 10f). The corresponding strain images are displayed at the bottom. The traditional rigid ultrasound probe cannot conform to the curved surface. The air gaps between the rigid base and the phantom surface cause poor acoustic coupling and thus information loss and artifacts inside the white dashed box. The resulting patterns (distinguishable by color in color renditions of the images) are random artifacts with abnormal strain values. In contrast, the intimate and seamless contact between the stretchable ultrasonic array and the phantom surface enables ideal acoustic coupling, leading to high-quality imaging with a comprehensive reconstruction of the internal structure.

FIG. 11 shows a schematic diagram of the exploded view of one transducer element. All components have been labelled to illustrate the structure of an element.

FIG. 12 shows the workflow of reconstructing elastographic images by the stretchable and/or flexible ultrasonic array. A multichannel Verasonics system is used to acquire the radiofrequency signals from the transducers. The pre-compression frame will be stored at the receive buffer 1 and the after-compression frame will be stored at the receive buffer 2. Then, receive beamforming will enhance the sonographic signal-to-noise ratio of these two frames. The beamformed radiofrequency data will generate the displacement field by using the normalized cross-correlation algorithm. The least-squares strain estimator is then applied to derive the strain field from the displacement field. The inverse elasticity problem calculation will reconstruct the modulus mapping based on the displacement field. The Amira software reconstructs the 3D image by integrating all slices of 2D images.

Figure 13A:
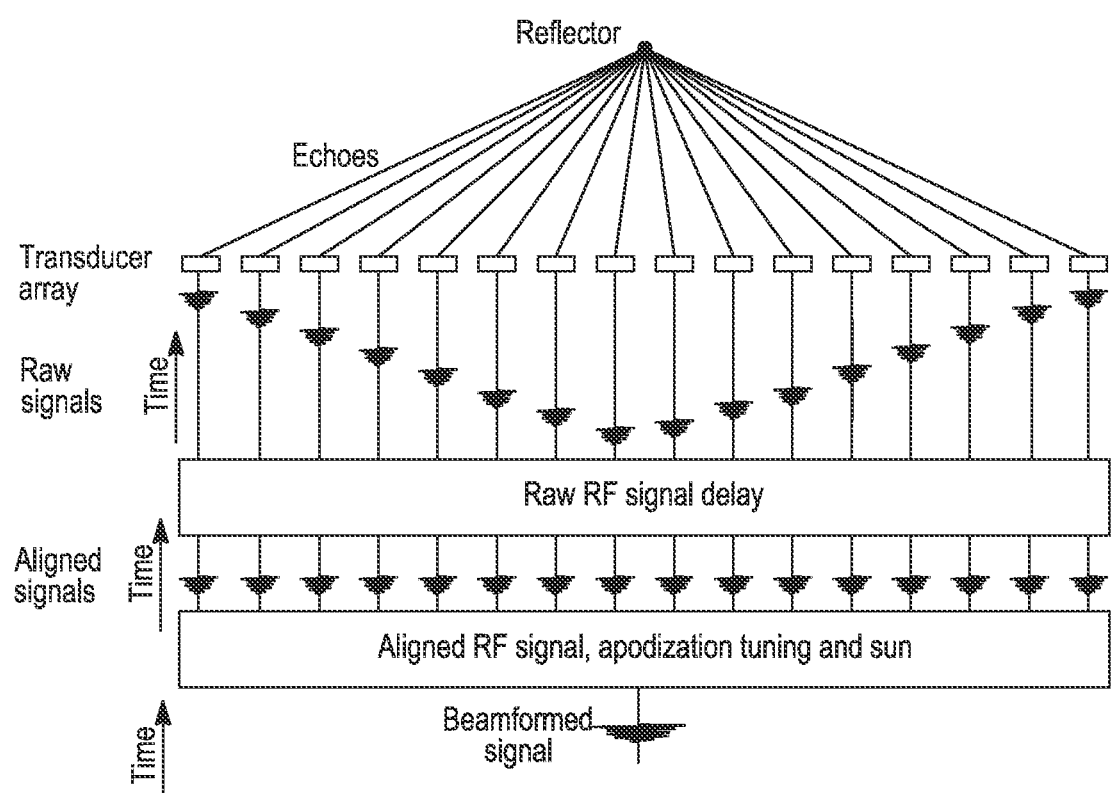

FIG. 13 shows the effects of the receive beamforming. In particular, FIG. 13(a) is a schematic plot showing the process of the receive beamforming. A phantom with a reflector inside is tested by a 1×16 linear array. The raw signals are captured by the transducer array showing a certain profile based on the element locations. These raw signals are then aligned by adding different time-delays and summed to obtain a beamformed radiofrequency signal. The reflected signals without (FIG. 13b) and with (FIG. 13c) receive beamforming are plotted. From the radiofrequency signals (top), it is obvious that the receive beamforming enhances the sonographic signal-to-noise ratio. Besides, from the 2D plot (bottom), the receive beamforming improves the lateral resolution.

Figure 14A:
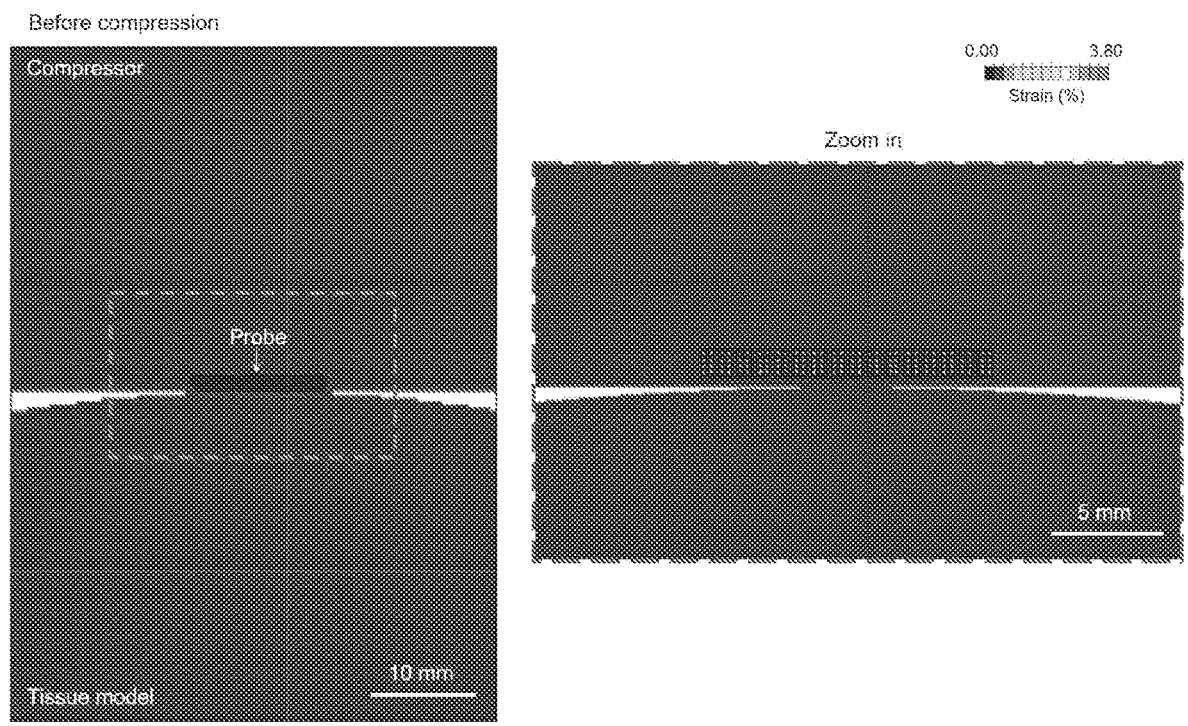
FIGS. 14A-14B show simulations of the change of the transducers' locations before and after compression by finite element analysis.
Figure 14B:
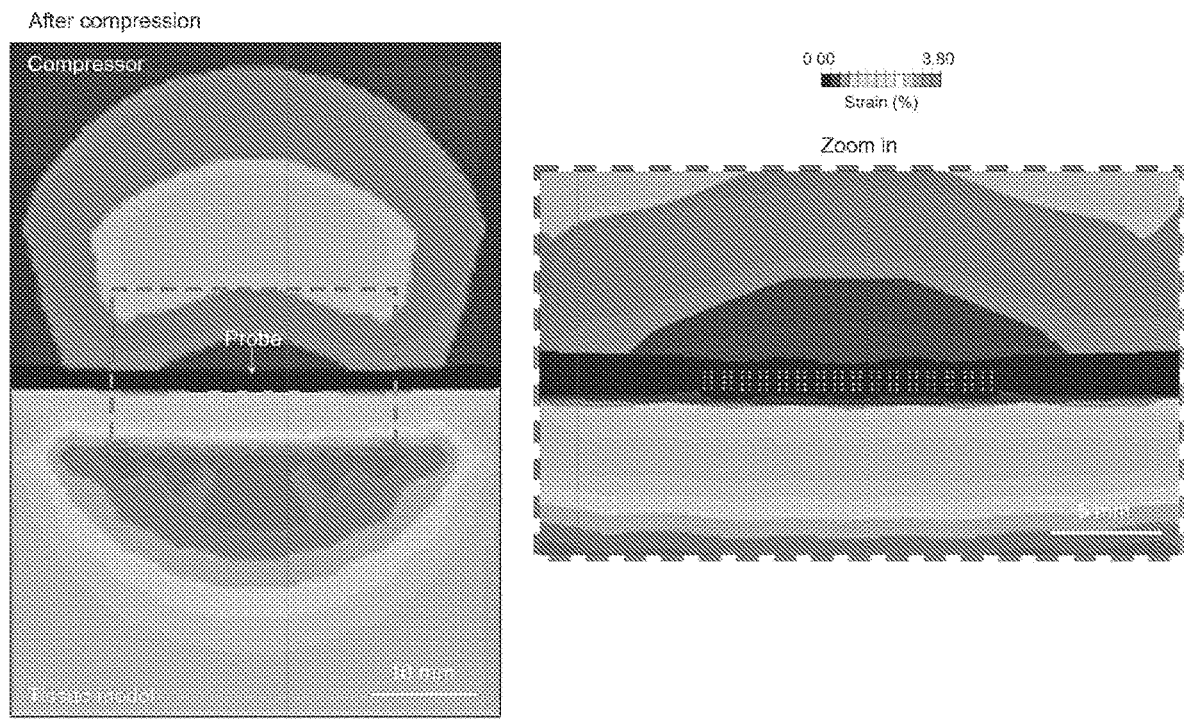

FIG. 14 shows a simulation of the change of transducers' locations by finite element analysis. After laminated with the device on the top, the tissue is deformed by a mildly applied force, so the strain is within the dynamic range. The strain distribution and locations of the transducer before (FIG. 14a) and after (FIG. 14b) compression are compared. The left column shows the entire strain field, and the right column illustrates details of the transducer array's locations. There is only ~0.02% change in the array's pitch after the compression, indicating minimal impact on the elastographic image quality after the compression. All images share the same grayscale bar.

FIG. 15 characterizes the skin curvature of a breast phantom. In particular, FIG. 15(a) is a schematic plot of the setup for scanning the surface curvature by a 3D scanner. The small defects at the lower-left corner are due to the light reflection. These defects can be compensated by interpolation and thus do not frustrate the curvature calculation of the entire intersected interfaces.

Figure 15A:
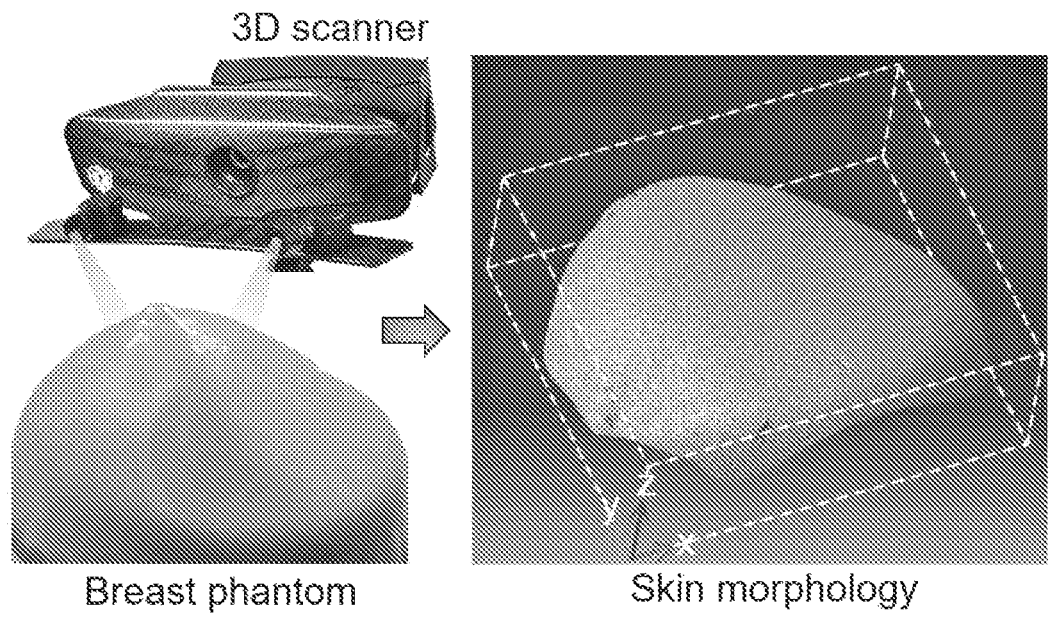
FIGS. 15A-15F shows schematics and data characterizing the skin curvature of a breast phantom.
Figure 15B:
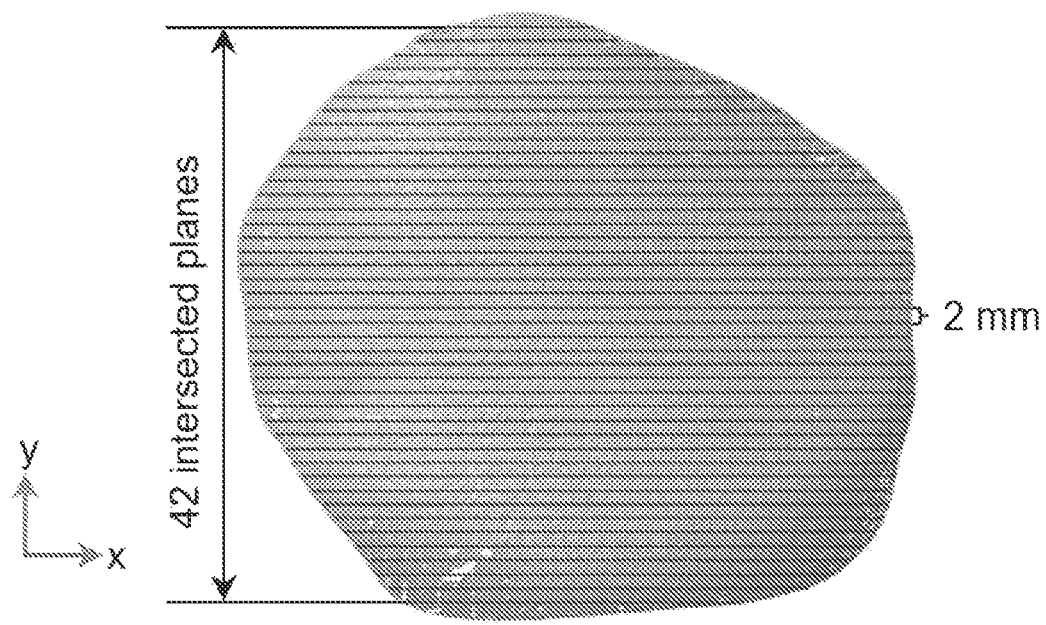
Figure 15C:
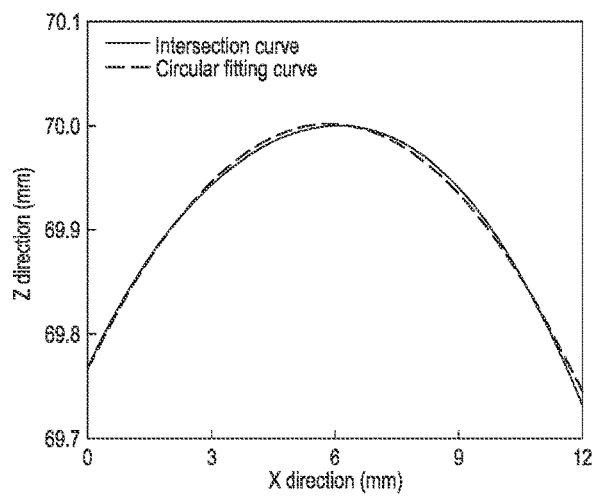
Figure 15D:
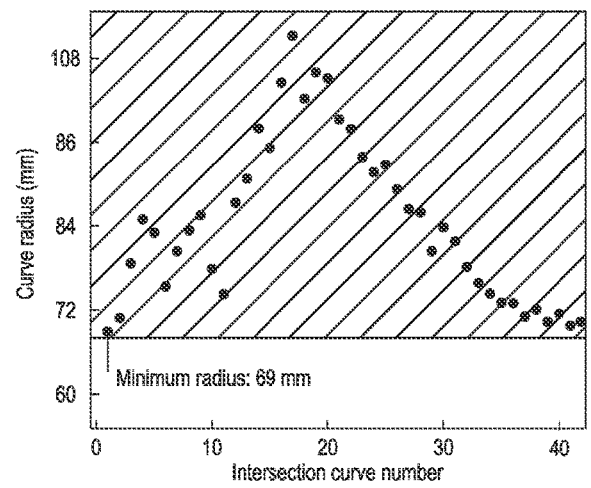
Figure 15E:
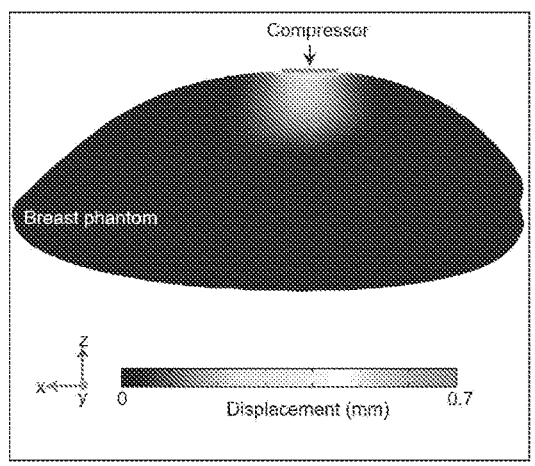

FIG. 15(b) shows the raw digital model, in top view, of the skin profile reconstructed by the 3D scanner. 42 datum planes with a 2 mm interval are applied to intersect the digital model. FIG. 15(c) shows the curvature of each intersection interface is extracted using circular curve-fitting. FIG. 15(d) shows the distribution of the skin curvature of the 42 datum planes. The minimum curvature radius (i.e., the maximum curvature) across the entire surface is 69 mm in this project. The corresponding curve has been extracted to study the maximum deformation tolerance of the stretchable ultrasonic array and to determine the time-delay profile before and after compression. FIG. 15(e) COMSOL simulation of a 3D breast phantom model with the maximum skin curvature (radius: 69 mm, before compression). The compressor executes the 0.7 mm uniaxial displacement (1% strain in the z direction) to the breast phantom model and the post-compressive surface morphology has therefore been obtained. FIG. 15(f) shows the surface profile of the phantom before and after compression.

FIG. 16 illustrates the determination of the time-delay profile. In particular, FIGS. 16(a) and 16(b) are simulated beamformed signals on planar and curvilinear surfaces before and after compression, respectively, and FIG. 16(c) shows their correlation coefficients. The high correlation coefficient of the signals from planar and curved surfaces means the time-delay profile on the planar surface is suitable for the curved surface. Using the same time-delay profile for both surfaces does not cause big distortions of the radiofrequency signals from the curved surface. FIG. 16(d) show simulated displacement fields on the curvilinear surface (left panel) and on a planar surface (middle panel). Both fields are derived by using the time-delay profile on the planar surface. The right panel shows the discrepancy in the distribution of the two fields.

Figure 17A:
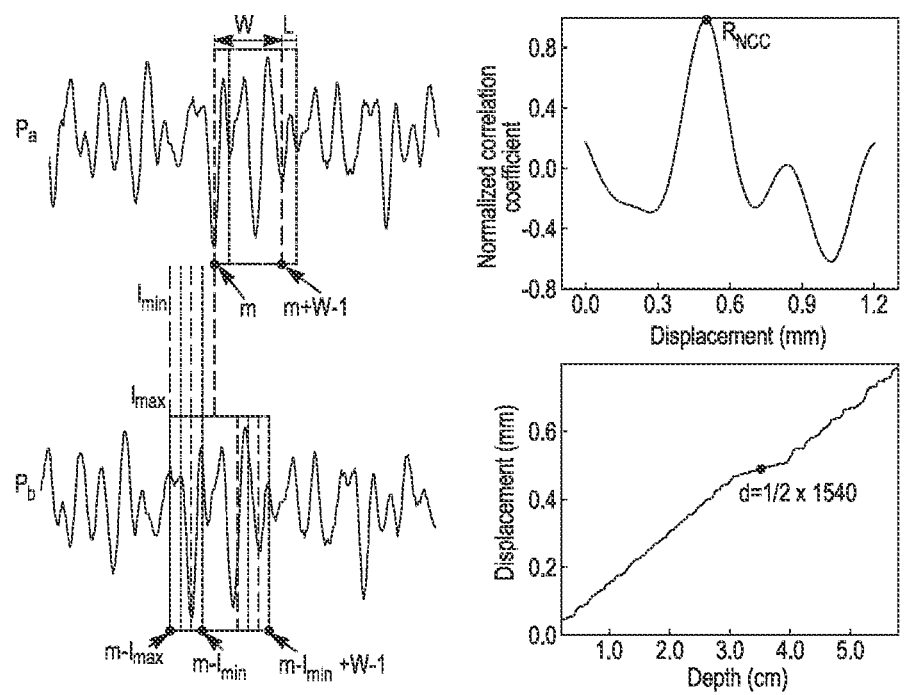

FIG. 17 Illustrates the normalized cross-correlation and least-squares strain estimator algorithms. In particular, FIG. 17(a) shows the process of displacement calculation. Sliding windows are applied to correlate the beamformed radiofrequency signals before and after compression. The displacement at a certain depth is defined as the one with the highest normalized correlation coefficient among all compared windows (top right panel). The displacement curve is derived by combing all displacement values along the depths (lower right panel). FIG. 17(b) is schematic figure showing the source of fluctuations in the displacement curve. Signals in windows 1, 2, and 3 are adjacent to each other. After compression, the pre-compression signals may correlate signals from window 1, or 2, or 3 since they are very similar and the corresponding correlation coefficients are almost the same. It causes some confusion to the normalized cross-correlation algorithm and thus leads to tiny fluctuations in the displacement curve. FIG. 17(c) shows the displacement along the axial direction and a window used to estimate the local strain. The inset image illustrates the raw (dots) and the fitted displacements by a least-squares strain estimator (red line), which can smooth out the fluctuations in the displacement. The calculated strain is the slope of the fitted displacement curve.

Figure 18A:
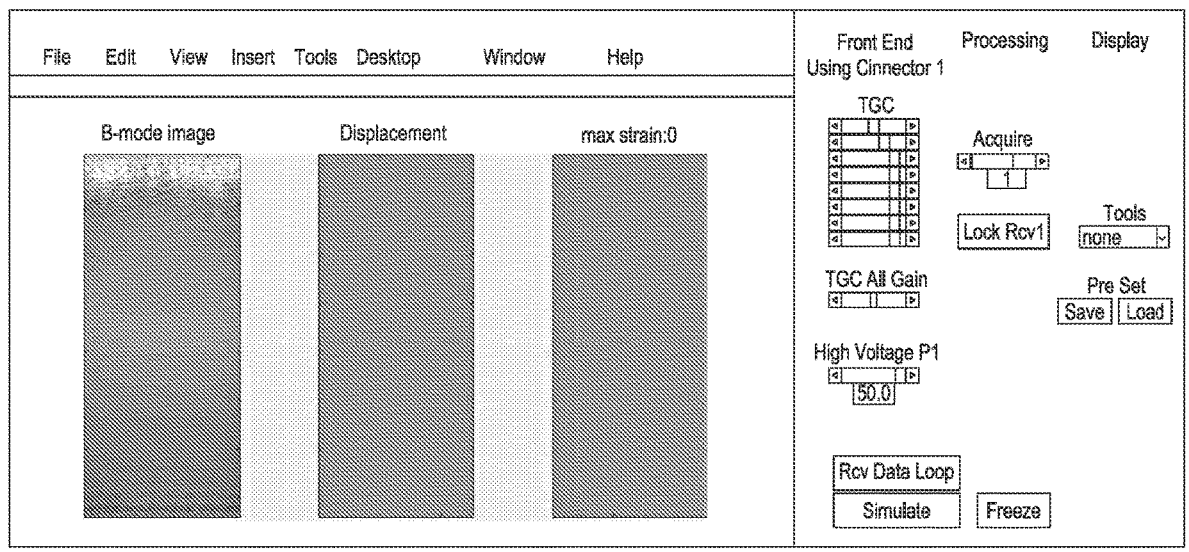
FIGS. 18A and 18B show the layout of the graphical user interface.
Figure 18B:
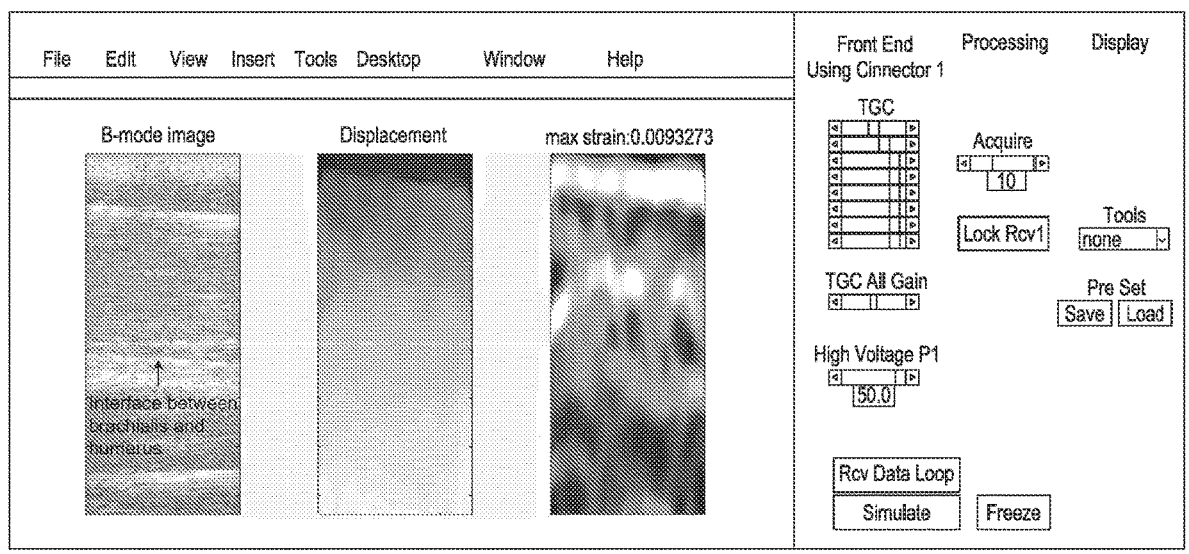

FIG. 18 shows the layout of the graphical user interface. In particular the figure shows the B-mode, displacement, and strain distributions before (FIG. 18a) and (FIG. 18b) after compression are shown on the left. The control panel is on the right.

FIG. 19 illustrates the determination of the curvature range of the stretchable array. The schematics show the pitch of transducer elements in different configurations, when they are on a planer surface (FIG. 19a) and on a curved surface (FIG. 19b). FIG. 19(c) is a schematic showing one unit of the array. FIG. 19(d) shows the relationship between the von-Mises stress and curvature radius. FIG. 19(e) shows mechanical simulations showing the maximum curvature that the stretchable electrodes can conform to and the stress distribution in the electrodes. FIG. 19(f) shows a COMSOL simulation of a 3D breast phantom model with different skin curvature. The compressor executes 0.7 mm uniaxial displacement to the breast phantom model. The post-compressive surface morphology has therefore been obtained. FIG. 19(g) shows simulated displacement fields on a planar surface (left panel) and on a curvilinear surface (middle panel). Both fields are derived by using the time-delay profile on the planar surface. The right panel shows the discrepancy in the distribution of the two fields.

Figure 20A:
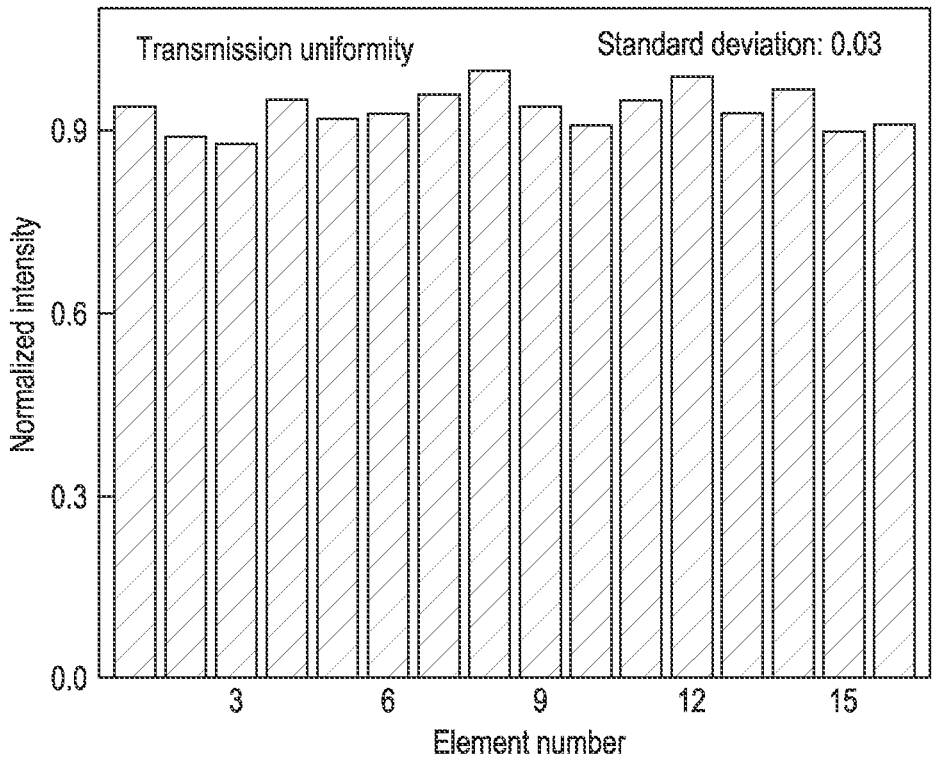
FIGS. 20A and 20B show data illustrating the transmission and receiving uniformity.
Figure 20B:
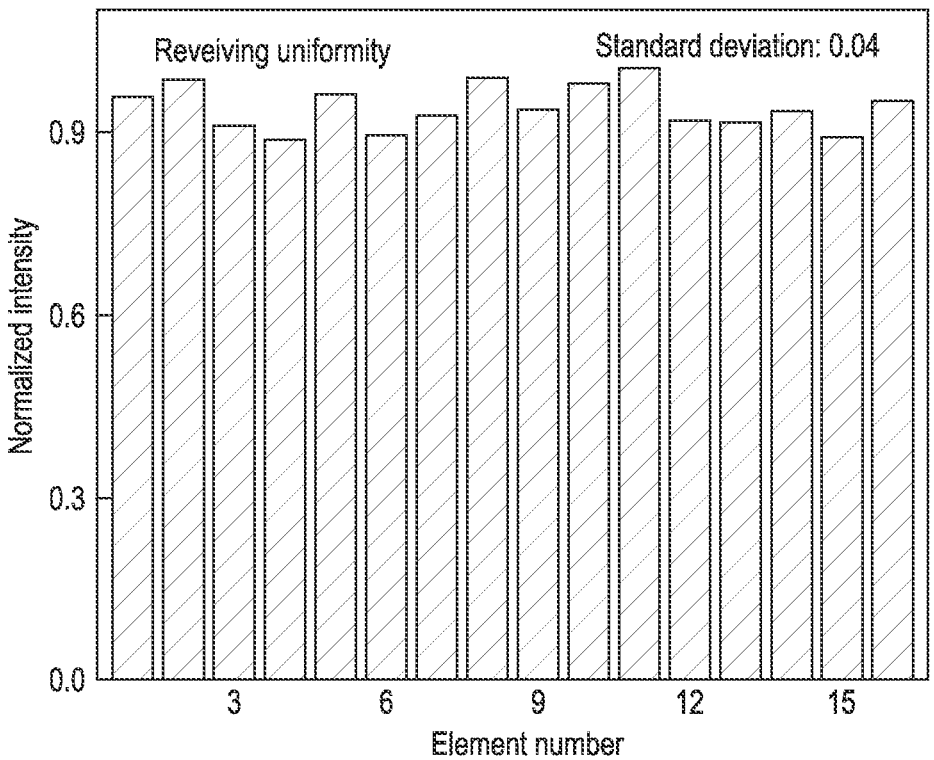
Figure 21A:
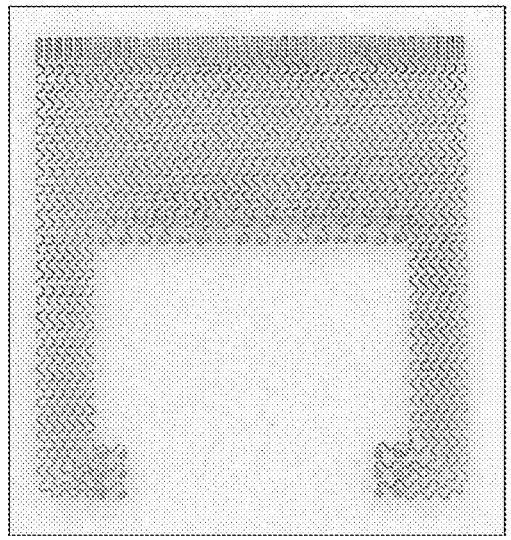
FIGS. 21A-21G show the design and fabrication of the seven-layered electrodes.
Figure 21B:
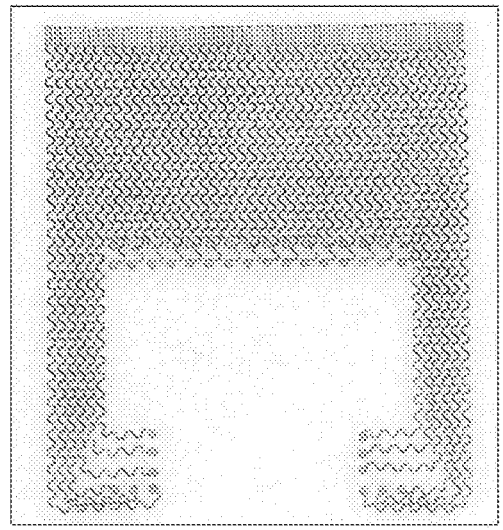
Figure 21C:
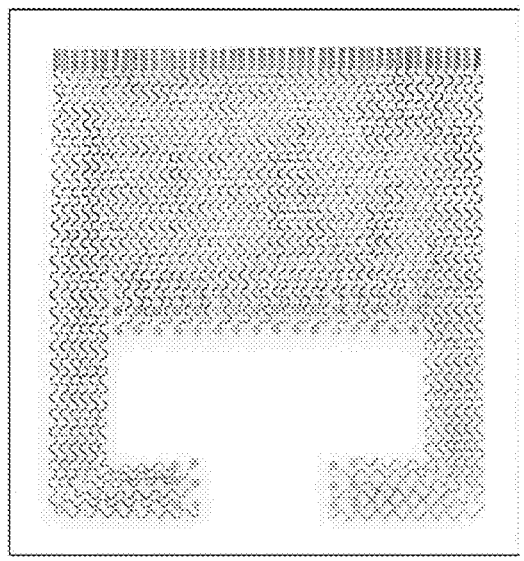
Figure 21D:
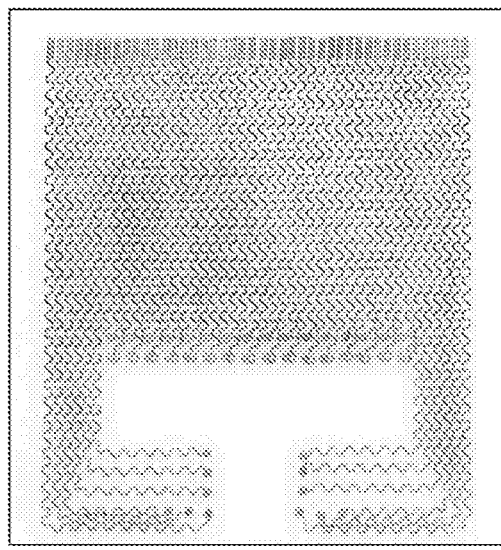
Figure 21E:
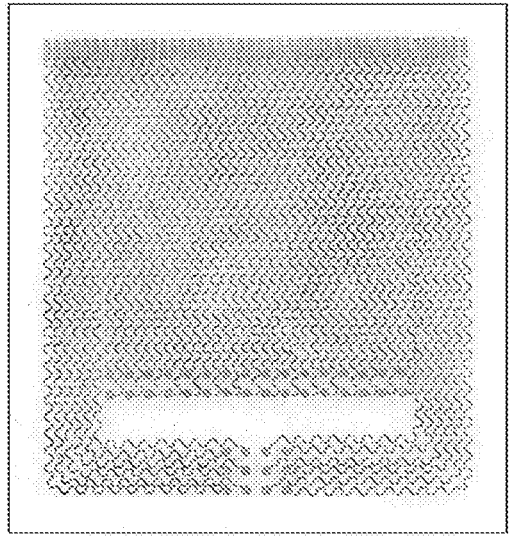
Figure 21F:
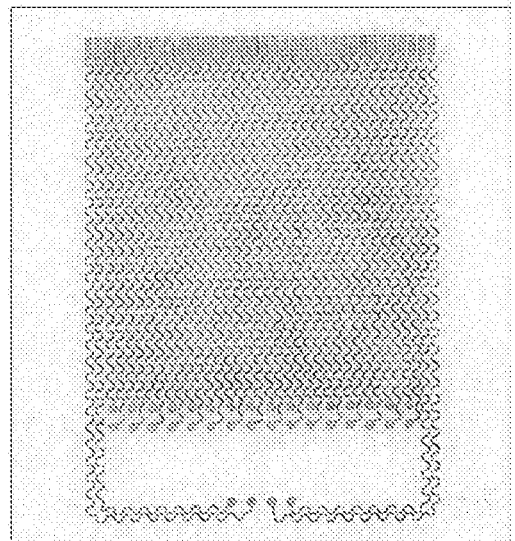
Figure 21G:
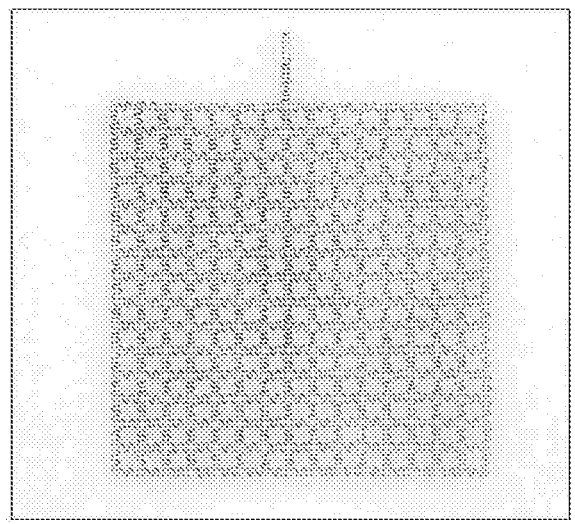

FIG. 20 illustrates the transmission and receiving uniformity. In particular, FIG. 20(a) shows the transmission uniformity with little standard deviation, owing to the new device fabrication process (e.g., the transducer dicing). FIG. 20(b) shows that apodization tuning greatly improves the receiving uniformity of the transducer array. The outstanding transmission and receiving uniformity significantly improve the beamforming quality to generate beamformed radiofrequency signals with high sonographic signal-to-noise ratios. Since the 3D testing is based on the integration of the 2D images from 16 linear arrays, one linear array is used as a representative example. The results of the other linear arrays are similar to this one.

Figure 22:
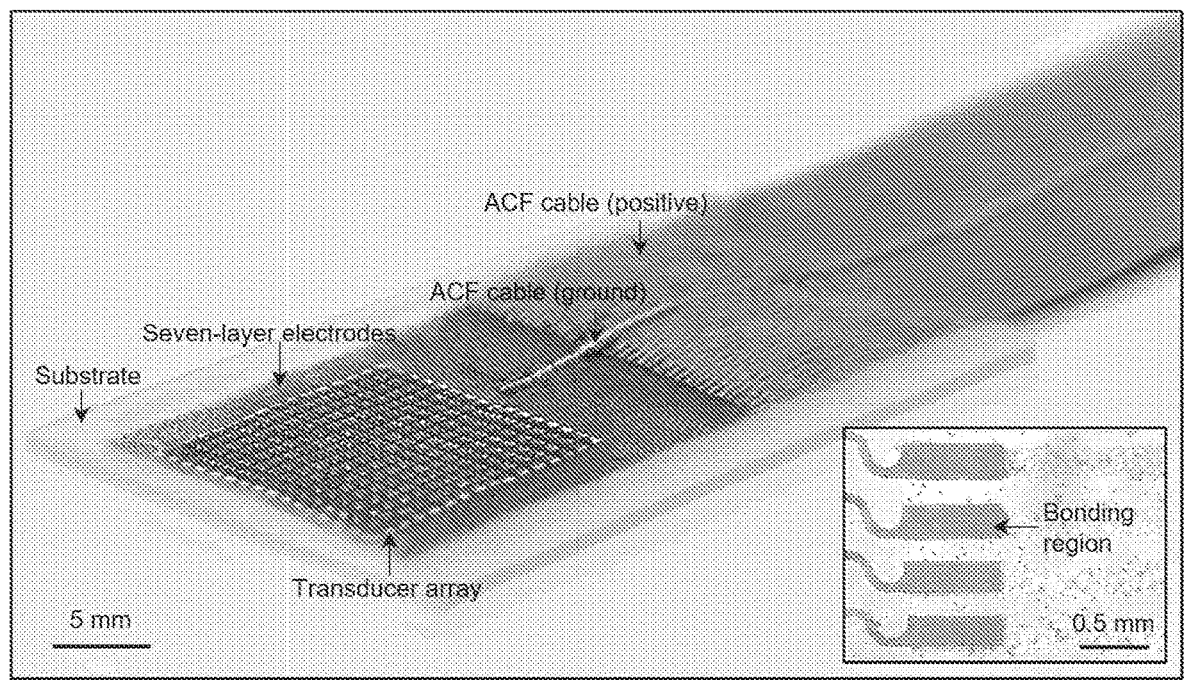
FIG. 22 shows optical images of the stretchable ultrasonic array bonded with anisotropic conductive films.

FIG. 21 shows the design and fabrication of the seven-layered electrodes. In particular, FIGS. 21a-21f show optical images of the six-layers of the activation electrodes, and FIG. 21(g) shows the bottom electrode as a common ground. This design permits individual activation with a particular time-delay profile for each element in the array while keeping the overall footprint small.

a. FIG. 22 shows optical images of the stretchable ultrasonic array bonded with anisotropic conductive films. The anisotropic conductive film (ACF) can bond to the Cu interconnects as a flexible interface between the stretchable ultrasonic array and the external power supply and data acquisition system. The inset image is the bonding interface.

Figure 23A:
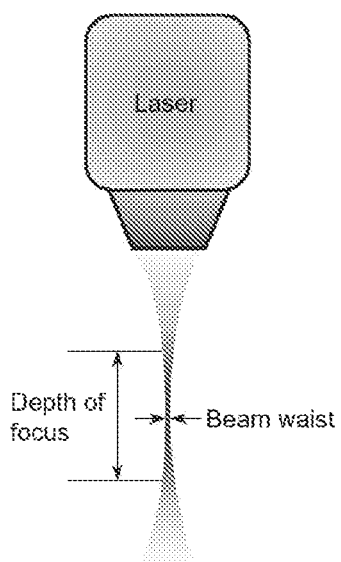
Figure 23B:
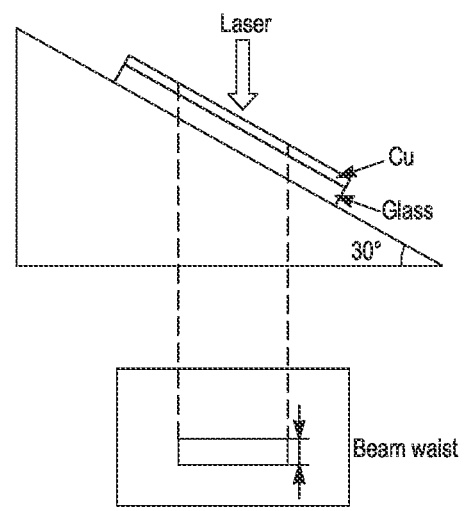

FIG. 23 shows an evaluation of the effective laser beam size and depth of focus. In particular, FIG. 23(a) shows a schematic figure of the laser beam, showing that the depth of focus and beam waist are two critical parameters for making the vertical interconnect accesses. FIG. 23(b) is a schematics of the experiment setup. A Cu foil is put on a wedge with a 30° tilting angle and ablated by the laser to determine the depth of focus and the beam waist. FIG. 23(c) shows the reflected and illumination of the ablation results and FIG. 23d shows the transmitted illumination of the ablation results. The 50 μm dot patterns are viewed as the reference to evaluate the beam waist and the depth of focus. The results show the beam waist is ~20 μm, providing accurate ablation with high spatial resolution. The depth of focus is ~686 μm that is long enough to make the vertical interconnect accesses of the top six-layered electrodes, whose total thickness is ~120 μm.

FIG. 24 shows electromechanical characterizations of the transducer array. FIG. 24(a) shows the dielectric loss of the 16×16 array. The average of the dielectric loss is 0.022 and the standard deviation is 0.002. Time- (FIG. 24b) and frequency-domain (FIG. 24c) characterizations of the echo signals shows the sensitivity and bandwidth of the transducer element.

Figure 25A:
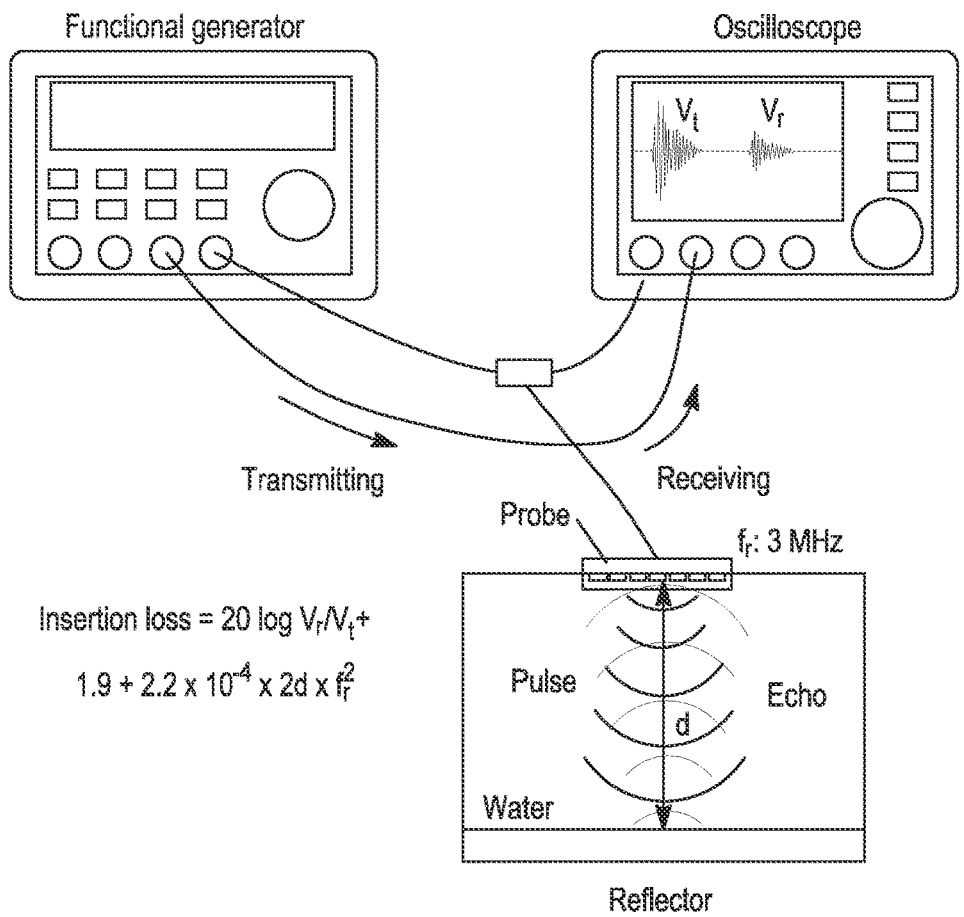
FIGS. 25A-25B show schematics of the setup for characterizing the transducers' sonographic sensitivity and the corresponding design of the electrical matching circuit.
Figure 25B:
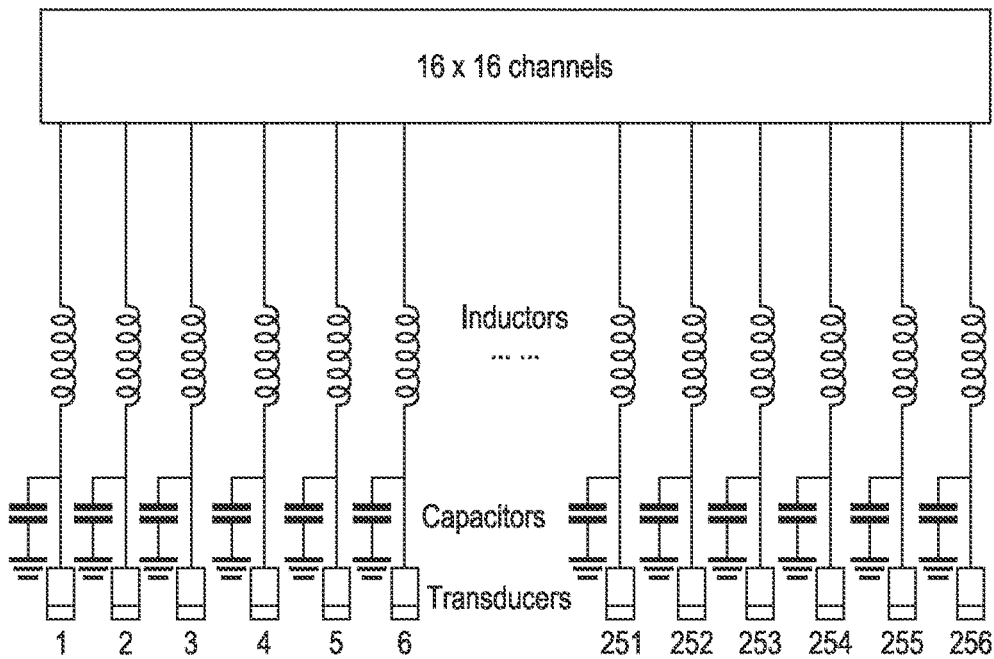

FIG. 25 shows a setup for characterizing the transducers' sonographic sensitivity and the corresponding design of the electrical matching circuit. FIG. 25(a) shows the insertion loss used to quantify the sonographic sensitivity of the transducers and these two variables are inversely proportional to each other. FIG. 25(b) is a schematic figure of the electrical matching circuit design. The matching circuit enhances the transmission efficiency of the electrical signals, resulting in a reduction of the power dissipation and an increase of the echoic intensity. The matching circuit reduces the insertion loss from 29.67 dB to 16.98 dB, significantly improving the sonographic sensitivity of the transducers.

Figure 26A:
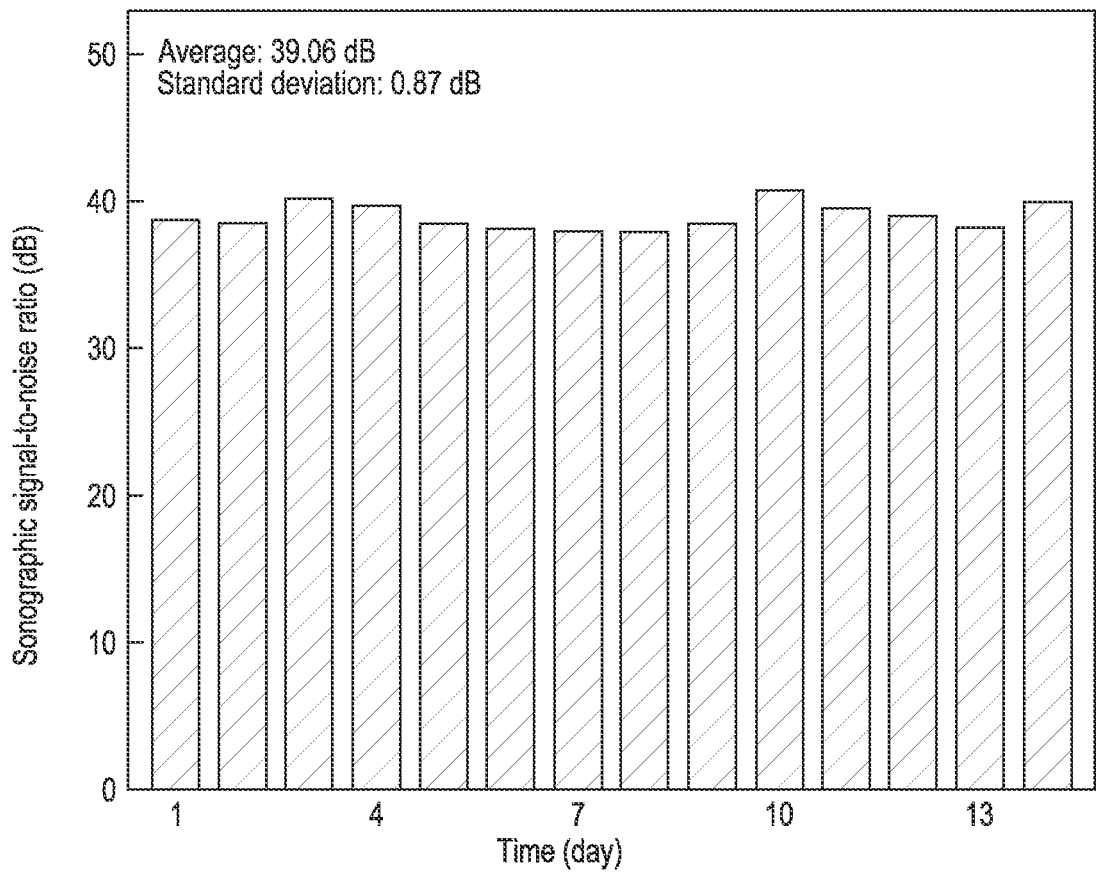
FIGS. 26A-26B show data and an image concerning the hydrophobicity characterization.
Figure 26B:
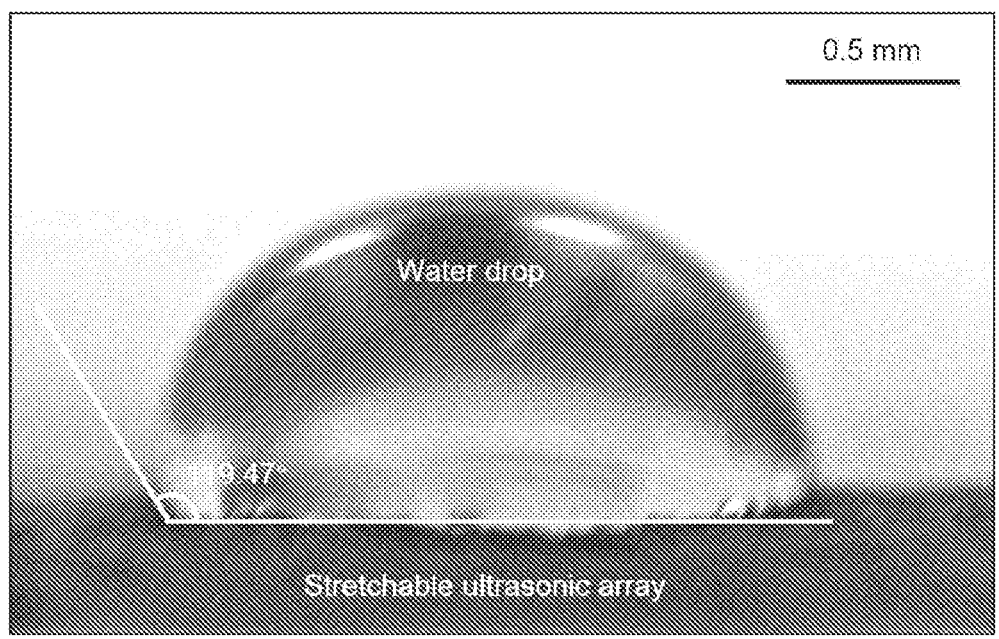
Figure 27A:
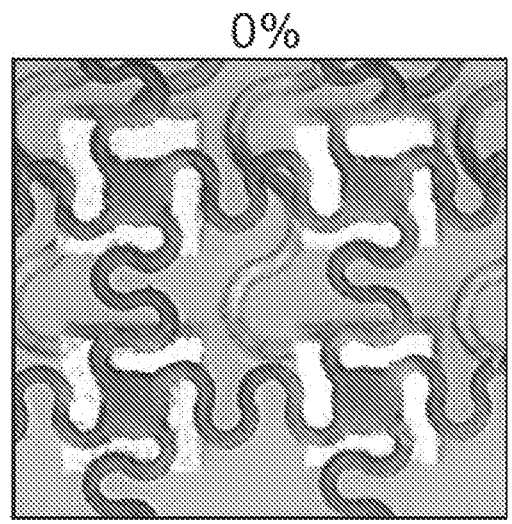
FIGS. 27A-27E show optical images of the stretchable ultrasonic array under stretchability tests.
Figure 27B:
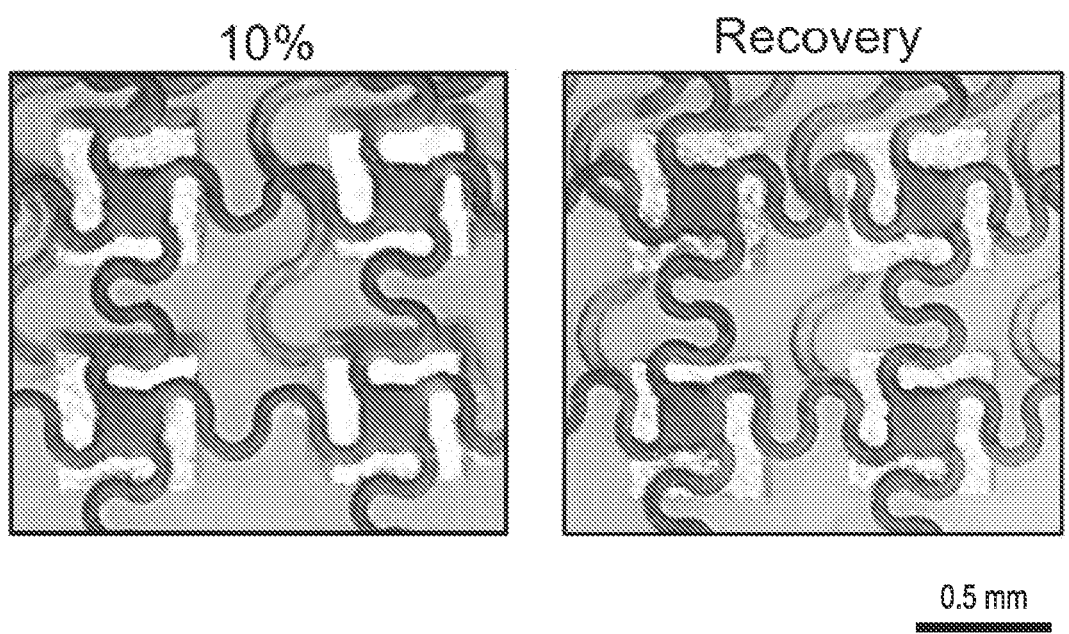
Figure 27C:
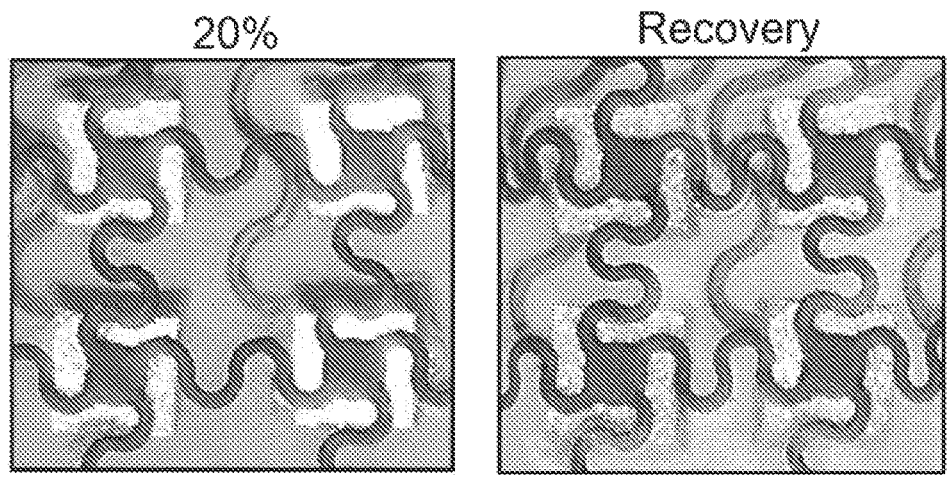
Figure 27D:
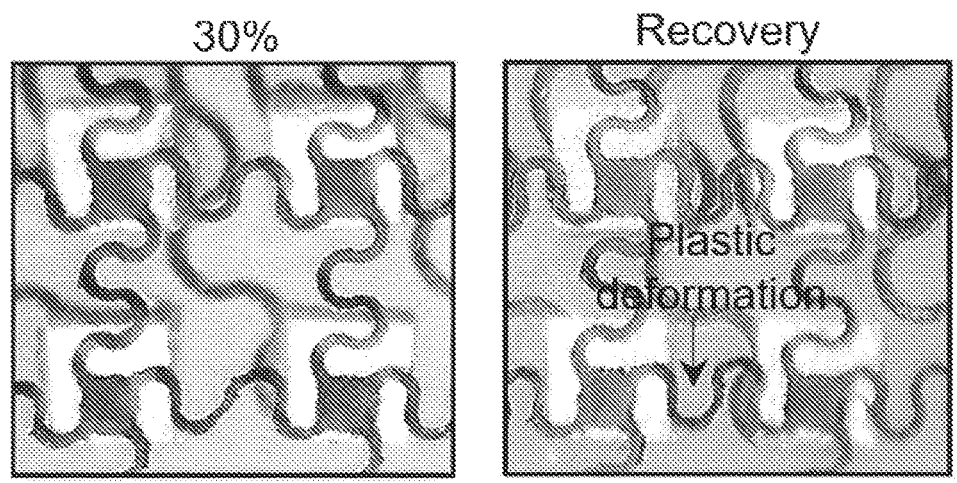
Figure 27E:
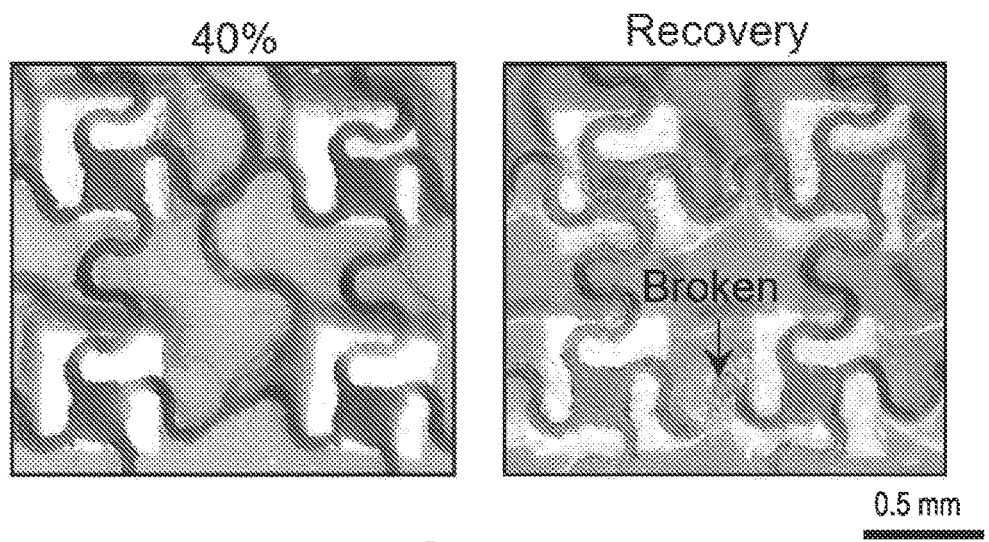

FIG. 26 shows a characterization of the hydrophobicity. In particular, FIG. 26(a) shows sonographic signal-to-noise ratios of the stretchable ultrasonic array measured underwater for two weeks. FIG. 26(b) shows an optical image showing the contact angle of 119.47° of a water droplet on the stretchable ultrasonic array. The hydrophobicity of the encapsulating silicone elastomer makes the stretchable ultrasonic array sweat-proof.

FIG. 27 shows optical images of the stretchable ultrasonic array under stretchability tests. In particular, FIG. 27(a) shows the device in its original state under 0% strain. FIG. 27(b) shows the device under 10% biaxial tensile strain (left) and after releasing the strain (right). FIG. 27(c) shows the device under 20% biaxial tensile strain (left) and after releasing the strain (right). FIG. 27(d) shows the device under 30% biaxial tensile strain (left) and after releasing the strain (right). Plastic deformation of the interconnects starts to show up. The results reveal that the device can withstand biaxial strain up to 30% without irreversible deformations. FIG. 27(e) shows the device under 40% biaxial tensile strain (left) and after releasing the strain (right), where the fracture is identified (right). All panels share the same scale bar of 0.5 mm. The 800 μm pitch balances the elastographic image quality and the stretchability: finer pitch ensures a higher lateral resolution and fewer image artifacts caused by side-lobes; larger pitch allows larger stretchability and better conformability to the human body.

Figure 28A:
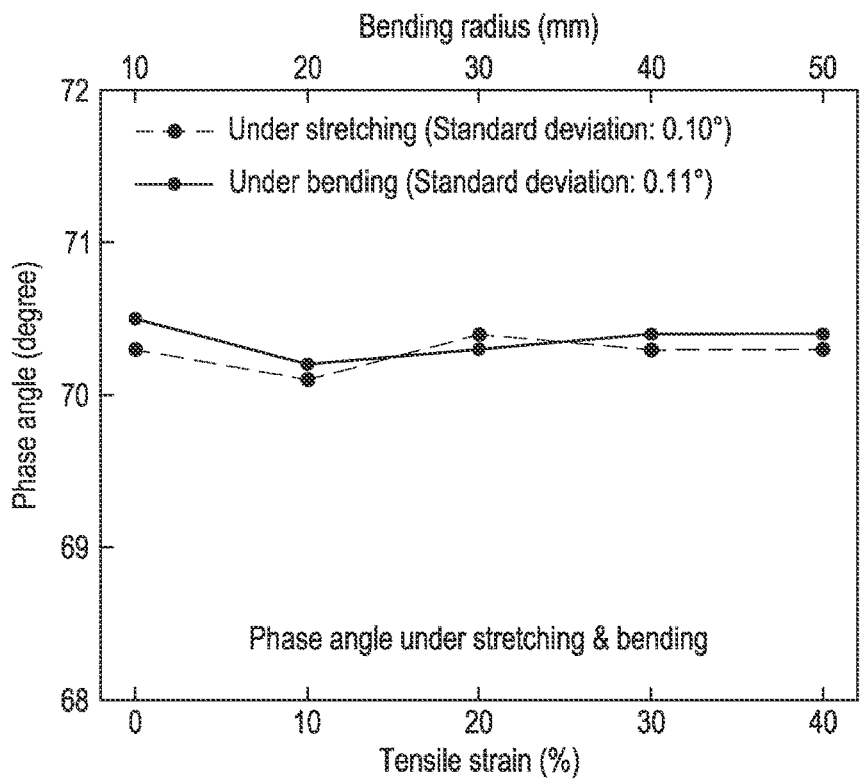
FIGS. 28A-28B shows performance characterization data for the transducers under deformation.
Figure 28B:
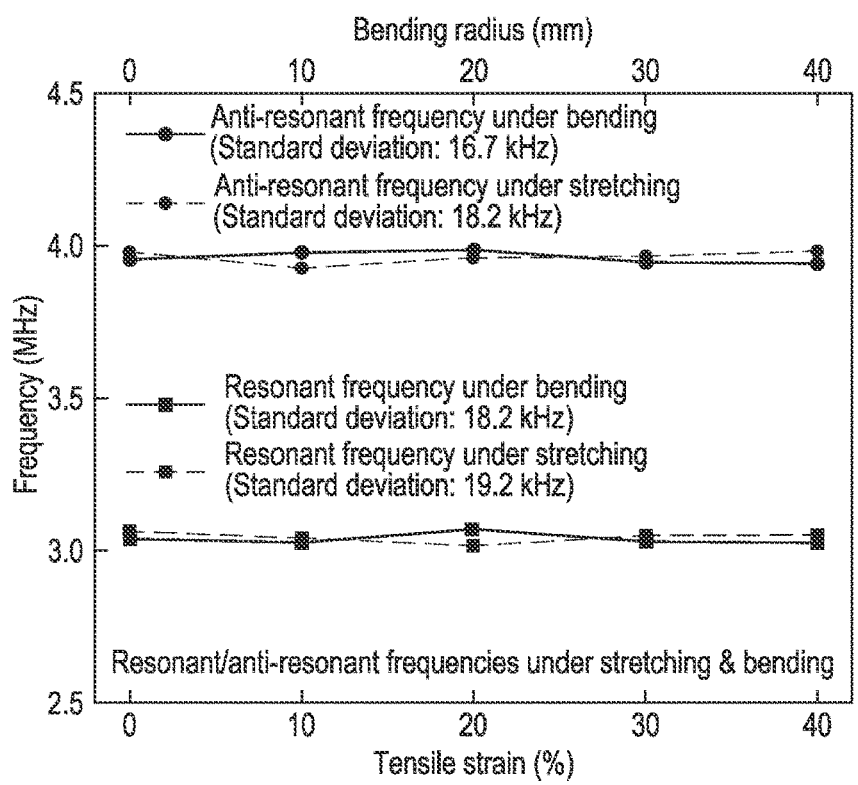

FIG. 28 shows the performance characterization of the transducers under deformation. In particular the figures show the phase angle (FIG. 28a) and resonant and anti-resonant frequencies (FIG. 28b) of the transducers under stretching and bending. The small standard deviations (0.10°, 0.11° for phase angles; 19.2 kHz, 18.2 kHz for resonant frequencies; and 18.2 kHz, 16.7 kHz for anti-resonant frequencies) show the stable electromechanical coupling performance of the transducers under various modes of mechanical deformation.

Figure 29A:
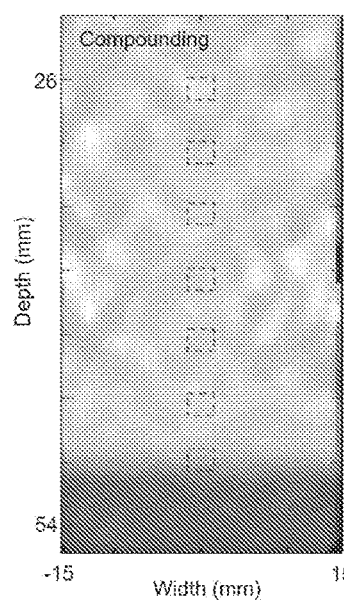
FIGS. 29A-29C show simulations comparing three different transmission modes.
Figure 29B:
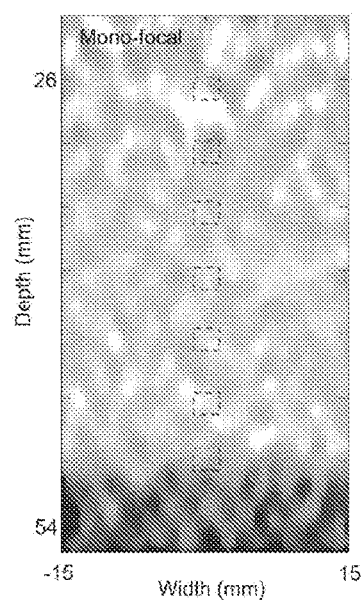
Figure 29C:
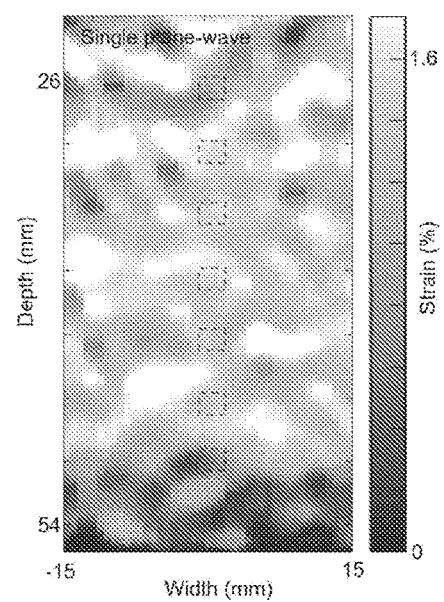

FIG. 29 shows a comparison of three different transmission modes. Strain distribution simulations using coherent plane wave compounding (FIG. 29a), mono-focus (FIG. 29b), and single plane-wave (FIG. 29c) transmission modes are shown. The dashed boxes are the locations of choice for comparison. The single plane wave mode has a high frame rate and a short image reconstruction time since it does not need to steer multiple angles. The mono-focal mode can achieve a high image quality at the focal depth. The coherent plane-wave compounding mode provides images with the best $SNR_e$ and $CNR_e$ than the other two modes so it is used herein as the transmission mode for elastography imaging.

Figure 30A:
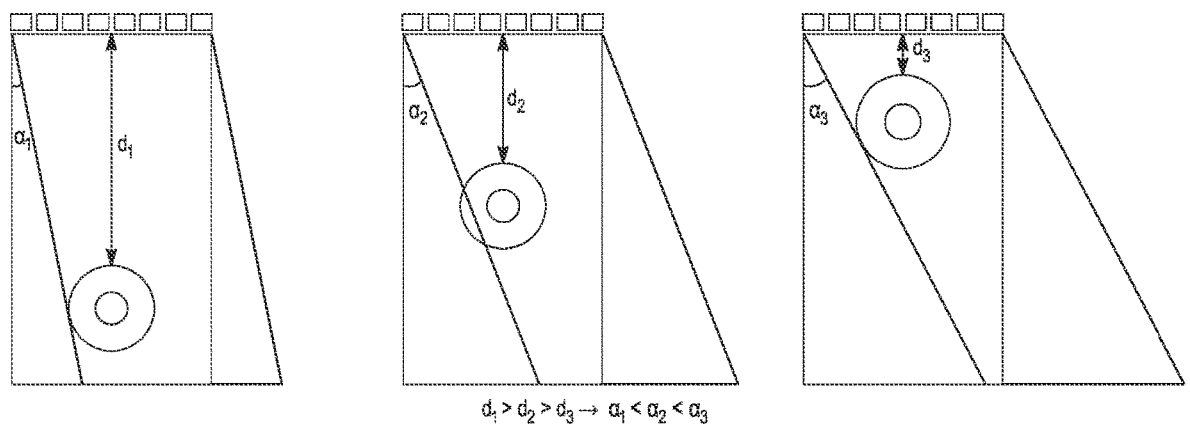
FIGS. 30A-30B illustrate factors affecting the step size and number of the compounding angle.
Figure 30B:
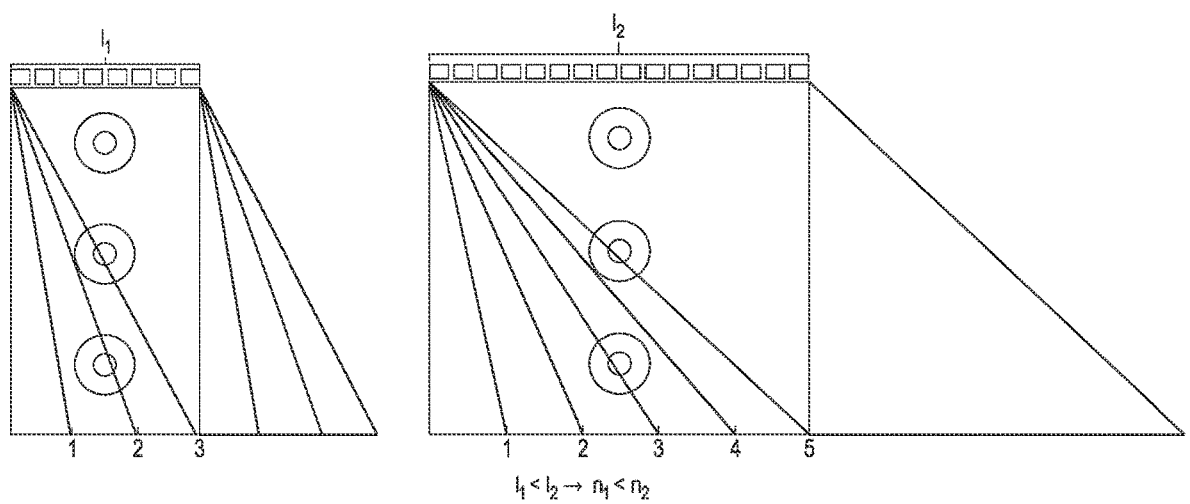
Figure 31A:
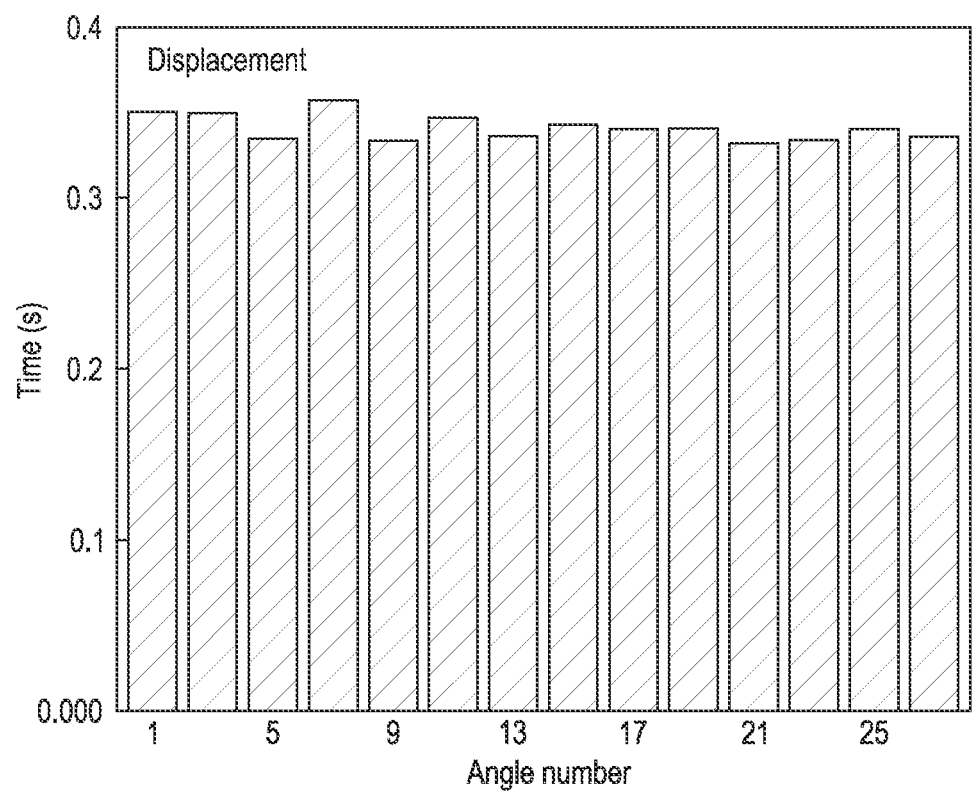
FIGS. 31A-31D illustrate the processing time for reconstructing images at different angle numbers
Figure 31B:
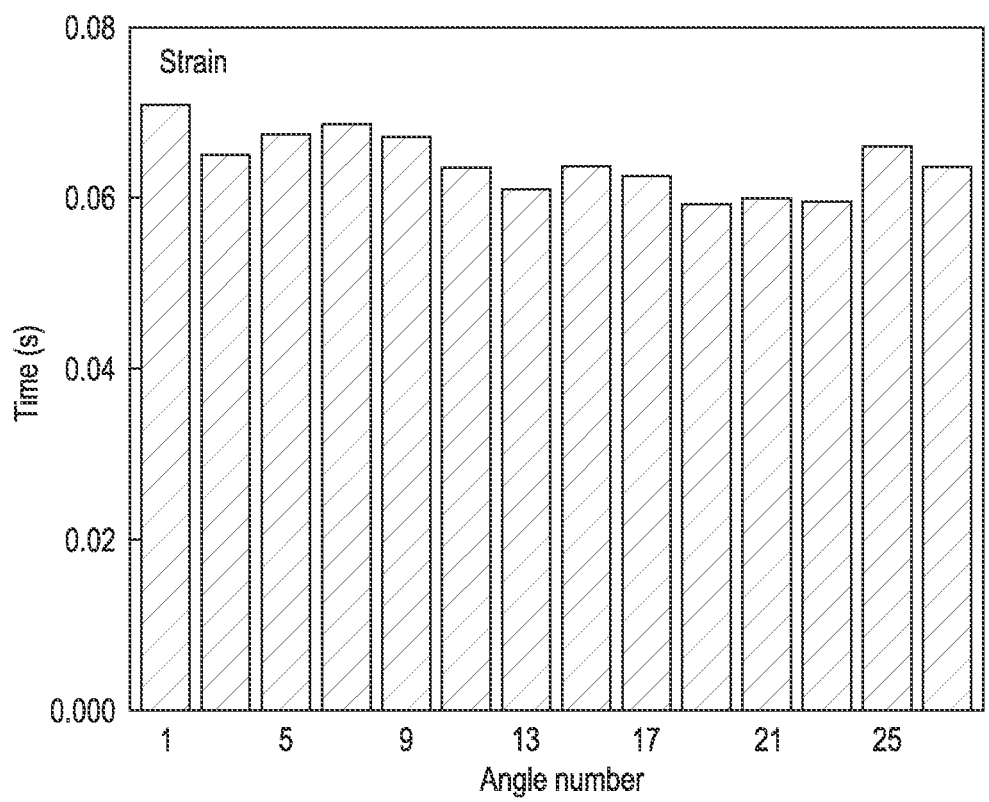
Figure 31C:
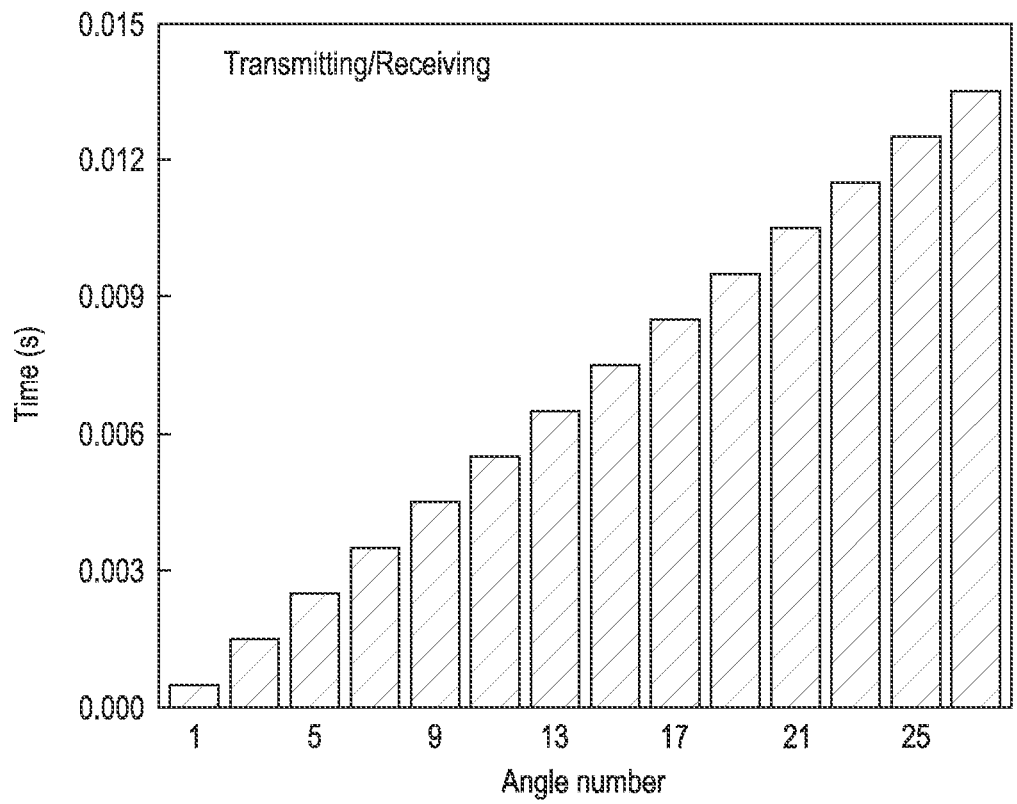
Figure 31D:
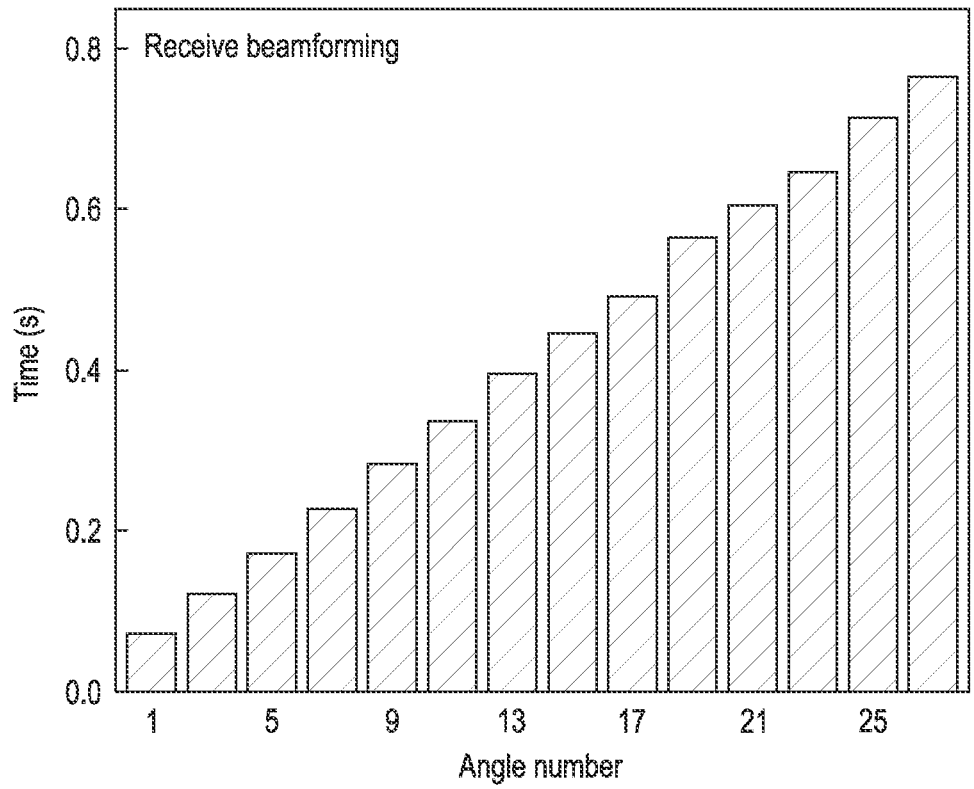
Figure 32A:
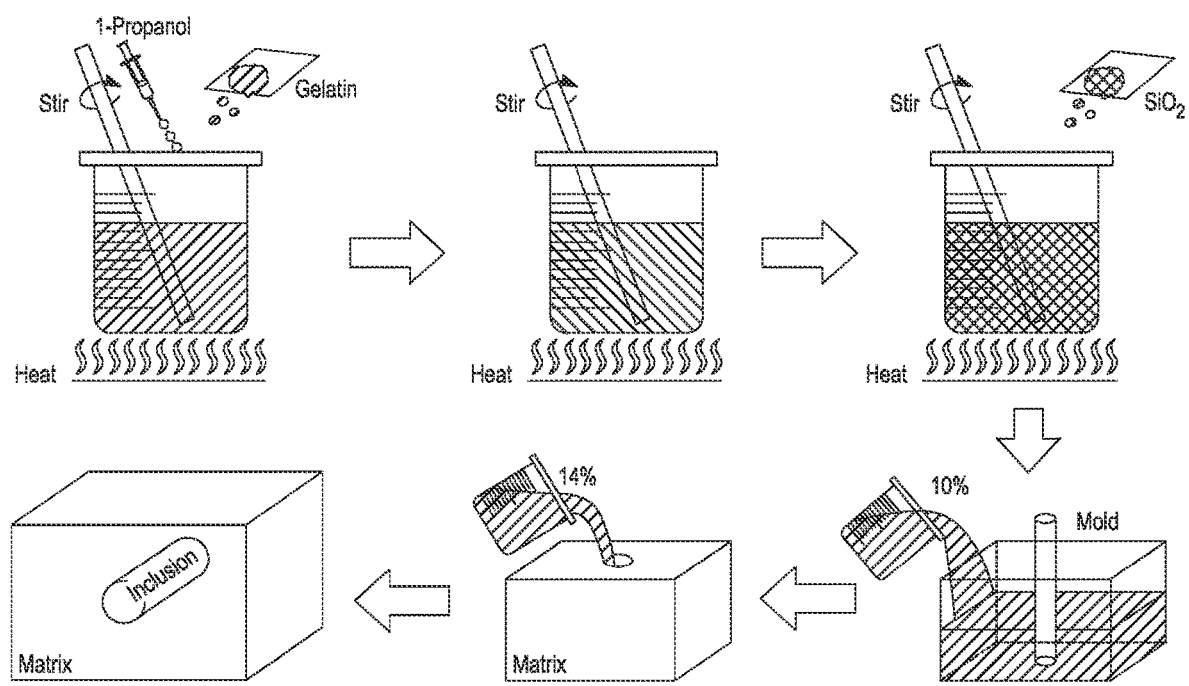
FIGS. 32A-32E show fabrication processes and optical images of tissue-mimic phantoms.
Figure 32B:
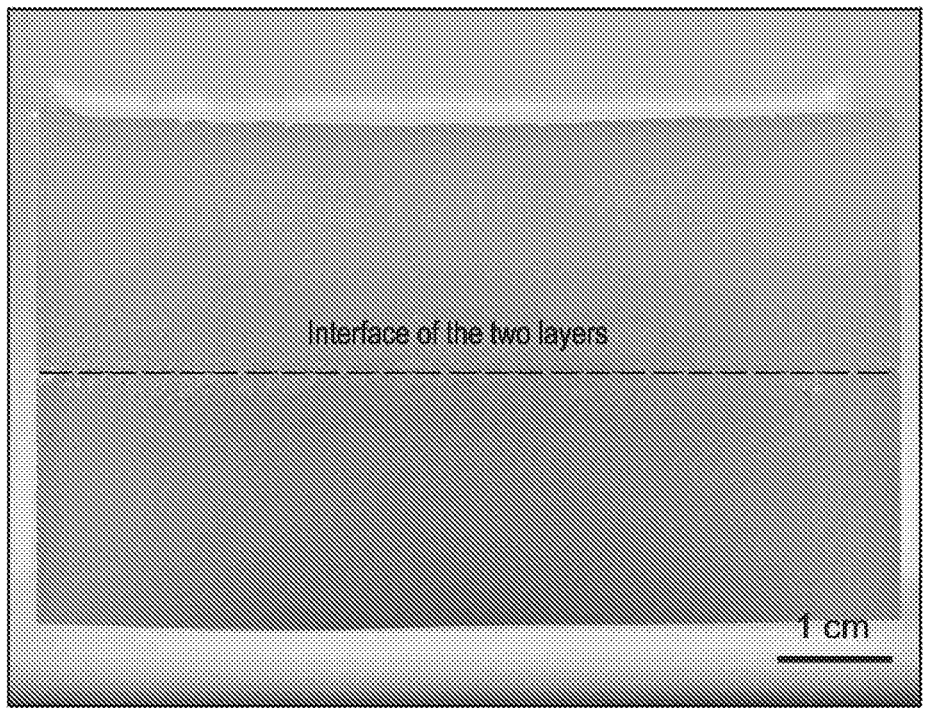
Figure 32C:
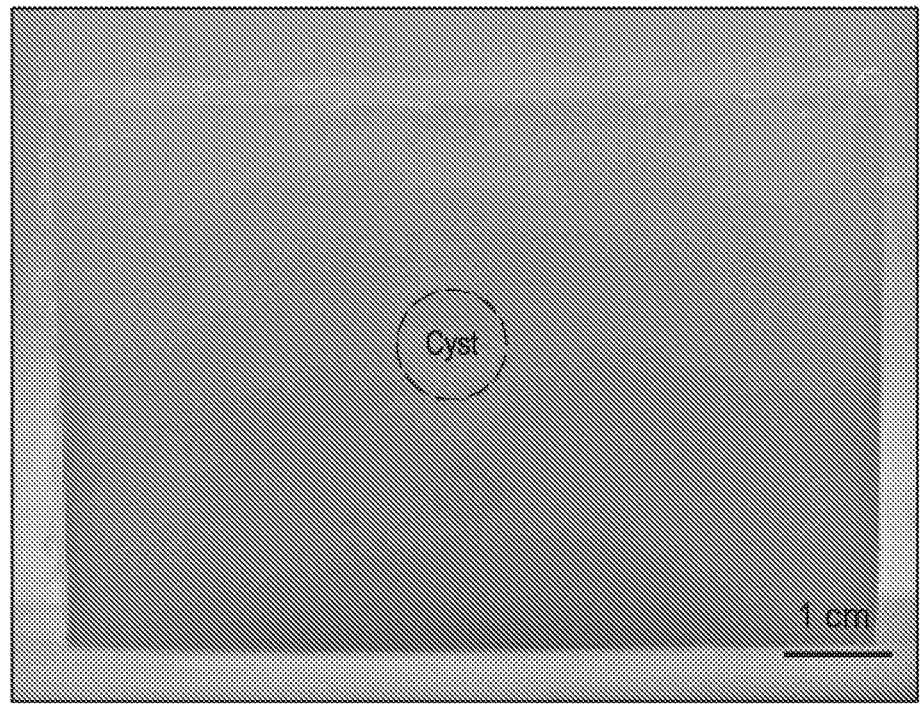
Figure 32D:
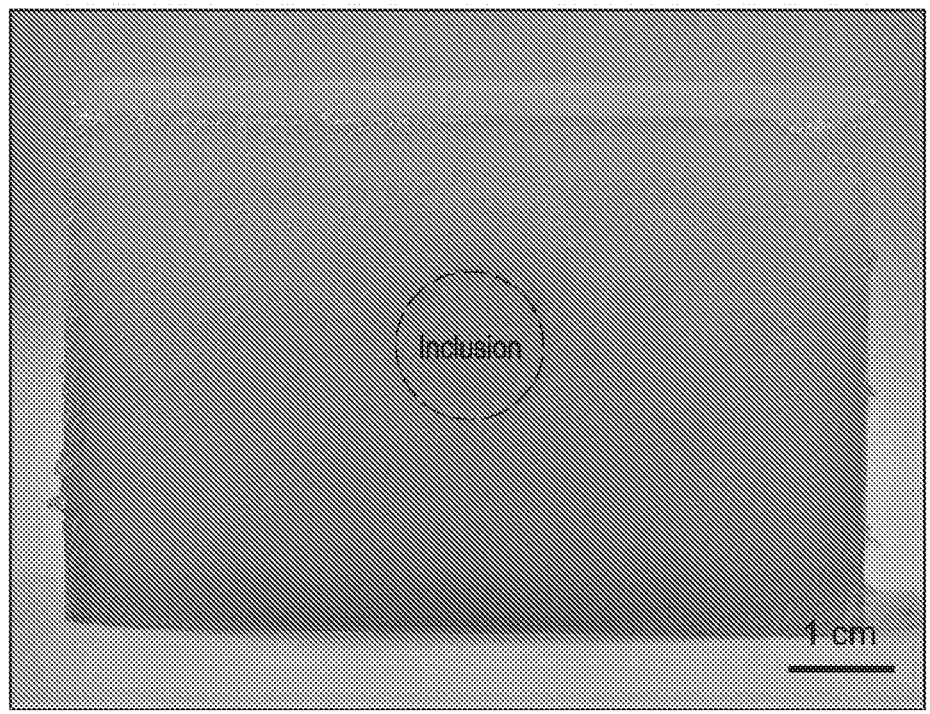
Figure 32E:
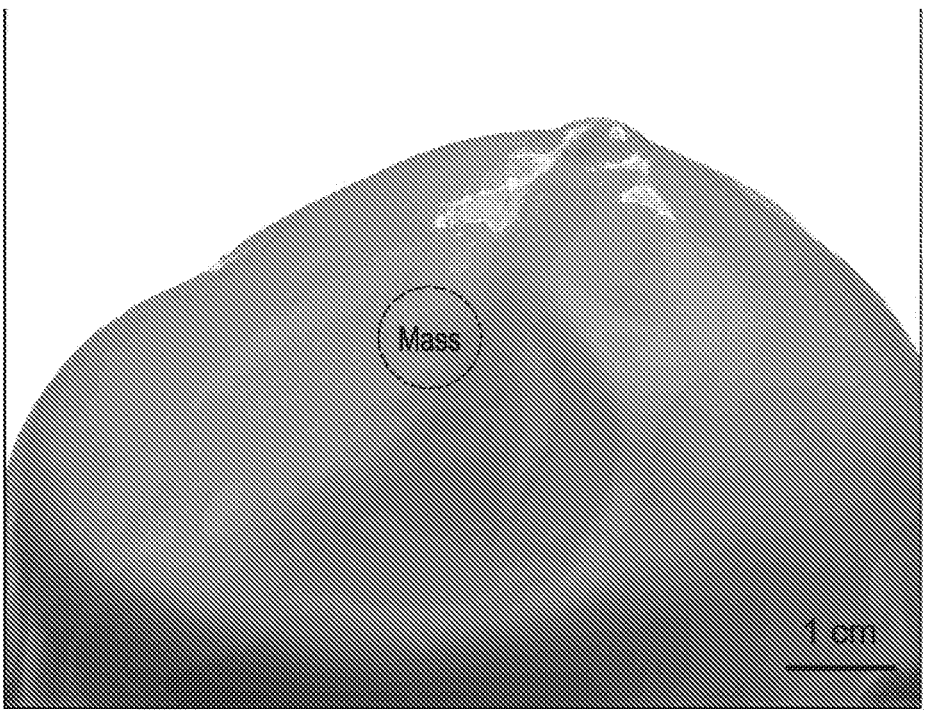

FIG. 30 shows factors affecting the step size and number of the compounding angle. In particular, FIG. 30(a) shows that the step size mainly relies on the position of the target region. The deeper region needs a smaller step size, so the majority of scanned frames coherently overlap in this region. d: depth, α: step size. FIG. 30(b) shows that the number of angles mainly relies on the aperture size of the transducer array. A larger aperture requires more angles, providing sufficient in sonification by the plane waves at target regions to obtain effective synthetic focusing quality. In this work, the compounding mode with 19 steering angles in total significantly improves the $SNR_e$ of the image. Without the steered angles, adding 19 slides of identical plane wave images together will increase the intensity of both useful signals and noises caused by the side-lobes, even though random noise will cancel with each other. With different steering angles, these noises caused by side-lobes are out of the overlapping area and will not add up. Therefore, the $SNR_e$ of the final image will be enhanced. Since the compounding mode has the synthetic focusing effect at the entire region, the lateral and axial resolutions of the elastography images keep constant at different locations in the target region. l: aperture length; In the figures, n denotes angle number.

FIG. 31 shows the processing time for reconstructing images at different angle numbers. In particular, the time for displacement calculation (FIG. 31a), strain calculation (FIG. 31b), transmitting/receiving (FIG. 31c), and receive beamforming (FIG. 31d) with different angle numbers are shown. Time for calculating the displacement and strain keeps constant at different angle numbers but for the transmitting/receiving processes and receive beamforming is increasing linearly with the angle number. Specifically, time for receive beamforming dominates. Balancing the overall time budget and the gain in $SNR_e$ at different numbers of steering angles, we use 19 angles for the compounding imaging in this work.

FIG. 32 shows fabrication processes and optical images of tissue-mimic phantoms. In particular, FIG. 32(a) shows that the tissue-mimic phantoms are made of gelatin and silicon dioxide particles. Optical images of a bilayer phantom (FIG. 32b), a phantom with cyst (fluid inside) (FIG. 32c), a phantom with inclusion (solid inside) (FIG. 32d), and a commercial breast phantom with a mass inside (CIRS Model 059) (FIG. 32e) are shown, corresponding to 1D, 2D, 2D, and 3D biological tissue elasticity models, respectively.

Figure 33A:
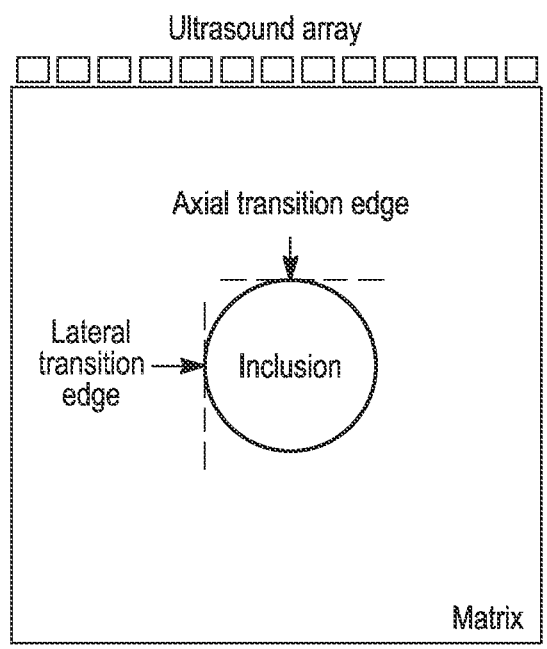
FIGS. 33A-33B show schematics and data for characterizing the elastographic spatial resolutions.
Figure 33B:
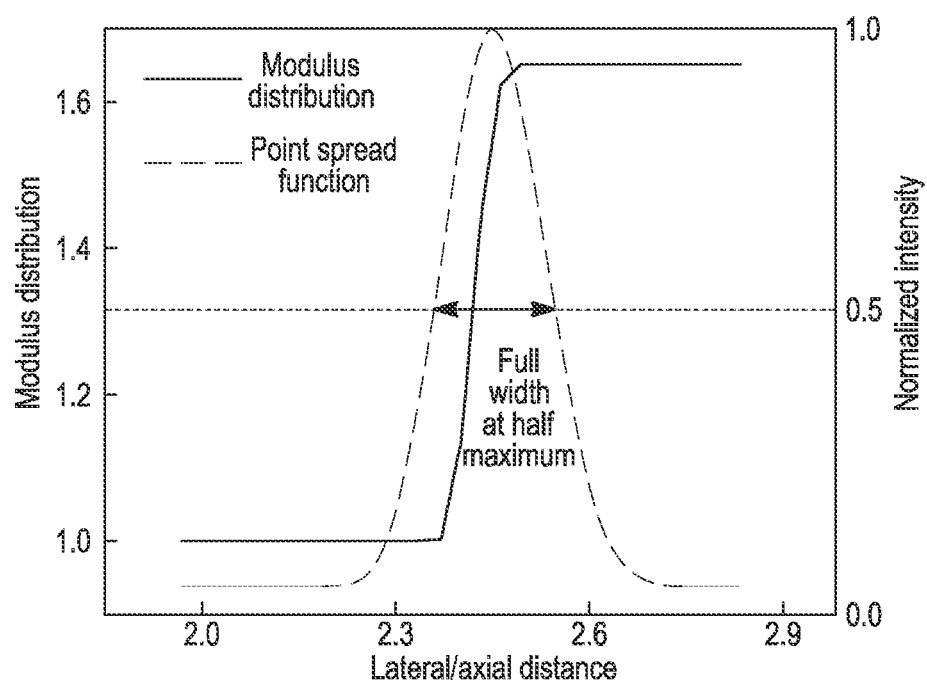

FIG. 33 characterizes the elastographic spatial resolutions. Schematic plots of the experiment setup (FIG. 33a) and curves of modulus distribution (FIG. 33b) and the corresponding point spread function are shown. The full widths at half maximum of the point spread functions are defined as the lateral and axial resolutions.

Figure 34:
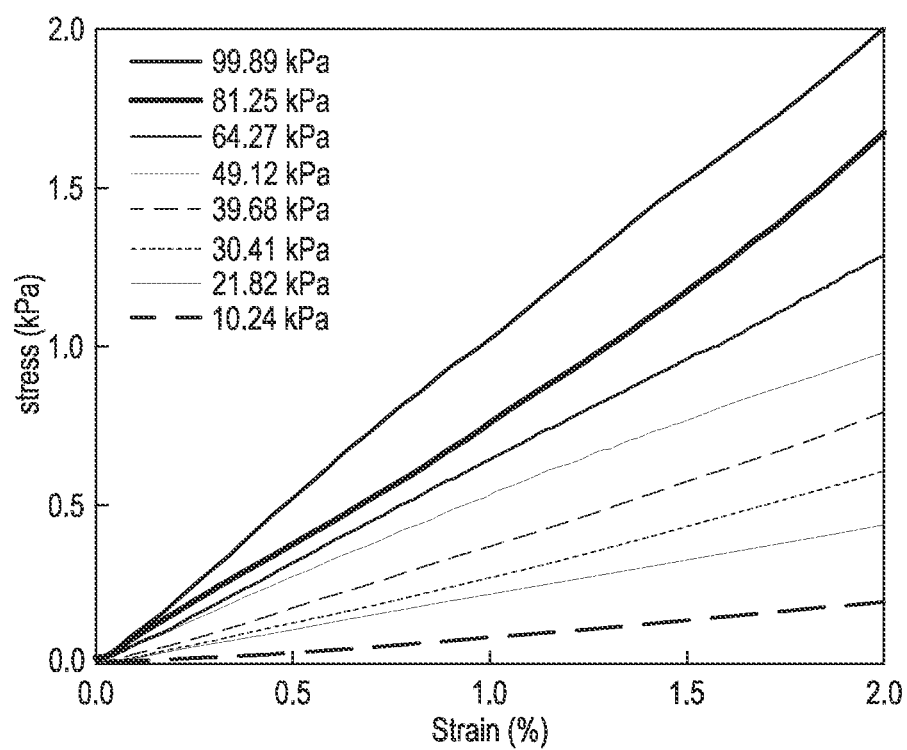
FIG. 34 show stress-strain plots of tissue-mimic gelatin phantoms in quasi-static strain rate regimes.

FIG. 34 show stress-strain plots of tissue-mimic gelatin phantoms in quasi-static strain rate regimes. We focus on the first 2% strain since within this range the phantom has a linear stress-strain behaviour. Young's moduli are yielded by calculating the slope of the curves. Non-linear behaviour shows up when the strain is larger. That non-linear part in the stress-strain curve will not be used for Young's modulus calculation.

Figure 35A:
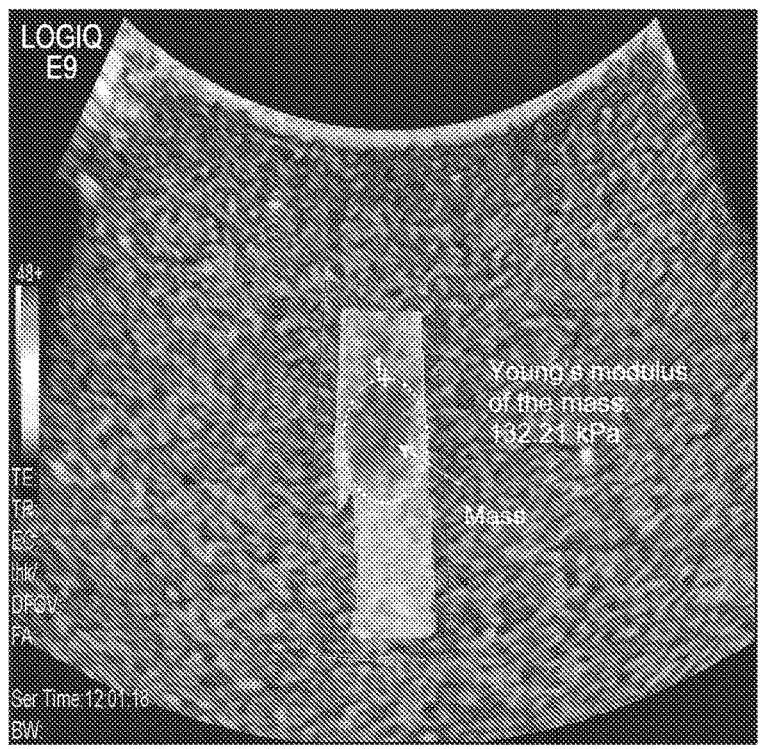
FIGS. 35A and 35B show modulus validation of a commercial breast phantom.
Figure 35B:
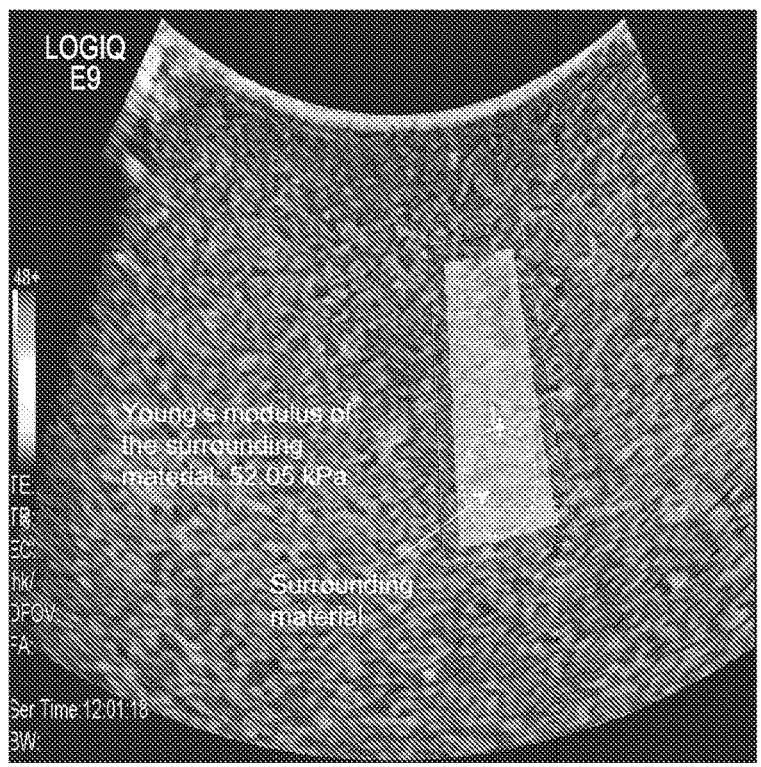

FIG. 35 shows the modulus validation of a commercial breast phantom. The validation of the moduli of the mass (FIG. 35a) and the surrounding material (FIG. 35b) by a medical shear-wave ultrasound system (GE Logiq E9 Ultrasound Machine) are shown. The Young's modulus equals to three times the shear modulus in soft tissues, which yields 132.21 kPa and 52.05 kPa of Young's moduli of the mass and the surrounding material, respectively FIG. 36 shows displacement and strain curves at the central lines of different phantoms. In particular, the displacement (left column) and strain curves (right column) of a bi-layer phantom (FIG. 36a), a cyst phantom (FIG. 36b), an inclusion phantom (FIG. 36c), and a breast phantom (FIG. 36d) are shown. The slope of the displacement curve of each component generally does not vary with the thickness, indicating the uniform Young's modulus of each component. The least-squares strain estimator with a piecewise linear curve fitting transforms the displacement to the strain. These curves at the central lines clearly show the difference in displacement and strain of each component in the phantoms. Particularly, certain regions depicted in color renditions in the cyst phantom is a unique artifact in cysts. The cyst region is devoid of echoes and mere random noises are detected, causing the displacements to be very small. The section where the large displacement transits to the small displacement produces a large negative strain due to the slope change in the displacement curve ("A" region). The small displacement generates close to zero strain ("B" region). And the transition section where the displacement raises from small to large yields large positive strain ("C" region). Analysis and discussions about regions "A" and "C" are in FIG. 37.

Figures 37A, 37B:
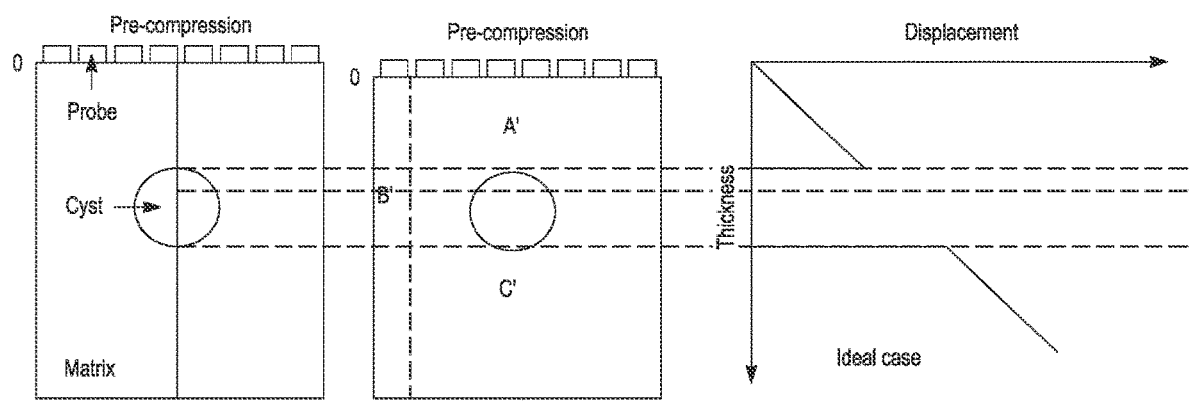
FIGS. 37A-37D are schematic plots showing the mechanism of generating the displacement curve in the cyst phantom.
Figure 37C:
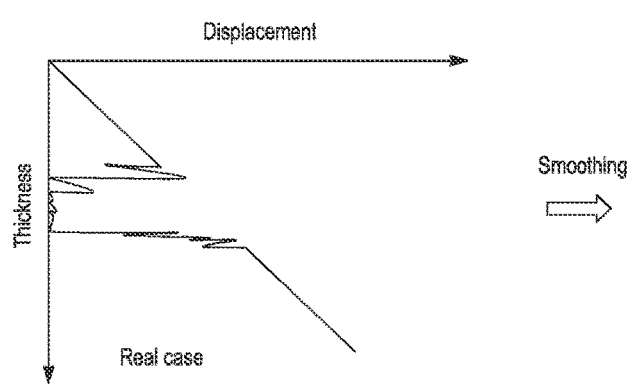
Figure 37D:
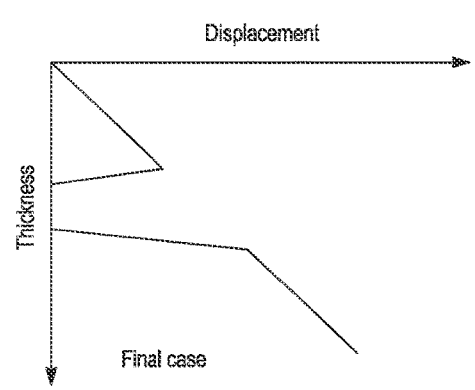

FIG. 37 shows schematic plots illustrating the mechanism of generating the displacement curve in the cyst phantom. In particular, FIG. 37a illustrates when a cyst phantom undergoes a mild compression. FIG. 37(b) illustrates the displacements of the transition between the matrix and the cyst ideally should go straight down and up. FIG. 37(c) shows that in the real case, since there are no echoes in the cyst region, the electrical noises from radiofrequency lines cause the displacement curve in this region very noisy. FIG. 37d shows that after smoothing, the curves with gradients have been yielded to connect the displacements between the matrix and the cyst.

Figure 38:
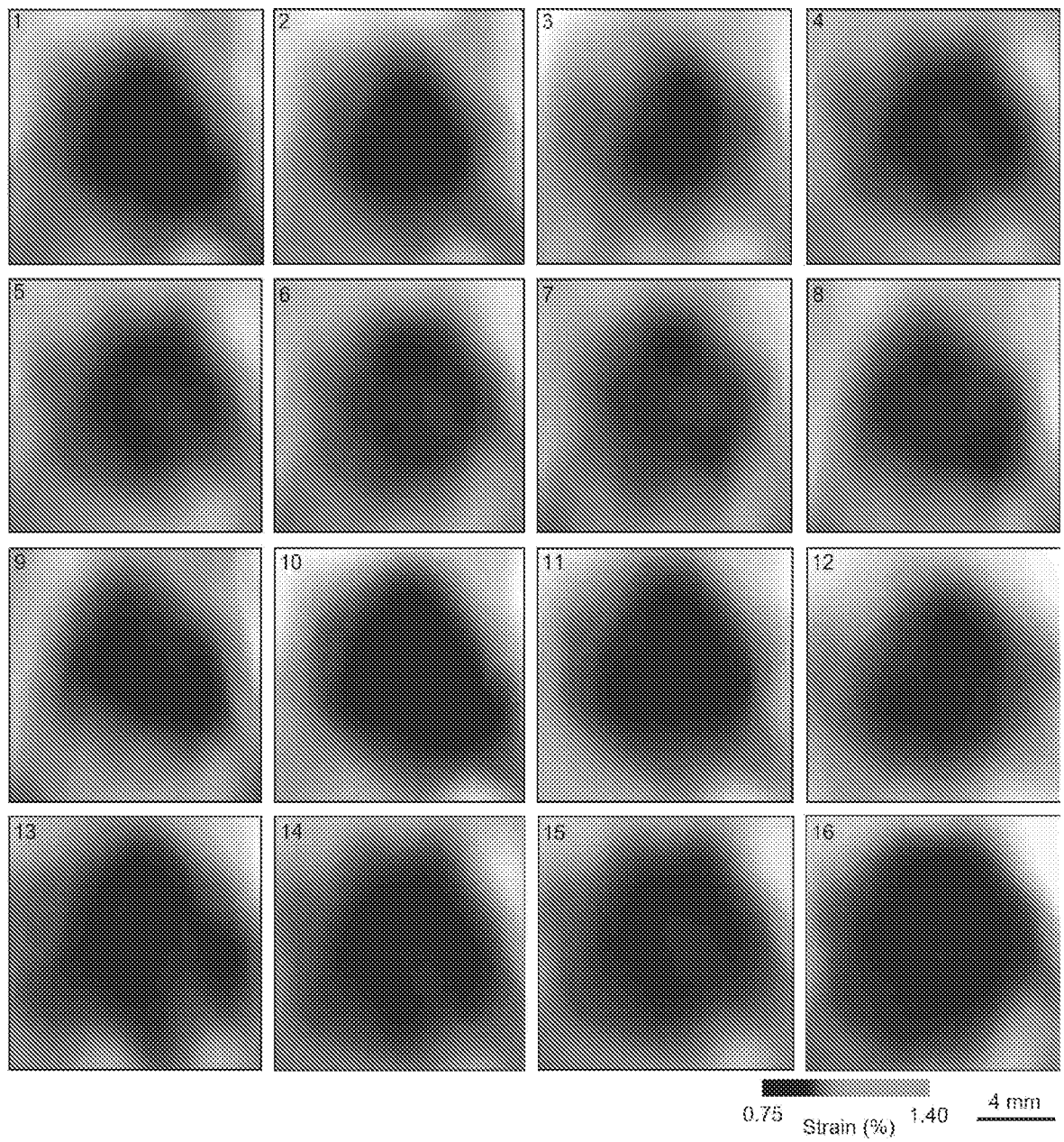
FIG. 38 shows 16 slices of 2D strain images of the inclusion phantom by the stretchable ultrasonic array.

FIG. 38 shows 16 slices of 2D strain images of the inclusion phantom by the stretchable ultrasonic array. Each slice of 2D strain image is generated by one 1×16 linear array in the stretchable ultrasonic array. 16 strain images with similar strain values and distribution demonstrate the stable and reliable performance of the stretchable ultrasonic array. These 2D images are used to reconstruct the 3D image. These figures share the same grayscale bar and scale bar.

Figure 39A:
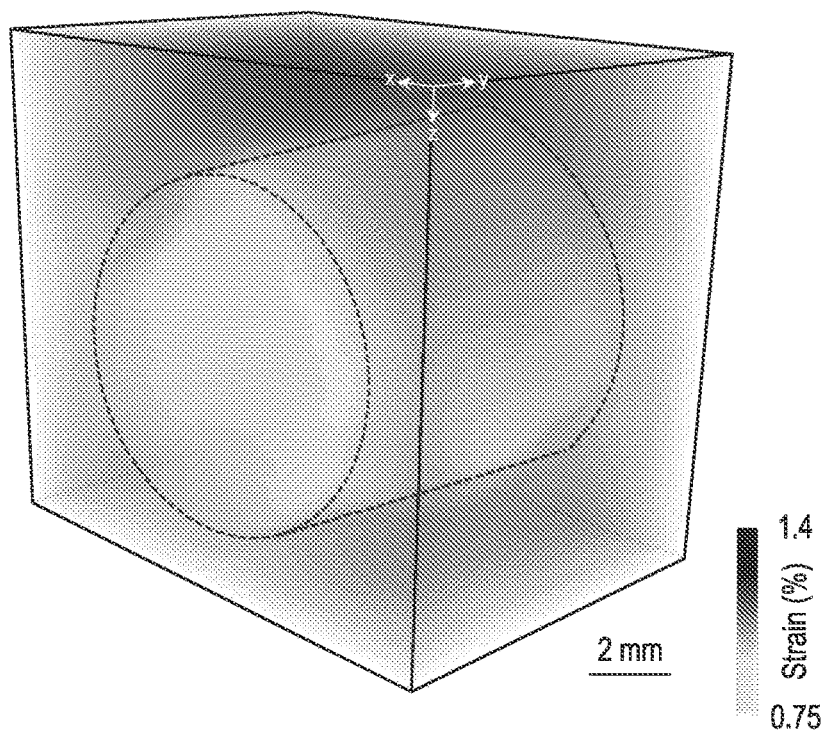
FIGS. 39A-39B show 3D strain images of an inclusion phantom by the stretchable and commercial ultrasonic probes.
Figure 39B:
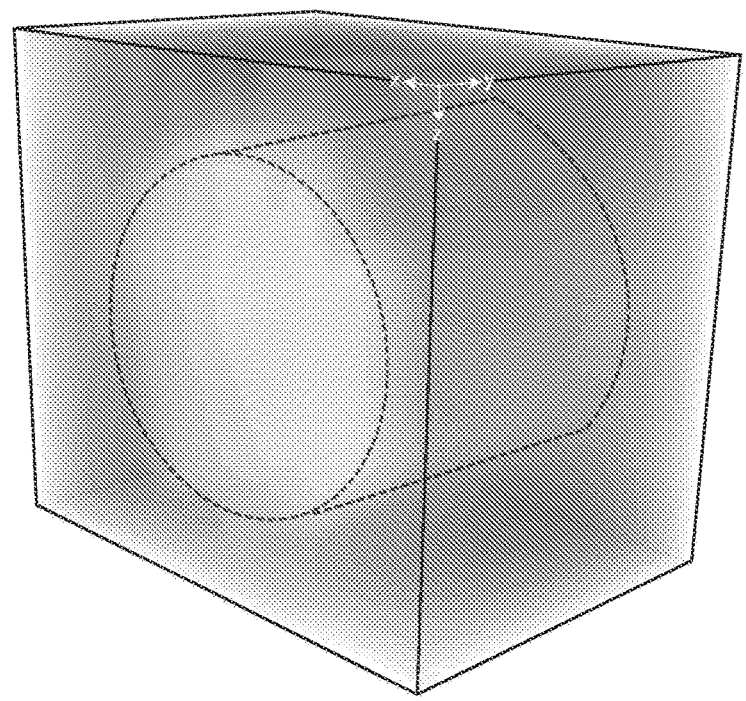

FIG. 39 shows 3D strain images of an inclusion phantom by the stretchable and commercial ultrasonic probes. The 3D strain images tested by the stretchable ultrasonic array (FIG. 39A) and a commercial ultrasound probe (FIG. 39B) show high correspondence to each other in size, geometry, and strain distribution of the inclusion phantom. Both figures share the same bar and scale bar.

Figure 40:
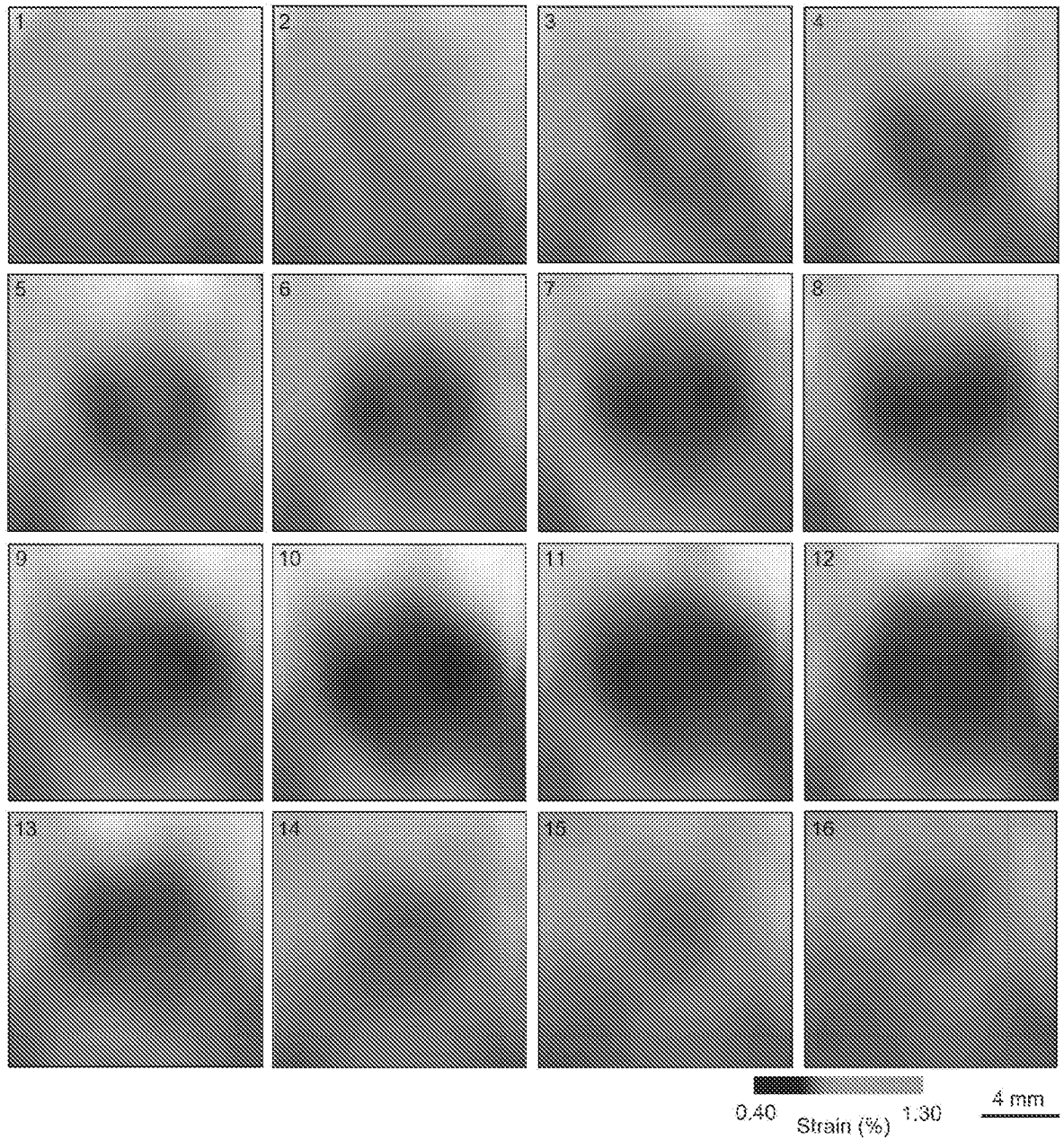
FIG. 40 show 16 slices of 2D strain images of the commercial breast phantom by the stretchable ultrasonic array.

FIG. 40 shows 16 slices of 2D strain images of the commercial breast phantom by the stretchable ultrasonic array. Each slice of 2D strain image is generated by each 1×16 linear array in the stretchable ultrasonic array. These 2D images are used to reconstruct the 3D image. These figures share the same grayscale bar and scale bar.

Figure 41A:
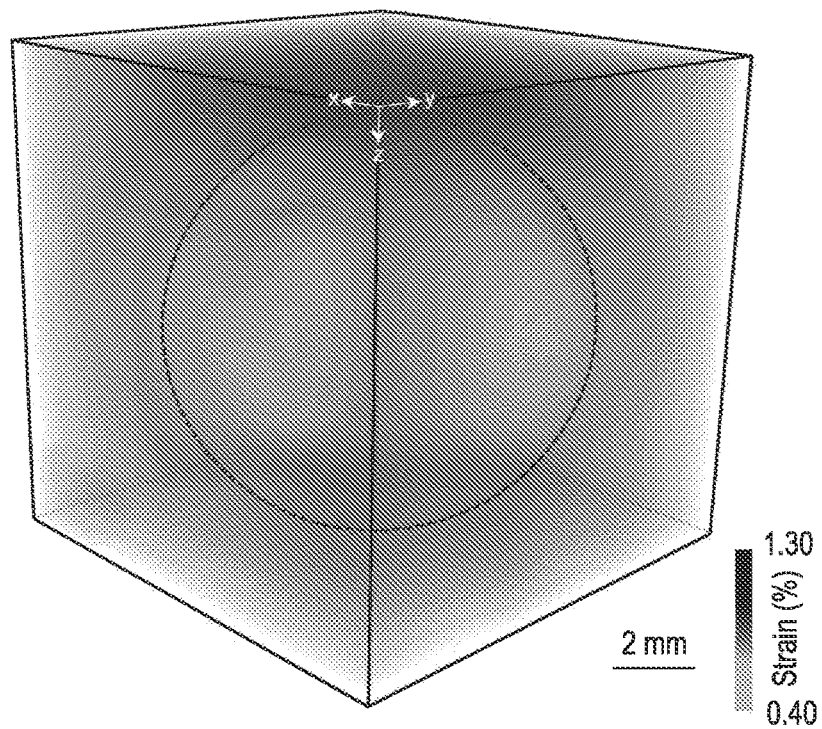
FIGS. 41A-41B show 3D strain images of the commercial breast phantom by the stretchable and commercial ultrasonic probes.
Figure 41B:
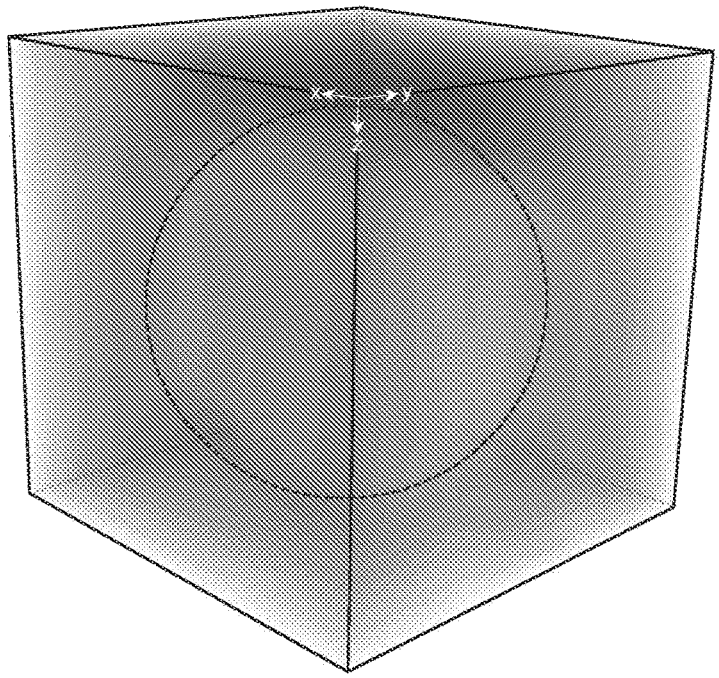

FIG. 41 shows 3D strain images of the commercial breast phantom by the stretchable and commercial ultrasonic probes. The results obtained by the stretchable ultrasonic array (FIG. 41a) and the commercial ultrasound probe (FIG. 41b) show high correspondence to each other in size, geometry, and strain distribution of the breast phantom. Both figures share the same colour bar and scale bar.

Figure 42A:
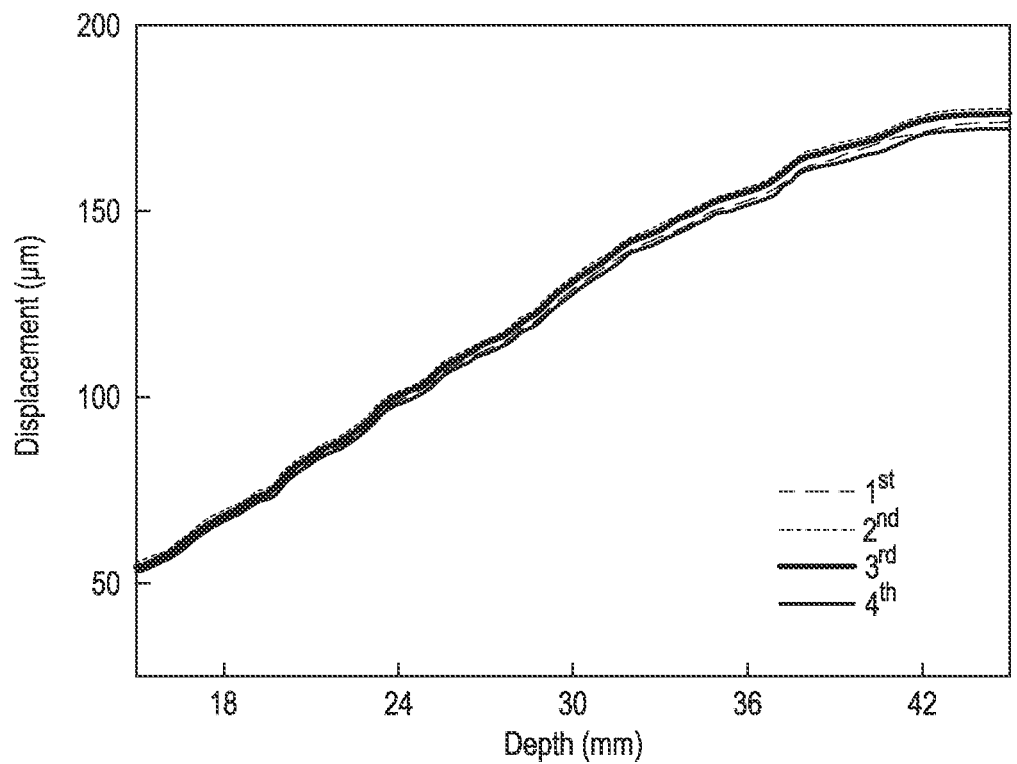
FIGS. 42A-42B show repetitive tests for the displacement and strain of a phantom.
Figure 42B:
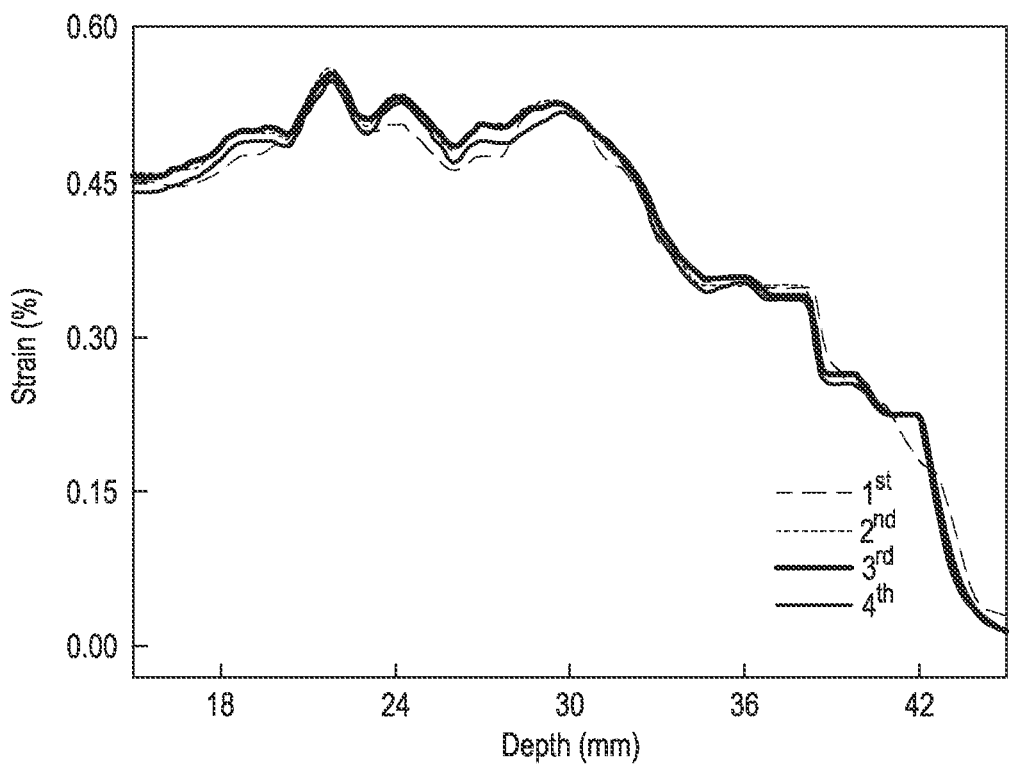

FIG. 42 show repetitive test result measurements of the displacement (FIG. 42a) and the strain (FIG. 42b) of a phantom for four times. There is a three-minute interval between each measurement to allow the phantom to relax from the compressive to the original states. These measurements are highly reproducible.

Figure 43:
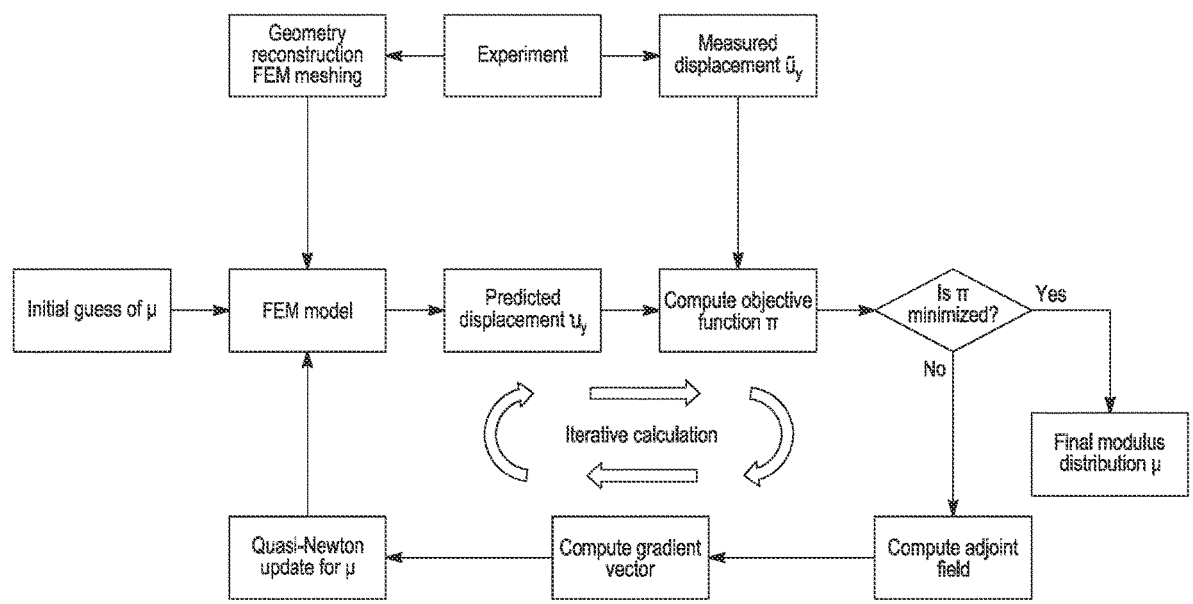
FIG. 43 is a flow chart of the process for calculating the forward and inverse elasticity problem.

FIG. 43 is a flow chart of the process for calculating the forward and inverse elasticity problem. Blue boxes demonstrate the workflow of developing synthetic specimens and solving the forward elasticity problems. Orange boxes demonstrate the workflow of calculating the inverse elasticity problem. Blue boxes demonstrate the interaction of the inverse elasticity problem with the experimental system. μ: modulus distribution; $u_{exact}$: exact displacement without adding noise; $u_{noise}$: the "measured" displacement field; $u_y$: the predicted displacement field; $ũ_y$: the measured displacement field; π: the objective function, as defined in equation 8.

FIG. 44 shows simulation results of uniform and nonuniform compressions. In particular, FIG. 44(a) shows a synthetic specimen with an inclusion that has a shear modulus 10 times higher than that of the surrounding matrix. The synthetic "measured" displacement fields are based on uniform compression (FIG. 44b) and non-uniform compression (FIG. 44c) on the specimen. FIGS. 44(d) and 44(e) show the strain distributions from uniform and non-uniform compression, respectively. The strain distributions vary upon different applied loads, which indicates that the strain-based elastography is a qualitative method only reflecting a relative stiffness of each component for a subject with inhomogeneous structures. The reconstructed modulus distributions obtained from solving inverse elasticity problems based on uniform compression (FIG. 44e) and non-uniform compression (FIG. 44f) are shown. FIG. 44(g) shows the results of a quantitative analysis of modulus contrasts and their deviations from the ground truth in FIG. 44(a).

Figure 45:
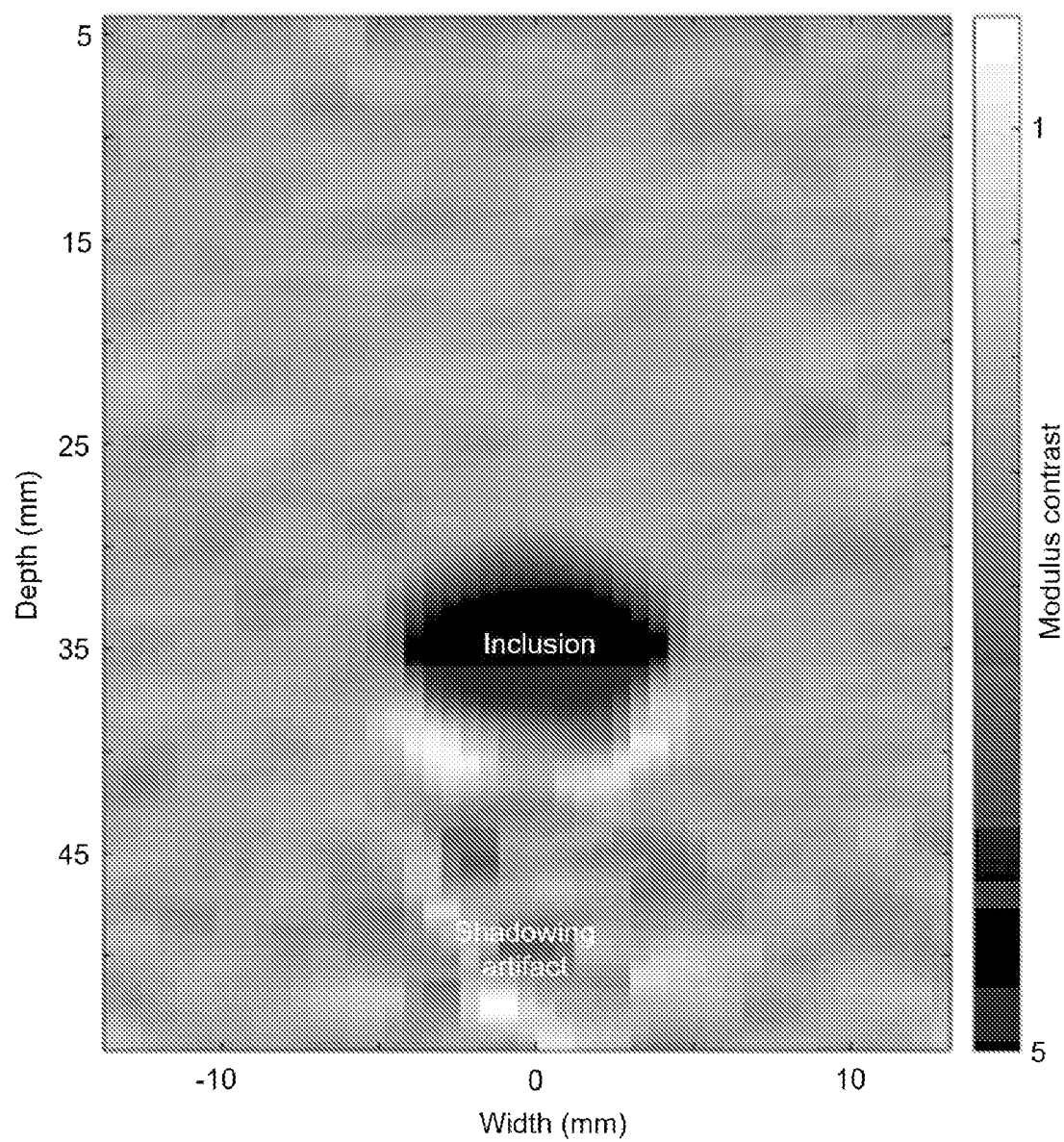
FIG. 45 shows simulated shadowing artifacts.

FIG. 45 shows simulated shadowing artifacts. Shadowing artifacts in the elastogram are usually caused by the shielding of the inclusion. Most of the ultrasound waves are bounced back by the inclusion. Only probes with high sonographic sensitivity can sense the weak signals below the inclusion and reconstruct the elastogram with minimal artifacts.

Figure 46:
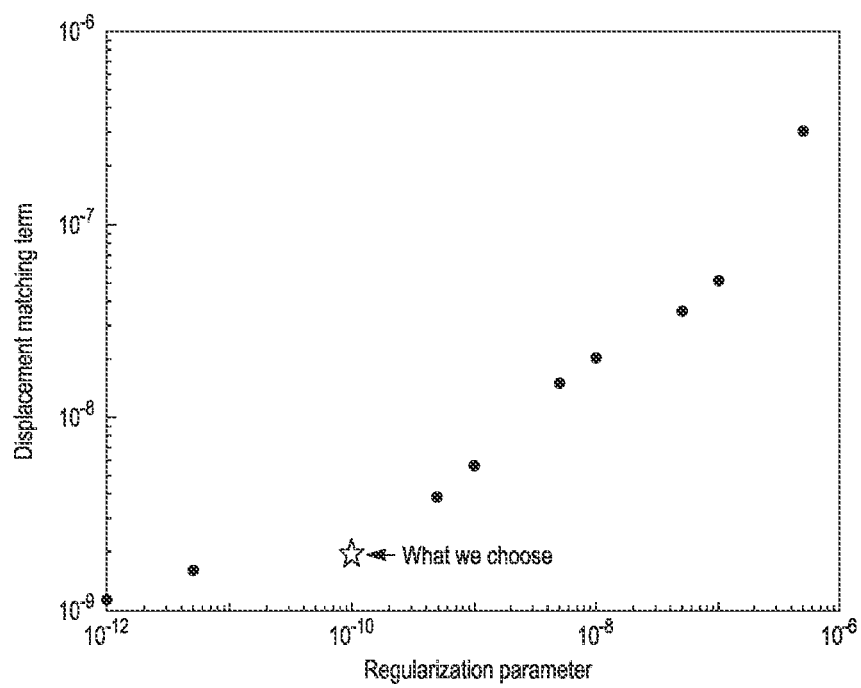
FIG. 46 shows the L-curve of calculating the inverse elasticity problem.

FIG. 46 shows the L-curve of calculating the inverse elasticity problem. An appropriate regularization parameter is required to reconstruct the displacement and modulus ratio fields. When selecting a large regularization parameter, the field will be very smooth but with small modulus contrast; and vice versa. In this work, we use $1 \times 10^{-10}$ to optimally harmonize the levels of smoothness and contrast to get the best matching of the measured and predicted results.

Figure 47A:
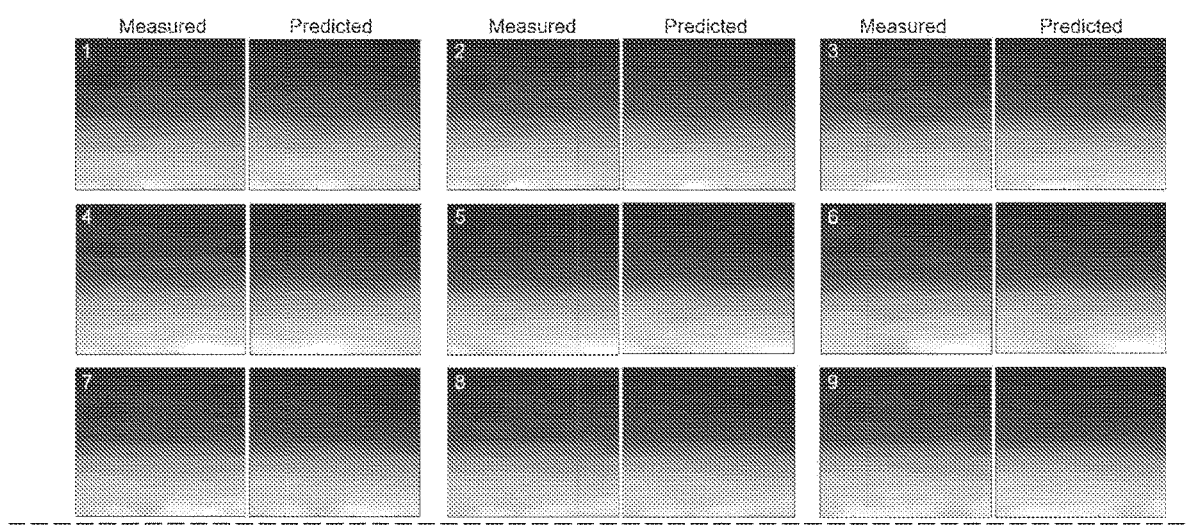
FIGS. 47A-47B show comparisons between the measured and predicted displacement fields of the porcine abdominal tissue.
Figure 47B:
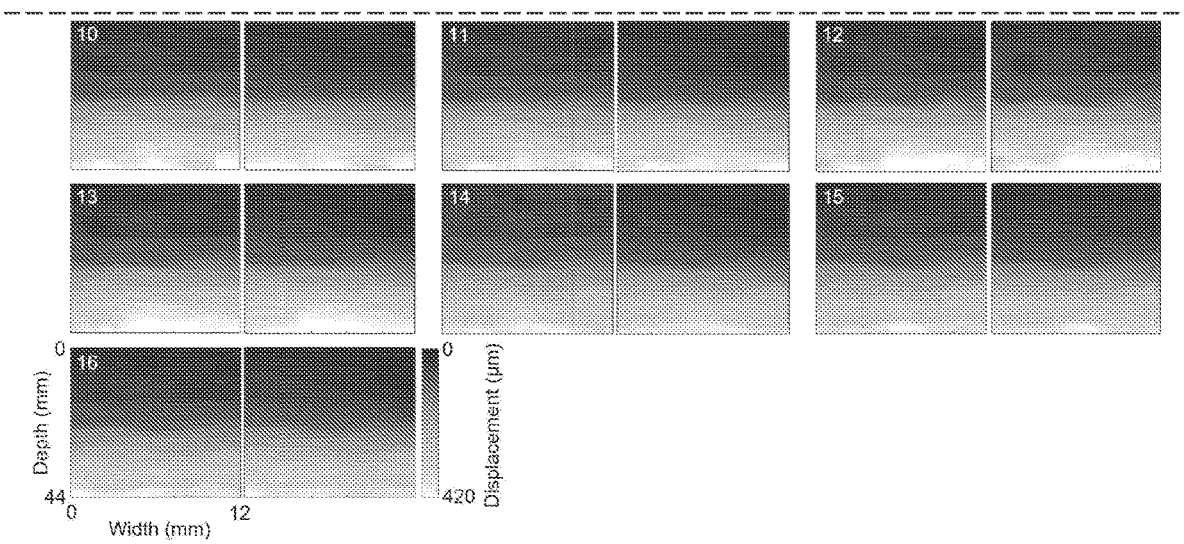

FIG. 47 shows a comparisons between the measured and predicted displacement fields of the porcine abdominal tissue. The prediction is by calculating the inverse elasticity problem. Each 1×16 linear array in the stretchable ultrasonic array produces a 2D cross-sectional displacement field using the coherent compounding imaging strategy. The >97% matching shows the high correspondence between the measured and predicted fields, providing a solid foundation for generating a reliable and accurate 3D modulus distribution in this work.

Figure 48A:
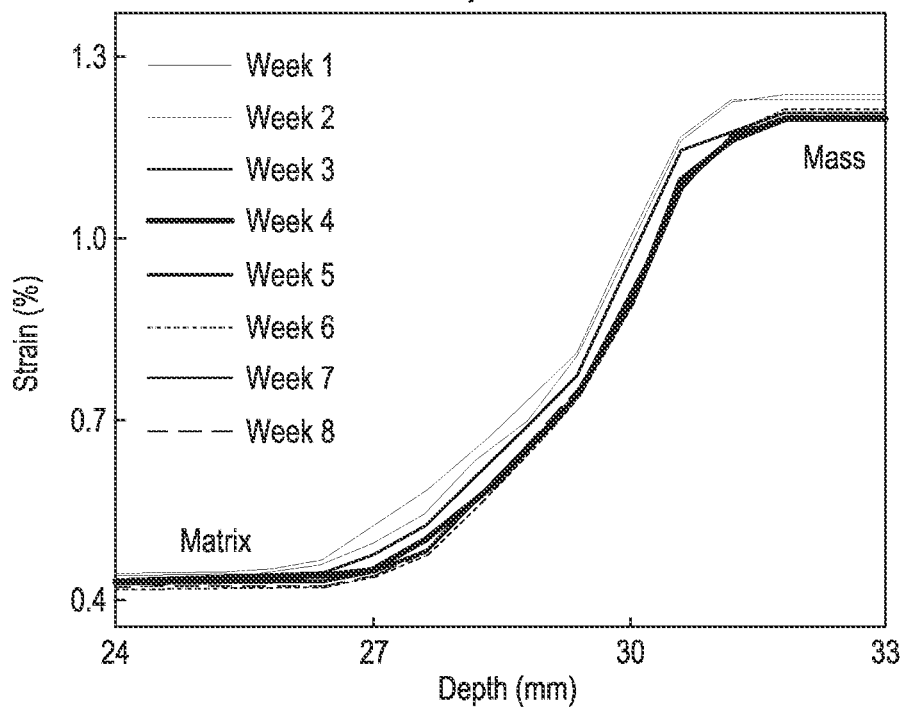
FIGS. 48A-48C shows the results of longitudinal studies of the strain curves of a commercial breast phantom.
Figure 48B:
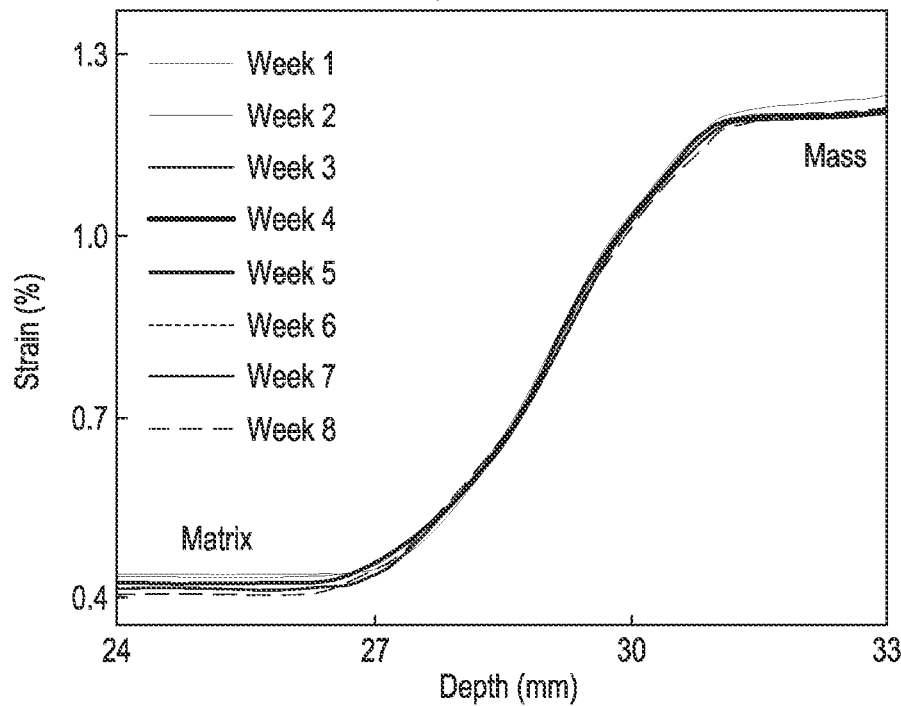
Figure 48C:
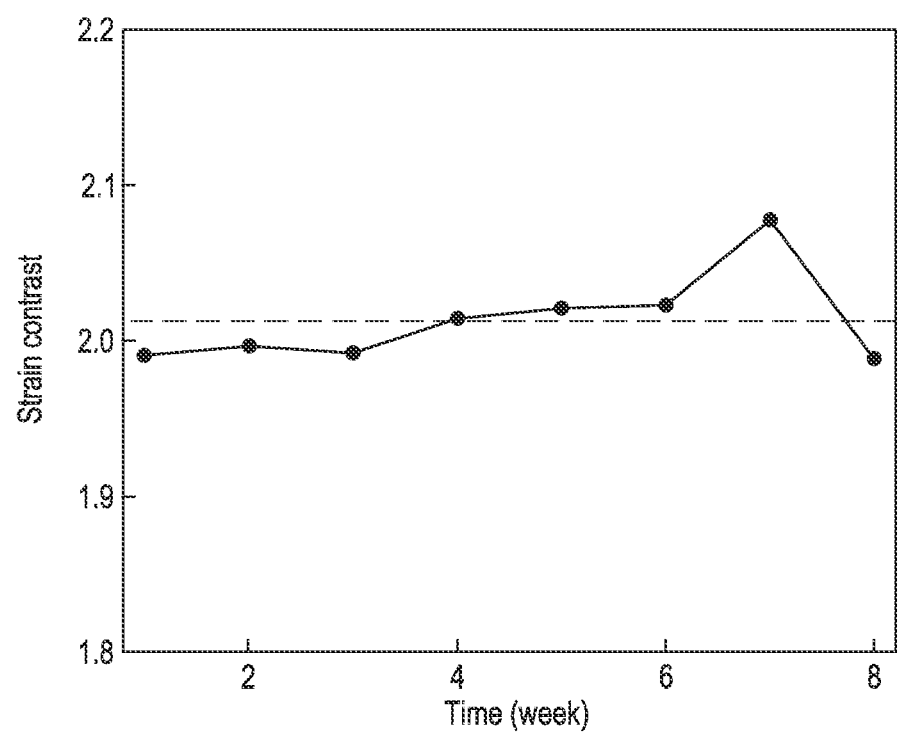

FIG. 48 show the results of longitudinal studies of the strain curves of a commercial breast phantom. In particular, FIG. 48a shows results for the stretchable ultrasonic array and FIG. 48(b) shows the results for a commercial ultrasonic probe to test the same commercial phantom over a duration of eight weeks, with one measurement per week. A linear motor was used for both devices to apply the same compressive strain to the target. Eight central lines of the strain fields, one per week, have been characterized, extracted, and plotted together. The results show the excellent accuracy and repeatability of the stretchable ultrasonic array for long-term monitoring. The little discrepancy of these curves from the stretchable ultrasonic array is probably due to the depolarization of the piezoelectric elements, which can potentially be fixed by re-poling with the strong electric field of 52.38 kV/cm for 15 minutes. FIG. 48(c) shows the strain contrast monitored by the stretchable ultrasonic array, demonstrating the excellent repeatability of the device in longitudinal studies.

Figure 49A:
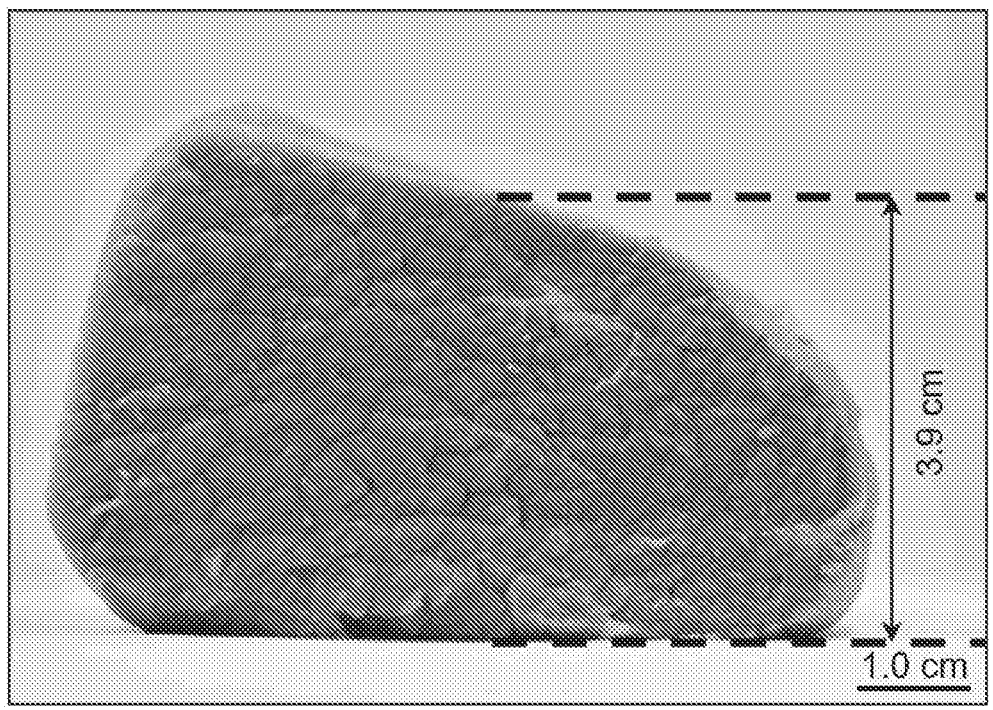
FIGS. 49A-49C show optical images and data concerning the serial monitoring of the modulus evolution of a bovine gluteobiceps muscle.
Figure 49B:
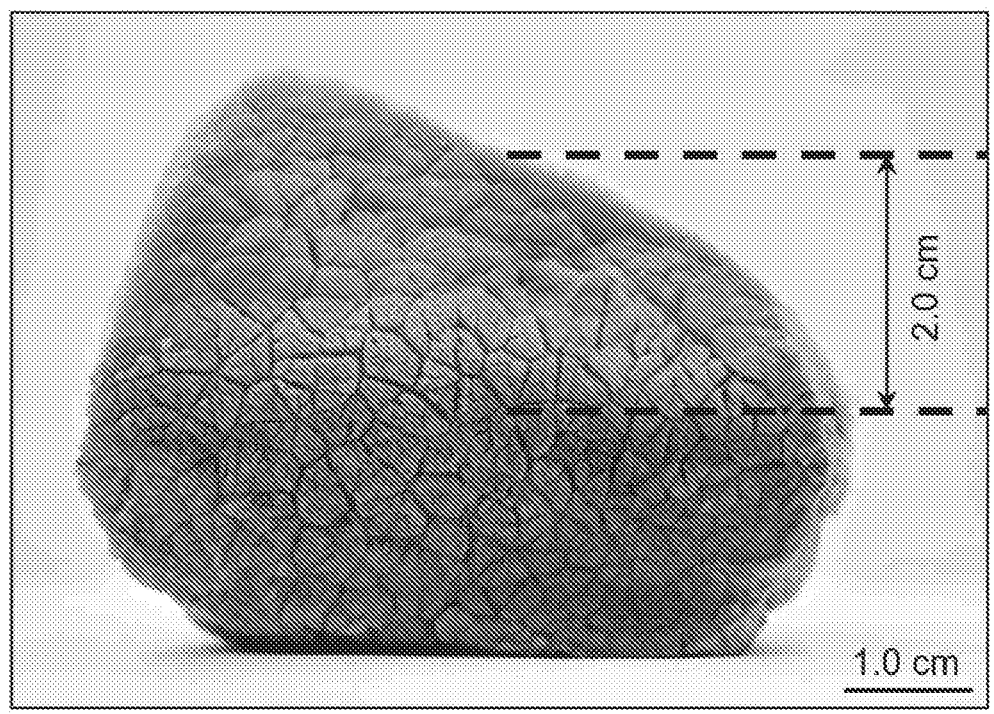
Figure 49C:
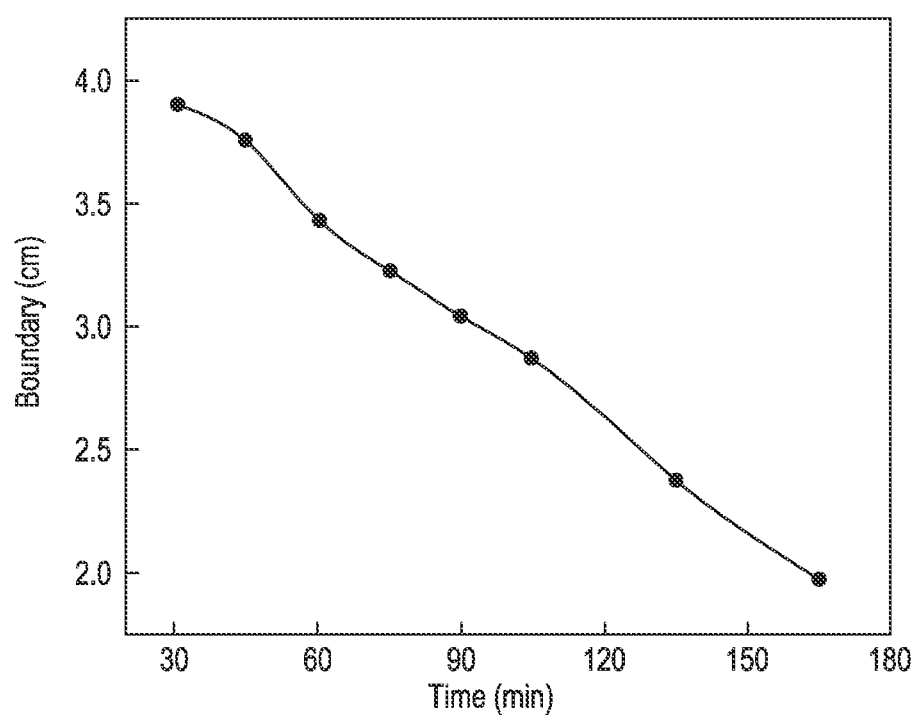

FIG. 49 shows the serial monitoring of the modulus evolution of a bovine gluteobiceps muscle. In particular, the figure shows optical images of the bovine gluteobiceps muscle before (FIG. 49a) and after (FIG. 49b) heating for 165 mins. The total thickness of the testing part is 3.9 cm. After heating, part of the specimen is stiffened, as evidenced by the boundary between stiff and soft tissues. FIG. 49(c) shows the boundary locations plotted with the heating time. The probe position is defined as the origin.

Figure 50:
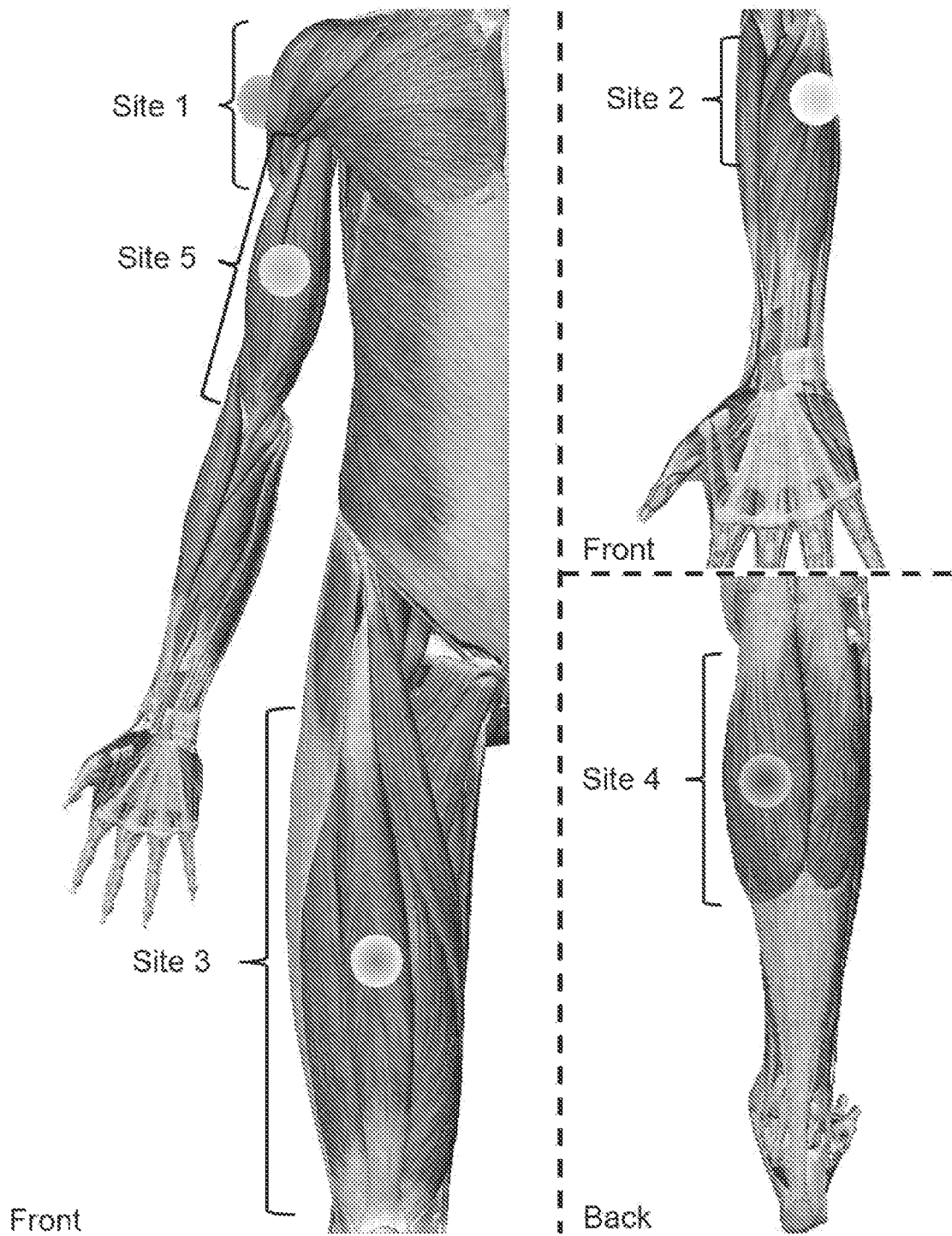
FIG. 50 shows a schematic plot demonstrating the anatomical structures and locations for in vivo measurements.

FIG. 50 shows a schematic plot demonstrating the anatomical structures and locations for in vivo measurements. Site 1: the later shoulder joint including the deltoid muscle belly. Site 2: the anterior arm including the palmaris longus muscle belly. Site 3: the anterior thigh from the upper pole of patella to the greater trochanter of femur. Site 4: the posterior calf including the medial head of the gastrocnemius. Site 5: the upper arm including the biceps brachii muscle belly.

FIG. 51 shows results validating the device's reliability on 10 subjects. Strain mapping results and the corresponding B-mode images of the upper arms of 10 subjects. Key anatomical structures are labelled in the strain images.

Figure 52A:
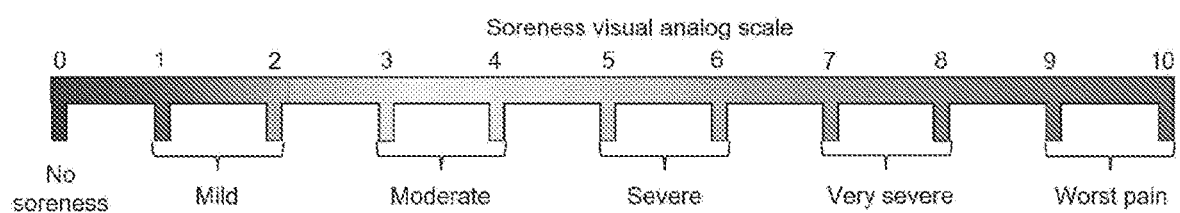
FIGS. 52A-52B show a soreness visual analog scale and testing protocol.
Figure 52B:
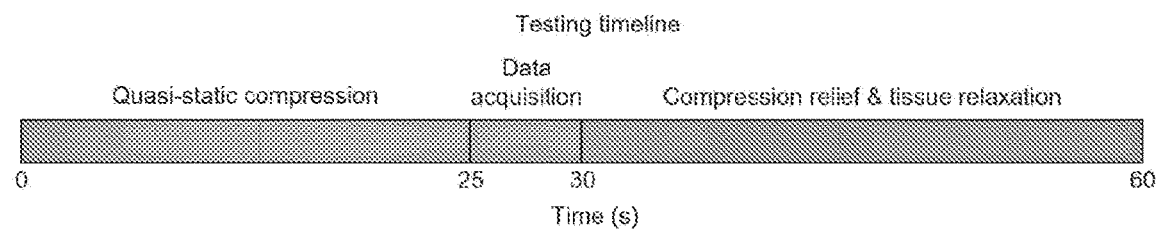

FIG. 52 shows a soreness visual analog scale and testing protocol. In particular, FIG. 52(a) shows a soreness visual analog scale interpreting the corresponding scores for different levels of soreness. FIG. 52(b) shows the testing protocol with all steps labelled. The test begins with quasi-static compression, which takes about 25 seconds. Then, multiple frames of data are acquired with a frame rate of 1 Hz. In the following ~30 s, the compression is relieved to make tissue recover to the original state.

Figure 53A:
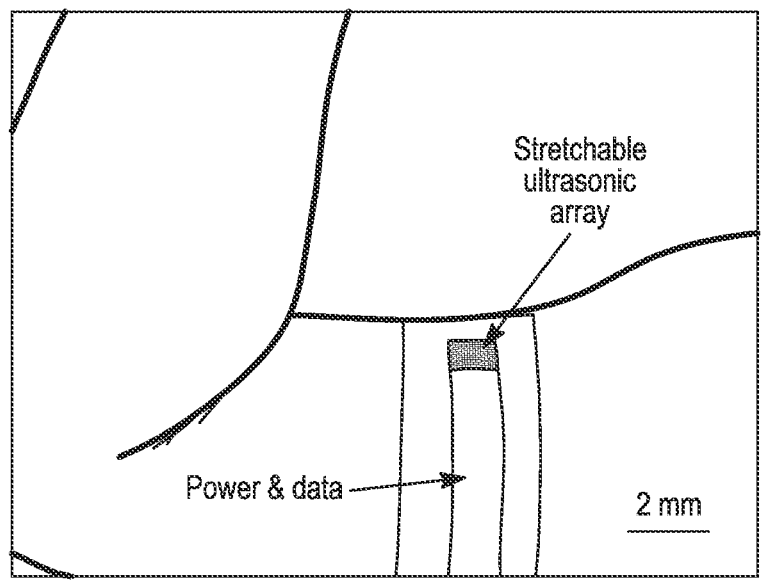
FIGS. 53A-53C show images concerning a 3D elastographic reconstruction of the upper arm.
Figure 53B:
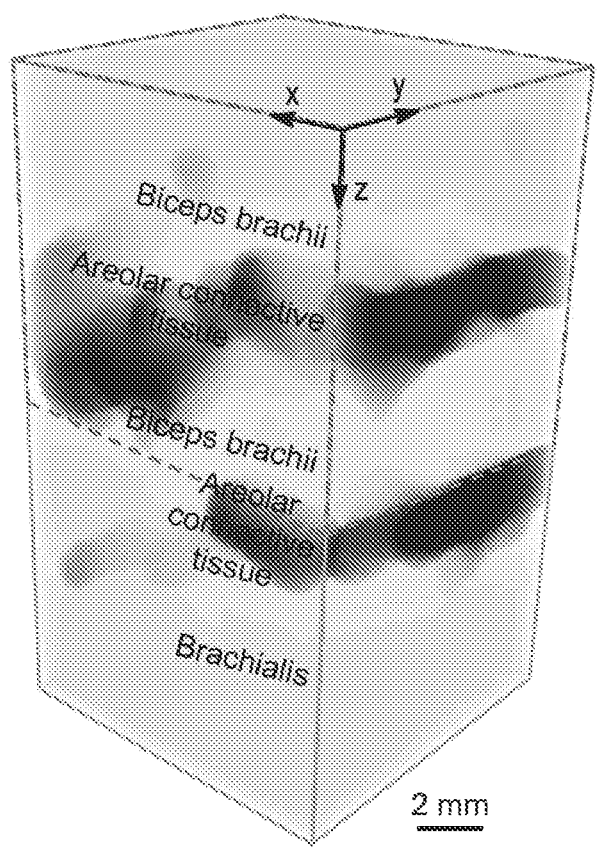
Figure 53C:
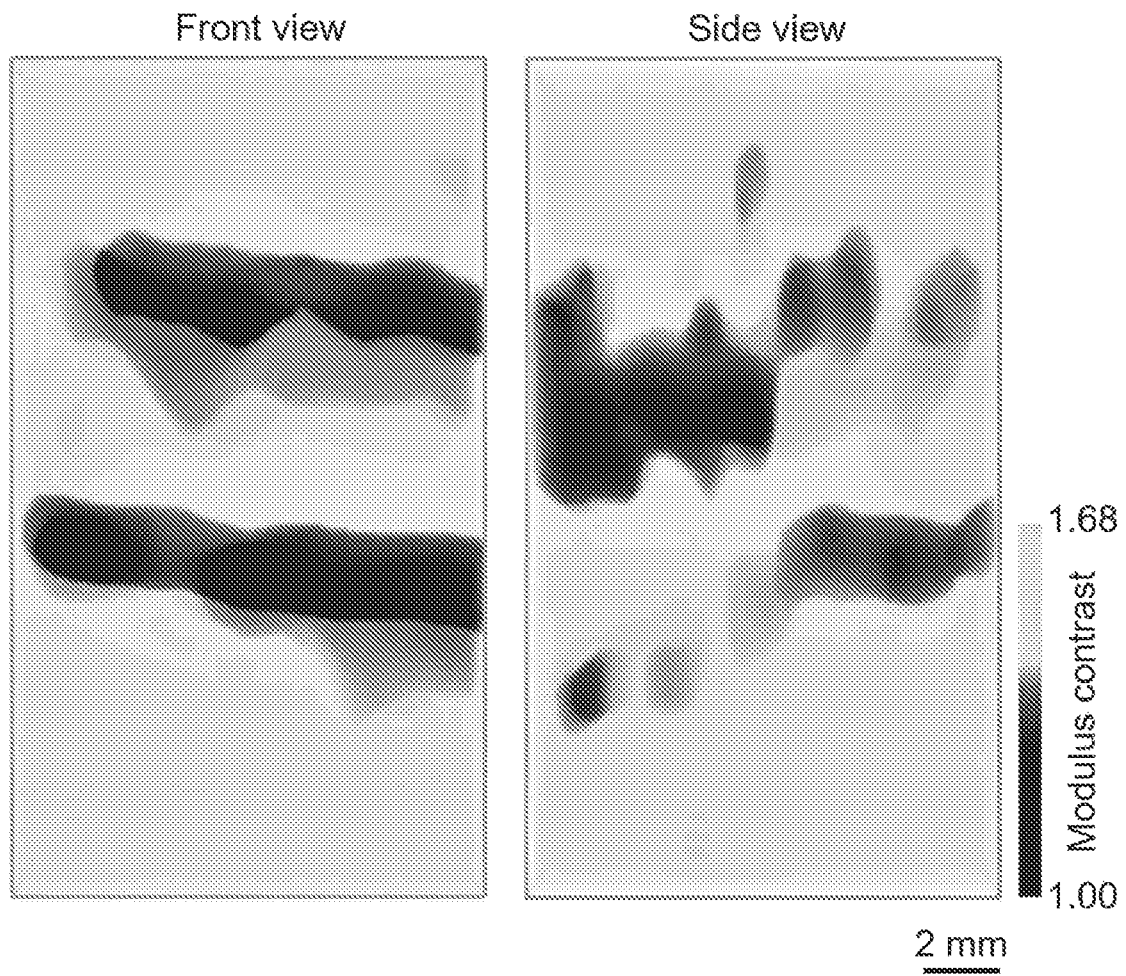

FIG. 53 shows a 3D elastographic reconstruction of the upper arm. In particular, FIG. 53(a) shows an optical image showing the device and the testing position. FIG. 53(b) shows a 3D modulus distribution of the upper arm mapped by the stretchable ultrasonic array and FIG. 53c shows its front and side views. The areolar connective tissues contain sparsely arranged fibers and collagens. In addition, the arm was bent at 90 degrees when testing in this study, which left the areolar connective tissue in a relaxed state with fibers unstretched. Therefore, it has a lower stiffness of than muscles.

Figure 54A:
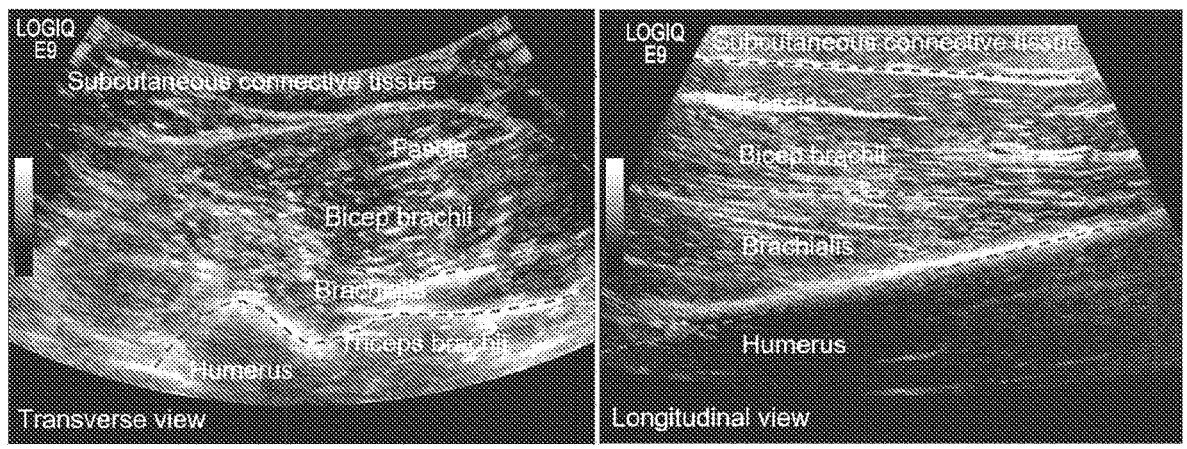
FIGS. 54A-54B show images providing a full view of the upper arm measured by a commercial ultrasonic system.
Figure 54B:
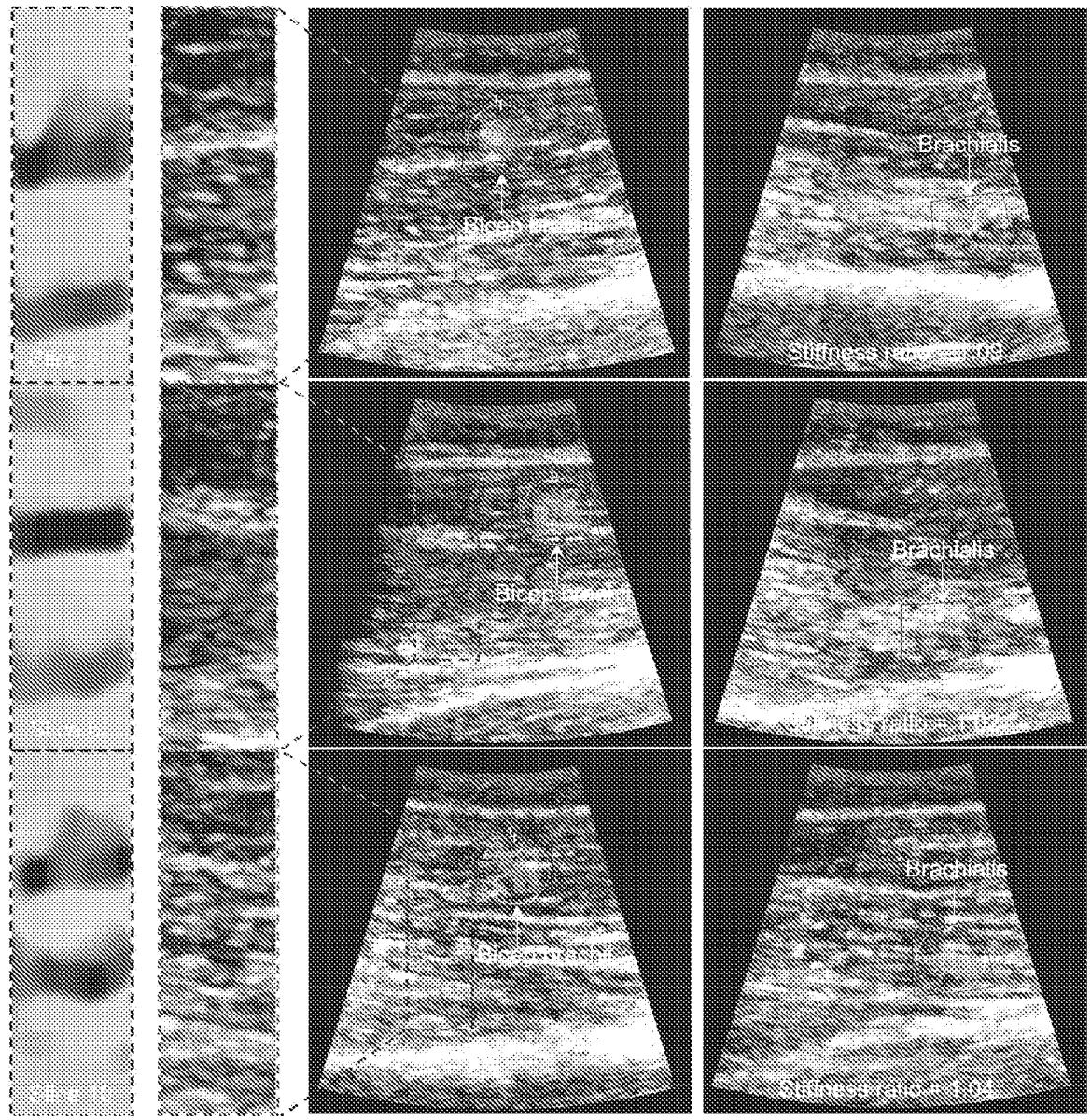

FIG. 54 shows a full view of the upper arm measured by a commercial ultrasonic system. In particular, FIG. 54(a) shows transverse and longitudinal B-mode images of the upper arm by a commercial ultrasonic system. Representative anatomical structures have been labelled. FIG. 54(b) shows B-mode images overlaid with corresponding modulus measurements. Representative structures and the stiffness ratio of bicep brachii and brachialis from the commercial system highly match with those from the stretchable ultrasonic patch.

Figure 55A:
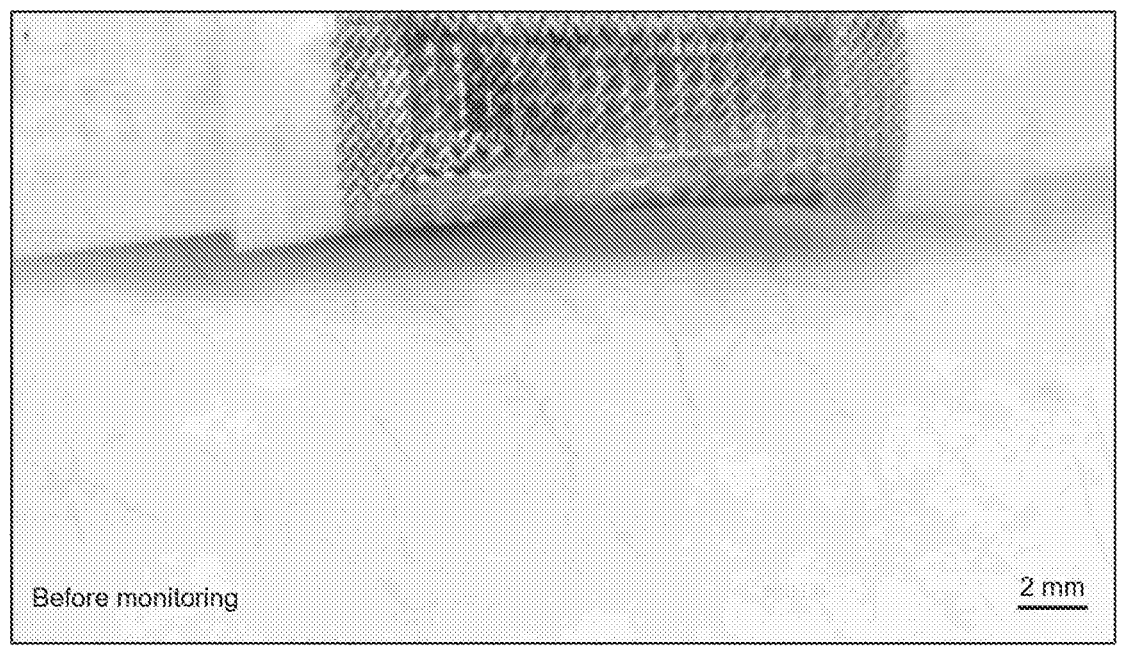
FIGS. 55A-55B show optical images of skin before and after monitoring.
Figure 55B:
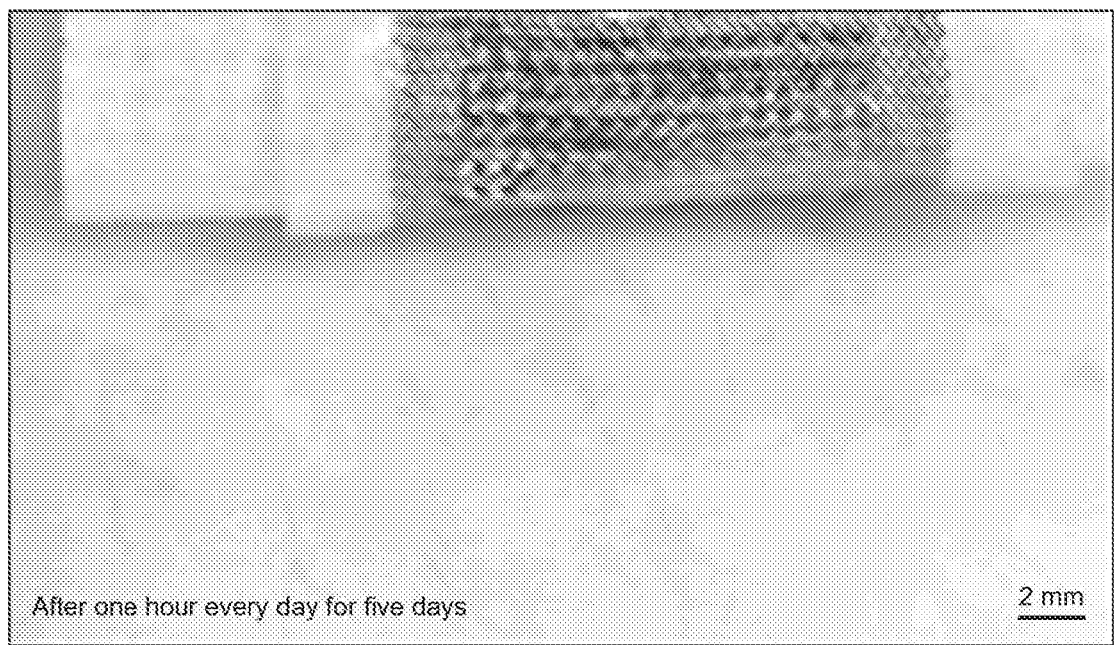
Figure 56A:
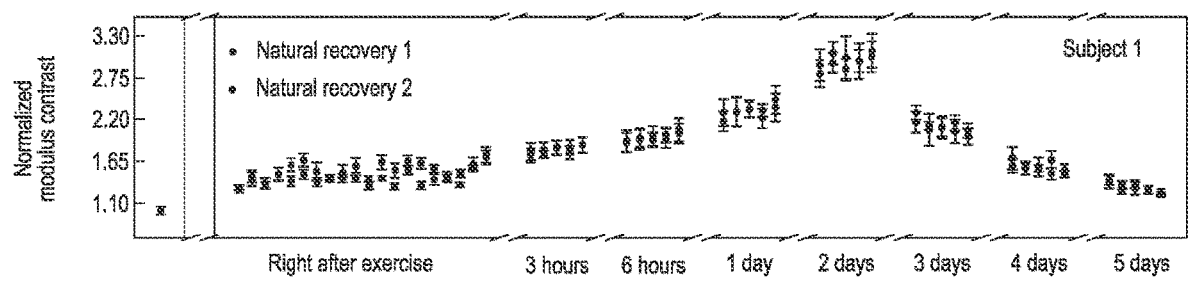
FIGS. 56A-56F show serial surveillance data of delayed onset muscle soreness in multiple subjects.
Figure 56B:
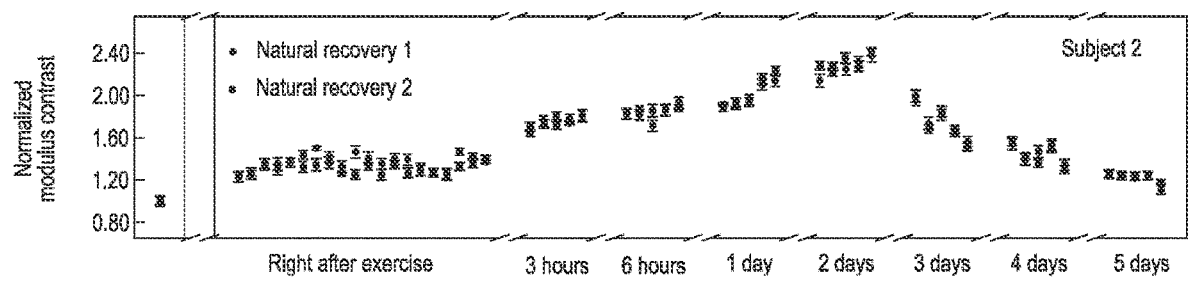
Figure 56C:
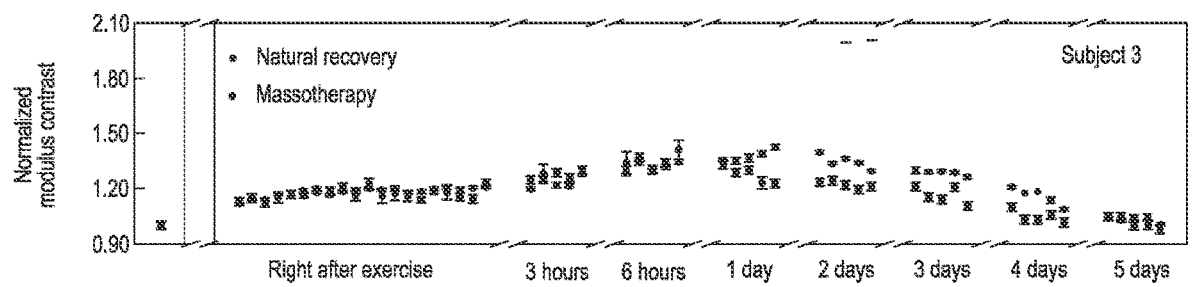
Figure 56D:
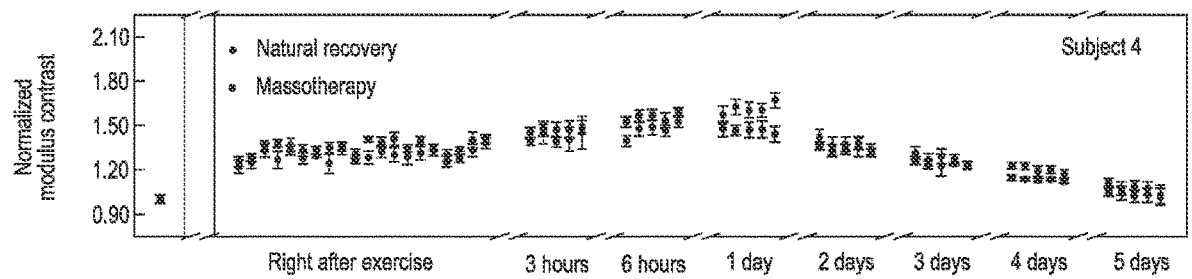
Figure 56E:
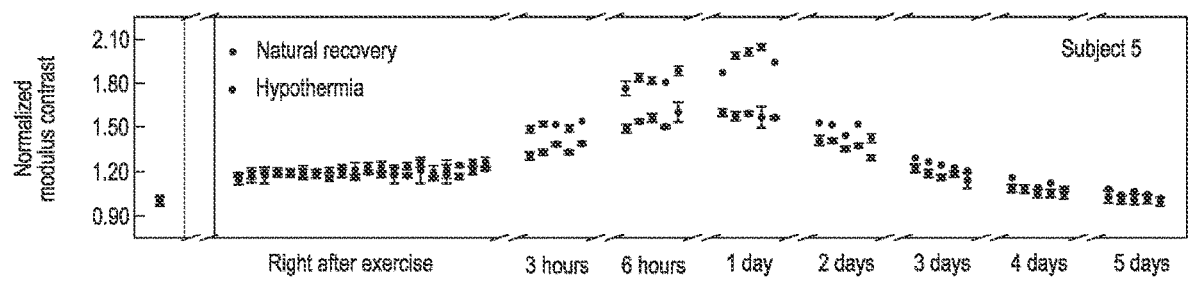
Figure 56F:
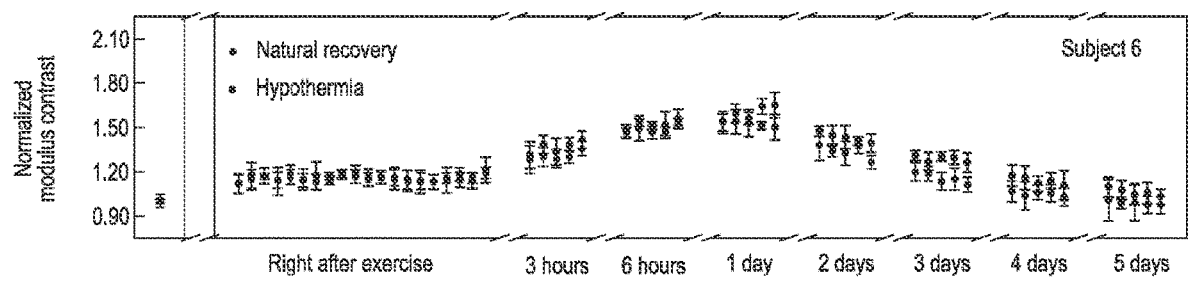

FIG. 55A shows an optical image of skin before monitoring and FIG. 55B shows an optical image of skin after monitoring. The device was mounted on the upper arm one hour every day for five days. No obvious skin irritation occurs, showing that the device is appropriate for long-time monitoring.

FIG. 56 shows serial surveillance data of delayed onset muscle soreness in multiple subjects. Serial monitoring results of normalized modulus contrast of the biceps brachii muscle before and after the eccentric exercise. All subjects did two rounds of experiments. In the first round, all subjects took the natural recovery after doing the exercise. In the second round, subjects in FIGS. 56(a) and 56(b) took natural recovery, subjects in FIGS. 56(c) 56(d) took massotherapy, and subjects in FIGS. 56(e) and 56(f) took hyperthermia.

FIG. 57 compares the coupling performance between ultrasonic gel and Silicone. In particular, received signals of the single transducer are shown with ultrasonic gel (FIG. 57a) and silicone (FIG. 57b) are shown. FIG. 57(c) shows a comparison of the corresponding signal-to-noise ratio of the received signals. Strain mapping of an upper arm by the stretchable ultrasonic array with different couplants are shown. The couplants of ultrasonic gel (FIG. 57d) and silicon (FIG. 57e) show similar results. Key anatomical structures are labelled.

FIG. 58 shows the length of the muscle fiber before and after compression. The schematics show the muscle fiber before (left) and after (right) compression. Muscle fibers will be extended along the axial direction after compression.

Additional Embodiments

The particular systems, devices and methods described herein for deriving a quantitative modulus distribution from which mechanical properties of tissue can be obtained have been presented for illustrative purposes only and not as a limitation on the systems, devices and method described herein.

More generally, in one aspect, a method is provided for determining one or more mechanical properties of tissue in an individual. In accordance with the method, a stretchable and/or flexible ultrasound imaging device is attached in a removable manner to the individual. The stretchable and/or flexible ultrasound imaging device includes at least a one-dimensional array of transducer elements. Ultrasound waves are transmitted into the individual using the transducer elements. A first series of ultrasound waves are received from the tissue in the individual using the transducer elements before applying a strain to the tissue by compression and a second series of ultrasound waves are received from the tissue in the individual using the transducer elements after applying the compression to the tissue. Data from the first series of ultrasound waves is compared to data from the second series of ultrasound waves to obtain displacement data of the tissue from which strain data representing strain applied to the tissue is obtainable. At least one 2D image representing a 2D modulus distribution within the tissue is generated using the displacement data of the tissue. One or more mechanical properties of the tissue is identified based on the 2D modulus distribution.

In another aspect, the mechanical property that is identified is a shear modulus or Young's modulus of the tissue.

In yet another aspect, the mechanical property that is identified is a viscoelasticity of the tissue.

In another aspect, a tissue type is determined from the identified one or more mechanical properties of the tissue.

In another aspect, the tissue type is determined to be cancerous tissue and the one or more mechanical properties of the tissue are used to distinguish between malignant and benign cancerous tissue.

In another aspect, the transmitting employs a beamforming scheme selected from the group including a coherent plane-wave compounding algorithm, a single plane-wave algorithm, and a mono-focus algorithm.

In another aspect, the receiving employs a beamforming scheme selected from group including a delay and sum algorithm, a delay multiply and sum algorithm, and a filtered-delay multiply and sum algorithm.

In another aspect, the comparing of data representing the first series of ultrasound waves to the data representing the second series of ultrasound waves uses a normalized cross-correlation algorithm to obtain the displacement data of the tissue.

In another aspect, the comparing of data representing the first series of ultrasound waves to the data representing the second series of ultrasound waves uses a least—squares strain estimator to obtain the strain data of the tissue.

In another aspect, an inverse elasticity problem calculation is used to generate at least one 2D modulus image slice using the displacement data of the tissue.

In another aspect, the strain applied to the tissue is about 1%.

In another aspect, generating the at least one 2D image includes generating a plurality of 2D image slices each representing a 2D modulus distribution within the tissue using the displacement data of the tissue.

In another aspect, a 3D image is generated from the plurality of 2D images slices, the 3D image representing a 3D modulus distribution within the tissue.

In another aspect, generating the 3D image from the plurality of 2D images slices uses cubic spline interpolation.

In another aspect, the stretchable and/or flexible ultrasound imaging device includes a two-dimensional array of transducer elements.

In another aspect, one or more mechanical properties of the tissue are monitored to identify changes to the tissue that are occurring over time by using the stretchable and/or flexible ultrasound imaging device.

In another aspect, the changes to the tissue that are occurring over time include an onset of microstructural damage of tissue or tissue recovery or tissue deterioration.

In another aspect, therapeutic treatments are adjusted based at least in part on changes to the tissue that are identified over time.

Certain aspects of the stretchable and/or flexible ultrasound imaging device described herein are presented in the foregoing description and illustrated in the accompanying drawing using electronic hardware, computer software, or any combination thereof. Whether such elements are implemented as hardware or software depends upon the particular application and design constraints imposed on the overall system. By way of example, such elements, or any portion of such elements, or any combination of such elements may be implemented with one or more processors or controllers. Examples of processors or controllers include microprocessors, microcontrollers, digital signal processors (DSPs), field programmable gate arrays (FPGAs), programmable logic devices (PLDs), state machines, gated logic, discrete hardware circuits, and any other suitable hardware configured to perform the various functionalities described throughout this disclosure. Examples of processors or controllers may also include general-purpose computers or computing platforms selectively activated or reconfigured by code to provide the necessary functionality.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalent of the appended claims.

The invention claimed is:

1. A method for determining one or more mechanical properties of tissue in an individual, comprising:
    attaching in a removable manner a stretchable and/or flexible ultrasound imaging device to the individual, the stretchable and/or flexible ultrasound imaging device including at least a one-dimensional array of transducer elements;
    transmitting ultrasound waves into the individual using the transducer elements;
    receiving a first series of ultrasound waves from the tissue in the individual using the transducer elements before applying a strain to the tissue by compression and a second series of ultrasound waves from the tissue in the individual using the transducer elements after applying the compression to the tissue;
    comparing data from the first series of ultrasound waves to data from the second series of ultrasound waves to obtain displacement data of the tissue from which strain data representing strain applied to the tissue is obtainable;
    generating at least one 2D image representing a 2D modulus distribution within the tissue using the displacement data of the tissue; and
    identifying one or more mechanical properties of the tissue based on the 2D modulus distribution.

2. The method of claim 1, wherein the mechanical property that is identified is a shear modulus or Young's modulus of the tissue.

3. The method of claim 1, wherein the mechanical property that is identified is a viscoelasticity of the tissue.

4. The method of claim 1, further comprising determining a tissue type from the identified one or more mechanical properties of the tissue.

5. The method of claim 4, wherein the tissue type is determined to be cancerous tissue and further comprising using the one or more mechanical properties of the tissue to distinguish between malignant and benign cancerous tissue.

6. The method of claim 1, wherein the transmitting employs a beamforming scheme selected from the group including a coherent plane-wave compounding algorithm, a single plane-wave algorithm, and a mono-focus algorithm.

7. The method of claim 1, wherein the receiving employs a beamforming scheme selected from group including a delay and sum algorithm, a delay multiply and sum algorithm, and a filtered-delay multiply and sum algorithm.

8. The method of claim 1, wherein the comparing of data representing the first series of ultrasound waves to the data representing the second series of ultrasound waves uses a normalized cross-correlation algorithm to obtain the displacement data of the tissue.

9. The method of claim 1, wherein the comparing of data representing the first series of ultrasound waves to the data representing the second series of ultrasound waves uses a least—squares strain estimator to obtain the strain data of the tissue.

10. The method of claim 1, further comprising using an inverse elasticity problem calculation to generate at least one 2D modulus image slice using the displacement data of the tissue.

11. The method of claim 1, wherein the strain applied to the tissue is about 1%.

12. The method of claim 1, wherein generating the at least one 2D image includes generating a plurality of 2D image slices each representing a 2D modulus distribution within the tissue using the displacement data of the tissue.

13. The method of claim 12, further comprising generating a 3D image from the plurality of 2D images slices, the 3D image representing a 3D modulus distribution within the tissue.

14. The method of claim 13, wherein generating the 3D image from the plurality of 2D images slices uses cubic spline interpolation.

15. The method of claim 1, wherein the stretchable and/or flexible ultrasound imaging device includes a two-dimensional array of transducer elements.

16. The method of claim 1, further comprising monitoring one or more mechanical properties of the tissue to identify changes to the tissue that are occurring over time by using the stretchable and/or flexible ultrasound imaging device.

17. The method of claim 16, wherein the changes to the tissue that are occurring over time include an onset of microstructural damage of tissue or tissue recovery or tissue deterioration.

18. The method of claim 16, further comprising adjusting therapeutic treatments based at least in part on changes to the tissue that are identified over time.

* * * * *